(12) United States Patent
Hennig et al.

(10) Patent No.: US 12,121,610 B2
(45) Date of Patent: *Oct. 22, 2024

(54) COMPOSITIONS AND METHODS FOR TARGETED DELIVERY TO CELLS

(71) Applicant: ReCode Therapeutics, Inc., Menlo Park, CA (US)

(72) Inventors: Mirko Hennig, Mountain View, CA (US); Vladimir Kharitonov, San Diego, CA (US); Brandon A. Wustman, San Diego, CA (US); Jackson Eby, Menlo Park, CA (US); Rumpa Bhattacharjee, Menlo Park, CA (US)

(73) Assignee: ReCode Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,616

(22) Filed: May 3, 2023

(65) Prior Publication Data

US 2023/0302138 A1 Sep. 28, 2023

Related U.S. Application Data

(63) Continuation of application No. PCT/US2022/021442, filed on Mar. 22, 2022.

(60) Provisional application No. 63/305,426, filed on Feb. 1, 2022, provisional application No. 63/229,497, filed on Aug. 4, 2021, provisional application No. 63/164,523, filed on Mar. 22, 2021.

(51) Int. Cl.
| | | |
|---|---|---|
| *A61K 47/14* | (2017.01) | |
| *A61K 9/00* | (2006.01) | |
| *A61K 9/127* | (2006.01) | |
| *A61K 9/51* | (2006.01) | |
| *A61K 31/7115* | (2006.01) | |
| *A61K 47/10* | (2017.01) | |
| *A61K 47/24* | (2006.01) | |
| *A61K 47/28* | (2006.01) | |
| *A61K 47/54* | (2017.01) | |
| *A61P 11/00* | (2006.01) | |
| *C07K 14/47* | (2006.01) | |
| *C12N 9/14* | (2006.01) | |
| *C12N 15/113* | (2010.01) | |
| *C12N 15/88* | (2006.01) | |

(52) U.S. Cl.
CPC .......... *A61K 9/0073* (2013.01); *A61K 9/1272* (2013.01); *A61K 9/51* (2013.01); *A61K 31/7115* (2013.01); *A61K 47/10* (2013.01); *A61K 47/14* (2013.01); *A61K 47/24* (2013.01); *A61K 47/28* (2013.01); *A61K 47/543* (2017.08); *A61K 47/544* (2017.08); *A61P 11/00* (2018.01); *C07K 14/47* (2013.01); *C12N 9/14* (2013.01); *C12N 15/113* (2013.01); *C12N 15/88* (2013.01); *C12Y 306/04002* (2013.01)

(58) Field of Classification Search
None
See application file for complete search history.

(56) References Cited

U.S. PATENT DOCUMENTS

| | | |
|---|---|---|
| 5,820,873 A | 10/1998 | Choi et al. |
| 5,962,429 A | 10/1999 | Welsh et al. |
| 8,450,298 B2 | 5/2013 | Mahon et al. |
| 8,691,966 B2 | 4/2014 | Kariko et al. |
| 8,748,089 B2 | 6/2014 | Kariko et al. |
| 8,835,108 B2 | 9/2014 | Kariko et al. |
| 9,750,824 B2 | 9/2017 | Kariko et al. |
| 10,137,086 B2 | 11/2018 | Derosa et al. |
| 10,232,055 B2 | 3/2019 | Kariko et al. |
| 10,717,982 B2 | 7/2020 | Eberle et al. |
| 10,898,574 B2 | 1/2021 | De Fougerolles et al. |
| 11,090,264 B2 | 8/2021 | Heartlein et al. |
| 11,135,312 B2 | 10/2021 | Von Der Mülbe et al. |
| 11,173,190 B2 | 11/2021 | Heartlein et al. |
| 11,247,968 B2 | 2/2022 | Siegwart et al. |
| 11,253,605 B2 | 2/2022 | Dias et al. |

(Continued)

FOREIGN PATENT DOCUMENTS

| | | |
|---|---|---|
| EP | 0941066 A1 | 9/1999 |
| EP | 2578685 B1 | 4/2019 |

(Continued)

OTHER PUBLICATIONS

Alabi et al. (Aug. 6, 2013) "Multiparametric Approach for the Evaluation of Lipid Nanoparticles for siRNA delivery", Proceedings of the National Academy of Sciences of the United States of America, 110(32):12881-12886.

Álvarez-Benedicto et al. (Jan. 18, 2022) "Optimization of Phospholipid Chemistry for Improved Lipid Nanoparticle (LNP) Delivery of Messenger RNA (mRNA)", Biomaterials Science, 10(2):549-559 (20 pages).

Arteta et al. (Mar. 27, 2018) "Successful Reprogramming of Cellular Protein Production Through mRNA Delivered by Functionalized Lipid Nanoparticles", Proceedings of the National Academy of Sciences of the United States of America, 115(15):E3351-E3360.

(Continued)

*Primary Examiner* — Celeste A Roney
(74) *Attorney, Agent, or Firm* — Mintz Levin Cohn Ferris Glovsky and Popeo, P.C.

(57) ABSTRACT

Described herein are compositions, kits, and methods for potent delivery to a cell of a subject. The cell can be of a particular cell type, such as a basal cell, a ciliated cell, or a secretory cell. In some cases, the cell can be a lung cell of a particular cell type. Also described herein are pharmaceutical compositions comprising a therapeutic or prophylactic agent assembled to a lipid composition. The lipid composition can comprise an ionizable cationic lipid, a phospholipid, and a selective organ targeting lipid. Further described herein are high-potency dosage forms of a therapeutic or prophylactic agent formulated with a lipid composition.

32 Claims, 62 Drawing Sheets

(56) References Cited

U.S. PATENT DOCUMENTS

| | | |
|---|---|---|
| 11,389,547 B2 | 7/2022 | Kariko et al. |
| 11,498,944 B2 | 11/2022 | Langedijk et al. |
| 11,510,880 B2 | 11/2022 | Cheng et al. |
| 11,510,997 B2 | 11/2022 | Lockhart et al. |
| 11,559,561 B2 | 1/2023 | Dias et al. |
| 11,642,421 B2 | 5/2023 | Lockhart et al. |
| 11,648,209 B2 | 5/2023 | Cheng et al. |
| 11,648,210 B2 | 5/2023 | Cheng et al. |
| 11,766,408 B2 | 9/2023 | Cheng et al. |
| 11,786,610 B2 | 10/2023 | Lockhart et al. |
| 11,858,884 B2 | 1/2024 | Siegwart et al. |
| 2015/0157565 A1 | 6/2015 | Heartlein et al. |
| 2018/0200186 A1 | 7/2018 | Chen et al. |
| 2019/0117796 A1 | 4/2019 | Lockhart et al. |
| 2019/0167811 A1* | 6/2019 | Benenato ............ A61K 31/713 |
| 2021/0259980 A1 | 8/2021 | Cheng et al. |
| 2021/0275689 A1* | 9/2021 | Karve .................. A61K 48/005 |
| 2022/0071916 A1 | 3/2022 | Cheng et al. |
| 2023/0293429 A1 | 9/2023 | Hennig et al. |
| 2023/0338411 A1 | 10/2023 | Hennig et al. |
| 2024/0010614 A1 | 1/2024 | Siegwart et al. |
| 2024/0025848 A1 | 1/2024 | Siegwart et al. |
| 2024/0043378 A1 | 2/2024 | Siegwart et al. |
| 2024/0083842 A1 | 3/2024 | Siegwart et al. |
| 2024/0116859 A1 | 4/2024 | Siegwart et al. |
| 2024/0116860 A1 | 4/2024 | Siegwart et al. |

FOREIGN PATENT DOCUMENTS

| | | | |
|---|---|---|---|
| EP | 3317411 B1 | 12/2020 | |
| EP | 2858679 B1 | 2/2021 | |
| EP | 3060257 B1 | 2/2021 | |
| EP | 3611266 B1 | 11/2022 | |
| WO | 2010144740 A1 | 12/2010 | |
| WO | 2011068810 A1 | 6/2011 | |
| WO | 2012170930 A1 | 12/2012 | |
| WO | 2013149140 A1 | 10/2013 | |
| WO | 2015095340 A1 | 6/2015 | |
| WO | 2015199952 A1 | 12/2015 | |
| WO | 2016004202 A1 | 1/2016 | |
| WO | 2016094342 A1 | 6/2016 | |
| WO | 2016118724 A1 | 7/2016 | |
| WO | 2016118725 A1 | 7/2016 | |
| WO | 2016205691 A1 | 12/2016 | |
| WO | 2017004143 A1 | 1/2017 | |
| WO | 2017048789 A1 | 3/2017 | |
| WO | 2017075531 A1 | 5/2017 | |
| WO | 2017117528 A1 | 7/2017 | |
| WO | 2017173054 A1 | 10/2017 | |
| WO | 2017201076 A1 | 11/2017 | |
| WO | 2017201091 A1 | 11/2017 | |
| WO | 2017205767 A1 | 11/2017 | |
| WO | 2019246203 A1 | 12/2019 | |
| WO | 2020051223 A1 | 3/2020 | |
| WO | WO-2020051220 A1 * | 3/2020 | ......... A61K 31/7105 |
| WO | 2020106946 A1 | 5/2020 | |
| WO | 2021205032 A1 | 10/2021 | |
| WO | 2021216577 A1 | 10/2021 | |
| WO | 2021222801 A2 | 11/2021 | |
| WO | 2021226463 A1 | 11/2021 | |
| WO | 2022032154 A2 | 2/2022 | |
| WO | 2022040641 A2 | 2/2022 | |
| WO | 2022169508 A1 | 8/2022 | |
| WO | 2022198099 A1 | 9/2022 | |
| WO | 2022204053 A1 | 9/2022 | |
| WO | 2022204215 A1 | 9/2022 | |
| WO | 2022204219 A1 | 9/2022 | |
| WO | 2022204270 A1 | 9/2022 | |
| WO | 2022204286 A1 | 9/2022 | |
| WO | 2022216619 A1 | 10/2022 | |
| WO | 2022226344 A1 | 10/2022 | |
| WO | 2022261185 A1 | 12/2022 | |

OTHER PUBLICATIONS

Battaglia et al. (Jan. 15, 2019) "Lipid Nano- and Microparticles: An Overview of Patent-Related Research", Journal of Nanomaterials, 2:1-22.

Bryson et al. (May 20, 2022) "Aerosolized Therapy Restores CFTR in Patient-derived Cells", Cystic Fibrosis News Today, 5 pages.

Cao et al. (Aug. 15, 2022) "Helper-Polymer Based Five-Element Nanoparticles (FNPs) for Lung-Specific mRNA Delivery with Long-Term Stability after Lyophilization", Nano Letters, 22(16):6580-6589.

Carrasco et al. (Aug. 11, 2021) "Ionization and Structural Properties of mRNA Lipid Nanoparticles Influence Expression in Intramuscular and Intravascular Administration", Communications Biology, 4(1):956 (15 pages).

Chahal et al. (Jul. 19, 2016) "Dendrimer-RNA Nanoparticles Generate Protective Immunity Against Lethal Ebola, H1N1 Influenza, and Toxoplasma Gondii Challenges With a Single Dose", Proceedings of the National Academy of Sciences of the United States of America, 113(29):E4133-4142.

Chang et al. (Oct. 6, 2021) "Lipid Nanoparticles for the Inhalation of mRNA", Nature Biomedical Engineering, 9:949-950.

Cheng et al. (Dec. 2018) "Dendrimer-Based Lipid Nanoparticles Deliver Therapeutic FAH mRNA to Normalize Liver Function and Extend Survival in a Mouse Model of Hepatorenal Tyrosinemia Type I", Advanced Materials, 30(52):e1805308 (10 pages).

Chow et al. (Oct. 2020) "Inhaled RNA Therapy: From Promise to Reality", Trends in Pharmacological Sciences, 41(10):715-729 (16 pages).

Dilliard et al. (Dec. 28, 2021) "On the Mechanism of Tissue-specific mRNA Delivery by Selective Organ Targeting Nanoparticles", Proceedings of the National Academy of Sciences of the United States of America, 118(52):e2109256118 (10 pages).

Farbiak et al. (Jun. 17, 2021) "All-In-One Dendrimer-Based Lipid Nanoparticles Enable Precise HDR-Mediated Gene Editing In Vivo", Advanced Materials, 33(30):e2006619 (8 pages).

Gary et al. (Aug. 2013) "The Effect of N/P Ratio on the In Vitro and In Vivo Interaction Properties of PEGylated Poly(2-(dimethylamino)ethyl methacrylate)-Based siRNA Complexes", Macromolecular Bioscience, 13(8):1059-1071 (28 pages).

Han et al. (Dec. 13, 2021) "An Ionizable Lipid Toolbox for RNA Delivery", Nature Communications, 12(1):7233 (6 pages).

Hashiba et al. (Nov. 2022) "Branching Ionizable Lipids Can Enhance the Stability, Fusogenicity, and Functional Delivery of mRNA", Small Science, 3(1):2200071 (12 pages).

Hou et al. (Aug. 10, 2021) "Lipid nanoparticles for mRNA delivery", Nature Reviews Materials, 6(12):1078-1094.

Khan et al. (Mar. 19, 2015) "Dendrimer-Inspired Nanomaterials for the in Vivo Delivery of siRNA to Lung Vasculature", Nano Letters, 15(5):3008-3016 (24 pages).

Khan et al. (Dec. 22, 2014) "Ionizable Amphiphilic Dendrimer-based Nanomaterials With Alkyl-chain-substituted Amines for Tunable siRNA delivery to the Liver Endothelium in Vivo", Angewandte Chemie, 53(52):14397-14402 (12 pages).

Kim et al. (Aug. 29, 2022) "Engineering Lipid Nanoparticles for Enhanced Intracellular Delivery of mRNA through Inhalation", ACS Nano, 16(9):14792-14806.

Liu et al. (Feb. 4, 2021) "Membrane-destabilizing Ionizable Phospholipids for Organ-selective mRNA Delivery and CRISPR-Cas Gene Editing", Nature Materials, 20(5):701-710 (24 pages).

Lokugamage et al. (Oct. 6, 2021) "Optimization of Lipid Nanoparticles for the Delivery of Nebulized Therapeutic mRNA to the Lungs", Nature Biomedical Engineering, 9:1059-1068 (23 pages).

Miller et al. (Jan. 19, 2017) "Non-Viral CRISPR/Cas Gene Editing In Vitro and In Vivo Enabled by Synthetic Nanoparticle Co-Delivery of Cas9 mRNA and sgRNA", Angewandte Chemie, 56(4):1059-1063 (12 pages).

Pardi et al. (Nov. 10, 2015) "Expression Kinetics of Nucleoside-modified mRNA Delivered in Lipid Nanoparticles to Mice by Various Routes", Journal of Controlled Release, 217:345-351 (18 pages).

(56) References Cited

OTHER PUBLICATIONS

Pei et al. (Mar. 2022) "Synthesis and Bioactivity of Readily Hydrolysable Novel Cationic Lipids for Potential Lung Delivery Application of mRNAs", Chemistry and Physics of Lipids, 243:105178 (12 pages).

Pillai et al. (Nov. 1998) "Ultrasonic Nebulization of Cationic Lipid-based Gene Delivery Systems for Airway Administration", Pharmaceutical Research, 15(11):1743-1747.

Qiu et al. (Feb. 22, 2022) "Lung-selective mRNA Delivery of Synthetic Lipid Nanoparticles for the Treatment of Pulmonary Lymphangioleiomyomatosis", Proceedings of the National Academy of Sciences of the United States of America, 119(8):e2116271119 (10 pages).

Samaridou et al. (2020) "Lipid Nanoparticles for Nucleic Acid Delivery: Current Perspectives", Advanced Drug Delivery Reviews, 154-155:37-63 (83 pages).

Sanchez et al. (Jan. 2023) "Substituting Racemic Ionizable Lipids With Stereopure Ionizable Lipids Can Increase mRNA Delivery", Journal of Controlled Release, 353:270-277.

Shaffer et al. (Oct. 2020) "Mist Begins to Clear for Lung Delivery of RNA", Nature Biotechnology, 38(10):1110-1112.

Tam et al. (Jun. 2022) "Lipid Nanoparticle Formulations for Optimal RNA-based Topical Delivery to Murine Airways", European Journal of Pharmaceutical Sciences, 176(20):106234 (10 pages).

Wang et al. (Oct. 31, 2022) "Preparation of Selective Organ-targeting (SORT) Lipid Nanoparticles (LNPs) Using Multiple Technical Methods for Tissue-specific mRNA Delivery", Nature Protocols, 18:265-291.

Whitehead et al. (Jun. 27, 2014) "Degradable Lipid Nanoparticles With Predictable in Vivo Sirna Delivery Activity", Nature Communications, 5:4277 (22 pages).

Zhou et al. (Jan. 19, 2016) "Modular Degradable Dendrimers Enable Small Rnas to Extend Survival in an Aggressive Liver Cancer Model", Proceedings of the National Academy of Sciences of the United States of America, 113(3):520-525.

McClellan, et al. (Apr. 16, 2010) Genetic Heterogeneity in Human Disease, Cell, 141(2):210-217.

Cheng, Q. et al., "Selective organ targeting (SORT) nanoparticles for tissue-specific mRNA delivery and CRISPR-Cas gene editing," Nature nanotechnology, Apr. 6, 2020, vol. 15, No. 4, pp. 313-320.

Graham, C. et al., "CRISPR/Cas9 gene editing therapies for cystic fibrosis," Expert opinion on biological therapy, Feb. 2, 2021 (online), vol. 21, No. 6, pp. 767-780.

Wei, T. et al., "Systemic nanoparticle delivery of CRISPR-Cas9 ribonucleoproteins for effective tissue specific genome editing," Nature communications, 2020, vol. 11, Article No. 3232, pp. 1-12.

International Search Report and Written Opinion for International Application No. PCT/US2022/021442, mailed Jul. 7, 2022 (12 pages).

Allen et al. (2013) "Liposomal Drug Delivery Systems: From Concept to Clinical Applications", Advanced Drug Delivery Reviews, 65(1):36-48.

Anderson et al. (Oct. 2019) "Inhalable Nanotherapeutics to Improve Treatment Efficacy for Common Lung Diseases", WIREs Nanomedicine and Nanobiotechnology, 12(1):e1586(29 pages).

Buschmann et al. (2021) "Nanomaterial Delivery Systems for mRNA Vaccines", Vaccines, 9(1):65(30 pages).

Chhin et al. (Mar. 20, 2009) "Ciliary Beating Recovery in Deficient Human Airway Epithelial Cells after Lentivirus Ex Vivo Gene Therapy", Plos Genetics, 5(3):e1000422(8 pages).

Danilovtseva et al. (Nov. 16, 2017) "Polymeric Amines and Ampholytes Derived from Poly(acryloyl chloride): Synthesis, Influence on Silicic Acid Condensation and Interaction with Nucleic Acid", Polymers, 9(11):624(18 pages).

Ferguson et al. (2018) "Co-Suspension Delivery Technology in Pressurized Metered-Dose Inhalers for Multi-drug Dosing in the Treatment of Respiratory Diseases", Respiratory Medicine, 134:16-23.

Guevara et al. (Oct. 23, 2020) "Advances in Lipid Nanoparticles for mRNA-Based Cancer Immunotherapy", Frontiers in Chemistry, 8(589959):17 pages.

Guo et al. (Aug. 2021) "Pharmaceutical Strategies to Extend Pulmonary Exposure of Inhaled Medicines", Acta Pharmaceutica Sinica B, 11(8):2565-2584.

Haque et al. (Nov. 13, 2018) "Chemically Modified hCFTR mRNAs Recuperate Lung Function in a Mouse Model of Cystic Fibrosis", Scientific reports, 8(1):1-14.

Jarzebinska et al. (Aug. 2016) "A Single Methylene Group in Oligoalkylamine-Based Cationic Polymers and Lipids Promotes Enhanced mRNA Delivery", Angewandte Chemie International Edition in English, 55(33):9591-9595.

Jayaraman et al. (2012) "Maximizing the Potency of siRNA Lipid Nanoparticles for Hepatic Gene Silencing In Vivo", Angewandte Chemie International Edition, 51(34):8529-8533.

Karra et al. (Dec. 2019) "Drug Delivery for Traditional and Emerging Airway Models", Organs-on-a-Chip, 1:100002(13 pages).

Leong et al. (Sep. 2022) "Lipid Nanoparticles as Delivery Vehicles for Inhaled Therapeutics", Biomedicines, 10(9):2179(25 pages).

Liu et al. (Jul. 2021) "Non-Viral Nanoparticles for RNA Interference: Principles of Design and Practical Guidelines", Advanced Drug Delivery Reviews, 174:576-612.

Micklefield, Jason (2001) "Backbone Modification of Nucleic Acids: Synthesis, Structure and Therapeutic Applications", Current Medicinal Chemistry, 8(10):1157-1179.

Paranjpe et al. (Apr. 2014) "Nanoparticle-Mediated Pulmonary Drug Delivery: A Review", International Journal of Molecular Sciences, 15(4):5852-5873.

Uner et al. (2007) "Importance of Solid Lipid Nanoparticles (SLN) in Various Administration Routes and Future Perspectives", International Journal of Nanomedicine, 2(3):289-300.

Robinson et al. (2018) "Lipid Nanoparticle-Delivered Chemically Modified mRNA Restores Chloride Secretion in Cystic Fibrosis", Molecular Therapy, 26(8):2034-2046.

Zhang, et al. (2020) "Aerosolizable Lipid Nanoparticles for Pulmonary Delivery of mRNA through Design of Experiments", Pharmaceutics, 12(11):1042(16 pages).

Hu Xiong, et al.; "Theranostic Dendrimer-Based Lipid Nanoparticles Containing PEGylated Bodipy Dyes for Tumor Imaging and Systemic mRNA delivery in Vivo"; J Control Release; Sep. 10, 2020; 17 pgs.

\* cited by examiner

Fig. 1
DOTAP
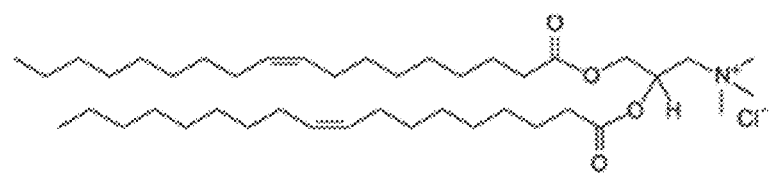
DODAP
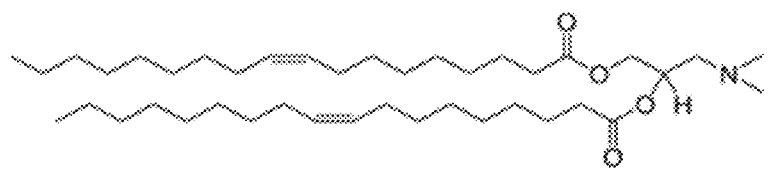
EPC
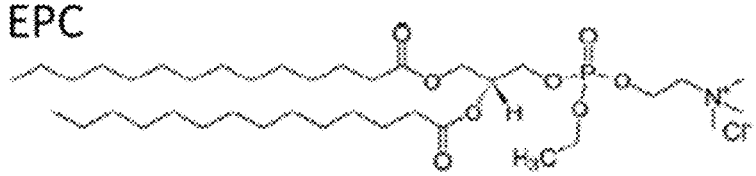

Fig. 3
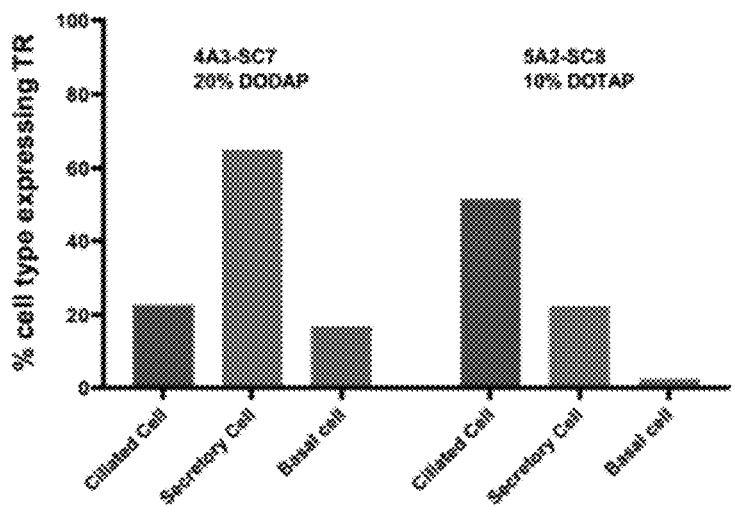
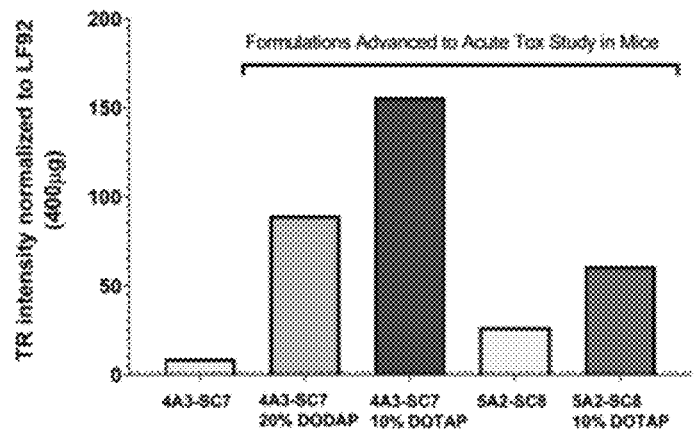

| STUDY GOALS | PARAMETERS | READOUTS |
|---|---|---|
| Compare multiple LNP formulations for:<br>1) biodistribution<br>2) expression in target cells<br>3) initial tolerability<br><br>Looking for:<br>• Good lung distribution of mRNA & protein<br>• Confirm mRNA to protein expression in target cells<br>• Tolerability findings that support further dose finding and repeat dosing studies | NHPs intubated and ventilated to ensure consistent delivered dose for comparison between formulations<br><br>Model: Cynomolgus macaques<br>Treatment:<br>• Short exposure: ≤ 9 minutes<br>• Single low dose: < 0.1 mg/kg<br>Formulations:<br>• LNP<br>Device: Aerogen solo | Readouts/necropsy at 6 and 24 hrs post

| No# | Designation (min) | Target dose TD (mg/kg) | Aerosol concentration $E_c$ (ug/L) | RMV (L) | BW (kg) | Delivered dose (mg/kg) | Animals |
|---|---|---|---|---|---|---|---|
| 1 | Vehicle 90 | 0 | 0 | 1.638 | 3.2 | 0 | Male |
|   |   |   |   | 1.417 | 2.7 | 0 | Female |
| 2 | Low 30 | 0.08 | 7.62 +/- 0.369 (5.2) | 1.550 | 3.0 | 0.12 | Male |
|   |   |   |   | 1.462 | 2.8 | 0.12 | Female |
| 4 | High 90 | 0.24 | 8.22 +/- 0.741 (5.2) | 1.594 | 3.1 | 0.38 | Male |
|   |   |   |   | 1.506 | 2.9 | 0.38 | Female |

0.38 mg/kg → 1.14 mg -25%→ 285 μg (RNA) → 8.55 mg total lipids

Fig. 18C

| RTX-00052/DNAI1 | Impactor (Mercer) | |
|---|---|---|
|  | MMAD (μm) | GSD |
| 2 | 1.7 | 1.88 |
| 3 | 2.3 | 1.92 |

G = gravimetric analysis

Fig. 22C

| No# | Designation (min) | Target dose TD (mg/kg) | Aerosol concentration $E_c$ (ug/L) | RMV (L) | BW (kg) | Delivered dose (mg/kg) | Animals |
|---|---|---|---|---|---|---|---|
| 1 | Vehicle 240 | 0 | 0 | 0.224 | 0.310 | 0 | Male |
|   |   |   |   | 0.158 | 0.205 | 0 | Female |
| 2 | Low 60 | 0.25 | 5.44 +/- 0.369 (5.5) | 0.223 | 0.308 | 0.24 | Male |
|   |   |   |   | 0.153 | 0.198 | 0.25 | Female |
| 3 | Mid 120 | 0.49 | 5.50 +/- 0.585 (5.5) | 0.255 | 0.311 | 0.48 | Male |
|   |   |   |   | 0.156 | 0.203 | 0.51 | Female |
| 4 | High 240 | 0.99 | 6.70 +/- 0.741 (5.5) | 0.227 | 0.315 | 1.16 | Male |
|   |   |   |   | 0.161 | 0.210 | 1.23 | Female |

Fig. 22D

| RTX00052/DNAI1-HA | Impactor (Mercer) | |
|---|---|---|
|  | MMAD (μm) | GSD |
| 2 | 1.3 | 1.97 |
| 3 | 1.1 | 2.00 |
| 4 | 1.4 | 1.89 |

| | Vehicle 24 h | | | High Dose: 1.2 mg/kg 6 h | | | High Dose: 1.2 mg/kg 24 h | | |
|---|---|---|---|---|---|---|---|---|---|
| Animal Number | ELISA Result (pg/100 µg total protein) | Western Blot Signal (Y/N) | | Animal Number | ELISA Result (pg/100 µg total protein) | Western Blot Signal (Y/N) | Animal Number | ELISA Result (pg/100 µg total protein) | Western Blot Signal (Y/N) |
| 1001 | n.d. | N | | 4001 | 0.47 | Y | 4006 | n.d. | N |
| 1002 | n.d. | N | | 4501 | n.d. | Y | 4506 | n.d. | N |
| 1003 | n.d. | N | | 4002 | n.d. | N | 4007 | n.d. | N |
| 1501 | n.d. | N | | 4502 | 1.10 | Y | 4507 | n.d. | N |
| 1502 | n.d. | N | | 4003 | 3.33 | Y | 4008 | n.d. | N |
| 1503 | n.d. | N | | 4503 | n.d. | N | 4508 | n.d. | N |
| | | | | 4004 | 0.34* | Y | 4009 | n.d. | N |
| | | | | 4504 | 1.01 | Y | 4509 | n.d. | N |
| | | | | 4005 | 0.09* | N | 4010 | n.d. | N |
| | | | | 4505 | n.d. | N | 4510 | n.d. | N |

*Below LOQ

Fig. 26A

| Group | Formulation | Animals | Delivery | [RNA] (mg/mL) | Total Dose | Aerosol delivery of substrate | # animals | Data collection |
|---|---|---|---|---|---|---|---|---|
| 1 | Control vehicle | Albino B6, naive | Nebulization 2 h 66.6 μL/min | none | 4 mL buffer 27 | - | n = 12 | For groups 1 to 7 - once a week (Mondays or Tuesdays) and after last dose: a) 2 mice @ 4h post-dosing = IVIS<br><br>For all groups – after last dose: a) 2 mice @ 4h post-last dose and post IVIS - perfuse and explant liver, spleen and lungs - half for RNAscope, half for protein assay<br><br>b) Histopath at 72h post-last dosing (5 mice) and 7 days post-last dosing (5 mice) |
| 2 | RTX00301 (95% DMA11-HA + 5% luciferase mRNA) | Albino B6, naive | Nebulization 2 h 66.6 μL/min | 0.5 mg/mL neb: 0.5 mg/mL | 4.0 mg per chamber | For 2 mice: 2 mL Luciferin @ 95 mM (30 mg/mL) | n = 12 | |
| 3 | RTX00051 (95% DMA11-HA + 5% luciferase mRNA) | Albino B6, naive | Nebulization 2 h 66.6 μL/min | 0.5 mg/mL neb: 0.5 mg/mL | 4.0 mg per chamber | For 2 mice: 2 mL Luciferin @ 95 mM (30 mg/mL) | n = 12 | |
| 4 | RTX00352 (95% DMA11-HA + 5% luciferase mRNA) | Albino B6, naive | Nebulization 2 h 66.6 μL/min | 0.5 mg/mL neb: 0.5 mg/mL | 4.0 mg per chamber | For 2 mice: 2 mL Luciferin @ 95 mM (30 mg/mL) | n = 12 | |

Selected measurements shown had a ≥2-fold change from baseline

Fig. 35

6 hr Necropsy Scores

| 6 HRS | O1 | | S1 | | S2 | |
|---|---|---|---|---|---|---|
| | M | F | M | F | M | F |
| Alveolar macrophages, increased | 0 | 0 | 0 | 0 | 0 | 1 |
| Infiltrate, mixed, interstitial | 1 | 0 | 0 | 0 | 0 | 0 |
| | | | | | | |
| | | | | | | |
| | | | | | | |
| Inflammation, neutrophilic, alveolar, multifocal | 2 | 2 | 1 | 2 | 2 | 2 |
| Inflammation, neutrophilic, terminal bronchiole | 1 | 1 | 1 | 0 | 2 | 2 |
| Ulceration, bronchiole | 0 | 0 | 0 | 0 | 1 | 0 |

72 hr Necropsy Scores

| 72 HRS | vehicle | | O1 | | S1 | | S2 | |
|---|---|---|---|---|---|---|---|---|
| | M | F | M | F | M | F | M | F |
| Alveolar macrophages, increased | 1 | 0 | 0 | 0 | 0 | 0 | 0 | 0 |
| Infiltrate, mixed, interstitial | 1 | 1 | 0 | 0 | 0 | 2 | 0 | 0 |
| Infiltrate, mixed, terminal bronchiole | 0 | 1 | 0 | 0 | 0 | 0 | 0 | 0 |
| Inflammation, mixed, alveolar, multifocal | 0 | 0 | 2 | 2 | 0 | 0 | 2 | 2 |
| Inflammation, mixed, interstitial, multifocal | 0 | 0 | 0 | 2 | 0 | 0 | 2 | 2 |
| Inflammation, mixed, terminal bronchiole | 0 | 0 | 0 | 1 | 0 | 0 | 0 | 0 |
| Inflammation, neutrophilic, alveolar, multifocal | 0 | 0 | 0 | 0 | 2 | 2 | 0 | 0 |
| Inflammation, neutrophilic, terminal bronchiole | 0 | 0 | 1 | 0 | 2 | 0 | 0 | 0 |

COMPOSITIONS AND METHODS FOR TARGETED DELIVERY TO CELLS

CROSS-REFERENCE

This application is a continuation of International Application No. PCT/US2022/021442 filed Mar. 22, 2022, which claims the benefits of U.S. Provisional Application No. 63/164,523 filed Mar. 22, 2021; U.S. Provisional Application No. 63/229,497 filed Aug. 4, 2021; and U.S. Provisional Application No. 63/305,426 filed on Feb. 1, 2022, each of which is entirely hereby incorporated by reference herein for all purposes.

BACKGROUND

Therapeutic approaches, such as the CRISPR/Cas (clustered regularly interspaced short palindromic repeat/CRISPR-associated protein (Cas)) technology, often require precise and potent delivery of therapeutic agent(s) to target organ(s) or cell(s), sometimes in a sequence dependent manner. To date, there remains a clear need to accomplish therapeutically safe and effective lipid-based carriers for achieving clinical outcomes in the context of genetic diseases and many other applications, particularly in the context of respiratory diseases.

SUMMARY

The present application generally concerns safe, efficacious, and potent delivery of a therapeutic or prophylactic agent such as a polynucleotide, a polypeptide, or a small molecule compound in lipid nanoparticles to target cell(s).

In certain aspects, the present application provides a method for potent delivery to a (e.g., lung) cell of a subject, comprising: administering to the subject a (e.g., aerosol) composition comprising a therapeutic agent assembled with a lipid composition which comprises: (i) an ionizable cationic lipid; and (ii) a selective organ targeting (SORT) lipid separate from the ionizable cationic lipid, wherein (e.g., an amount of) the SORT lipid effects delivery of the therapeutic agent to the cell of the subject characterized by a (e.g., about 1.1- or 10-fold) greater therapeutic effect compared to that achieved with a reference lipid composition (e.g., without the amount of the SORT lipid). In some embodiments, the lipid composition further comprises a phospholipid.

In another aspect, the present application provides a method for potent delivery to (e.g., lung) cells of a subject, comprising: administering to the subject a (e.g., aerosol) composition comprising a therapeutic agent assembled with a lipid composition which comprises: (i) an ionizable cationic lipid; and (ii) a selective organ targeting (SORT) lipid separate from the ionizable cationic lipid, wherein (e.g., an amount of) the SORT lipid effects delivery of the therapeutic agent to cells of the subject characterized by a therapeutic effect in a (e.g., about 1.1- or 10-fold) greater plurality of (e.g., lung) cells compared to that achieved with a reference lipid composition (e.g., without the amount of the SORT lipid). In some embodiments, the lipid composition further comprises a phospholipid.

In another aspect, the present application provides a method for targeted delivery to (e.g., lung) cells of a subject, comprising: administering to the subject a (e.g., aerosol) composition comprising a therapeutic agent assembled with a lipid composition which comprises: (i) an ionizable cationic lipid; and (ii) a selective organ targeting (SORT) lipid separate from the ionizable cationic lipid, wherein (e.g., an amount of) the SORT lipid effects delivery of the therapeutic agent to a greater proportion of cell types as compared to that achieved with a reference lipid composition. In some embodiments, the lipid composition further comprises a phospholipid.

In another aspect, the present application provides a method for targeted delivery to (e.g., lung) cells of a subject, comprising: administering to the subject a (e.g., aerosol) composition comprising a therapeutic agent assembled with a lipid composition which comprises: (i) an ionizable cationic lipid; and (ii) a selective organ targeting (SORT) lipid separate from the ionizable cationic lipid, wherein (e.g., an amount of) the SORT lipid effects delivery of the therapeutic agent to cells of the subject characterized by a therapeutic effect in a first plurality of (e.g., lung) cells of a first cell type and in a (e.g., about 1.1- or 10-fold) greater second plurality of (e.g., lung) cells of a second cell type. In some embodiments, the lipid composition further comprises a phospholipid.

In another aspect, the present application provides a method for targeted delivery to (e.g., lung) cells of a subject, comprising: administering to the subject a (e.g., aerosol) composition comprising a therapeutic agent assembled with a lipid composition which comprises: (i) an ionizable cationic lipid; and (ii) a selective organ targeting (SORT) lipid separate from the ionizable cationic lipid, wherein (e.g., an amount of) the SORT lipid effects a delivery of the therapeutic agent to cells of the subject characterized by a (e.g., about 1.1- or 10-fold) greater therapeutic effect in a first (e.g., lung) cell of a first cell type of the subject compared to that in a second (e.g., lung) cell of a second cell type of the subject, wherein the first cell type is different from the second cell type. In some embodiments, the lipid composition further comprises a phospholipid.

In another aspect, the present application provides a pharmaceutical composition comprising a therapeutic agent assembled with a lipid composition, which lipid composition comprises: (i) an ionizable cationic lipid; and (ii) a selective organ targeting (SORT) lipid separate from the ionizable cationic lipid, wherein the SORT lipid is configured to effect a delivery of the therapeutic agent characterized by one or more of the following: (a) a (e.g., 1.1- or 10-fold) greater therapeutic effect in a (e.g., lung) cell of the subject compared to that achieved with a reference lipid composition; (b) a therapeutic effect in a (e.g., 1.1- or 10-fold) greater plurality of (e.g., lung) cells (e.g., of a cell type) of the subject compared to that achieved with a reference lipid composition; (c) a therapeutic effect in a first plurality of (e.g., lung) cells of a first cell type and in a (e.g., 1.1- or 10-fold) greater second plurality of (e.g., lung) cells of a second cell type; and (d) a (e.g., 1.1- or 10-fold) greater therapeutic effect in a first (e.g., lung) cell of a first cell type of the subject compared to that in a second (e.g., lung) cell of a second cell type of the subject. In some embodiments, the lipid composition further comprises a phospholipid.

In another aspect, the present disclosure provided a high-potency dosage form of a therapeutic agent formulated with a selective organ targeting (SORT) lipid, the dosage form comprising: the therapeutic agent assembled with a lipid composition that comprises: (i) an ionizable cationic lipid; and (ii) the SORT lipid separate from the ionizable cationic lipid, wherein the SORT lipid is present in the dosage form in an amount sufficient to achieve a therapeutic effect at a dose of the therapeutic agent (e.g., at least about 1.1- or 10-fold) lower than that required with a reference lipid composition. In some embodiments, the lipid composition further comprises a phospholipid.

In another aspect, the present disclosure provided a high-potency dosage form of a therapeutic agent formulated with a selective organ targeting (SORT) lipid, the dosage form comprising: the therapeutic agent assembled with a lipid composition that comprises: (i) an ionizable cationic lipid; and (ii) the SORT lipid separate from the ionizable cationic lipid, wherein the therapeutic agent (e.g., heterologous polynucleotide) is present in the dosage form at a dose of no more than about 2 milligram per kilogram (mg/kg, or mpk) body weight. In some embodiments, the lipid composition further comprises a phospholipid.

In another aspect, the present application provided a method for delivery to (e.g., lung) basal cells of a subject, comprising: (e.g., systemically) administering to the subject a therapeutic agent assembled with a lipid composition that comprises: (i) an ionizable cationic lipid; and (ii) a selective organ targeting (SORT) lipid separate from the ionizable cationic lipid, thereby delivering the therapeutic agent to an organ or tissue (e.g., lung) of the subject to result in a therapeutic effect detectable in at least about 5%, 10%, or 15% basal cells in the organ or tissue of the subject.

Provided herein in some embodiments include a method for delivery by nebulization to lung cell(s) of a subject, the method comprising: administering to said subject a (e.g., pharmaceutical) composition comprising a therapeutic agent assembled with a lipid composition, which lipid composition comprises: (i) an ionizable cationic lipid; and (ii) a selective organ targeting (SORT) lipid separate from said ionizable cationic lipid, thereby delivering said therapeutic agent to said lung cell(s) of a lung of said subject. In some embodiments, the method provides a (e.g., therapeutically) effective amount or activity of said therapeutic agent in at least about 5%, 10%, 15%, or 20% lung epithelial cells of said subject. In some embodiments, the method provides a (e.g., therapeutically) effective amount or activity of said therapeutic agent in at least about 2%, 5%, or 10% lung ciliated cells of said subject. In some embodiments, the method provides a (e.g., therapeutically) effective amount or activity of said therapeutic agent in at least about 5%, 10%, 15%, or 20% lung secretory cells of said subject. In some embodiments, the method provides a (e.g., therapeutically) effective amount or activity of said therapeutic agent in at least about 5%, 10%, 15%, or 20% lung club cells of said subject. In some embodiments, the method provides a (e.g., therapeutically) effective amount or activity of said therapeutic agent in at least about 5%, 10%, 15%, or 20% lung goblet cells of said subject. In some embodiments, the method provides a (e.g., therapeutically) effective amount or activity of said therapeutic agent in at least about 5%, 10%, 15%, or 20% lung basal cells of said subject. In some embodiments, the lipid composition comprises a phospholipid. In some embodiments, the (e.g., pharmaceutical) composition comprising said therapeutic agent assembled with said lipid composition is an aerosol composition.

Additional aspects and advantages of the present application will become readily apparent to those skilled in this art from the following detailed description, wherein only illustrative embodiments of the present application are shown and described. As will be realized, the present application is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. The patent or application file contains at least one drawing executed in color. Copies of this patent or patent application publication with color drawing(s) will be provided by the Office upon request and payment of the necessary fee. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 1 shows the chemical structures of lipids.

FIG. 3 shows a chart of cells type and expression levels of a delivered mRNA using different compositions of LNP.

FIG. 10E illustrates data collected from experiments demonstrating functional restoration of cilia, tolerability, and selectivity of lipid compositions described herein.

FIG. 35 illustrates summary of tolerability as determined by clinical observations and organ weights for the single dose inhalation study.

DETAILED DESCRIPTION

Figure 2:
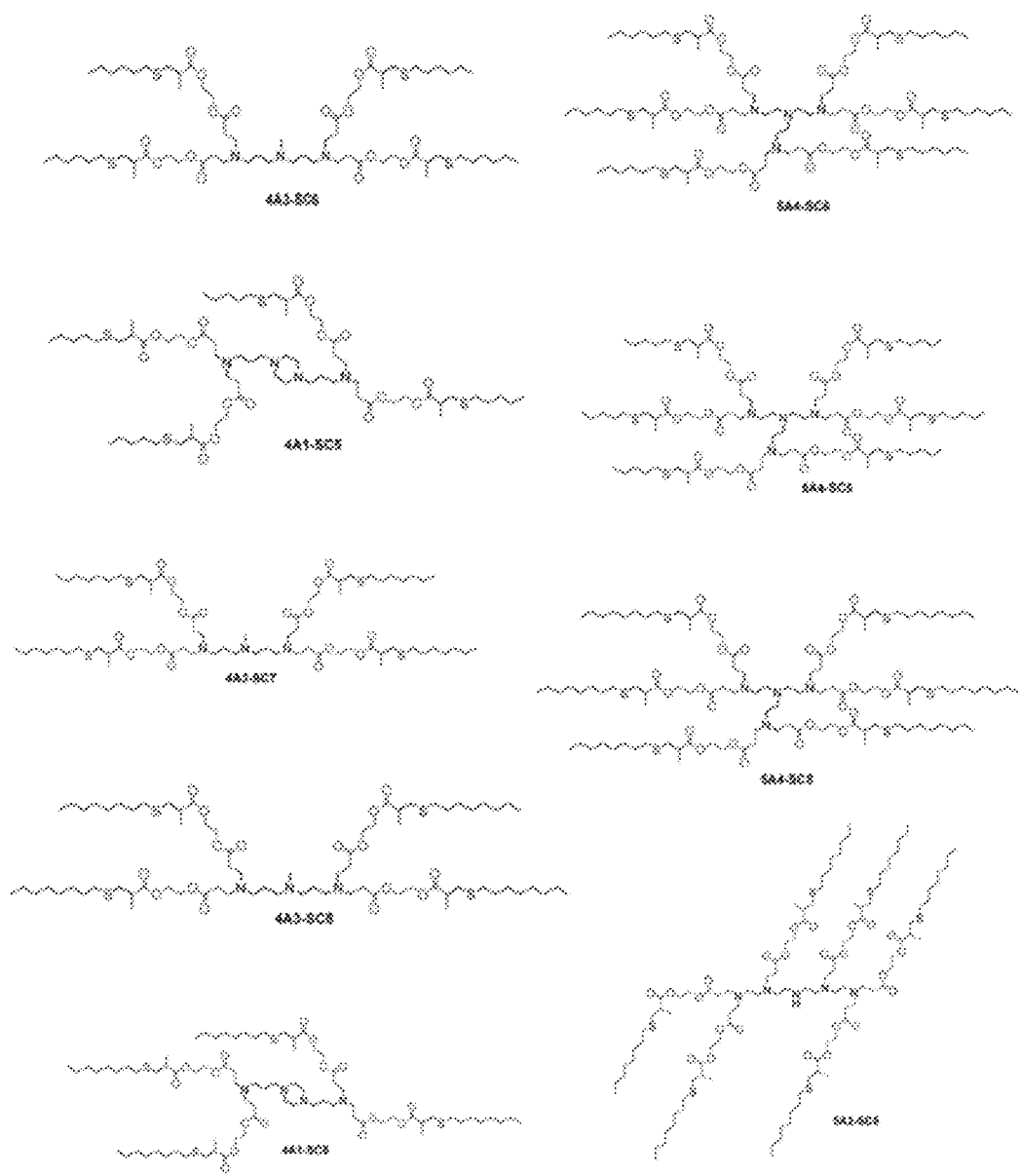
FIG. 2 shows the chemical structures of dendrimer or dendron lipids

Before the embodiments of the disclosure are described, it is to be understood that such embodiments are provided by way of example only, and that various alternatives to the embodiments of the disclosure described herein may be employed in practicing the invention. Numerous variations, changes, and substitutions will now occur to those skilled in the art without departing from the invention.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

In the context of the present application, the following terms have the meanings ascribed to them unless specified otherwise:

As used throughout the specification and claims, the terms "a", "an" and "the" are generally used in the sense that they mean "at least one", "at least a first", "one or more" or "a plurality" of the referenced components or steps, except in instances wherein an upper limit is thereafter specifically stated. For example, a "cleavage sequence", as used herein, means "at least a first cleavage sequence" but includes a plurality of cleavage sequences. The operable limits and parameters of combinations, as with the amounts of any single agent, will be known to those of ordinary skill in the art in light of the present application.

The terms "polypeptide", "peptide", and "protein" are used interchangeably herein to generally refer to polymers of amino acids of any length. The polymer may be linear or branched, it may comprise modified amino acids, and it may be interrupted by non-amino acids. The terms also encompass an amino acid polymer that has been modified, for example, by disulfide bond formation, glycosylation, lipidation, acetylation, phosphorylation, or any other manipulation, such as conjugation with a labeling component.

As used herein in the context of the structure of a polypeptide, "N-terminus" (or "amino terminus") and "C-terminus" (or "carboxyl terminus") generally refer to the extreme amino and carboxyl ends of the polypeptide, respectively.

The term "N-terminal end sequence," as used herein with respect to a polypeptide or polynucleotide sequence of interest, generally means that no other amino acid or nucleotide residues precede the N-terminal end sequence in the polypeptide or polynucleotide sequence of interest at the N-terminal end. The term "C-terminal end sequence," as used herein with respect to a polypeptide or polynucleotide sequence of interest, generally means that no other amino acid or nucleotide residues follows the C-terminal end sequence in the polypeptide or polynucleotide sequence of interest at the C-terminal end.

The terms "non-naturally occurring" and "non-natural" are used interchangeably herein. The term "non-naturally occurring" or "non-natural," as used herein with respect to a therapeutic agent or prophylactic agent, generally means that the agent is not biologically derived in mammals (including but not limited to human). The term "non-naturally occurring" or "non-natural," as applied to sequences and as used herein, means polypeptide or polynucleotide sequences that do not have a counterpart to, are not complementary to, or do not have a high degree of homology with a wild-type or naturally-occurring sequence found in a mammal. For example, a non-naturally occurring polypeptide or fragment may share no more than 99%, 98%, 95%, 90%, 80%, 70%, 60%, 50% or even less amino acid sequence identity as compared to a natural sequence when suitably aligned.

"Physiological conditions" refers to a set of conditions in a living host as well as in vitro conditions, including temperature, salt concentration, pH, that mimic those conditions of a living subject. A host of physiologically relevant conditions for use in in vitro assays have been established. Generally, a physiological buffer contains a physiological concentration of salt and is adjusted to a neutral pH ranging from about 6.5 to about 7.8, and preferably from about 7.0 to about 7.5. A variety of physiological buffers are listed in Sambrook et al. (2001). Physiologically relevant temperature ranges from about 25° C. to about 38° C., and preferably from about 35° C. to about 37° C.

As used herein, the terms "treatment" or "treating," or "palliating" or "ameliorating" are used interchangeably herein. These terms generally refer to an approach for obtaining beneficial or desired results including but not limited to a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms or improvement in one or more clinical parameters associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect" or "therapeutic benefit," as used herein, generally refers to a physiologic effect, including but not limited to the mitigation, amelioration, or prevention of disease or an improvement in one or more clinical parameters associated with the underlying disorder in humans or other animals, or to otherwise enhance physical or mental wellbeing of humans or animals, resulting from administration of a polypeptide of the disclosure other than the ability to induce the production of an antibody against an antigenic epitope possessed by the biologically active protein. For prophylactic benefit, the compositions may be administered to a subject at risk of developing a particular disease, a recurrence of a former disease, condition or symptom of the disease, or to a subject reporting one or more of the physiological symptoms of a disease, even though a diagnosis of this disease may not have been made.

The terms "therapeutically effective amount" and "therapeutically effective dose", as used herein, generally refer to an amount of a drug or a biologically active protein, either alone or as a part of a polypeptide composition, that is capable of having any detectable, beneficial effect on any symptom, aspect, measured parameter or characteristics of a disease state or condition when administered in one or repeated doses to a subject. Such effect need not be absolute to be beneficial. Determination of a therapeutically effective amount is well within the capability of those skilled in the art, especially in light of the detailed disclosure provided herein.

The term "equivalent molar dose" generally means that the amounts of materials administered to a subject have an equivalent amount of moles, based on the molecular weight of the material used in the dose.

The term "therapeutically effective and non-toxic dose," as used herein, generally refers to a tolerable dose of the compositions as defined herein that is high enough to cause depletion of tumor or cancer cells, tumor elimination, tumor shrinkage or stabilization of disease without or essentially without major toxic effects in the subject. Such therapeutically effective and non-toxic doses may be determined by dose escalation studies described in the art and should be below the dose inducing severe adverse side effects.

The terms "cancer" and "cancerous" refer to or describe the physiological condition in mammals that is typically characterized by unregulated cell growth/proliferation.

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof, "mercapto" means —SH; and "thio" means =S; "sulfonyl" means —S(O)$_2$—; "hydroxysulfonyl" means —S(O)$_2$OH; "sulfonamide" means —S(O)$_2$NH$_2$; and "sulfinyl" means —S(O)—.

In the context of chemical formulas, the symbol "—" means a single bond, "=" means a double bond, and "≡" means triple bond. The symbol " ---- " represents an optional bond, which if present is either single or double. The symbol " ==== " represents a single bond or a double bond. Thus, for example, the formula

includes

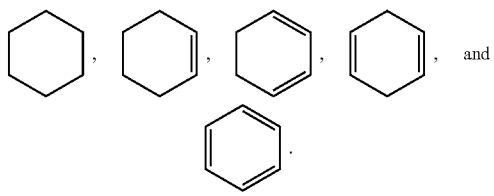

And it is understood that no one such ring atom forms part of more than one double bond. Furthermore, it is noted that the covalent bond symbol "-", when connecting one or two stereogenic atoms, does not indicate any preferred stereochemistry. Instead, it covers all stereoisomers as well as mixtures thereof. The symbol "∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄" means a single bond where the group attached to the thick end of the wedge is "out of the page." The symbol "⦀" means a single bond where the group attached to the thick end of the wedge is "into the page". The symbol "∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

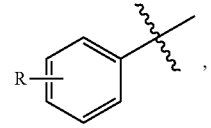

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

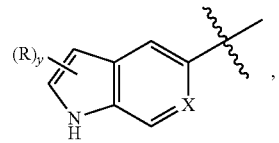

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, the carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). The term "cycloalkanediyl" when used without the "substituted" modifier refers to a divalent saturated aliphatic group with two carbon atoms as points of attachment, no carbon-carbon double or triple bonds, and no atoms other than carbon and hydrogen. The group

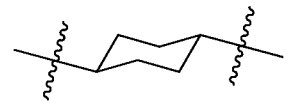 [SMILES: *C1CCC(*)CC1]

is a non-limiting example of cycloalkanediyl group. A "cycloalkane" refers to the class of compounds having the formula H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkenyl" when used without the "substituted" modifier refers to an monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly the terms "terminal alkene" and "α-olefin" are synonymous and refer to an alkene having just one carbon-carbon double bond, wherein that bond is part of a vinyl group at an end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —CH=CHF, —CH=CHCl and —CH=CHBr are non-limiting examples of substituted alkenyl groups.

The term "alkynyl" when used without the "substituted" modifier refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aryl" when used without the "substituted" modifier refers to a monovalent unsaturated aromatic group with an aromatic carbon atom as the point of attachment, the carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, the carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

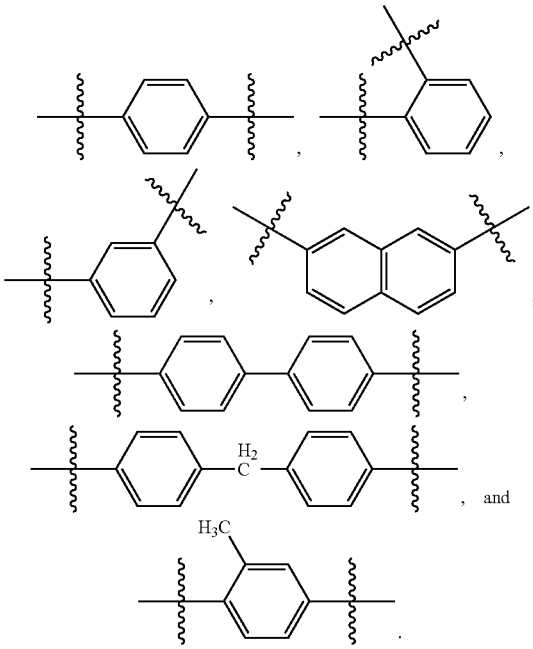

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "aralkyl" when used without the "substituted" modifier refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, the carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. Heteroaryl rings may contain 1, 2, 3, or 4 ring atoms selected from are nitrogen, oxygen, and sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, the atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

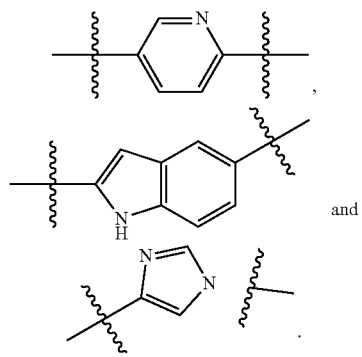

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "heterocycloalkyl" when used without the "substituted" modifier refers to a monovalent non-aromatic group with a carbon atom or nitrogen atom as the point of attachment, the carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur.

Heterocycloalkyl rings may contain 1, 2, 3, or 4 ring atoms selected from nitrogen, oxygen, or sulfur. If more than one ring is present, the rings may be fused or unfused. As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group. The term "heterocycloalkanediyl" when used without the "substituted" modifier refers to an divalent cyclic group, with two carbon atoms, two nitrogen atoms, or one carbon atom and one nitrogen atom as the two points of attachment, the atoms forming part of one or more ring structure(s) wherein at least one of the ring atoms is nitrogen, oxygen or sulfur, and wherein the divalent group consists of no atoms other than carbon, hydrogen, nitrogen, oxygen and sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl groups (carbon number limitation permitting) attached to the ring or ring system. Also, the term does not preclude the presence of one or more double bonds in the ring or ring system, provided that the resulting group remains non-aromatic. Non-limiting examples of heterocycloalkanediyl groups include:

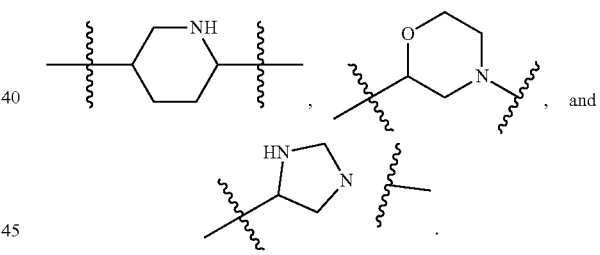

When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group.

When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), —OC(CH$_3$)$_3$ (tert-butoxy), —OCH(CH$_2$)$_2$, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$.

The term "alkylamino" when used without the "substituted" modifier refers to the group —NHR, in which R is an alkyl, as that term is defined above. Non-limiting examples include: —NHCH$_3$ and —NHCH$_2$CH$_3$.

The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The term "alkylaminodiyl" refers to the divalent group —NH-alkanediyl-, —NH-alkanediyl-NH—, or -alkanediyl-NH-alkanediyl-. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The groups —NHC(O)OCH$_3$ and —NHC(O)NHCH$_3$ are non-limiting examples of substituted amido groups.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the present specification and attached claims are approximations that can vary depending upon the desired properties sought to be obtained by the present application. Generally the term "about," as used herein when referring to a measurable value such as an amount of weight, time, dose, etc. is meant to encompass in one example variations of ±20% or ±10%, in another example ±5%, in another example ±1%, and in yet another example ±0.1% from the specified amount, as such variations are appropriate to perform the disclosed method.

As used in this application, the term "average molecular weight" refers to the relationship between the number of moles of each polymer species and the molar mass of that species. In particular, each polymer molecule may have different levels of polymerization and thus a different molar mass. The average molecular weight can be used to represent the molecular weight of a plurality of polymer molecules. Average molecular weight is typically synonymous with average molar mass. In particular, there are three major types of average molecular weight: number average molar mass, weight (mass) average molar mass, and Z-average molar mass. In the context of this application, unless otherwise specified, the average molecular weight represents either the number average molar mass or weight average molar mass of the formula. In some embodiments, the average molecular weight is the number average molar mass. In some embodiments, the average molecular weight may be used to describe a PEG component present in a lipid.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate (e.g., non-human primate). In certain embodiments, the patient or subject is a human. Non-limiting examples of human subjects are adults, juveniles, infants and fetuses.

The term "assemble" or "assembled," as used herein, in context of delivery of a payload to target cell(s) generally refers to covalent or non-covalent interaction(s) or association(s), for example, such that a therapeutic or prophylactic agent be complexed with or encapsulated in a lipid composition.

As used herein, the term "lipid composition" generally refers to a composition comprising lipid compound(s), including but not limited to, a lipoplex, a liposome, a lipid particle. Examples of lipid compositions include suspensions, emulsions, and vesicular compositions.

For example, as used herein, "RTX0001" refers to an example lipid composition tested herein. RTX0001 is a 5-component lipid nanoparticle composition comprising about 19.05% 4A3-SC7 (ionizable cationic lipid), about 20% DODAP (SORT lipid), about 19.05% DOPE, about 38.9% cholesterol, and about 3.81% DMG-PEG (PEG conjugated lipid), wherein each lipid component is defined as mol % of the total lipid composition.

As another example, as used herein, "RTX0004" refers to an example lipid composition tested herein. RTX0004 is a 4-component lipid nanoparticle composition comprising about 23.81% 5A2-SC8 (ionizable cationic lipid), about 23.81% DOPE, about 47.62% cholesterol, and about 4.76% DMG-PEG (PEG conjugated lipid), wherein each lipid component is defined as mol % of the total lipid composition.

As another example, as used herein, "RTX0051" refers to an example lipid composition tested herein. RTX0051 is a 5-component lipid nanoparticle composition comprising about 19.05% 4A3-SC7 (ionizable cationic lipid), about 20% 14:0 EPC (SORT lipid), about 19.05% DOPE, about 38.9% cholesterol, and about 3.81% DMG-PEG (PEG conjugated lipid), wherein each lipid component is defined as mol % of the total lipid composition.

As yet another example, as used herein, "RTX0052" refers to an example lipid composition tested herein. RTX0052 is a 5-component lipid nanoparticle composition comprising about 19.05% 4A3-SC7 (ionizable cationic lipid), about 20% 14:0 TAP (SORT lipid), about 19.05% DOPE, about 38.9% cholesterol, and about 3.81% DMG-PEG (PEG conjugated lipid), wherein each lipid component is defined as mol % of the total lipid composition.

As used herein, the term "detectable" refers to an occurrence of, or a change in, a signal that is directly or indirectly detectable either by observation or by instrumentation. Typically, a detectable response is an occurrence of a signal wherein the fluorophore is inherently fluorescent and does not produce a change in signal upon binding to a metal ion or biological compound. Alternatively, the detectable response is an optical response resulting in a change in the wavelength distribution patterns or intensity of absorbance or fluorescence or a change in light scatter, fluorescence lifetime, fluorescence polarization, or a combination of the above parameters. Other detectable responses include, for example, chemiluminescence, phosphorescence, radiation from radioisotopes, magnetic attraction, and electron density The term "potent" or "potency," as used herein in connection with delivery of therapeutic agent(s), generally refers to a greater ability of a delivery system (e.g., a lipid composition) to achieve or bring about a desired amount, activity, or effect of a therapeutic agent or prophylactic agent (such as a desired level of translation, transcription, production, expression, or activity of a protein or gene) in cells (e.g., targeted cells) to any measurable extent, e.g., relative to a reference delivery system. For example, a lipid composition with a higher potency may achieve a desired therapeutic effect in a greater population of relevant cells, within a shorter response time, or that last a longer period of time.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present application which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, $-[-CH_2CH_2-]_n-$, the repeat unit is $-CH_2CH_2-$. The subscript "n" denotes the degree of polymerization, that is, the number of repeat units linked together. When the value for "n" is left undefined or where "n" is absent, it simply designates repetition of the formula within the brackets as well as the polymeric nature of the material. The concept of a repeat unit applies equally to where the connectivity between the repeat units extends three dimensionally, such as in metal organic frameworks, modified polymers, thermosetting polymers, etc. Within the context of the dendrimer or dendron, the repeating unit may also be described as the branching unit, interior layers, or generations. Similarly, the terminating group may also be described as the surface group.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the disclosure in terms such that one of ordinary skill can appreciate the scope and practice the present application.

Compositions

Lipid Compositions

In one aspect, provided herein is a lipid composition comprising: (i) an ionizable cationic lipid; and (iii) a selective organ targeting (SORT) lipid separate from the ionizable cationic lipid. The lipid composition may further comprise a phospholipid.

Ionizable Cationic Lipids

In some embodiments of the lipid composition of the present application, the lipid composition comprises an ionizable cationic lipid. In some embodiments, the cationic ionizable lipids contain one or more groups which is protonated at physiological pH but may deprotonated and has no charge at a pH above 8, 9, 10, 11, or 12. The ionizable cationic group may contain one or more protonatable amines which are able to form a cationic group at physiological pH. The cationic ionizable lipid compound may also further comprise one or more lipid components such as two or more fatty acids with $C_6$-$C_{24}$ alkyl or alkenyl carbon groups. These lipid groups may be attached through an ester linkage or may be further added through a Michael addition to a sulfur atom. In some embodiments, these compounds may be a dendrimer, a dendron, a polymer, or a combination thereof.

In some embodiments of the lipid composition of the present application, the ionizable cationic lipids refer to lipid and lipid-like molecules with nitrogen atoms that can acquire charge (pKa). These lipids may be known in the literature as cationic lipids. These molecules with amino groups typically have between 2 and 6 hydrophobic chains, often alkyl or alkenyl such as $C_6$-$C_{24}$ alkyl or alkenyl groups, but may have at least 1 or more that 6 tails. In some embodiments, these cationic ionizable lipids are dendrimers, which are a polymer exhibiting regular dendritic branching, formed by the sequential or generational addition of branched layers to or from a core and are characterized by a core, at least one interior branched layer, and a surface branched layer. (See *Petar R. Dvornic and Donald A. Tomalia in Chem. in Britain*, 641-645, August 1994.) In other embodiments, the term "dendrimer" as used herein is intended to include, but is not limited to, a molecular architecture with an interior core, interior layers (or "generations") of repeating units regularly attached to this initiator core, and an exterior surface of terminal groups attached to the outermost generation. A "dendron" is a species of dendrimer having branches emanating from a focal point which is or can be joined to a core, either directly or through a linking moiety to form a larger dendrimer. In some embodiments, the dendrimer structures have radiating repeating groups from a central core which doubles with each repeating unit for each branch. In some embodiments, the dendrimers described herein may be described as a small molecule, medium-sized molecules, lipids, or lipid-like material. These terms may be used to described compounds described herein which have a dendron like appearance (e.g. molecules which radiate from a single focal point).

While dendrimers are polymers, dendrimers may be preferable to traditional polymers because they have a controllable structure, a single molecular weight, numerous and controllable surface functionalities, and traditionally adopt a globular conformation after reaching a specific generation. Dendrimers can be prepared by sequentially reactions of each repeating unit to produce monodisperse, tree-like and/or generational structure polymeric structures. Individual dendrimers consist of a central core molecule, with a dendritic wedge attached to one or more functional sites on that central core. The dendrimeric surface layer can have a variety of functional groups disposed thereon including anionic, cationic, hydrophilic, or lipophilic groups, according to the assembly monomers used during the preparation.

Modifying the functional groups and/or the chemical properties of the core, repeating units, and the surface or terminating groups, their physical properties can be modulated. Some properties which can be varied include, but are not limited to, solubility, toxicity, immunogenicity and bioattachment capability. Dendrimers are often described by their generation or number of repeating units in the branches. A dendrimer consisting of only the core molecule is referred to as Generation 0, while each consecutive repeating unit along all branches is Generation 1, Generation 2, and so on until the terminating or surface group. In some embodiments, half generations are possible resulting from only the first condensation reaction with the amine and not the second condensation reaction with the thiol.

Preparation of dendrimers requires a level of synthetic control achieved through series of stepwise reactions comprising building the dendrimer by each consecutive group. Dendrimer synthesis can be of the convergent or divergent type. During divergent dendrimer synthesis, the molecule is assembled from the core to the periphery in a stepwise process involving attaching one generation to the previous and then changing functional groups for the next stage of reaction. Functional group transformation is necessary to prevent uncontrolled polymerization. Such polymerization would lead to a highly branched molecule that is not monodisperse and is otherwise known as a hyperbranched polymer. Due to steric effects, continuing to react dendrimer repeat units leads to a sphere shaped or globular molecule, until steric overcrowding prevents complete reaction at a specific generation and destroys the molecule's monodispersity. Thus, in some embodiments, the dendrimers of G1-G10 generation are specifically contemplated. In some embodiments, the dendrimers comprise 1, 2, 3, 4, 5, 6, 7, 8, 9, or 10 repeating units, or any range derivable therein. In some embodiments, the dendrimers used herein are G0, G1, G2, or G3. However, the number of possible generations (such as 11, 12, 13, 14, 15, 20, or 25) may be increased by reducing the spacing units in the branching polymer.

Additionally, dendrimers have two major chemical environments: the environment created by the specific surface groups on the termination generation and the interior of the dendritic structure which due to the higher order structure can be shielded from the bulk media and the surface groups. Because of these different chemical environments, dendrimers have found numerous different potential uses including in therapeutic applications.

In some embodiments of the lipid composition of the present application, the dendrimers or dendrons are assembled using the differential reactivity of the acrylate and methacrylate groups with amines and thiols. The dendrimers or dendrons may include secondary or tertiary amines and thioethers formed by the reaction of an acrylate group with a primary or secondary amine and a methacrylate with a mercapto group. Additionally, the repeating units of the dendrimers or dendrons may contain groups which are degradable under physiological conditions. In some embodiments, these repeating units may contain one or more germinal diethers, esters, amides, or disulfides groups. In some embodiments, the core molecule is a monoamine which allows dendritic polymerization in only one direction. In other embodiments, the core molecule is a polyamine with multiple different dendritic branches which each may comprise one or more repeating units. The dendrimer or dendron may be formed by removing one or more hydrogen atoms from this core. In some embodiments, these hydrogen atoms are on a heteroatom such as a nitrogen atom. In some embodiments, the terminating group is a lipophilic groups such as a long chain alkyl or alkenyl group. In other embodiments, the terminating group is a long chain haloalkyl or haloalkenyl group. In other embodiments, the terminating group is an aliphatic or aromatic group containing an ionizable group such as an amine ($-NH_2$) or a carboxylic acid ($-CO_2H$). In still other embodiments, the terminating group is an aliphatic or aromatic group containing one or more hydrogen bond donors such as a hydroxide group, an amide group, or an ester.

The cationic ionizable lipids of the present application may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Cationic ionizable lipids may occur as racemates and racemic mixtures, single enantiomers, diastereomeric mixtures and individual diastereomers. In some embodiments, a single diastereomer is obtained. The chiral centers of the cationic ionizable lipids of the present application can have the S or the R configuration. Furthermore, it is contemplated that one or more of the cationic ionizable lipids may be present as constitutional isomers. In some embodiments, the compounds have the same formula but different connectivity to the nitrogen atoms of the core. Without wishing to be bound by any theory, it is believed that such cationic ionizable lipids exist because the starting monomers react first with the primary amines and then statistically with any secondary amines present. Thus, the constitutional isomers may present the fully reacted primary amines and then a mixture of reacted secondary amines.

Chemical formulas used to represent cationic ionizable lipids of the present application will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given formula, and regardless of which one is most prevalent, all tautomers of a given chemical formula are intended.

The cationic ionizable lipids of the present application may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the cationic ionizable lipids of the present application are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a cationic ionizable lipids provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

In some embodiments of the lipid composition of the present application, the ionizable cationic lipid is a dendrimer or dendron. In some embodiments, the ionizable cationic lipid comprises an ammonium group which is positively charged at physiological pH and contains at least two hydrophobic groups. In some embodiments, the ammonium group is positively charged at a pH from about 6 to about 8. In some embodiments, the ionizable cationic lipid is a dendrimer or dendron. In some embodiments, the ionizable cationic lipid comprises at least two $C_6$-$C_{24}$ alkyl or alkenyl groups.

Dendrimers or Dendrons of Formula (I)

In some embodiments of the lipid composition, the ionizable cationic lipid comprises at least two $C_8$-$C_{24}$ alkyl groups. In some embodiments, the ionizable cationic lipid is a dendrimer or dendron further defined by the formula:
Core-Repeating Unit-Terminating Group (D-I)
   wherein the core is linked to the repeating unit by removing one or more hydrogen atoms from the core and replacing the atom with the repeating unit and wherein: the core has the formula:

(D-II)

wherein:
X$_1$ is amino or alkylamino$_{(C \leq 12)}$, dialkylamino$_{(C \leq 12)}$, heterocycloalkyl$_{(C \leq 12)}$, heteroaryl$_{(C \leq 12)}$, or a substituted version thereof;
R$_1$ is amino, hydroxy, or mercapto, or alkylamino$_{(C \leq 12)}$, dialkylamino$_{(C \leq 12)}$, or a substituted version of either of these groups; and
a is 1, 2, 3, 4, 5, or 6; or
the core has the formula:

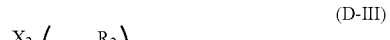

(D-III)

wherein:
X$_2$ is N(R$_5$)$_y$;
R$_5$ is hydrogen, alkyl$_{(C \leq 18)}$, or substituted alkyl$_{(C \leq 18)}$; and
y is 0, 1, or 2, provided that the sum of y and z is 3;
R$_2$ is amino, hydroxy, or mercapto, or alkylamino$_{(C \leq 12)}$, dialkylamino$_{(C \leq 12)}$, or a substituted version of either of these groups;
b is 1, 2, 3, 4, 5, or 6; and
z is 1, 2, 3; provided that the sum of z and y is 3; or
the core has the formula:

(D-IV)

wherein:
X$_3$ is —NR$_6$—, wherein R$_6$ is hydrogen, alkyl$_{(C \leq 8)}$, or substituted alkyl$_{(C \leq 8)}$, —O—, or alkylaminodiyl$_{(C \leq 8)}$, alkoxydiyl$_{(C \leq 8)}$, arenediyl$_{(C \leq 8)}$, heteroarenediyl$_{(C \leq 8)}$, heterocycloalkanediyl$_{(C \leq 8)}$, or a substituted version of any of these groups;
R$_3$ and R$_4$ are each independently amino, hydroxy, or mercapto, or alkylamino$_{(C \leq 12)}$, dialkylamino$_{(C \leq 12)}$, or a substituted version of either of these groups; or a group of the formula: —N(R$_f$)(CH$_2$CH$_2$N(R$_c$))$_e$R$_d$,

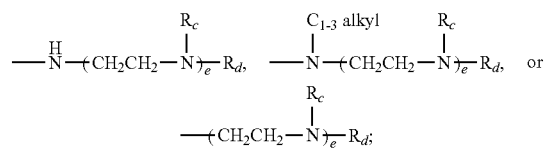

wherein:
e and f are each independently 1, 2, or 3; provided that the sum of e and f is 3;
R$_c$, R$_d$, and R$_f$ are each independently hydrogen, alkyl$_{(C \leq 6)}$, or substituted alkyl$_{(C \leq 6)}$;
c and d are each independently 1, 2, 3, 4, 5, or 6; or
the core is alkylamine$_{(C \leq 18)}$, dialkylamine$_{(C \leq 36)}$, heterocycloalkane$_{(C \leq 12)}$, or a substituted version of any of these groups;
wherein the repeating unit comprises a degradable diacyl and a linker; the degradable diacyl group has the formula:

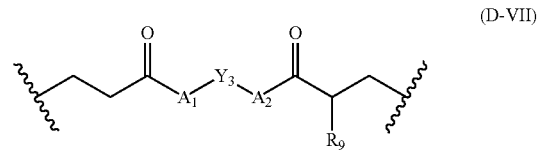

(D-VII)

wherein:
A$_1$ and A$_2$ are each independently —O—, —S—, or —NR$_a$—, wherein:
R$_a$ is hydrogen, alkyl$_{(C \leq 6)}$, or substituted alkyl$_{(C \leq 6)}$;
Y$_3$ is alkanediyl$_{(C \leq 12)}$, alkenediyl$_{(C \leq 12)}$, arenediyl$_{(C \leq 12)}$, or a substituted version of any of these groups; or a group of the formula:

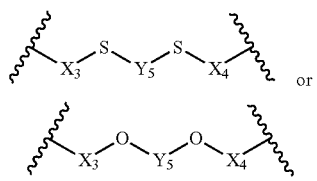

or wherein:
X$_3$ and X$_4$ are alkanediyl$_{(C \leq 12)}$, alkenediyl$_{(C \leq 12)}$, arenediyl$_{(C \leq 12)}$, or a substituted version of any of these groups;
Y$_5$ is a covalent bond, alkanediyl$_{(C \leq 12)}$, alkenediyl$_{(C \leq 12)}$, arenediyl$_{(C \leq 12)}$, or a substituted version of any of these groups; and
R$_9$ is alkyl$_{(C \leq 8)}$ or substituted alkyl$_{(C \leq 8)}$;
the linker group has the formula:

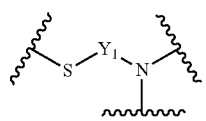

(D-VI)

wherein:
Y$_1$ is alkanediyl$_{(C \leq 12)}$, alkenediyl$_{(C \leq 12)}$, arenediyl$_{(C \leq 12)}$, or a substituted version of any of these groups; and
wherein when the repeating unit comprises a linker group, then the linker group comprises an independent degradable diacyl group attached to both the nitrogen and the sulfur atoms of the linker group if n is greater than 1, wherein the first group in the repeating unit is a degradable diacyl group, wherein for each linker group, the next repeating unit comprises two degradable diacyl groups attached to the nitrogen atom of the linker group; and wherein n is the number of linker groups present in the repeating unit; and
the terminating group has the formula:

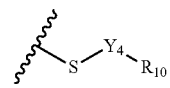

(D-VIII)

wherein:
Y$_4$ is alkanediyl$_{(C \leq 18)}$ or an alkanediyl$_{(C \leq 18)}$ wherein one or more of the hydrogen atoms on the alkanediyl$_{(C \leq 18)}$ has been replaced with —OH, —F, —Cl, —Br, —I, —SH, —OCH$_3$, —OCH$_2$CH$_3$, —SCH$_3$, or —OC(O)CH$_3$;
R$_{10}$ is hydrogen, carboxy, hydroxy, or aryl$_{(C \leq 12)}$, alkylamino$_{(C \leq 12)}$, dialkylamino$_{(C \leq 12)}$, N-heterocycloalkyl$_{(C \leq 12)}$, —C(O)N(R$_{11}$)-alkanediyl$_{(C \leq 6)}$-heterocycloalkyl$_{(C \leq 12)}$, —C(O)-alkyl-amino$_{(C \leq 12)}$, —C(O)-dialkylamino$_{(C \leq 12)}$, —C(O)—N-heterocycloalkyl$_{(C \leq 12)}$, wherein:
R$_{11}$ is hydrogen, alkyl$_{(C \leq 6)}$, or substituted alkyl$_{(C \leq 6)}$;
wherein the final degradable diacyl in the chain is attached to a terminating group; n is 0, 1, 2, 3, 4, 5, or 6;

or a pharmaceutically acceptable salt thereof. In some embodiments, the terminating group is further defined by the formula:

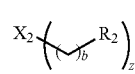

(D-VIII)

wherein:
Y$_4$ is alkanediyl$_{(C \leq 18)}$; and
R$_{10}$ is hydrogen. In some embodiments, A$_1$ and A$_2$ are each independently —O— or —NR$_a$—.
In some embodiments of the dendrimer or dendron of formula (D-I), the core is further defined by the formula:

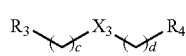

(D-III)

wherein:
X$_2$ is N(R$_5$)$_y$;
R$_5$ is hydrogen or alkyl$_{(C \leq 8)}$, or substituted alkyl$_{(C \leq 18)}$; and
y is 0, 1, or 2, provided that the sum of y and z is 3;
R$_2$ is amino, hydroxy, or mercapto, or alkylamino$_{(C \leq 12)}$, dialkylamino$_{(C \leq 12)}$, or a substituted version of either of these groups;
b is 1, 2, 3, 4, 5, or 6; and
z is 1, 2, 3; provided that the sum of z and y is 3.
In some embodiments of the dendrimer or dendron of formula (D-I), the core is further defined by the formula:

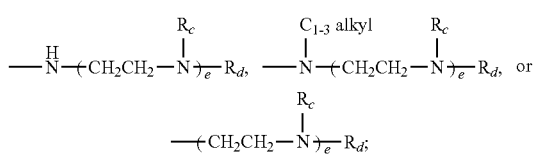

(D-IV)

wherein:
X$_3$ is —NR$_6$—, wherein R$_6$ is hydrogen, alkyl$_{(C \leq 8)}$, or substituted alkyl$_{(C \leq 8)}$, —O—, or alkylaminodiyl$_{(C \leq 8)}$, alkoxydiyl$_{(C \leq 8)}$, arenediyl$_{(C \leq 8)}$, heteroarenediyl$_{(C \leq 8)}$, heterocycloalkanediyl$_{(C \leq 8)}$, or a substituted version of any of these groups;
R$_3$ and R$_4$ are each independently amino, hydroxy, or mercapto, or alkylamino$_{(C \leq 12)}$, dialkylamino$_{(C \leq 12)}$, or a substituted version of either of these groups; or a group of the formula: —N(R$_f$)(CH$_2$CH$_2$N(R$_c$))$_e$R$_d$, wherein:
e and f are each independently 1, 2, or 3; provided that the sum of e and f is 3;
R$_c$, R$_d$, and R$_f$ are each independently hydrogen, alkyl$_{(C \leq 6)}$, or substituted alkyl$_{(C \leq 6)}$;
c and d are each independently 1, 2, 3, 4, 5, or 6.

In some embodiments of the dendrimer or dendron of formula (I), the terminating group is represented by the formula:

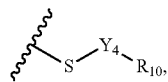

(D-VIII)

wherein:

$Y_4$ is alkanediyl$_{(C \leq 18)}$; and $R_{10}$ is hydrogen.

In some embodiments of the dendrimer or dendron of formula (D-I), the core is further defined as:

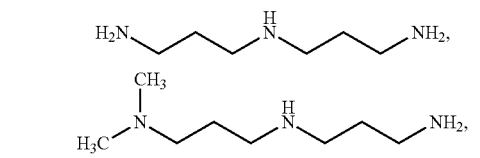

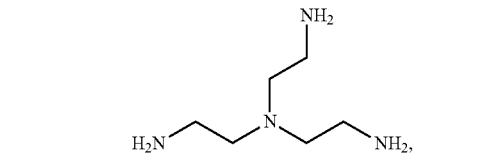

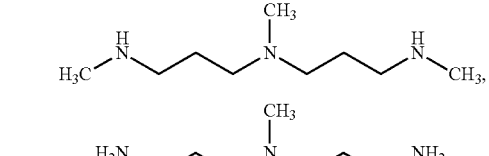

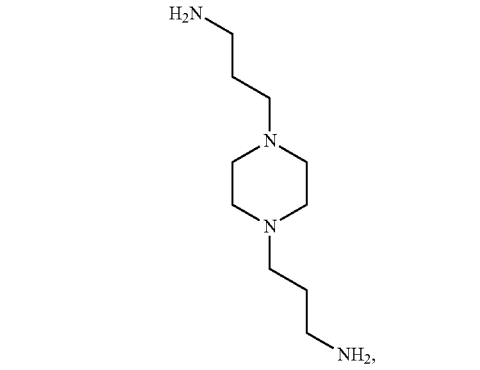


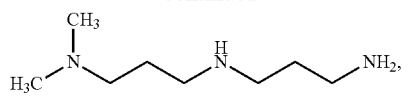

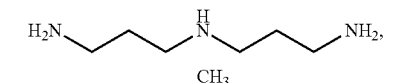

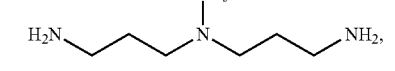

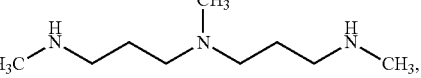

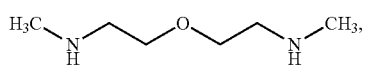

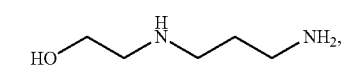

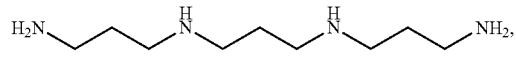

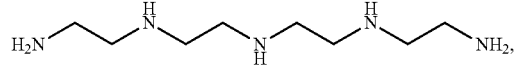

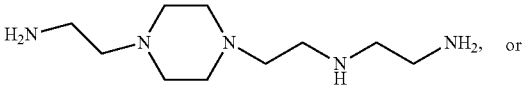

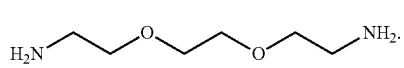

In some embodiments of the dendrimer or dendron of formula (D-I), the degradable diacyl is further defined as:

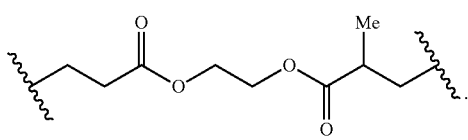 [SMILES: *CCC(=O)OCCOC(=O)C(C)C*]

In some embodiments of the dendrimer or dendron of formula (D-I), the linker is further defined as

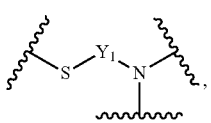

(D-VI)

wherein $Y_1$ is alkanediyl$_{(C \leq 8)}$ or substituted alkanediyl$_{(C \leq 8)}$.

In some embodiments of the dendrimer or dendron of formula (D-I), the dendrimer or dendron is selected from the group consisting of:
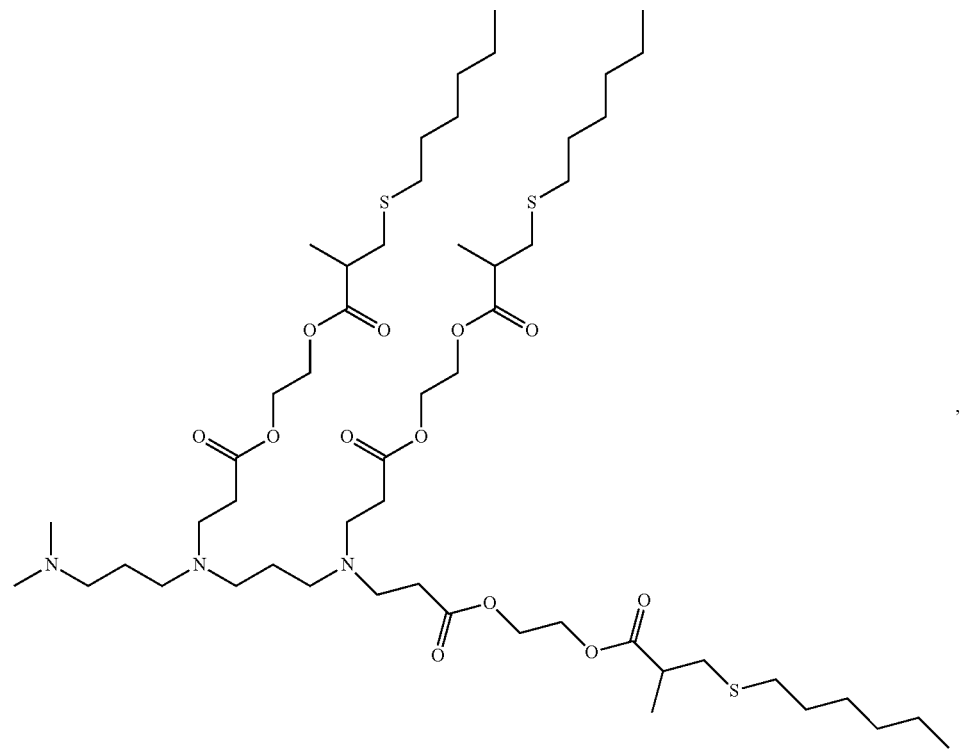
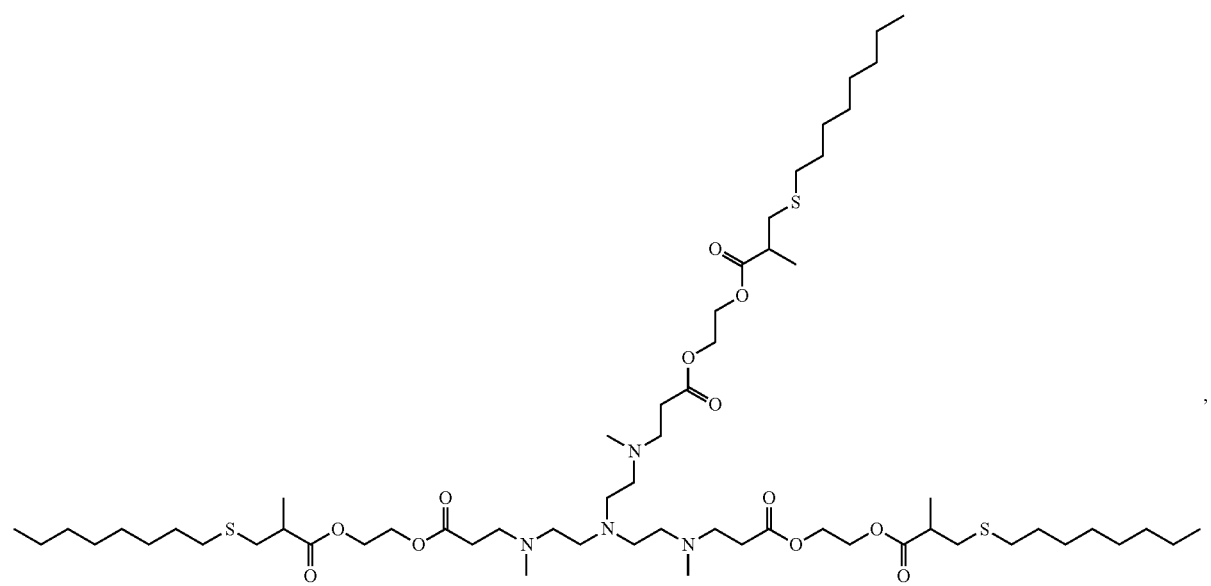

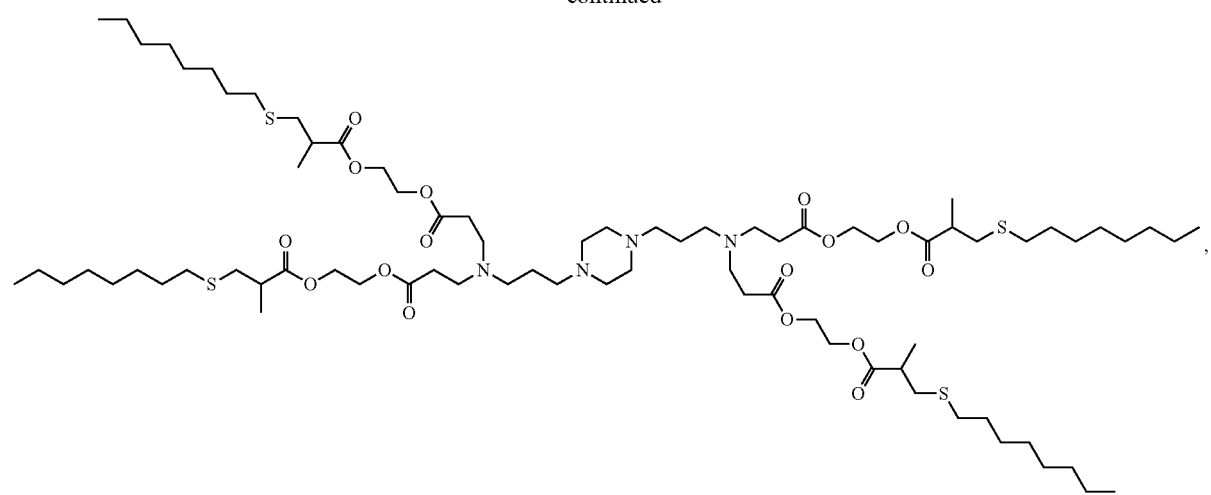
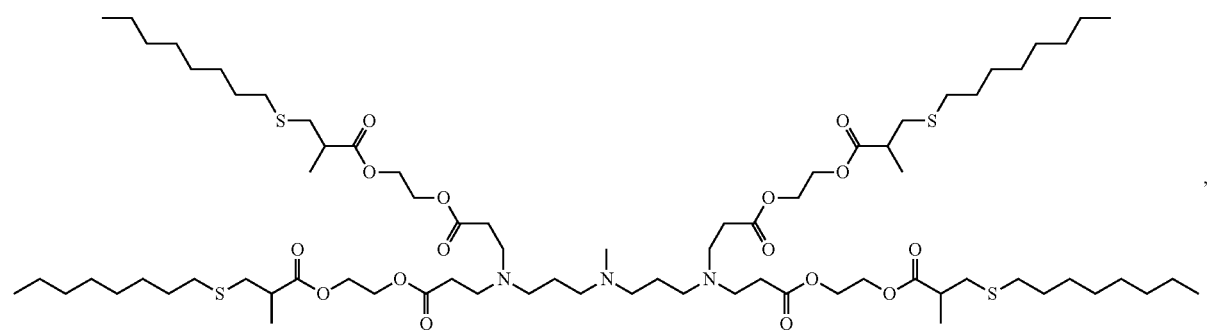
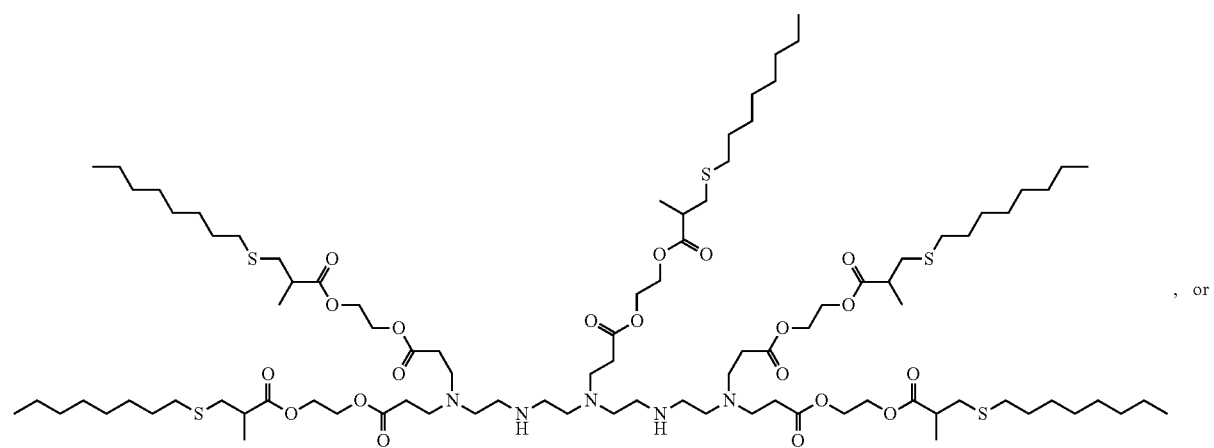

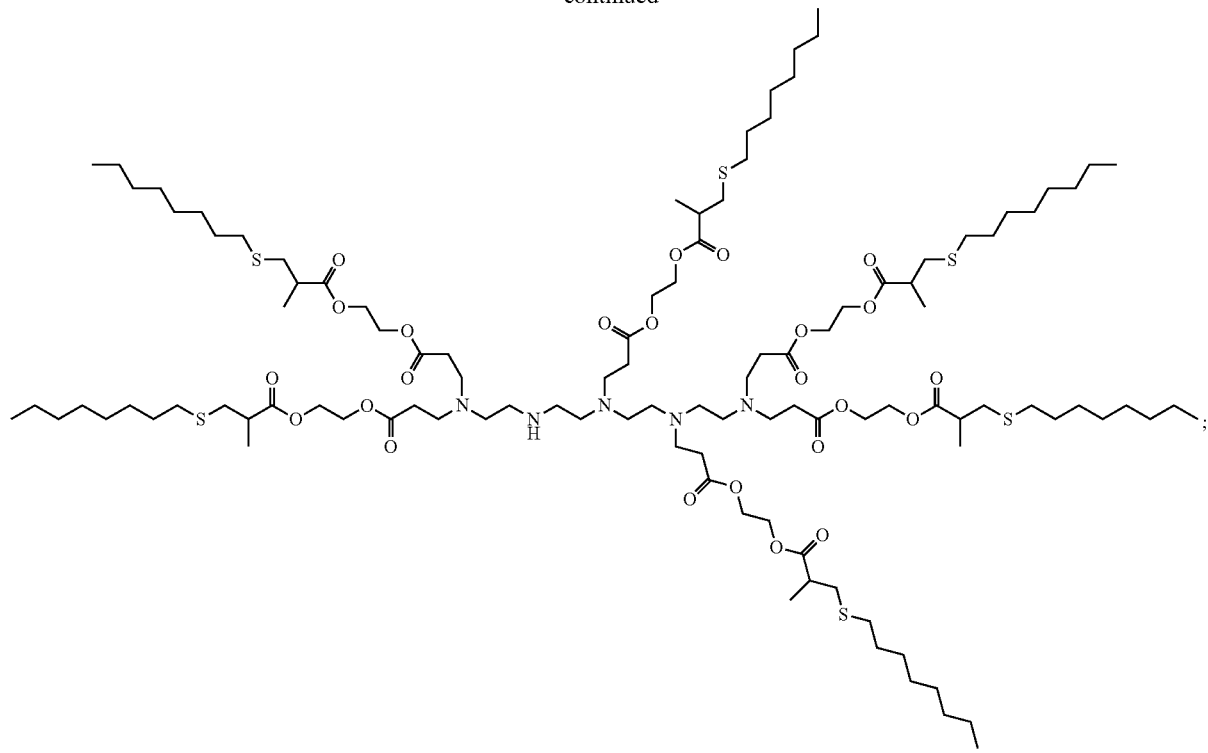

and pharmaceutically acceptable salts thereof.

Dendrimers or Dendrons of Formula (X)

In some embodiments of the lipid composition, the ionizable cationic lipid is a dendrimer or dendron of the formula Core–(Branch)$_N$. In some embodiments, the ionizable cationic lipid is a dendrimer or dendron of the formula

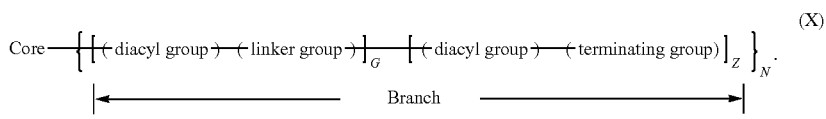

(X)

In some embodiments of the lipid composition, the ionizable cationic lipid is a dendrimer or dendron of a generation (g) having a structural formula:

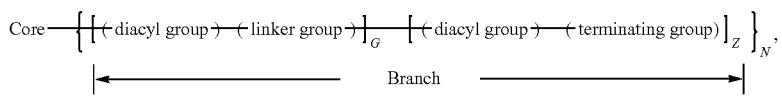

or a pharmaceutically acceptable salt thereof, wherein:
(a) the core comprises a structural formula ($X_{Core}$):

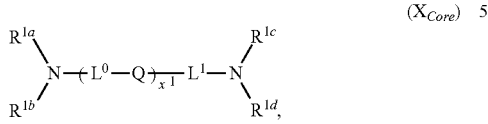

($X_{Core}$)

wherein:
Q is independently at each occurrence a covalent bond, —O—, —S—, —NR$^2$—, or —CR$^{3a}$R$^{3b}$—;
R$^2$ is independently at each occurrence R$^{1g}$ or -L$^2$-NR$^{1e}$R$^{1f}$; R$^{3a}$ and R$^{3b}$ are each independently at each occurrence hydrogen or an optionally substituted (e.g., C$_1$-C$_6$, such as C$_1$-C$_3$) alkyl;
R$^{1a}$, R$^{1b}$, R$^{1c}$, R$^{1d}$, R$^{1e}$, R$^{1f}$, and R$^{1g}$ (if present) are each independently at each occurrence a point of connection to a branch, hydrogen, or an optionally substituted (e.g., C$_1$-C$_{12}$) alkyl;
L$^0$, L$^1$, and L$^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of L$^1$ form a (e.g., C$_4$-C$_6$) heterocycloalkyl (e.g., containing one or two nitrogen atoms and, optionally, an additional heteroatom selected from oxygen and sulfur) with one of R$^{1c}$ and R$^{1d}$; and
x$^1$ is 0, 1, 2, 3, 4, 5, or 6; and
(b) each branch of the plurality (N) of branches independently comprises a structural formula ($X_{Branch}$):

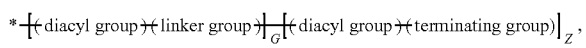

($X_{Branch}$)

wherein:
* indicates a point of attachment of the branch to the core;
g is 1, 2, 3, or 4;
Z=2$^{(g-1)}$;
G=0, when g=1; or G=$\Sigma_{i=0}^{1=g-2}$ 2$^i$, when g≠1;
(c) each diacyl group independently comprises a structural formula

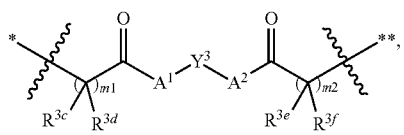

wherein:
* indicates a point of attachment of the diacyl group at the proximal end thereof;
** indicates a point of attachment of the diacyl group at the distal end thereof;
Y$^3$ is independently at each occurrence an optionally substituted (e.g., C$_1$-C$_{12}$) alkylene, an optionally substituted (e.g., C$_1$-C$_{12}$) alkenylene, or an optionally substituted (e.g., C$_1$-C$_{12}$) arenylene;

A$^1$ and A$^2$ are each independently at each occurrence —O—, —S—, or —NR$^4$—, wherein:
R$^4$ is hydrogen or optionally substituted (e.g., C$_1$-C$_6$) alkyl;
m$^1$ and m$^2$ are each independently at each occurrence 1, 2, or 3; and
R$^{3c}$, R$^{3d}$, R$^{3e}$, and R$^{3f}$ are each independently at each occurrence hydrogen or an optionally substituted (e.g., C$_1$-C$_8$) alkyl; and
(d) each linker group independently comprises a structural formula

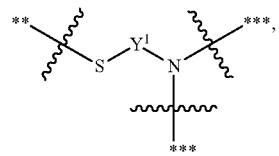

wherein:
** indicates a point of attachment of the linker to a proximal diacyl group;
*** indicates a point of attachment of the linker to a distal diacyl group; and
Y$_1$ is independently at each occurrence an optionally substituted (e.g., C$_1$-C$_{12}$) alkylene, an optionally substituted (e.g., C$_1$-C$_{12}$) alkenylene, or an optionally substituted (e.g., C$_1$-C$_{12}$) arenylene; and
(e) each terminating group is independently selected from optionally substituted (e.g., C$_1$-C$_{18}$, such as C$_4$-C$_{18}$) alkylthiol, and optionally substituted (e.g., C$_1$-C$_{18}$, such as C$_4$-C$_{18}$) alkenylthiol.

In some embodiments of $X_{Core}$, Q is independently at each occurrence a covalent bond, —O—, —S—, —NR$^2$—, or —CR$^{3a}$R$^{3b}$. In some embodiments of $X_{Core}$ Q is independently at each occurrence a covalent bond. In some embodiments of $X_{Core}$ Q is independently at each occurrence an —O—. In some embodiments of $X_{Core}$ Q is independently at each occurrence a —S—. In some embodiments of $X_{Core}$ Q is independently at each occurrence a —NR$^2$ and R$^2$ is independently at each occurrence R$^{1g}$ or -L$^2$-NR$^{1e}$R$^{1f}$. In some embodiments of $X_{Core}$ Q is independently at each occurrence a —CR$^{3a}$R$^{3b}$R$^{3a}$, and R$^{3a}$ and R$^{3b}$ are each independently at each occurrence hydrogen or an optionally substituted alkyl (e.g., C$_1$-C$_6$, such as C$_1$-C$_3$).

In some embodiments of $X_{Core}$, R$^{1a}$, R$^{1b}$, R$^{1c}$, R$^{1d}$, R$^{1e}$, R$^{1f}$, and R$^{1g}$ (if present) are each independently at each occurrence a point of connection to a branch, hydrogen, or an optionally substituted alkyl. In some embodiments of $X_{Core}$, R$^{1a}$, R$^{1b}$, R$^{1c}$, R$^{1d}$, R$^{1e}$, R$^{1f}$, and R$^{1g}$ (if present) are each independently at each occurrence a point of connection to a branch, hydrogen. In some embodiments of $X_{Core}$, R$^{1a}$, R$^{1b}$, R$^{1c}$, R$^{1d}$, R$^{1e}$, R$^{1f}$, and R$^{1g}$ (if present) are each independently at each occurrence a point of connection to a branch an optionally substituted alkyl (e.g., C$_1$-C$_{12}$).

In some embodiments of $X_{Core}$, L$^0$, L$^1$, and L$^2$ are each independently at each occurrence selected from a covalent bond, alkylene, heteroalkylene, [alkylene]-[heterocycloalkyl]-[alkylene], [alkylene]-(arylene)-[alkylene], heterocycloalkyl, and arylene; or, alternatively, part of L$^1$ form a heterocycloalkyl (e.g., C$_4$-C$_6$ and containing one or two nitrogen atoms and, optionally, an additional heteroatom selected from oxygen and sulfur) with one of R$^{1c}$ and R$^{1d}$. In some embodiments of $X_{Core}$, L$^0$, L$^1$, and L$^2$ are each independently at each occurrence can be a covalent bond. In some embodiments of $X_{Core}$, $L^0$, $L^1$, and $L^2$ are each independently at each occurrence can be a hydrogen. In some embodiments of $X_{Core}$, $L^0$, $L^1$, and $L^2$ are each independently at each occurrence can be an alkylene (e.g., $C_1$-$C_{12}$, such as $C_1$-$C_6$ or $C_1$-$C_3$). In some embodiments of $X_{Core}$, $L^0$, $L^1$, and $L^2$ are each independently at each occurrence can be a heteroalkylene (e.g., $C_1$-$C_{12}$, such as $C_1$-$C_8$ or $C_1$-$C_6$). In some embodiments of $X_{Core}$, $L^0$, $L^1$, and $L^2$ are each independently at each occurrence can be a heteroalkylene (e.g., $C_2$-$C_8$ alkyleneoxide, such as oligo(ethyleneoxide)). In some embodiments of $X_{Core}$, $L^0$, $L^1$, and $L^2$ are each independently at each occurrence can be a [alkylene]-[heterocycloalkyl]-[alkylene] [(e.g., $C_1$-$C_6$) alkylene]-[(e.g., $C_4$-$C_6$) heterocycloalkyl]-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene] [(e.g., $C_1$-$C_6$) alkylene]-(arylene)-[(e.g., $C_1$-$C_6$) alkylene]. In some embodiments of $X_{Core}$, $L^0$, $L^1$, and $L^2$ are each independently at each occurrence can be a [alkylene]-(arylene)-[alkylene] (e.g., [(e.g., $C_1$-$C_6$) alkylene]-phenylene-[(e.g., $C_1$-$C_6$) alkylene]). In some embodiments of $X_{Core}$, $L^0$, $L^1$, and $L^2$ are each independently at each occurrence can be a heterocycloalkyl (e.g., $C_4$-$C_6$heterocycloalkyl). In some embodiments of $X_{Core}$, $L^0$, $L^1$, and $L^2$ are each independently at each occurrence can be an arylene (e.g., phenylene). In some embodiments of $X_{Core}$, part of $L^1$ form a heterocycloalkyl with one of $R^{1c}$ and $R^{1d}$. In some embodiments of $X_{Core}$, part of $L^1$ form a heterocycloalkyl (e.g., $C_4$-$C_6$ heterocycloalkyl) with one of $R^{1c}$ and $R^{1d}$ and the heterocycloalkyl can contain one or two nitrogen atoms and, optionally, an additional heteroatom selected from oxygen and sulfur.

In some embodiments of $X_{Core}$, $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as —($CH_2CH_2O$)$_{1-4}$—($CH_2CH_2$)—), [($C_1$-$C_4$) alkylene]-[($C_4$-$C_6$) heterocycloalkyl]-[($C_1$-$C_4$) alkylene]

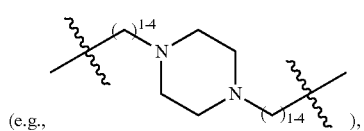

(e.g., and [($C_1$-$C_4$) alkylene]-phenylene-[($C_1$-$C_4$) alkylene]

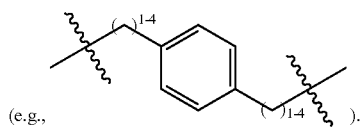

(e.g.,

In some embodiments of $X_{Core}$, $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-. In some embodiments of $X_{Core}$, $L^0$, $L^1$, and $L^2$ are each independently at each occurrence $C_1$-$C_6$ alkylene (e.g., $C_1$-$C_3$ alkylene). In some embodiments, $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$—($C_1$-$C_3$ alkylene)). In some embodiments of $X_{Core}$, $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene] (e.g., —($C_1$-$C_3$ alkylene)-phenylene-($C_1$-$C_3$ alkylene)-) and [($C_1$-$C_4$) alkylene]-[($C_4$-$C_6$) heterocycloalkyl]-[($C_1$-$C_4$) alkylene] (e.g., —($C_1$-$C_3$ alkylene)-piperazinyl-($C_1$-$C_3$ alkylene)-).

In some embodiments of $X_{Core}$, $x^1$ is 0, 1, 2, 3, 4, 5, or 6. In some embodiments of $X_{Core}$, $x^1$ is 0. In some embodiments of $X_{Core}$, $x^1$ is 1. In some embodiments of $X_{Core}$, $x^1$ is 2. In some embodiments of $X_{Core}$, $x^1$ is 0, 3. In some embodiments of $X_{Core}$ $x^1$ is 4. In some embodiments of $X_{Core}$ $x^1$ is 5. In some embodiments of $X_{Core}$, $x^1$ is 6.

In some embodiments of $X_{Core}$, the core comprises a structural formula:

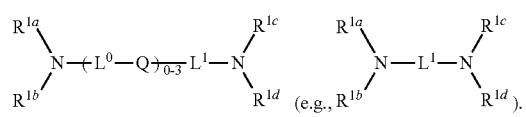

In some embodiments of $X_{Core}$, the core comprises a structural formula:

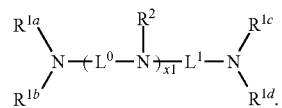

In some embodiments of $X_{Core}$, the core comprises a structural formula:

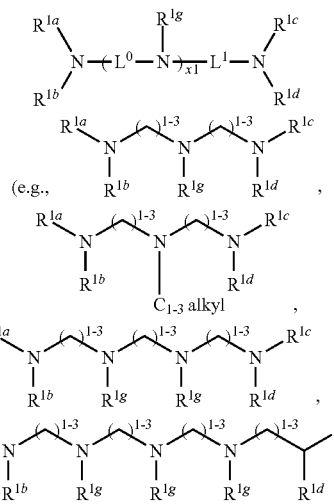

In some embodiments of $X_{Core}$, the core comprises a structural formula:

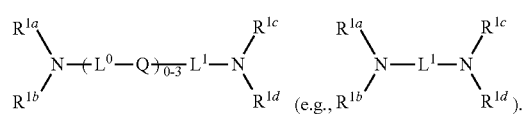

In some embodiments of $X_{Core}$, the core comprises a structural formula:

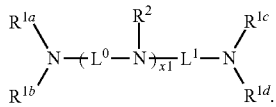

In some embodiments of $X_{Core}$, the core comprises a structural formula:

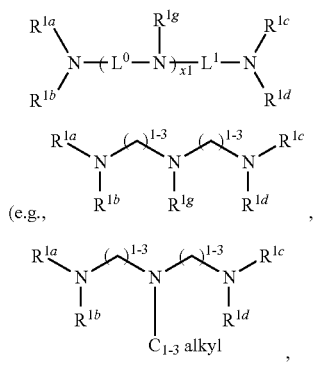

(e.g.,

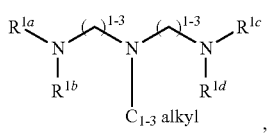

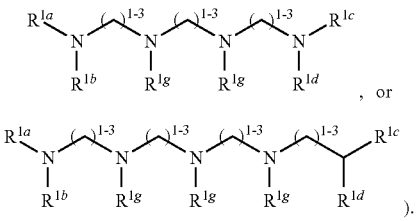

, or

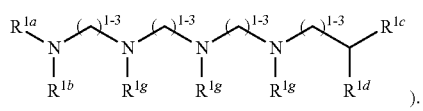

).

In some embodiments of $X_{Core}$, the core comprises a structural formula:

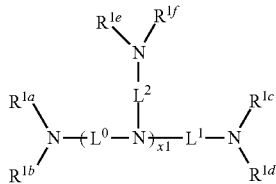

(e.g.,

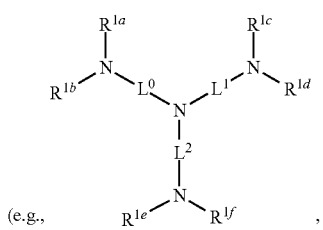

, such as

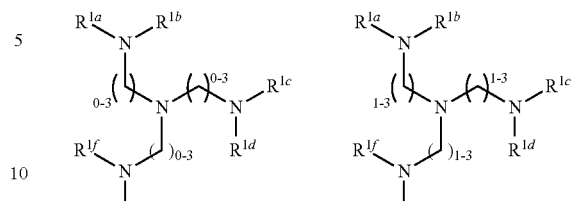

).

In some embodiments of $X_{Core}$, the core comprises a structural formula:

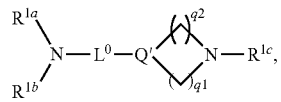

wherein Q' is $-NR^2-$ or $-CR^{3a}R^{3b}-$; $q^1$ and $q^2$ are each independently 1 or 2. In some embodiments of $X_{Core}$, the core comprises a structural formula:

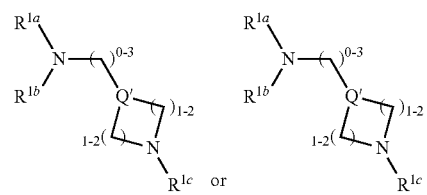

(e.g.,

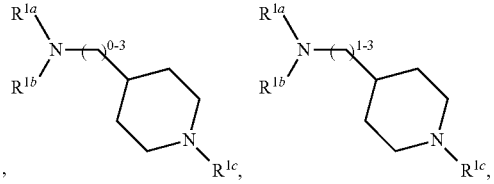

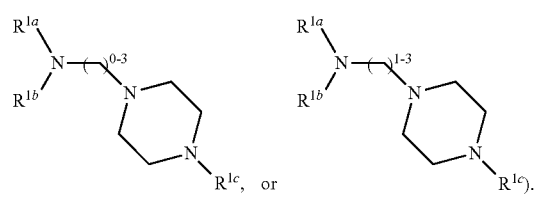

).

In some embodiments of $X_{Core}$, the core comprises a structural formula

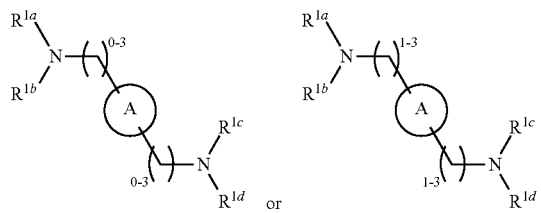

(e.g., 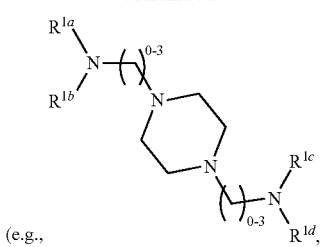

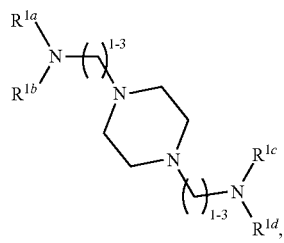

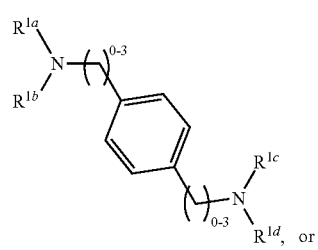, or

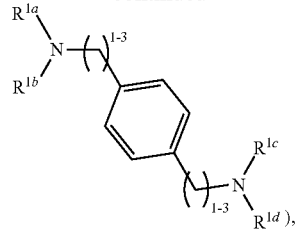

wherein ring A is an optionally substituted aryl or an optionally substituted (e.g., $C_3$-$C_{12}$, such as $C_3$-$C_5$) heteroaryl. In some embodiments of $X_{Core}$, the core comprises has a structural formula

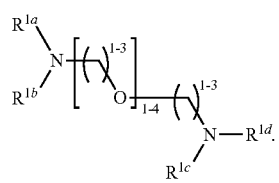

In some embodiments of $X_{Core}$, the core comprises a structural formula set forth in Table. 1 and pharmaceutically acceptable salts thereof, wherein * indicates a point of attachment of the core to a branch of the plurality of branches. In some embodiments, the example cores of Table. 1 are not limited to the stereoisomers (i.e. enantiomers, diastereomers) listed.

TABLE 1

Example core structures

| ID # | Structure |
|---|---|
| 1A1 | 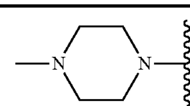 |
| 1A2-1 | 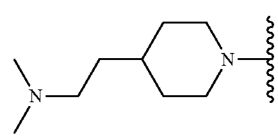 [SMILES: *N1CCC(CCN(C)C)CC1] |
| 1A2-2 | 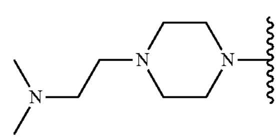 [SMILES: *N1CCN(CCN(C)C)CC1] |
| 1A3-1 | 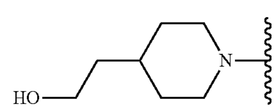 [SMILES: *N1CCC(CCO)CC1] |
| 1A3-2 | 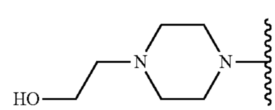 [SMILES: *N1CCN(CCO)CC1] |
| 1A4 | 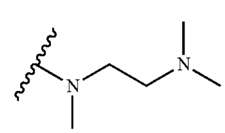 [SMILES: *N(C)CCN(C)C] |

TABLE 1-continued

Example core structures

| ID # | Structure |
|---|---|
| 1A5-1 | 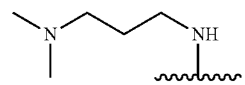 [SMILES: *NCCCN(C)C] |
| 1A5-2 | 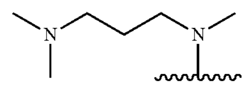 |
| 2A1-1 | 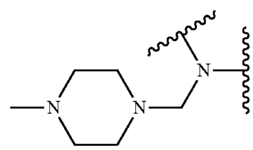 [SMILES: *N(*)CN1CCN(C)CC1] |
| 2A1-2 | 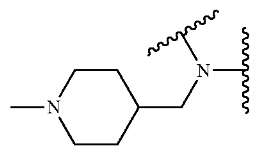 [SMILES: *N(*)CC1CCN(C)CC1] |
| 2A2-1 | 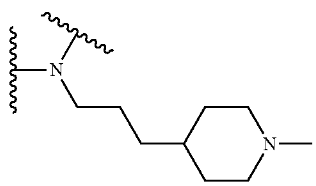 [SMILES: *N(*)CCCC1CCN(C)CC1] |
| 2A2-2 | 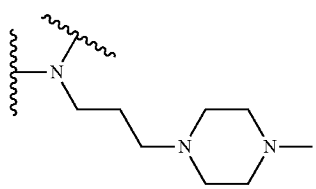 [SMILES: *N(*)CCCN1CCN(C)CC1] |
| 2A3 | 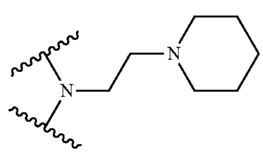 [SMILES: *N(*)CCN1CCCCC1] |
| 2A4 | 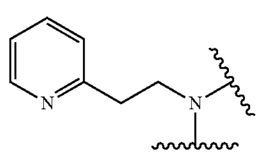 [SMILES: *N(*)CCc1ccccn1] |
| 2A5 | 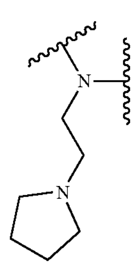 [SMILES: *N(*)CCN1CCCC1] |

TABLE 1-continued
Example core structures
| ID # | Structure |
|---|---|
| 2A6 | 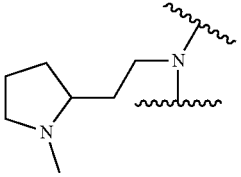 [SMILES: *N(*)CCC1CCCN1C] |
| 2A7-1 | 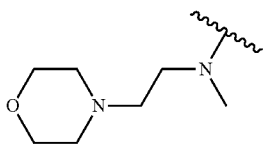 [SMILES: *N(C)CCN1CCOCC1] |
| 2A7-2 | 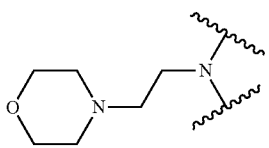 [SMILES: *N(*)CCN1CCOCC1] |
| 2A8 | 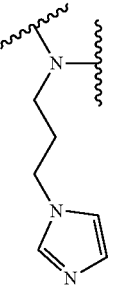 [SMILES: *N(*)CCCn1ccnc1] |
| 2A9 | 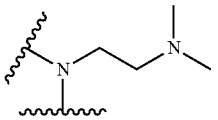 |
| 2A9V | 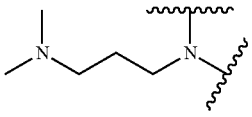 [SMILES: *N(*)CCCN(C)C] |
| 2A10 | 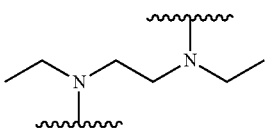 [SMILES: *N(CC)CCN(*)CC] |
| 2A11 | 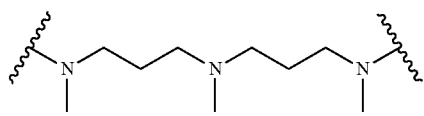 [SMILES: *N(C)CCCN(C)CCCN(*)C] |
| 2A12 | 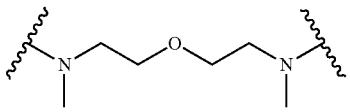 [SMILES: *N(C)CCOCCN(*)C] |

TABLE 1-continued

Example core structures

| ID # | Structure |
|---|---|
| 3A1 | (structure) |
| 3A2 | (structure) |
| 3A3 | (structure) |
| 3A4 | (structure) |
| 3A5 | (structure) |
| 3A6 | (structure) |
| 3A7 | (structure) |
| 4A1 | (structure) |
| 4A2 | (structure) |

TABLE 1-continued

Example core structures

| ID # | Structure |
|---|---|
| 4A3 | (structure) |
| 4A4 | (structure) |
| 5A1 | (structure) |
| 5A2-1 (5-arm) | (structure) |
| 5A2-2 (5-arm) | (structure) |
| 5A2-3 (5-arm) | (structure) |
| 5A2-4 (5-arm) | (structure) |
| 5A3-1 (5-arm) | (structure) |
| 5A4-1 (5-arm) | (structure) |
| 5A5 | (structure) |

TABLE 1-continued
Example core structures
| ID # | Structure |
|---|---|
| 5A6 | 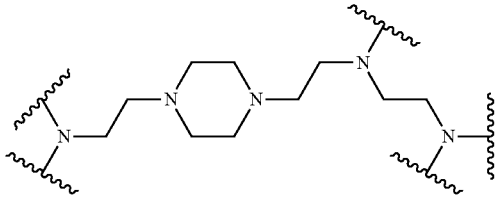 [SMILES: *N(*)CCN(*)CCN1CCN(CCN(*)*)CC1] |
| 5A2-4 (6 arm) | 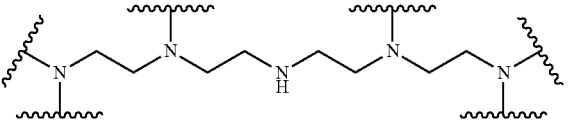 [SMILES: *N(*)CCN(*)CCNCCN(*)CCN(*)*] |
| 5A2-5 (6 arm) | 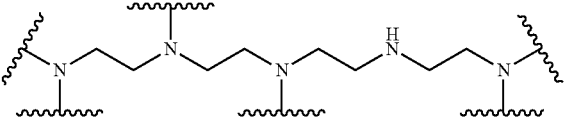 [SMILES: *N(*)CCNCCN(*)CCN(*)CCN(*)*] |
| 5A2-6 (6 arm) | 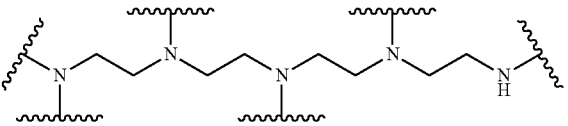 [SMILES: *NCCN(*)CCN(*)CCN(*)CCN(*)*] |
| 5A3-2 (6 arm) | 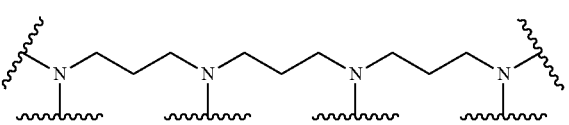 [SMILES: *N(*)CCCN(*)CCCN(*)CCCN(*)*] |
| 5A4-2 (6 arm) | 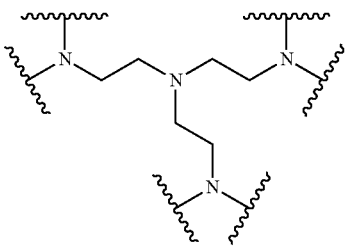 [SMILES: *N(*)CCN(CCN(*)*)CCN(*)*] |
| 6A4 | 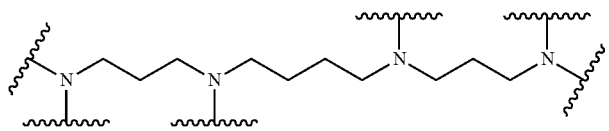 [SMILES: *N(*)CCCN(*)CCCCN(*)CCCN(*)*] |
| 1H1 | 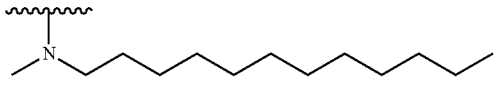 [SMILES: *N(C)CCCCCCCCCCCC] |
| 1H2 | 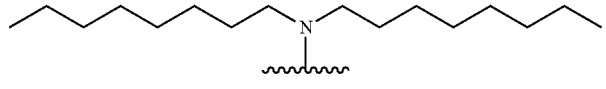 [SMILES: *N(CCCCCCCC)CCCCCCCC] |
| 1H3 | 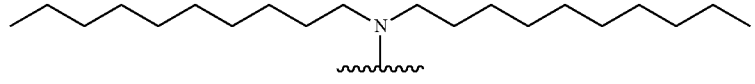 [SMILES: *N(CCCCCCCCCC)CCCCCCCCCC] |
| 2H1 | 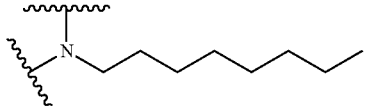 [SMILES: *N(*)CCCCCCCC] |

TABLE 1-continued
Example core structures
| ID # | Structure |
|---|---|
| 2H2 | 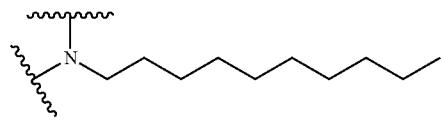 [SMILES: *N(*)CCCCCCCCCC] |
| 2H3 | 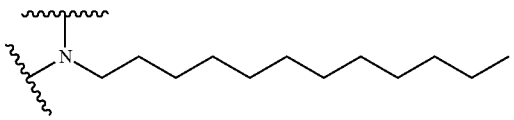 [SMILES: *N(*)CCCCCCCCCCCC] |
| 2H4 | 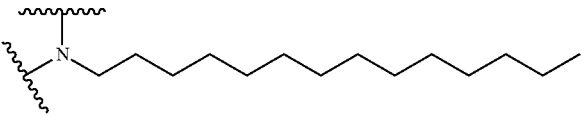 [SMILES: *N(*)CCCCCCCCCCCCCC] |
| 2H5 | 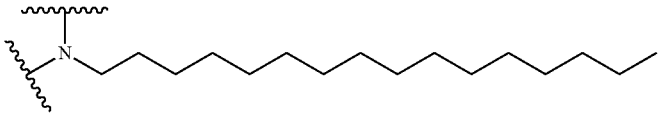 [SMILES: *N(*)CCCCCCCCCCCCCCCC] |
| 2H6 | 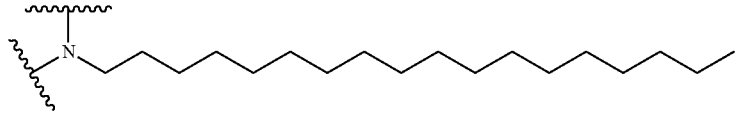 |
In some embodiments of $X_{Core}$, the core comprises a structural formula selected from the group consisting of:
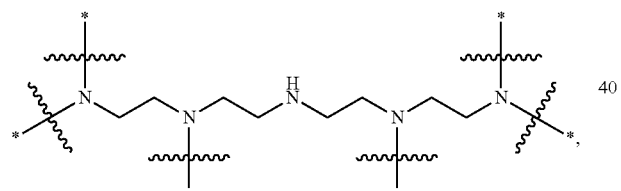
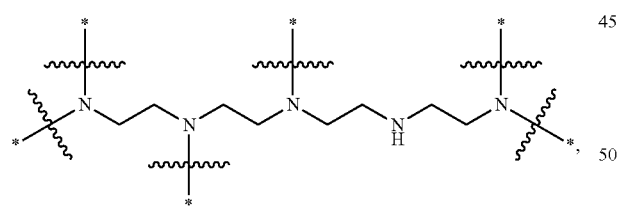
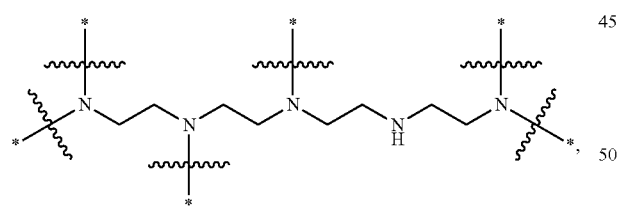
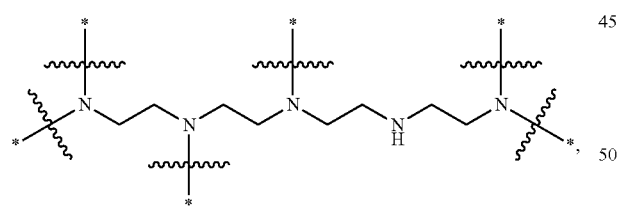

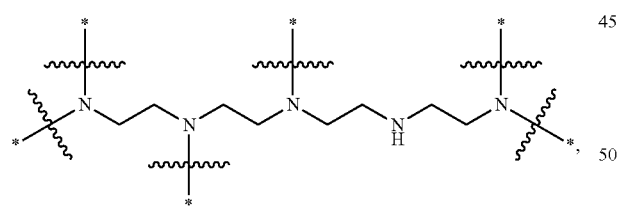
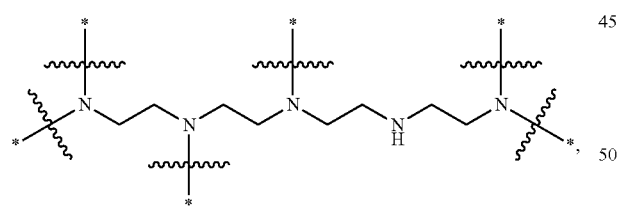
-continued
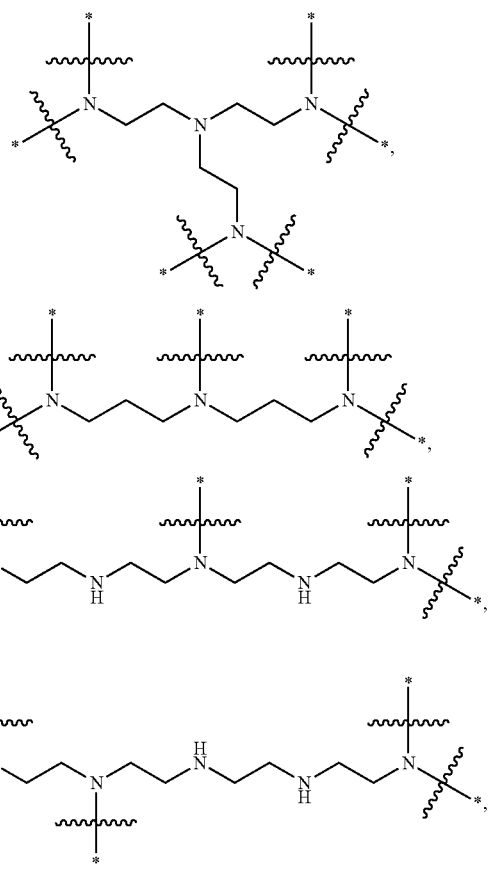

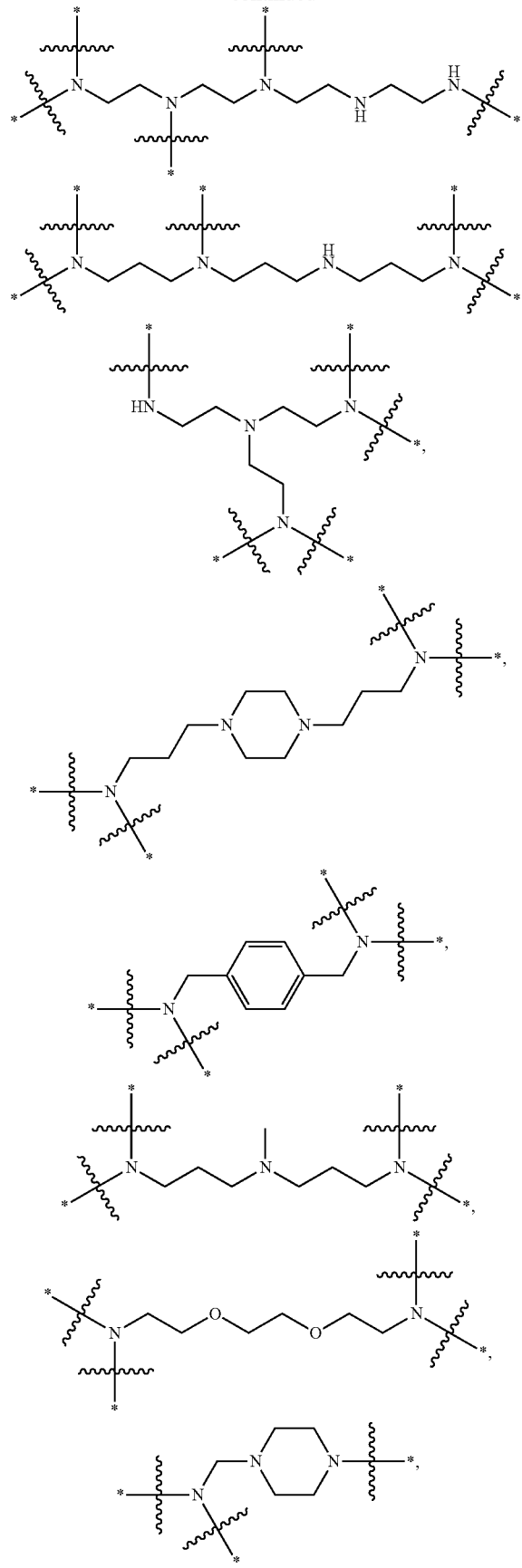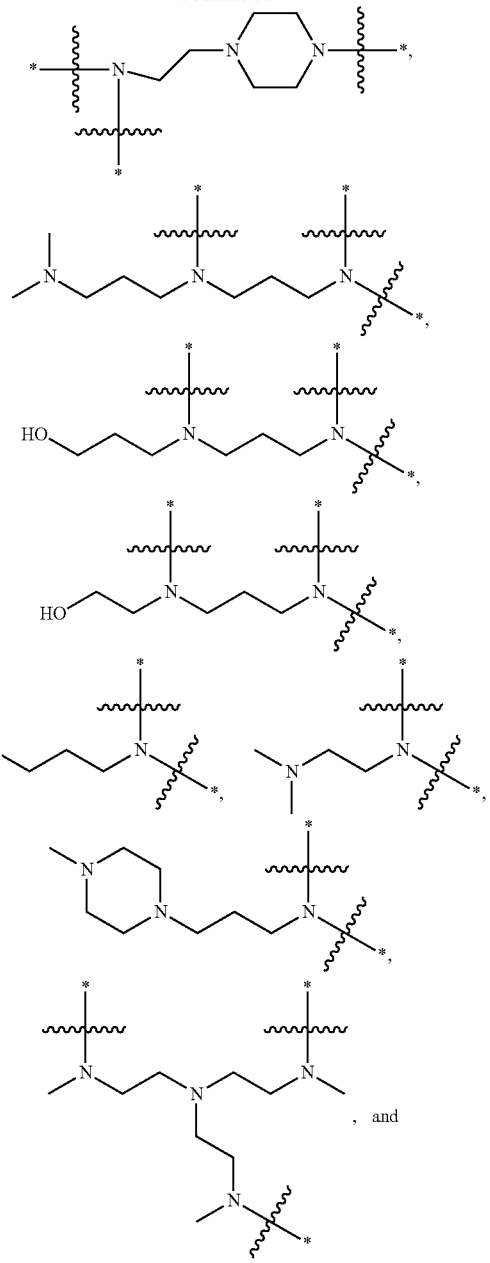

pharmaceutically acceptable salts thereof, wherein * indicates a point of attachment of the core to a branch of the plurality of branches or H. In some embodiments, wherein * indicates a point of attachment of the core to a branch of the plurality of branches.

In some embodiments of $X_{Core}$, the core has the structure

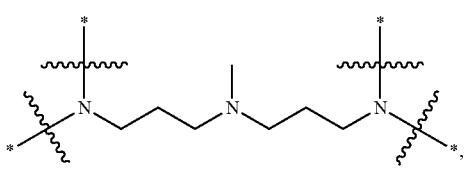

wherein * indicates a point of attachment of the core to a branch of the plurality of branches or H. In some embodiments, at least 2 branches are attached to the core. In some embodiments, at least 3 branches are attached to the core. In some embodiments, at least 4 branches are attached to the core.

In some embodiments of $X_{Core}$, the core has the structure

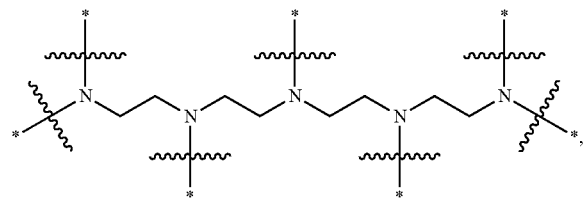

wherein * indicates a point of attachment of the core to a branch of the plurality of branches or H. In some embodiments, at least 4 branches are attached to the core. In some embodiments, at least 5 branches are attached to the core. In some embodiments, at least 6 branches are attached to the core.

In some embodiments, the plurality (N) of branches comprises at least 3 branches, at least 4 branches, at least 5 branches. In some embodiments, the plurality (N) of branches comprises at least 3 branches. In some embodiments, the plurality (N) of branches comprises at least 4 branches. In some embodiments, the plurality (N) of branches comprises at least 5 branches.

In some embodiments of $X_{Branch}$, g is 1, 2, 3, or 4. In some embodiments of $X_{Branch}$, g is 1. In some embodiments of $X_{Branch}$, g is 2. In some embodiments of $X_{Branch}$, g is 3. In some embodiments of $X_{Branch}$, g is 4.

In some embodiments of $X_{Branch}$, $Z=2^{(g-1)}$ and when g=1, G=0. In some embodiments of $X_{Branch}$, $Z=2^{(g-1)}$ and $G=\Sigma_{i=0}^{i=g-2} 2^i$, when g≠1.

In some embodiments of $X_{Branch}$, g=1, G=0, Z=1, and each branch of the plurality of branches comprises a structural formula each branch of the plurality of branches comprises a structural formula *—(diacyl group)—(terminating group).

In some embodiments of $X_{Branch}$, g=2, G=1, Z=2, and each branch of the plurality of branches comprises a structural formula

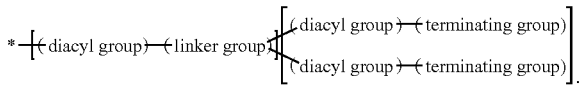

In some embodiments of $X_{Branch}$, g=3, G=3, Z=4, and each branch of the plurality of branches comprises a structural formula

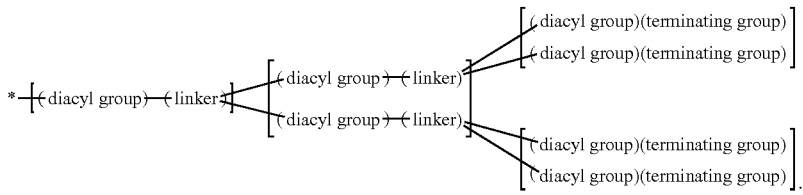

In some embodiments of $X_{Branch}$, g=4, G=7, Z=8, and each branch of the plurality of branches comprises a structural formula

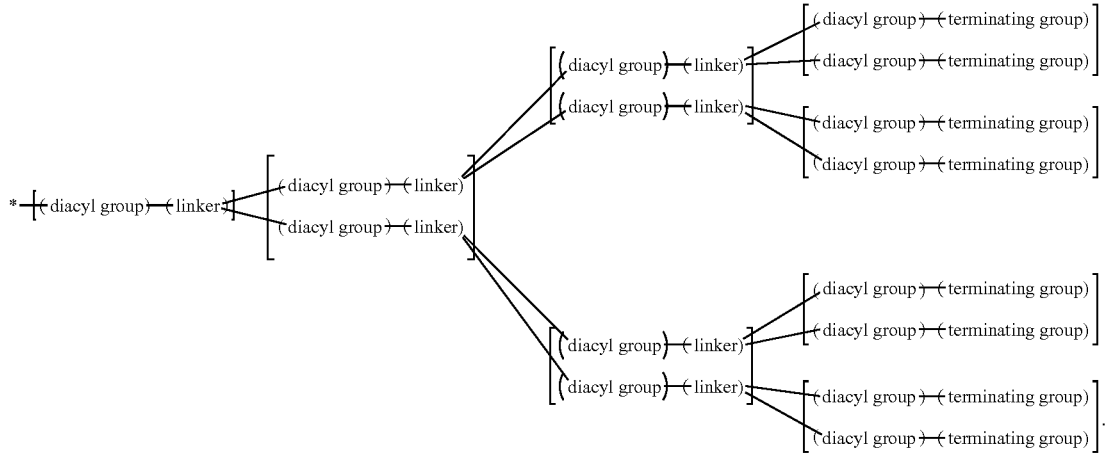

In some embodiments, the dendrimers or dendrons described herein with a generation (g)=1 has the structure:

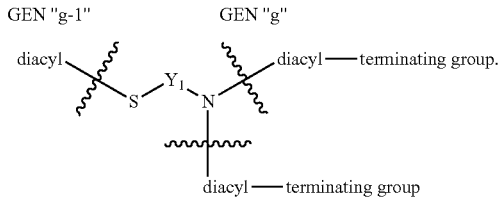

In some embodiments, the dendrimers or dendrons described herein with a generation (g)=1 has the structure:

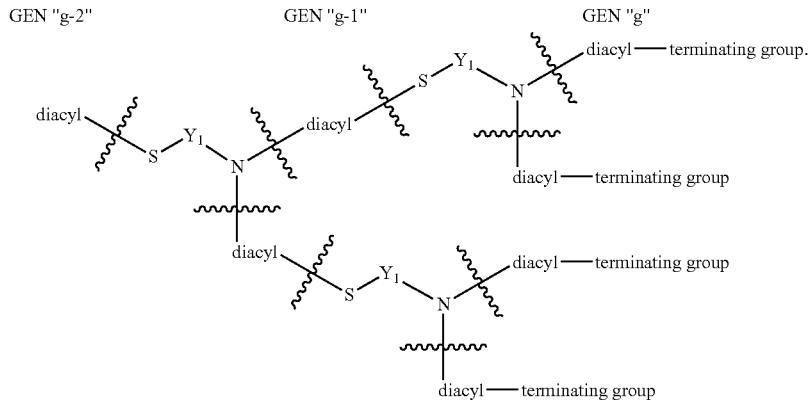

An example formulation of the dendrimers or dendrons described herein for generations 1-4 is shown in Table 2. The number of diacyl groups, linker groups, and terminating groups can be calculated based on g.

TABLE 2

Formulation of Dendrimer or Dendron Groups Based on Generation (g)

| | g = 1 | g = 2 | g = 3 | g = 4 | |
|---|---|---|---|---|---|
| # of diacyl grp | 1 | 1 + 2 = 3 | $1 + 2 + 2^2 = 7$ | $1 + 2 + 2^2 + 2^3 = 15$ | $1 + 2 + \ldots + 2^{g-1}$ |
| # of linker grp | 0 | 1 | 1 + 2 | $1 + 2 + 2^2$ | $1 + 2 + \ldots + 2^{g-2}$ |
| # of terminating grp | 1 | 2 | $2^2$ | $2^3$ | $2^{(g-1)}$ |

In some embodiments, the diacyl group independently comprises a structural formula

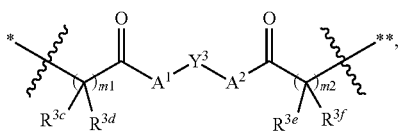

* indicates a point of attachment of the diacyl group at the proximal end thereof, and ** indicates a point of attachment of the diacyl group at the distal end thereof.

In some embodiments of the diacyl group of $X_{Branch}$, $Y^3$ is independently at each occurrence an optionally substituted; alkylene, an optionally substituted alkenylene, or an optionally substituted arenylene. In some embodiments of the diacyl group of $X_{Branch}$, $Y^3$ is independently at each occurrence an optionally substituted alkylene (e.g., $C_1$-$C_{12}$). In some embodiments of the diacyl group of $X_{Branch}$, $Y^3$ is independently at each occurrence an optionally substituted alkenylene (e.g., $C_1$-$C_{12}$). In some embodiments of the diacyl group of $X_{Branch}$, $Y^3$ is independently at each occurrence an optionally substituted arenylene (e.g., $C_1$-$C_{12}$).

In some embodiments of the diacyl group of $X_{Branch}$, $A^1$ and $A^2$ are each independently at each occurrence —O—, —S—, or —NR$^4$—. In some embodiments of the diacyl group of $X_{Branch}$, $A^1$ and $A^2$ are each independently at each occurrence —O—. In some embodiments of the diacyl group of $X_{Branch}$, $A^1$ and $A^2$ are each independently at each occurrence —S—. In some embodiments of the diacyl group of $X_{Branch}$, $A^1$ and $A^2$ are each independently at each occurrence —NR$^4$— and $R^4$ is hydrogen or optionally substituted alkyl (e.g., $C_1$-$C_6$). In some embodiments of the diacyl group of $X_{Branch}$, $m^1$ and $m^2$ are each independently at each occurrence 1, 2, or 3. In some embodiments of the diacyl group of $X_{Branch}$, $m^1$ and $m^2$ are each independently at each occurrence 1. In some embodiments of the diacyl group of $X_{Branch}$, $m^1$ and $m^2$ are each independently at each occurrence 2. In some embodiments of the diacyl group of $X_{Branch}$, $m^1$ and $m^2$ are each independently at each occurrence 3. In some embodiments of the diacyl group of $X_{Branch}$, $R^{3c}$, $R^{3d}$, $R^{3e}$, and $R^{3f}$ are each independently at each occurrence hydrogen or an optionally substituted alkyl. In some embodiments of the diacyl group of $X_{Branch}$, $R^{3c}$, $R^{3d}$, $R^{3e}$, and $R^{3f}$ are each independently at each occurrence hydrogen. In some embodiments of the diacyl group of $X_{Branch}$, $R^{3c}$, $R^{3d}$, $R^{3e}$, and $R^{3f}$ are each independently at each occurrence an optionally substituted (e.g., $C_1$-$C_8$) alkyl.

In some embodiments of the diacyl group, $A^1$ is —O— or —NH—. In some embodiments of the diacyl group, $A^1$ is —O—. In some embodiments of the diacyl group, $A^2$ is —O— or —NH—. In some embodiments of the diacyl group, $A^2$ is —O—. In some embodiments of the diacyl group, $Y^3$ is $C_1$-$C_{12}$ (e.g., $C_1$-$C_6$, such as $C_1$-$C_3$) alkylene.

In some embodiments of the diacyl group, the diacyl group independently at each occurrence comprises a structural formula

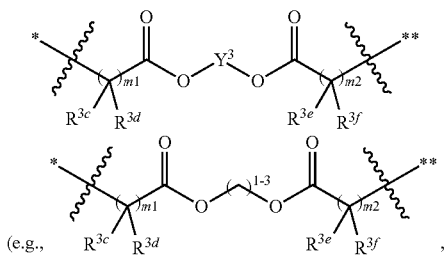

(e.g.,

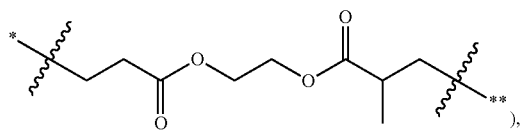

such as

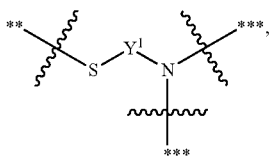

and optionally $R^{3c}$, $R^{3d}$, $R^{3e}$, and $R^{3f}$ are each independently at each occurrence hydrogen or $C_1$-$C_3$ alkyl.

In some embodiments, linker group independently comprises a structural formula

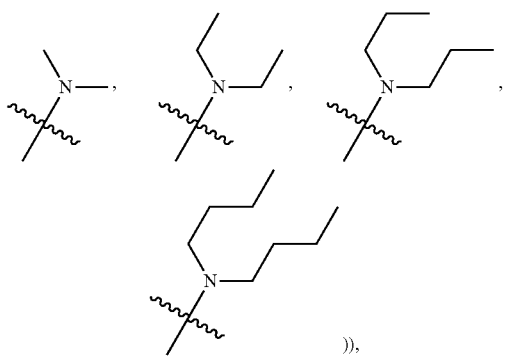

indicates a point of attachment of the linker to a proximal diacyl group, and * indicates a point of attachment of the linker to a distal diacyl group.

In some embodiments of the linker group of $X_{Branch}$ if present, $Y^1$ is independently at each occurrence an optionally substituted alkylene, an optionally substituted alkenylene, or an optionally substituted arenylene. In some embodiments of the linker group of $X_{Branch}$ if present, $Y_1$ is independently at each occurrence an optionally substituted alkylene (e.g., $C_1$-$C_{12}$). In some embodiments of the linker group of $X_{Branch}$ if present, $Y^1$ is independently at each occurrence an optionally substituted alkenylene (e.g., $C_1$-$C_{12}$). In some embodiments of the linker group of $X_{Branch}$ if present, $Y^1$ is independently at each occurrence an optionally substituted arenylene (e.g., $C_1$-$C_{12}$).

In some embodiments of the terminating group of $X_{Branch}$, each terminating group is independently selected from optionally substituted alkylthiol and optionally substituted alkenylthiol. In some embodiments of the terminating group of $X_{Branch}$, each terminating group is an optionally substituted alkylthiol (e.g., $C_1$-$C_{18}$, such as $C_4$-$C_{18}$). In some embodiments of the terminating group of $X_{Branch}$, each terminating group is optionally substituted alkenylthiol (e.g., $C_1$-$C_{18}$, such as $C_4$-$C_{18}$).

In some embodiments of the terminating group of $X_{Branch}$, each terminating group is independently $C_1$-$C_{18}$ alkenylthiol or $C_1$-$C_{18}$ alkylthiol, and the alkyl or alkenyl moiety is optionally substituted with one or more substituents each independently selected from halogen, $C_6$-$C_{12}$ aryl, $C_1$-$C_{12}$ alkylamino, $C_4$-$C_6$ N-heterocycloalkyl, —OH, —C(O)OH, —C(O)N($C_1$-$C_3$ alkyl)-($C_1$-$C_6$ alkylene)-($C_1$-$C_{12}$ alkylamino), —C(O)N($C_1$-$C_3$ alkyl)-($C_1$-$C_6$ alkylene)-($C_4$-$C_6$ N-heterocycloalkyl), —C(O)—($C_1$-$C_{12}$ alkylamino), and —C(O)—($C_4$-$C_6$ N-heterocycloalkyl), and the $C_4$-$C_6$ N-heterocycloalkyl moiety of any of the preceding substituents is optionally substituted with $C_1$-$C_3$ alkyl or $C_1$-$C_3$ hydroxyalkyl.

In some embodiments of the terminating group of $X_{Branch}$, each terminating group is independently $C_1$-$C_{18}$ (e.g., $C_4$-$C_{18}$) alkenylthiol or $C_1$-$C_{18}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —NHCH$_2$CH$_2$CH$_2$CH$_3$) or $C_1$-$C_8$ di-alkylamino (such as

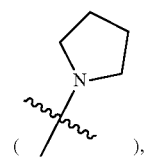

)), $C_4$-$C_6$ N-heterocycloalkyl (e.g., N-pyrrolidinyl

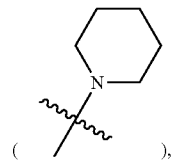

N-piperidinyl

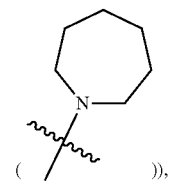 [SMILES: *N1CCCCCC1]

N-azepanyl

—OH—, —C(O)OH, —C(O)N(C₁-C₃ alkyl)-(C₁-C₆ alkylene)-(C₁-C₁₂ alkylamino (e.g., mono- or di-alkylamino))

(e.g., 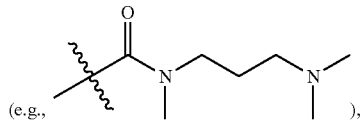 [SMILES: *C(=O)N(C)CCCN(C)C]),

—C(O)N(C₁-C₃ alkyl)-(C₁-C₆ alkylene)-(C₄-C₆ N-heterocycloalkyl)

(e.g., 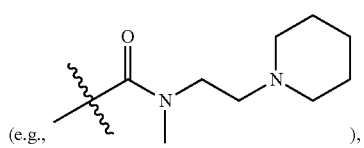 [SMILES: *C(=O)N(C)CCN1CCCCC1]),

—C(O)—(C₁-C₁₂ alkylamino (e.g., mono- or di-alkylamino)), and —C(O)—(C₄-C₆ N-heterocycloalkyl)

(e.g., 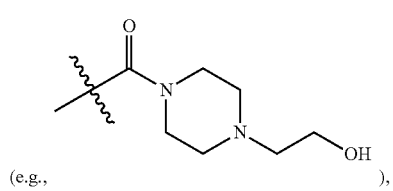 [SMILES: *C(=O)N1CCN(CCO)CC1]), wherein the C₄-C₆ N-heterocycloalkyl moiety of any of the preceding substituents is optionally substituted with C₁-C₃ alkyl or C₁-C₃ hydroxyalkyl. In some embodiments of the terminating group of X$_{Branch}$, each terminating group is independently C₁-C₁₈ (e.g., C₄-C₁₈) alkylthiol, wherein the alkyl moiety is optionally substituted with one substituent —OH. In some embodiments of the terminating group of X$_{Branch}$, each terminating group is independently C₁-C₁₈ (e.g., C₄-C₁₈) alkylthiol, wherein the alkyl moiety is optionally substituted with one substituent selected from C₁-C₁₂ (e.g., C₁-C₈) alkylamino (e.g., C₁-C₆ mono-alkylamino (such as —NHCH₂CH₂CH₂CH₃) or C₁-C₈ di-alkylamino (such as -continued ( 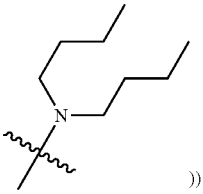 ))

and C₄-C₆ N-heterocycloalkyl (e.g., N-pyrrolidinyl ( 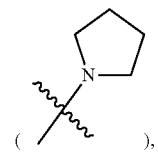 ),

N-piperidinyl ( 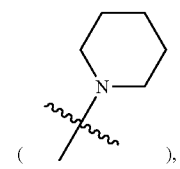 ),

N-azepanyl ( 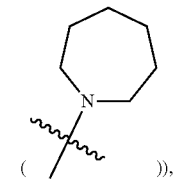 )),

In some embodiments of the terminating group of X$_{Branch}$, each terminating group is independently C₁-C₁₈ (e.g., C₄-C₁₈) alkenylthiol or C₁-C₁₈ (e.g., C₄-C₁₈) alkylthiol. In some embodiments of the terminating group of X$_{Branch}$, each terminating group is independently C₁-C₁₈ (e.g., C₄-C₁₈) alkylthiol.

In some embodiments of the terminating group of X$_{Branch}$, each terminating group is independently a structural set forth in Table 3. In some embodiments, the dendrimers or dendrons described herein can comprise a terminating group or pharmaceutically acceptable salt, or thereof selected in Table 3. In some embodiments, the example terminating group of Table 3 are not limiting of the stereoisomers (i.e. enantiomers, diastereomers) listed.

TABLE 3

| ID # | Example terminating group/peripheries structures Structure |
|---|---|
| SC1 | |

TABLE 3-continued
Example terminating group/peripheries structures
| ID # | Structure |
|---|---|
| SC2 | 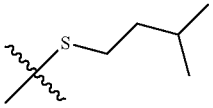 [SMILES: *SCCC(C)C] |
| SC3 | 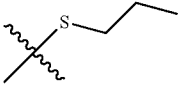 [SMILES: *SCCC] |
| SC4 | 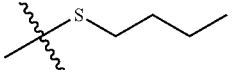 [SMILES: *SCCCC] |
| SC5 | 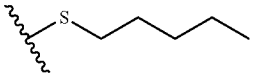 [SMILES: *SCCCCC] |
| SC6 | 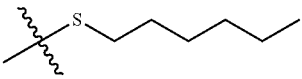 [SMILES: *SCCCCCC] |
| SC7 | 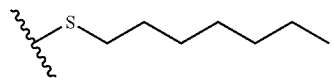 [SMILES: *SCCCCCCC] |
| SC8 | 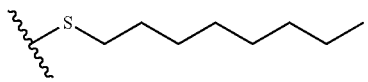 [SMILES: *SCCCCCCCC] |
| SC9 | 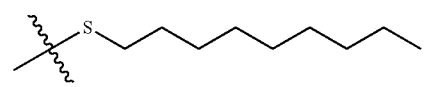 [SMILES: *SCCCCCCCCC] |
| SC10 | 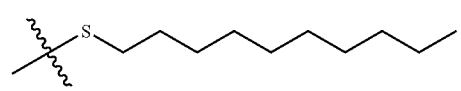 [SMILES: *SCCCCCCCCCC] |
| SC11 | 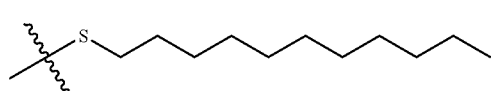 [SMILES: *SCCCCCCCCCCC] |
| SC12 | 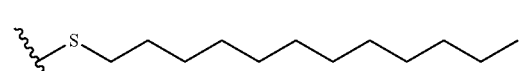 |
| SC14 | 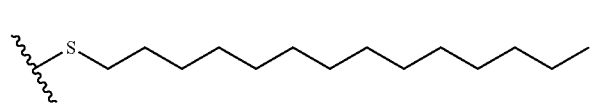 [SMILES: *SCCCCCCCCCCCCCC] |
| SC16 | 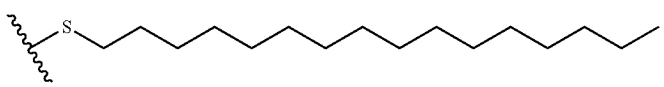 [SMILES: *SCCCCCCCCCCCCCCCC] |
| SC18 | 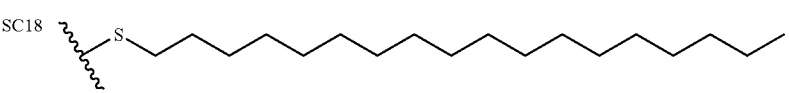 |
| SC19 | 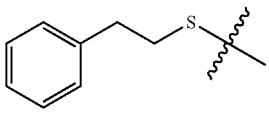 [SMILES: *SCCc1ccccc1] |

TABLE 3-continued

Example terminating group/peripheries structures

| ID # | Structure |
|---|---|
| SO1 | ~S-CH₂-CH₂-C(=O)-OH |
| SO2 | ~S-(CH₂)₄-C(=O)-OH |
| SO3 | ~S-(CH₂)₁₀-C(=O)-OH |
| SO4 | ~S-CH₂-CH₂-OH |
| SO5 | ~S-CH₂-CH(OH)-CH₂-OH |
| SO6 | ~S-CH₂-CH₂-CH₂-OH |
| SO7 | ~S-(CH₂)₄-OH |
| SO8 | ~S-(CH₂)₆-OH |
| SO9 | ~S-(CH₂)₁₁-OH |
| SN1 | ~S-CH₂-CH₂-N(CH₃)₂ |
| SN2 | ~S-CH₂-CH₂-NH-(CH₂)₃-CH₃ |
| SN3 | ~S-CH₂-CH₂-N(CH₂CH₃)₂ |
| SN4 | ~S-CH₂-CH₂-N(pyrrolidine) |

TABLE 3-continued
Example terminating group/peripheries structures
| ID # | Structure |
|---|---|
| SN5 | 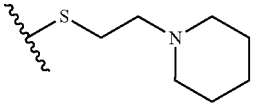 [SMILES: *SCCN1CCCCC1] |
| SN6 | 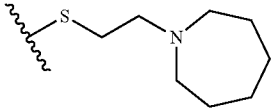 [SMILES: *SCCN1CCCCCC1] |
| SN7 | 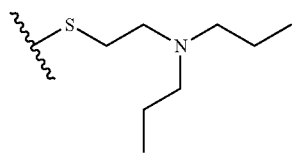 [SMILES: *SCCN(CCC)CCC] |
| SN8 | 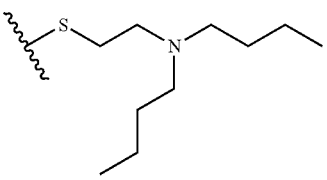 [SMILES: *SCCN(CCCC)CCCC] |
| SN9 | 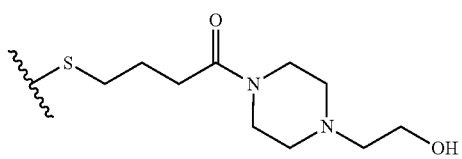 [SMILES: *SCCCC(=O)N1CCN(CCO)CC1] |
| SN10 | 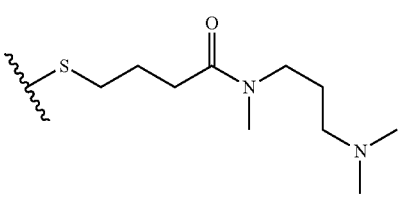 [SMILES: *SCCCC(=O)N(C)CCCN(C)C] |
| SN11 | 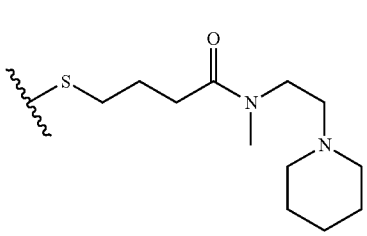 [SMILES: *SCCCC(=O)N(C)CCN1CCCCC1] |
In some embodiments, the dendrimer or dendron of Formula (X) is selected from those set forth in Table 4 and pharmaceutically acceptable salts thereof.

TABLE 4

Example ionizable cationic lipo-dendrimers or lipo-dendrons

| ID # | Structure |
|---|---|
| 2A2-SC14 | 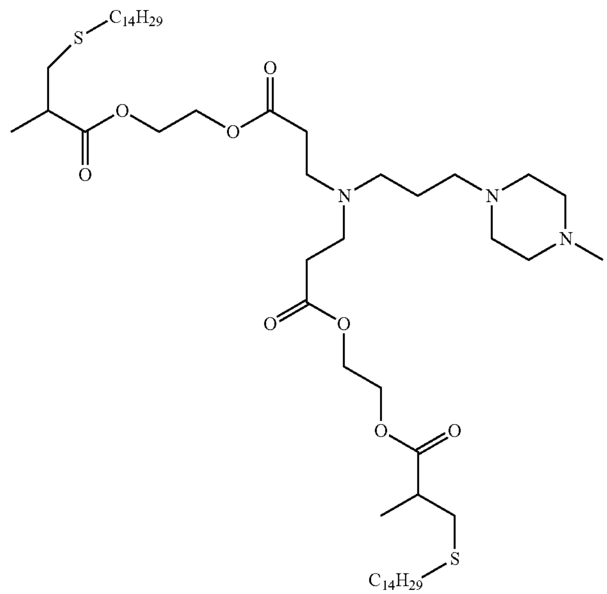 |
| 2A6-SC14 | 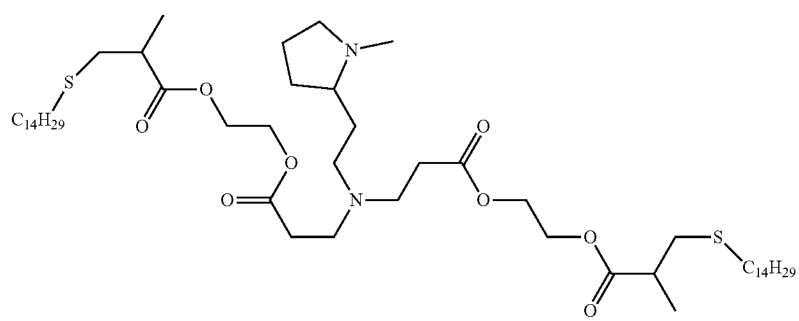 |
| 2A9-SC14 | 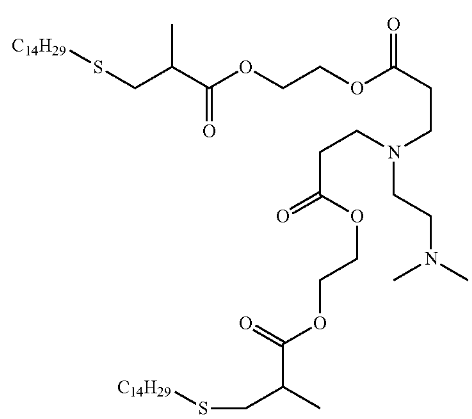 |

TABLE 4-continued
Example ionizable cationic lipo-dendrimers or lipo-dendrons
| ID # | Structure |
|---|---|
| 3A3-SC10 | 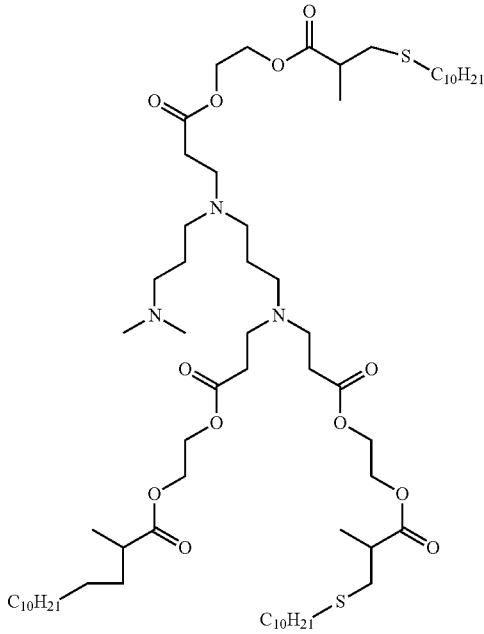 |
| 3A3-SC14 | 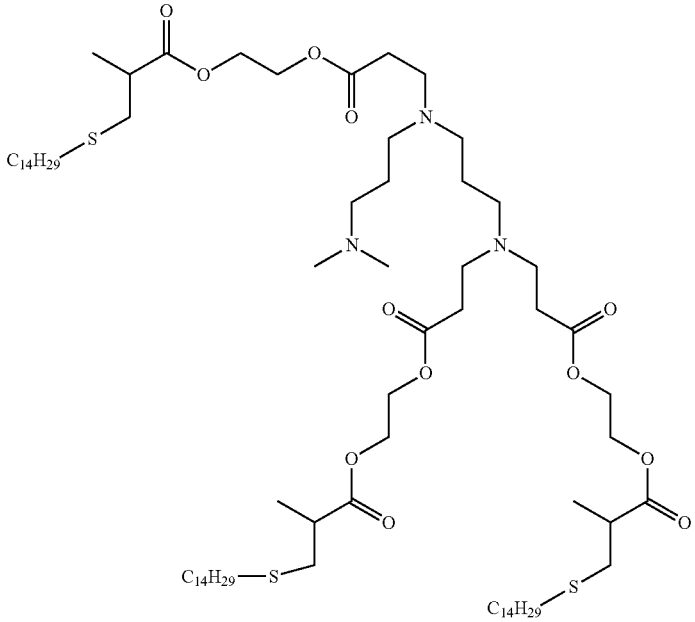 |

TABLE 4-continued

Example ionizable cationic lipo-dendrimers or lipo-dendrons

| ID # | Structure |
|---|---|
| 3A5-SC10 | 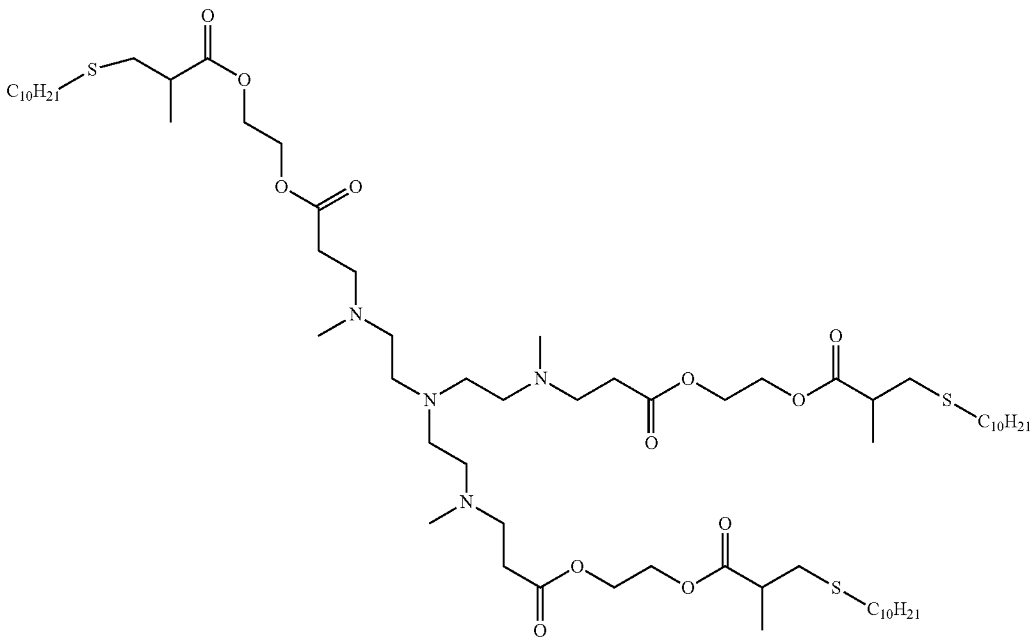 |
| 3A5-SC14 | 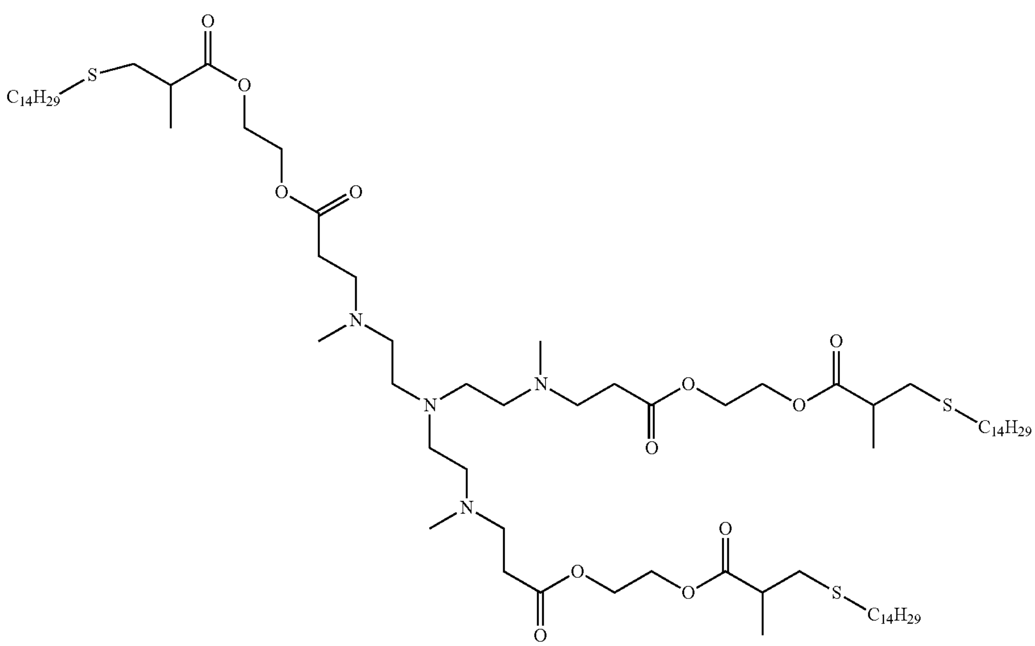 |

TABLE 4-continued
Example ionizable cationic lipo-dendrimers or lipo-dendrons
| ID # | Structure |
|---|---|
| 4A1-SC12 | 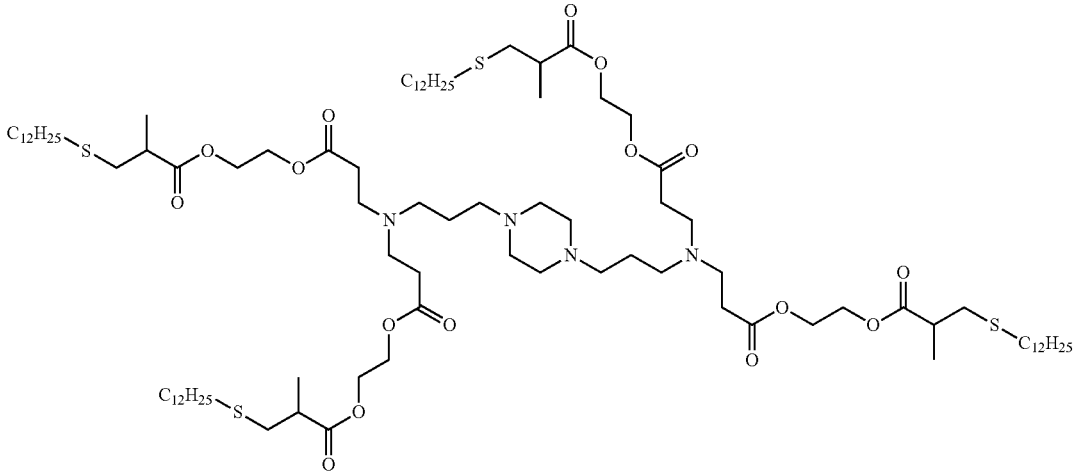 |
| 4A3-SC12 | 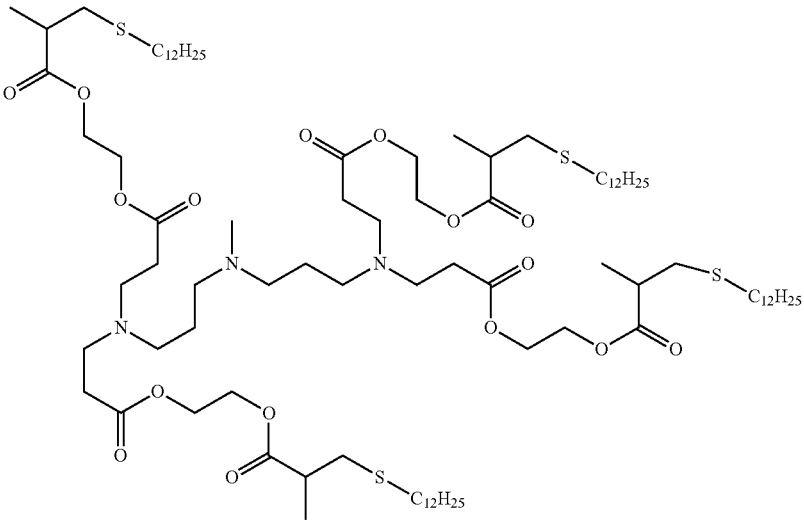 |
| 5A1-SC12 | 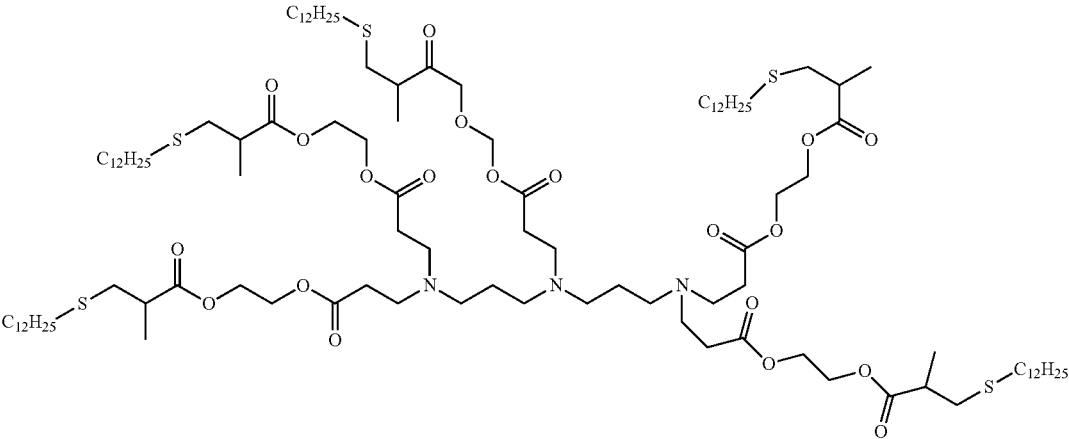 |

TABLE 4-continued
Example ionizable cationic lipo-dendrimers or lipo-dendrons
| ID # | Structure |
|---|---|
| 5A1-SC8 | 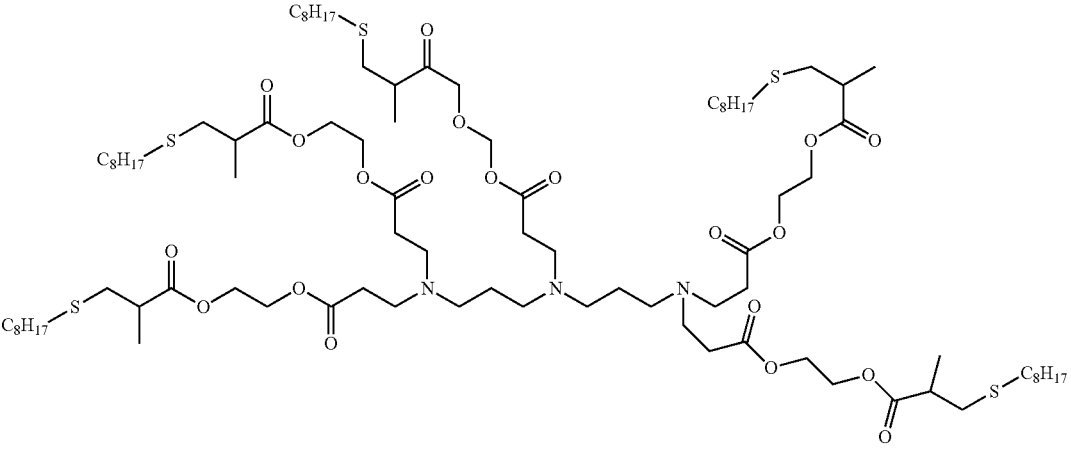 |
| 5A2-2-SC12 (5-arm) | 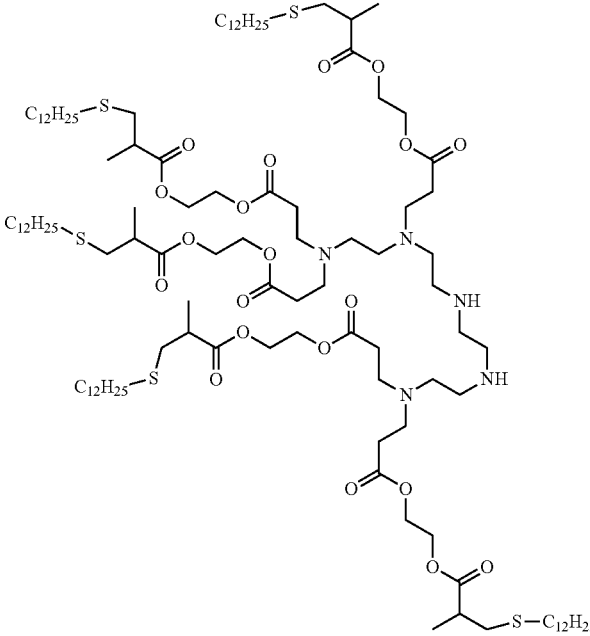 |

TABLE 4-continued

Example ionizable cationic lipo-dendrimers or lipo-dendrons

| ID # | Structure |
|---|---|
| 5A3-1-SC12 (5 arm) | 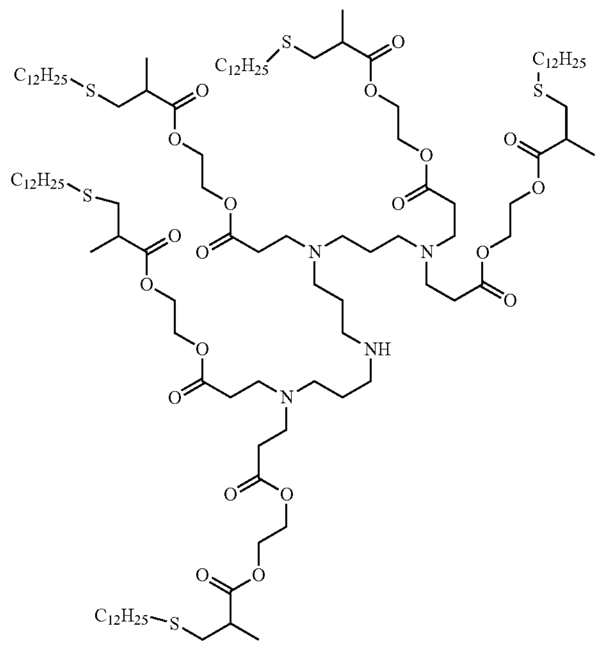 |
| 5A3-1-SC8 (5-arm) | 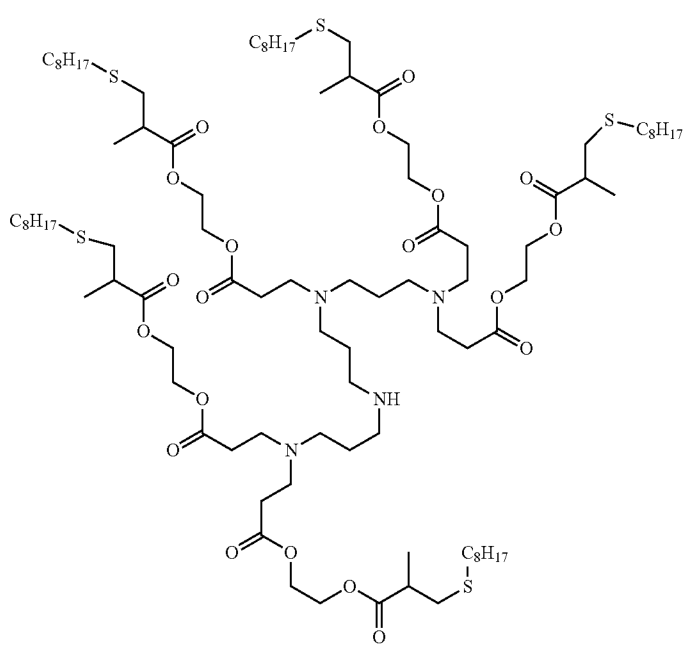 |

TABLE 4-continued

Example ionizable cationic lipo-dendrimers or lipo-dendrons

| ID # | Structure |
| --- | --- |
| 5A4-1-SC12 (5-arm) | *(chemical structure)* |
| 5A4-1-SC8 (5-arm) | *(chemical structure)* |

TABLE 4-continued
Example ionizable cationic lipo-dendrimers or lipo-dendrons
| ID # | Structure |
|---|---|
| 5A5-SC8 | 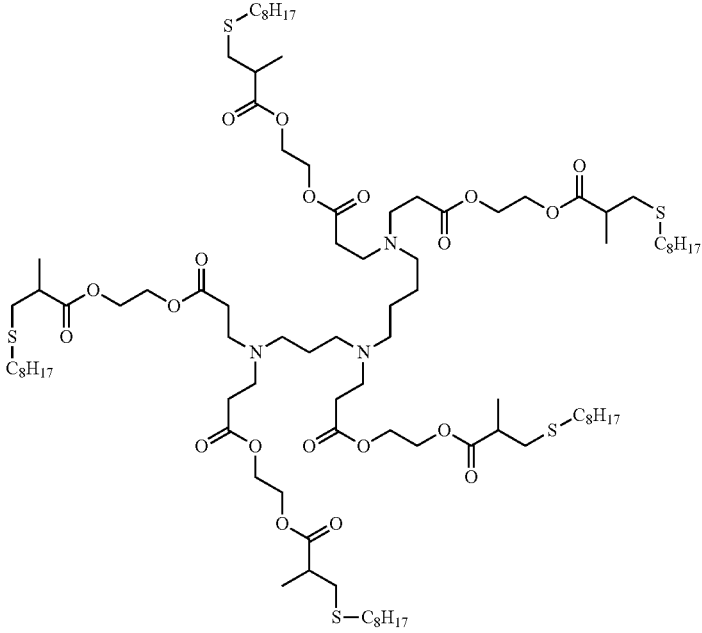 |
| 5A5-SC12 | 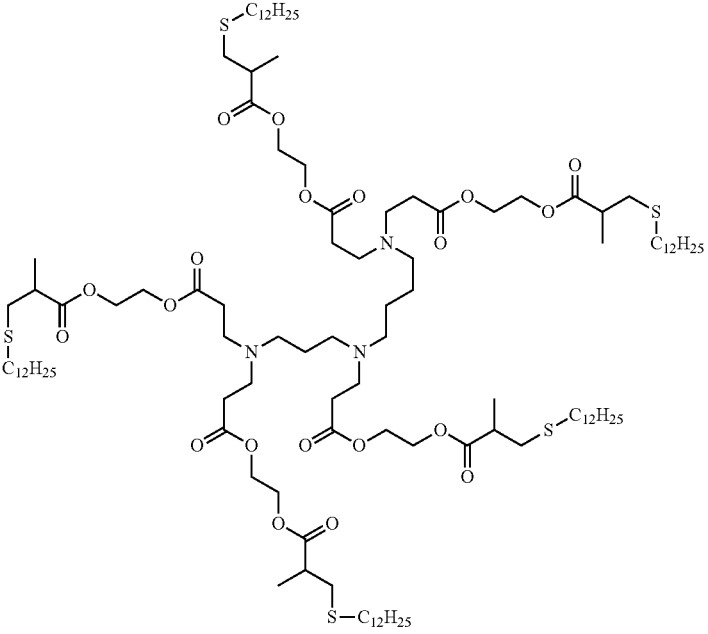 |

TABLE 4-continued
Example ionizable cationic lipo-dendrimers or lipo-dendrons
| ID # | Structure |
|---|---|
| 5A2-4-SC12 (6-arm) | 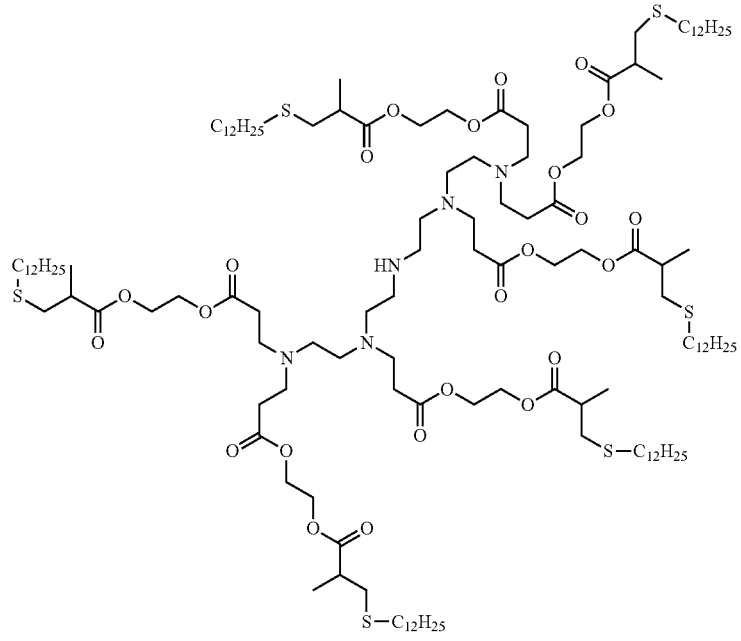 |
| 5A2-4-SC10 (6-arm) | 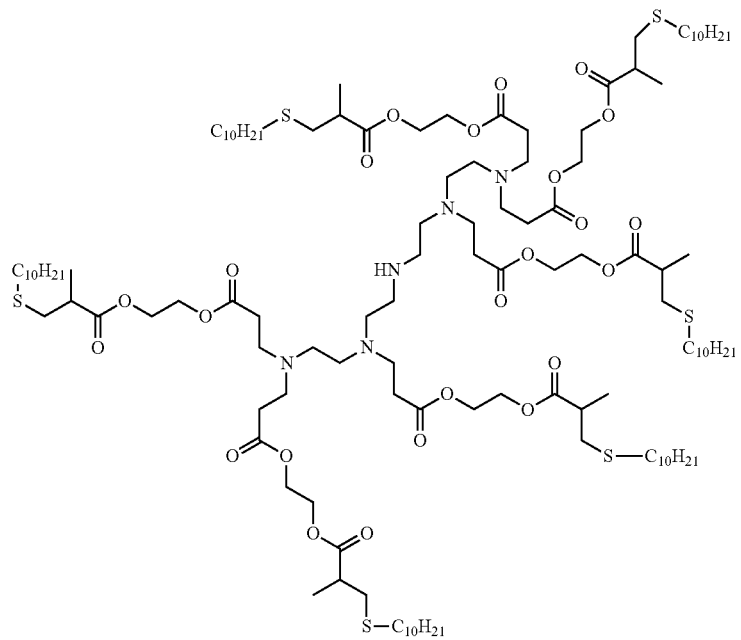 |

TABLE 4-continued

Example ionizable cationic lipo-dendrimers or lipo-dendrons

| ID # | Structure |
| --- | --- |
| 5A3-2-SC8 (6-arm) | (chemical structure) |
| 5A3-2-SC12 (6-arm) | (chemical structure) |

TABLE 4-continued

Example ionizable cationic lipo-dendrimers or lipo-dendrons

| ID # | Structure |
|---|---|
| 5A4-2-SC8 (6-arm) | (chemical structure) |
| 5A4-2-SC12 (6-arm) | (chemical structure) |

TABLE 4-continued
Example ionizable cationic lipo-dendrimers or lipo-dendrons
| ID # | Structure |
|---|---|
| 6A4-SC8 | 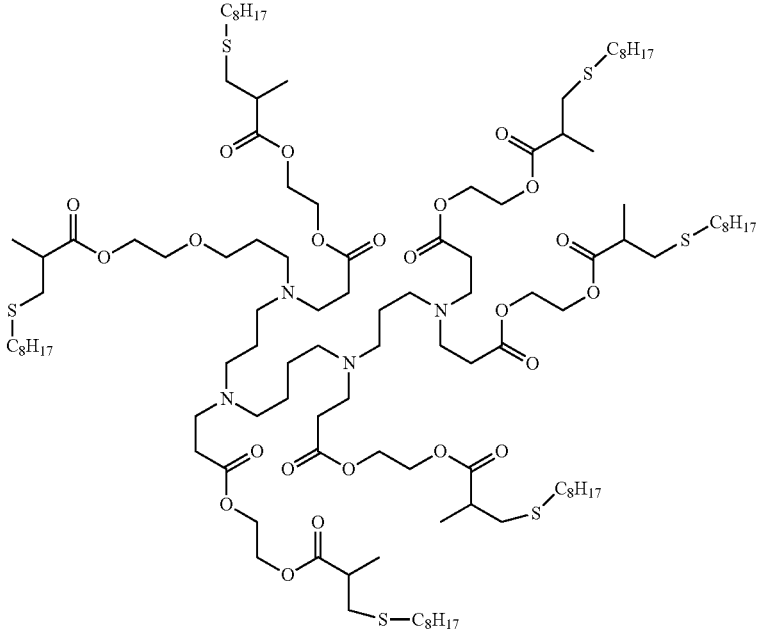 |
| 6A4-SC12 | 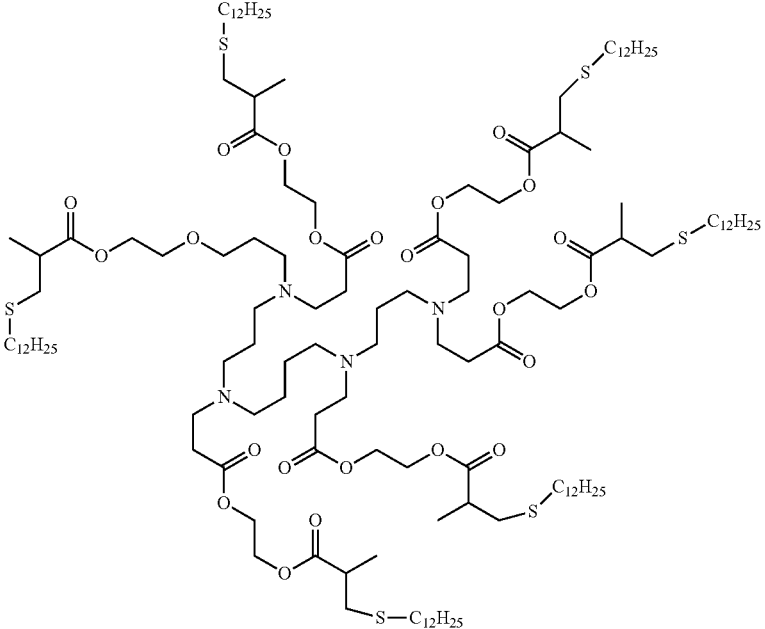 |

TABLE 4-continued
Example ionizable cationic lipo-dendrimers or lipo-dendrons
| ID # | Structure |
|---|---|
| 2A2-g2-SC12 | 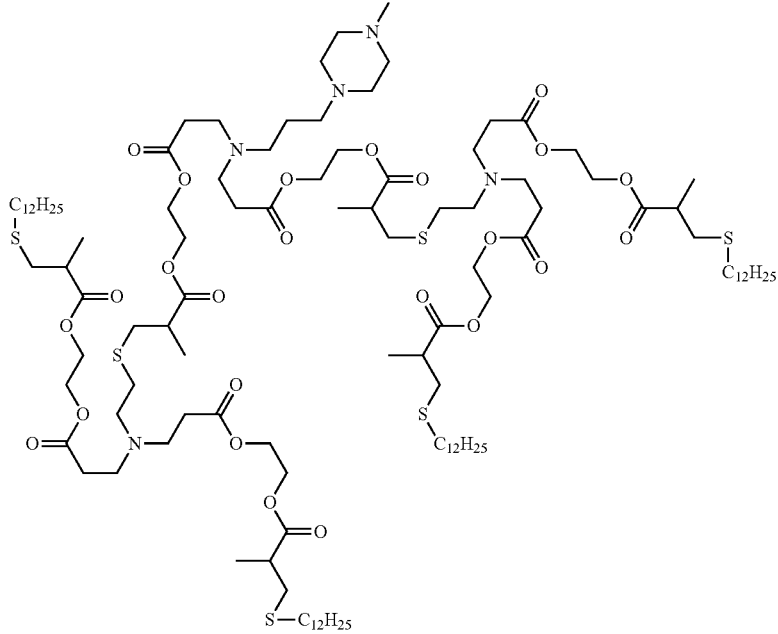 |
| 2A2-g2-SC8 | 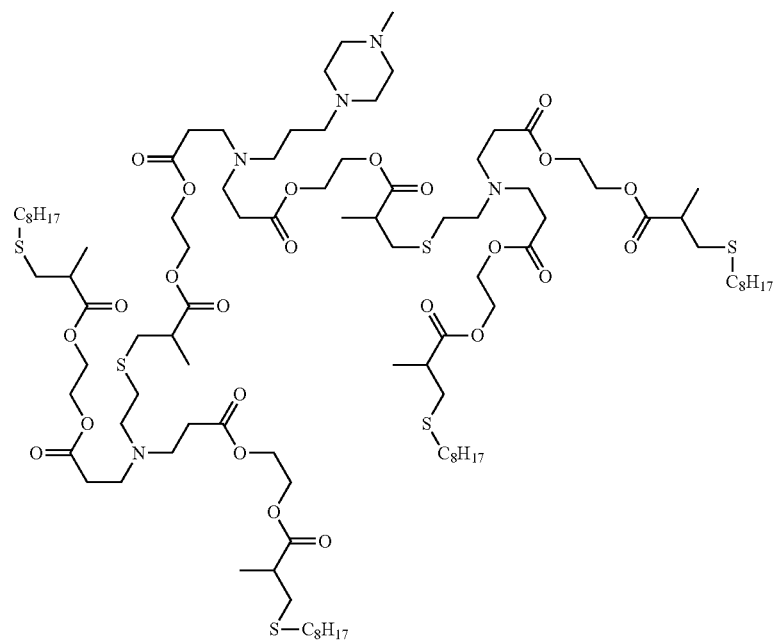 |

TABLE 4-continued
Example ionizable cationic lipo-dendrimers or lipo-dendrons
| ID # | Structure |
|---|---|
| 2A11-g2-SC12 | 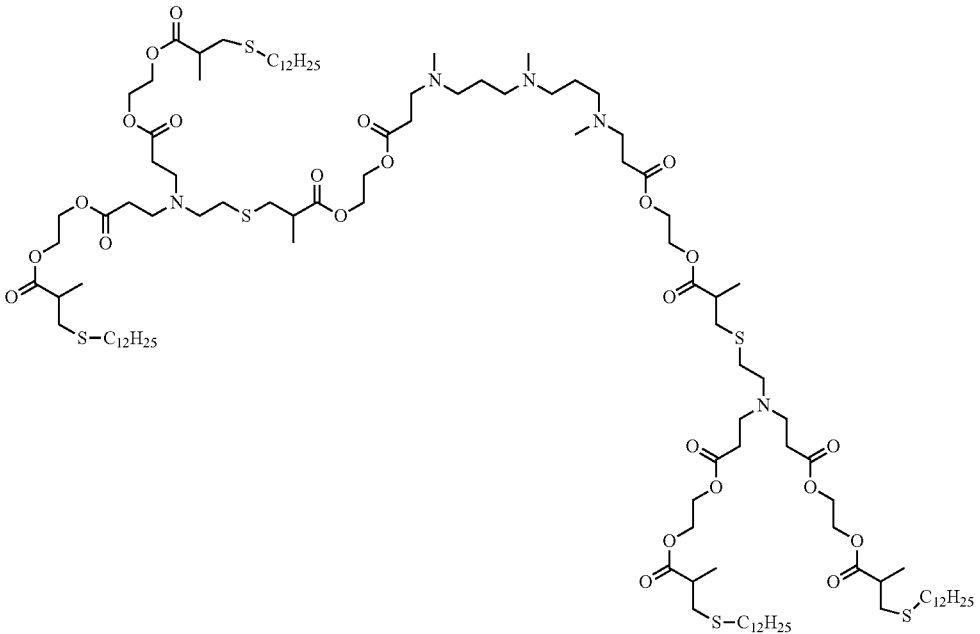 |
| 2A11-g2-SC8 | 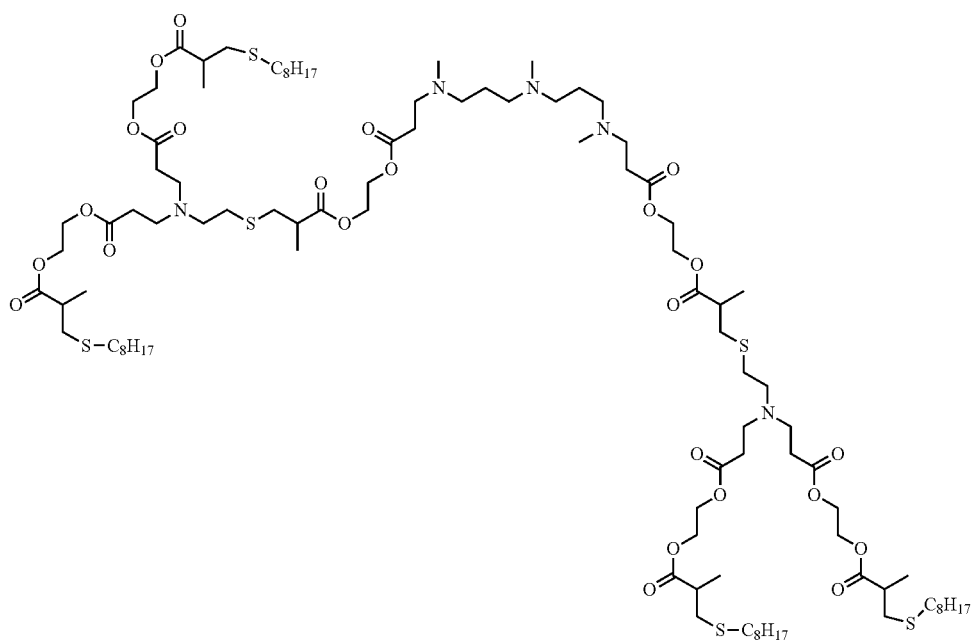 |

TABLE 4-continued
Example ionizable cationic lipo-dendrimers or lipo-dendrons
| ID # | Structure |
|---|---|
| 3A3-g2-SC12 | 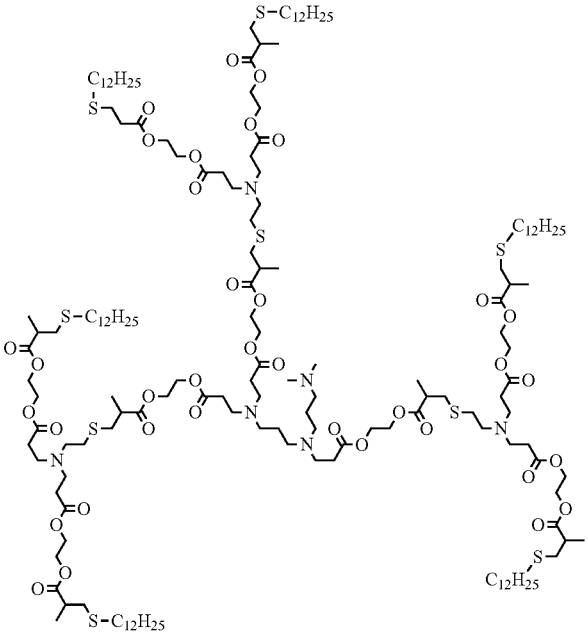 |
| 3A3-g2-SC8 | 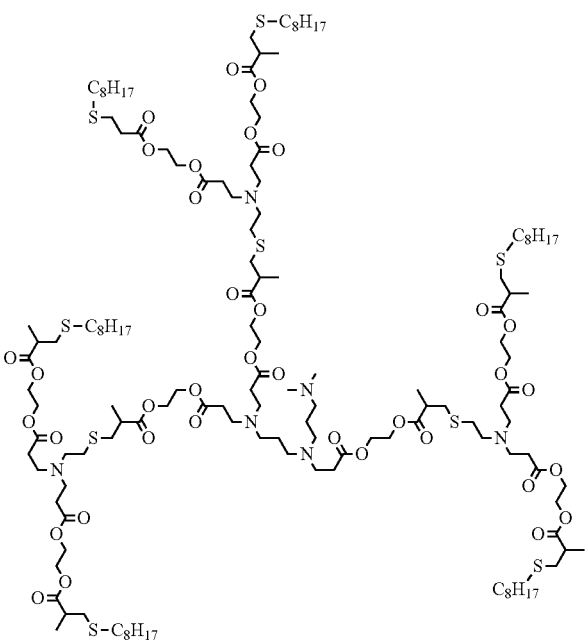 |

TABLE 4-continued

Example ionizable cationic lipo-dendrimers or lipo-dendrons

| ID # | Structure |
|---|---|
| 3A5-g2-SC12 | *(chemical structure)* |
| 2A11-g3-SC12 | *(chemical structure)* |

TABLE 4-continued

Example ionizable cationic lipo-dendrimers or lipo-dendrons

| ID # | Structure |
|---|---|
| 2A11-g3-SC8 | *(chemical structure)* |
| 1A2-g4-SC12 | *(chemical structure)* |

TABLE 4-continued
Example ionizable cationic lipo-dendrimers or lipo-dendrons
| ID # | Structure |
|---|---|
| 4A1-g2-SC12 | 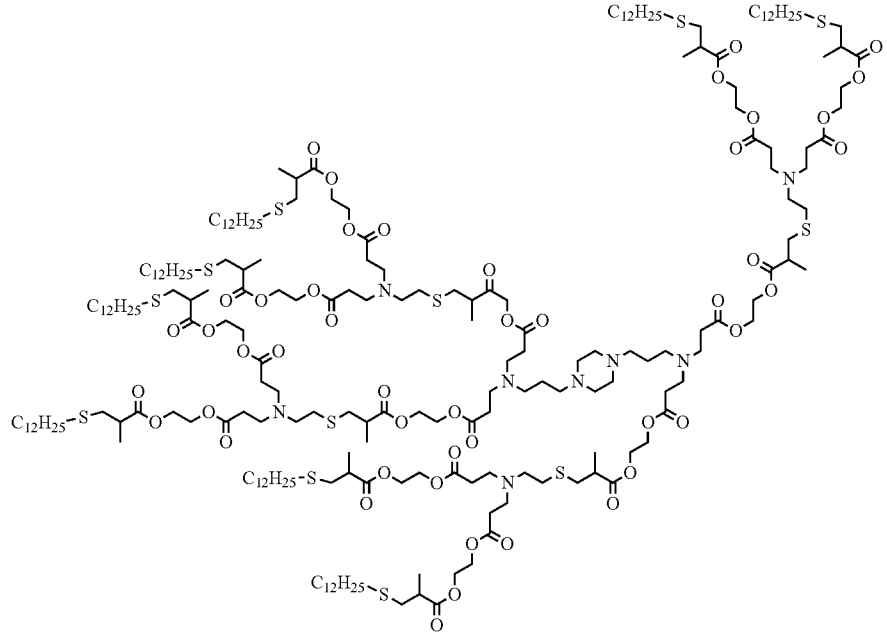 |
| 1A2-g4-SC8 | 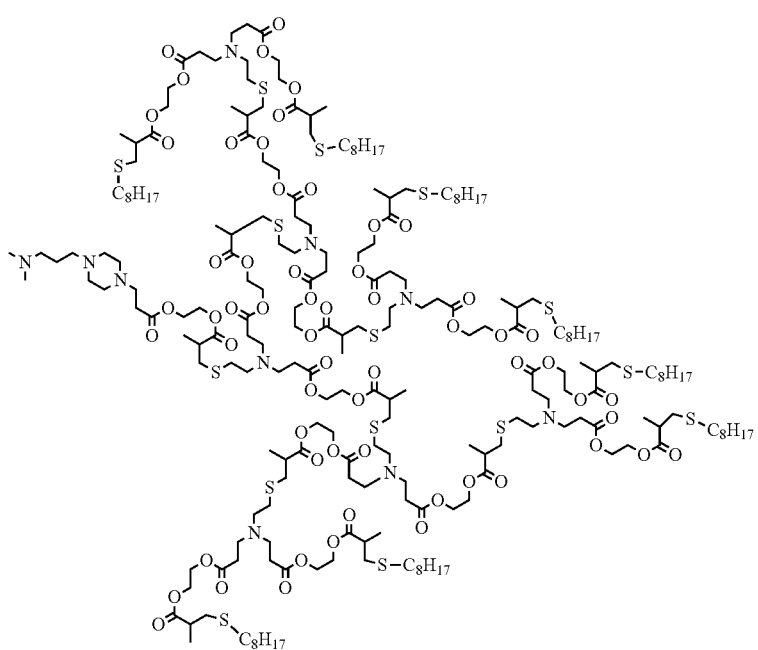 |

TABLE 4-continued

Example ionizable cationic lipo-dendrimers or lipo-dendrons

| ID # | Structure |
| --- | --- |
| 4A1-g2-SC8 | *(chemical structure)* |
| 4A3-g2-SC12 | *(chemical structure)* |

TABLE 4-continued
Example ionizable cationic lipo-dendrimers or lipo-dendrons
| ID # | Structure |
|---|---|
| 4A3-g2-SC8 | 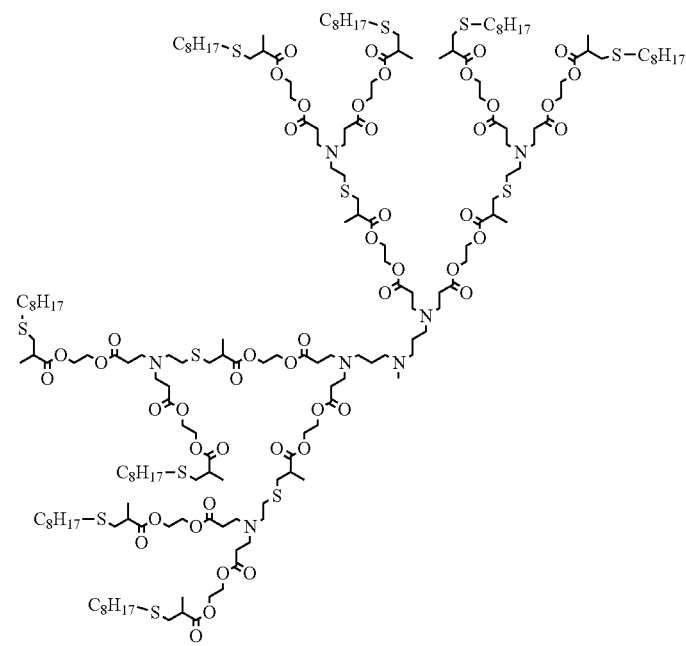 |
| 1A2-g3-SC12 | 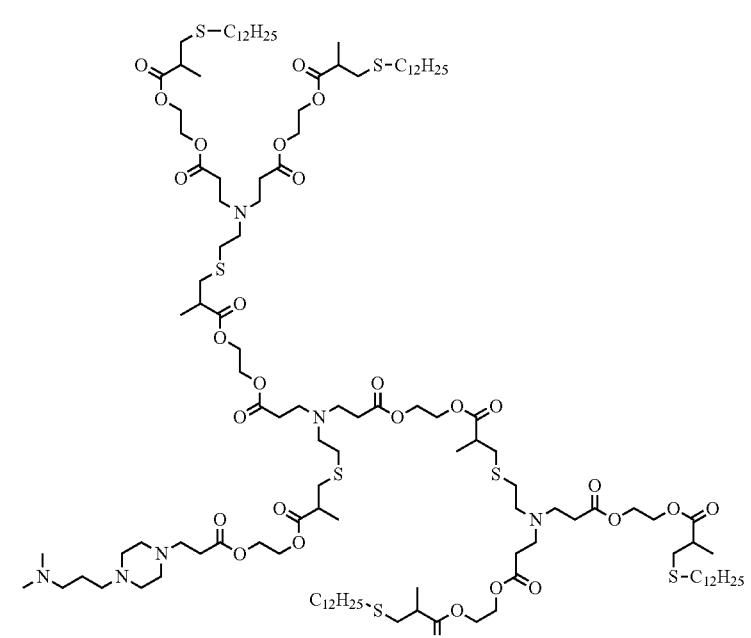 |

TABLE 4-continued
Example ionizable cationic lipo-dendrimers or lipo-dendrons
| ID # | Structure |
|---|---|
| 1A2-g3-SC8 | 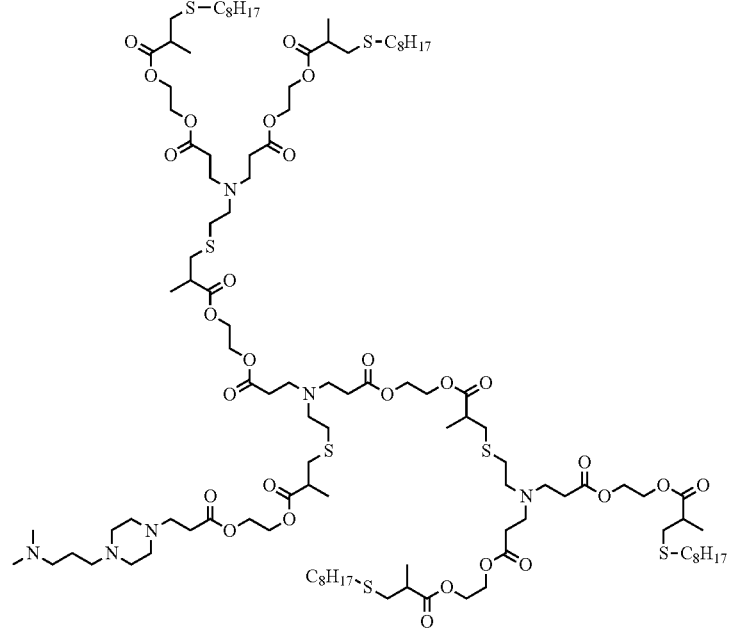 |
| 2A2-g3-SC12 | 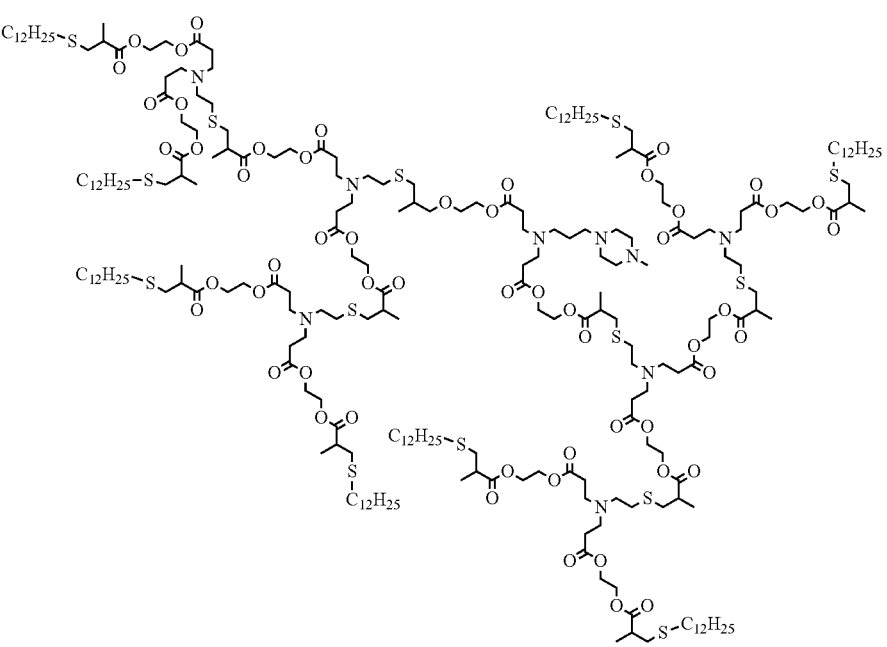 |

TABLE 4-continued

Example ionizable cationic lipo-dendrimers or lipo-dendrons

| ID # | Structure |
|---|---|
| 2A2-g3-SC8 | 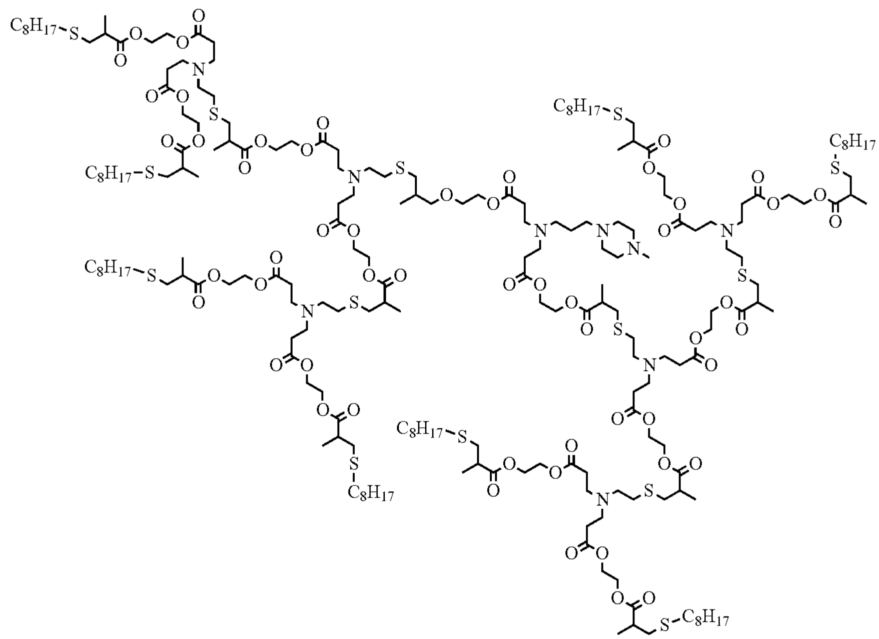 |
| 5A2-4-SC8 (6-arm) | 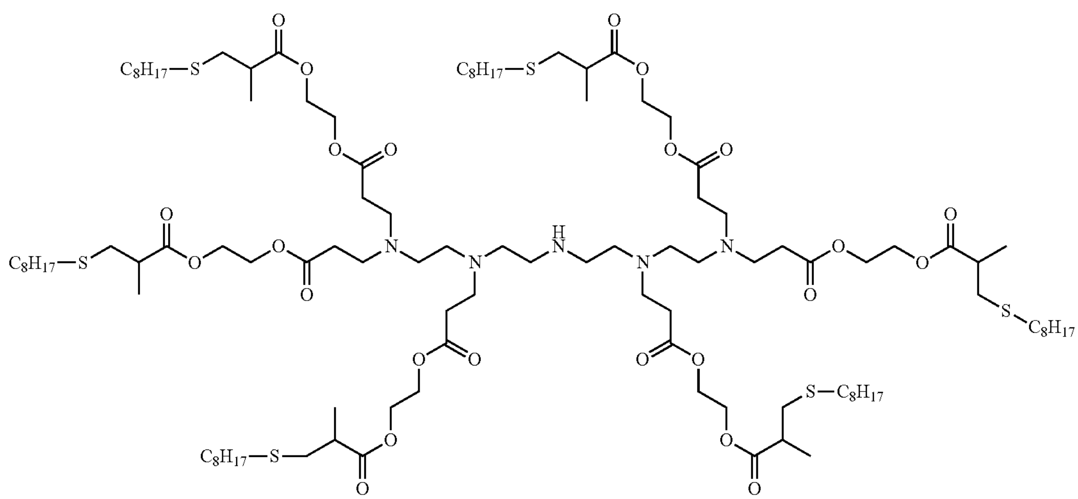 |
| 5A-5-SC8 (6 arm) | 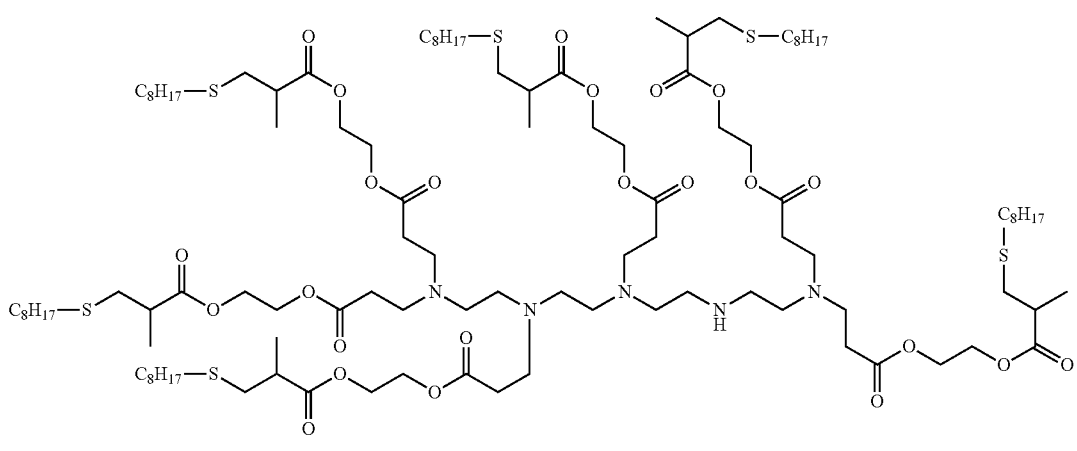 |

TABLE 4-continued

Example ionizable cationic lipo-dendrimers or lipo-dendrons

| ID # | Structure |
| --- | --- |
| 5A2-6-SC8 (6 arm) | 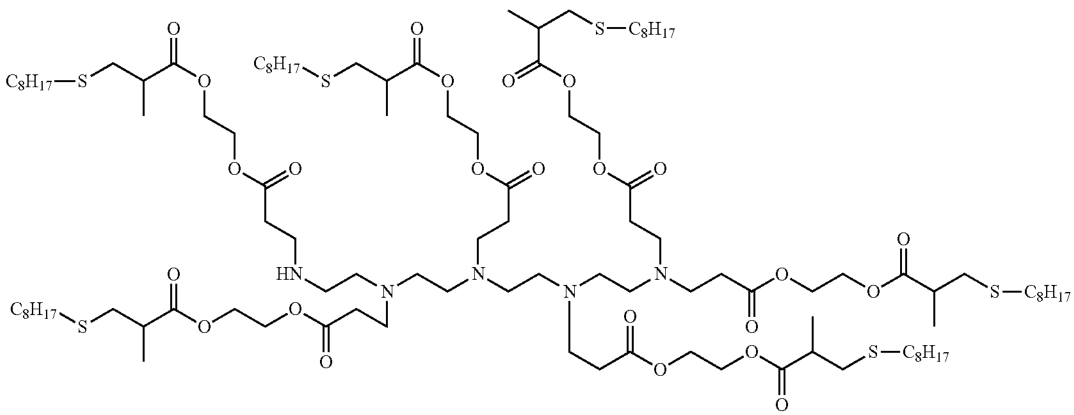 |
| 5A2-1-SC8 (5-arm) | 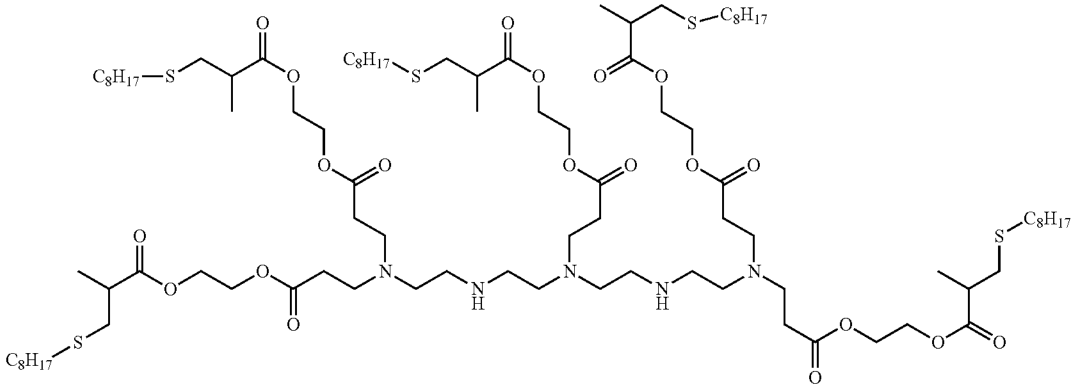 |
| 5A2-2-SC8 | 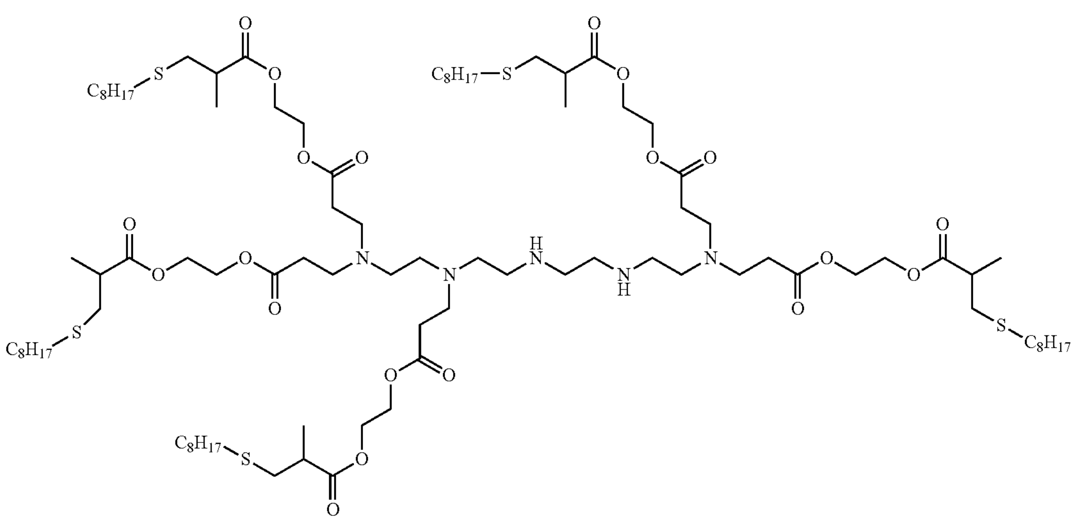 |

TABLE 4-continued
Example ionizable cationic lipo-dendrimers or lipo-dendrons
| ID # | Structure |
|---|---|
| 4A1-SC5 | 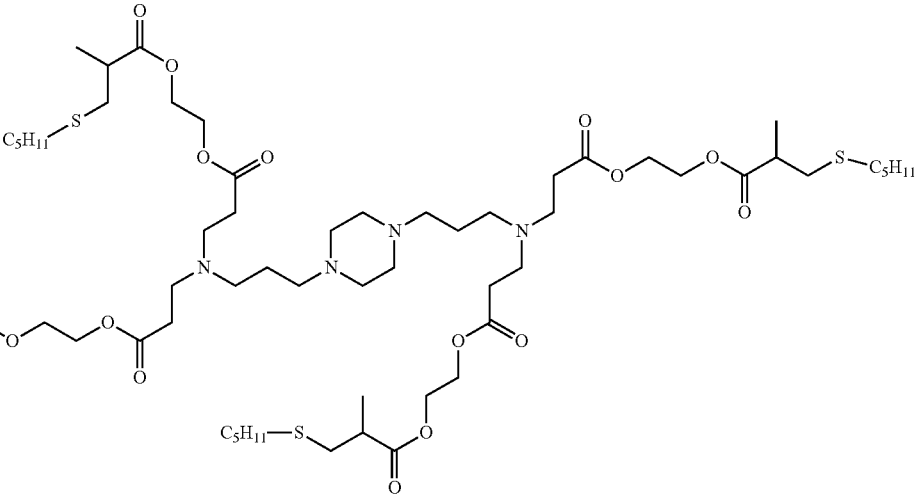 |
| 4A1-SC8 | 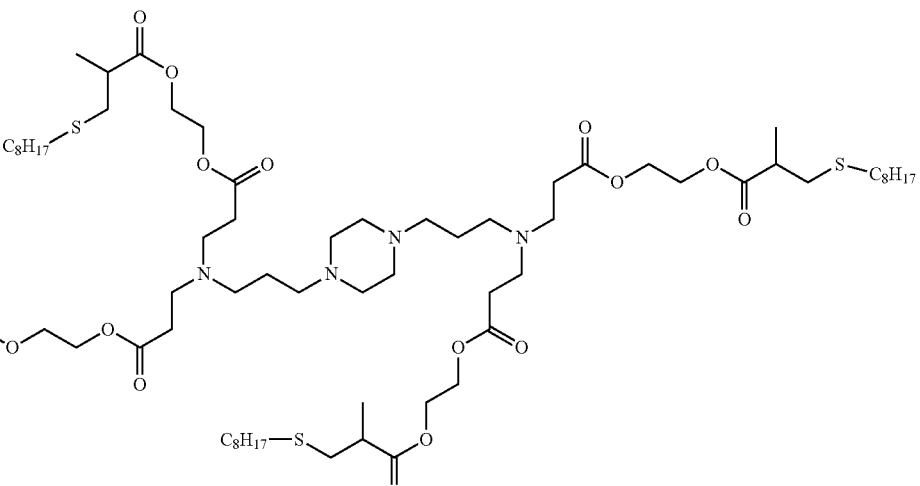 |
| 4A3-SC6 | 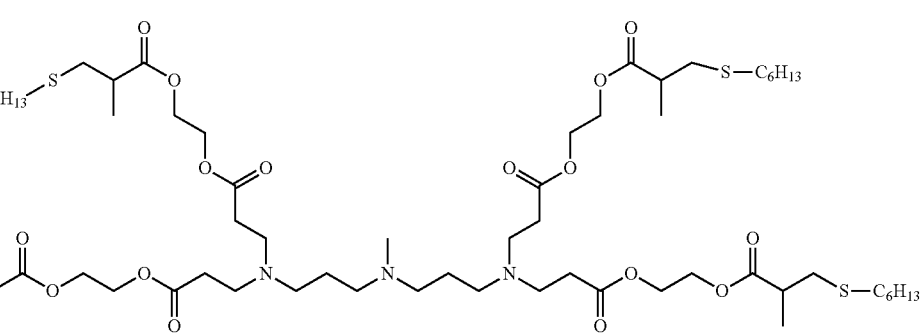 |

TABLE 4-continued
Example ionizable cationic lipo-dendrimers or lipo-dendrons
| ID # | Structure |
| --- | --- |
| 4A3-SC7 | 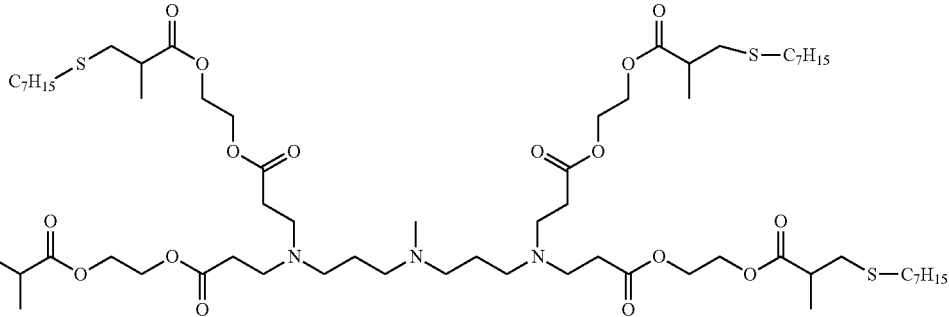 |
| 4A3-SC8 | 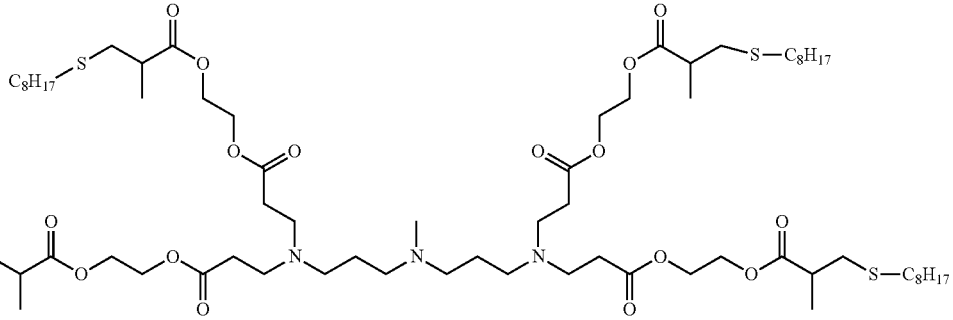 |
| 5A4-2-SC5 (6 arm) | 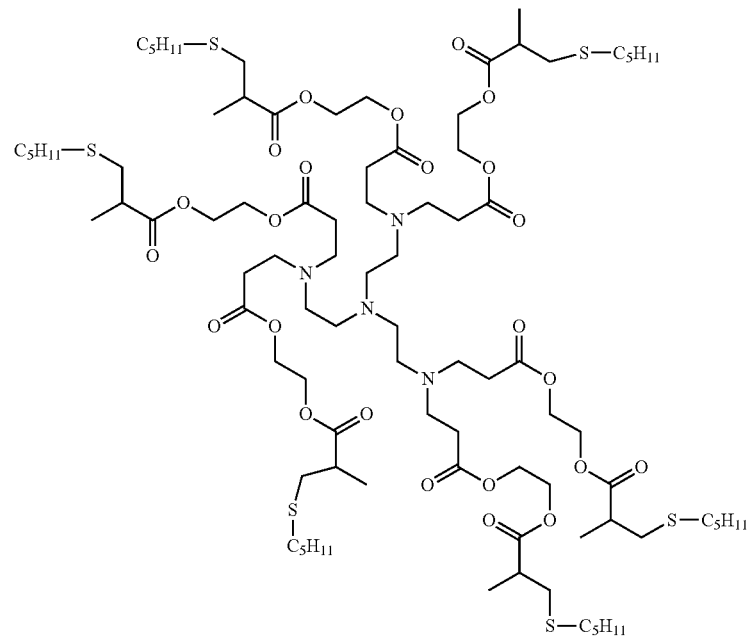 |

TABLE 4-continued

Example ionizable cationic lipo-dendrimers or lipo-dendrons

| ID # | Structure |
| --- | --- |
| 5A4-2-SC6 (6 arm) | (chemical structure) |
| 5A2-4-SC8 (5-arm) | (chemical structure) |

TABLE 4-continued

Example ionizable cationic lipo-dendrimers or lipo-dendrons

| ID # | Structure |
|---|---|
| 3A5-g2-SC8 | 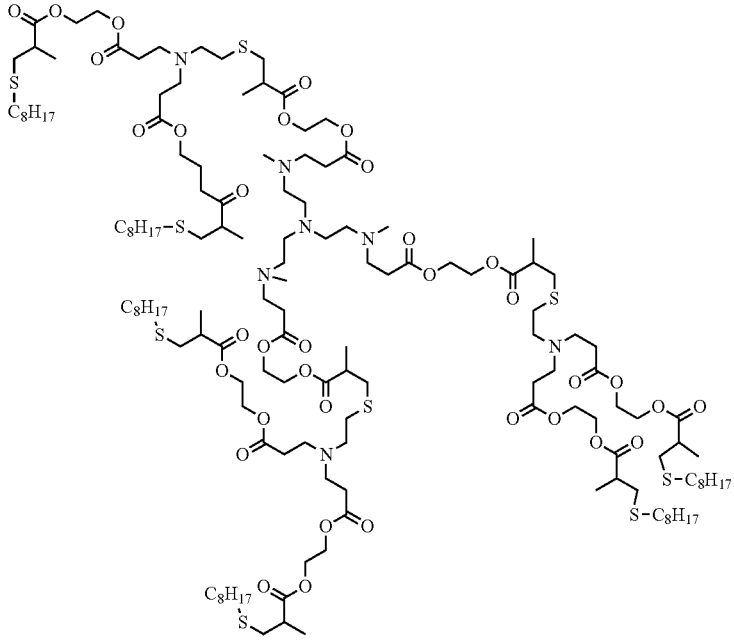 |

Other Ionizable Cationic Lipids

In some embodiments of the lipid composition, the cationic lipid comprises a structural formula (D-I'):

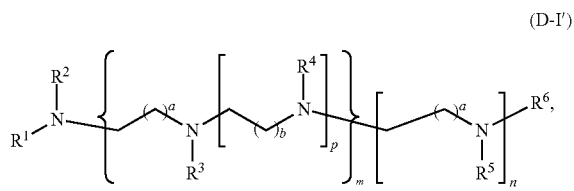

(D-I')

wherein:
- a is 1 and b is 2, 3, or 4; or, alternatively, b is 1 and a is 2, 3, or 4;
- m is 1 and n is 1; or, alternatively, m is 2 and n is 0; or, alternatively, m is 2 and n is 1; and
- $R^1$, $R^2$, $R^3$, $R^4$, $R^5$, and $R^6$ are each independently selected from the group consisting of H, —$CH_2CH(OH)R^7$, —$CH(R^7)CH_2OH$, —$CH_2CH_2C(=O)OR^7$, —$CH_2CH_2C(=O)NHR^7$, and —$CH_2R^7$, wherein $R^7$ is independently selected from $C_3$-$C_{18}$ alkyl, $C_3$-$C_{18}$ alkenyl having one C=C double bond, a protecting group for an amino group, —$C(=NH)NH_2$, a poly(ethylene glycol) chain, and a receptor ligand;
- provided that at least two moieties among $R^1$ to $R^6$ are independently selected from —$CH_2CH(OH)R^7$, —$CH(R^7)CH_2OH$, —$CH_2CH_2C(=O)OR^7$, —$CH_2CH_2C(=O)NHR^7$, or —$CH_2R^7$, wherein $R^7$ is independently selected from $C_3$-$C_{18}$ alkyl or $C_3$-$C_{18}$ alkenyl having one C=C double bond; and wherein one or more of the nitrogen atoms indicated in formula (D-I') may be protonated to provide a cationic lipid.

In some embodiments of the cationic lipid of formula (D-I'), a is 1. In some embodiments of the cationic lipid of formula (D-I'), b is 2. In some embodiments of the cationic lipid of formula (D-I'), m is 1. In some embodiments of the cationic lipid of formula (D-I'), n is 1. In some embodiments of the cationic lipid of formula (D-I'), $R^1$, $R^2$, $R^3$, $R^4$, $R^5$, and $R^6$ are each independently H or —$CH_2CH(OH)R^7$. In some embodiments of the cationic lipid of formula (D-I'), $R^1$, $R^2$, $R^3$, $R^4$, $R^5$, and $R^6$ are each independently H or

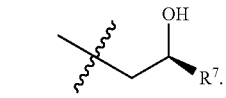

In some embodiments of the cationic lipid of formula (D-I'), $R^1$, $R^2$, $R^3$, $R^4$, $R^5$, and $R^6$ are each independently H or

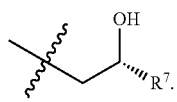

In some embodiments of the cationic lipid of formula (D-I'), $R^7$ is $C_3$-$C_{18}$ alkyl (e.g., $C_6$-$C_{12}$ alkyl).

In some embodiments, the cationic lipid of formula (D-I') is 13,16,20-tris(2-hydroxydodecyl)-13,16,20,23-tetraazapentatricontane-11,25-diol:

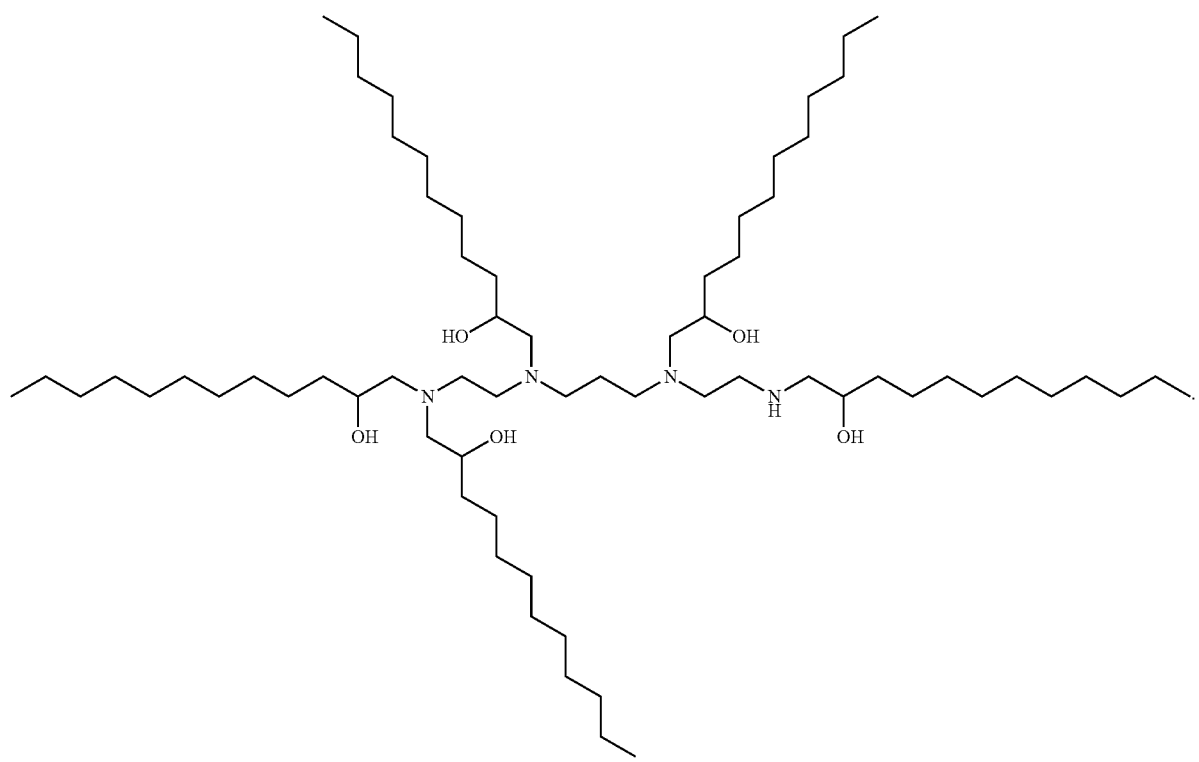 [SMILES: CCCCCCCCCCC(O)CNCCN(CCCN(CCN(CC(O)CCCCCCCCCC)CC(O)CCCCCCCCCC)CC(O)CCCCCCCCCC)CC(O)CCCCCCCCCC]
In some embodiments, the cationic lipid of formula (D-I')
is (11R,25R)-13,16,20-tris((R)-2-hydroxydodecyl)-13,16,
20,23-tetraazapentatricontane-11,25-diol:
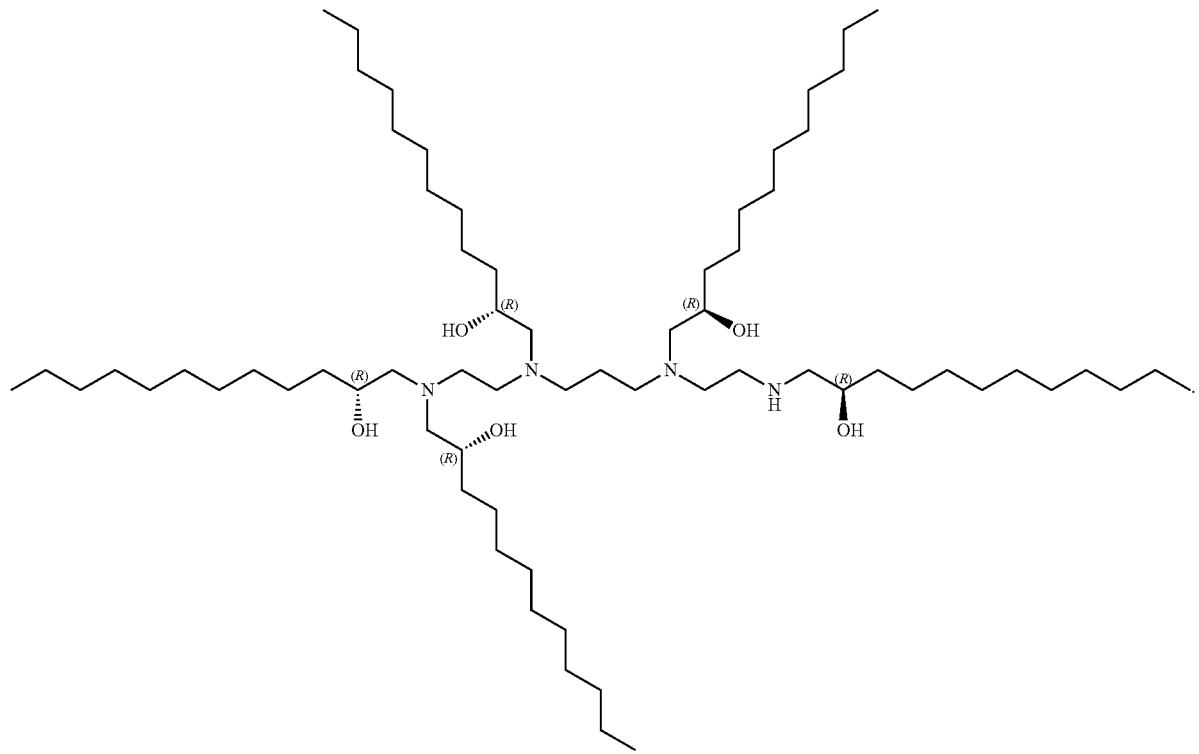

Additional cationic lipids that can be used in the compositions and methods of the present application include those cationic lipids as described in J. McClellan, M. C. King, Cell 2010, 141, 210-217, and International Patent Publication WO 2010/144740, WO 2013/149140, WO 2016/118725, WO 2016/118724, WO 2013/063468, WO 2016/205691, WO 2015/184256, WO 2016/004202, WO 2015/199952, WO 2017/004143, WO 2017/075531, WO 2017/117528, WO 2017/049245, WO 2017/173054 and WO 2015/095340, which are incorporated herein by reference for all purposes. Examples of those ionizable cationic lipids include but are not limited to those as shown in Table 5.

TABLE 5

Example ionizable cationic lipids

| # | Structure of example ionizable cationic lipid |
|---|---|
| 1 | (structure) |
| 2 | (structure) |
| 3 | (structure) |
| 4 | (HGT-5000) |
| 5 | (HGT-5001) |
| 6 | (HGT-5002) |
| 7 | (structure) |
| 8 | (structure) |
| 9 | (structure) |

TABLE 5-continued

Example ionizable cationic lipids

| # | Structure of example ionizable cationic lipid |
|---|---|
| 10 | |
| 11 | |
| 12 | |

TABLE 5-continued
Example ionizable cationic lipids
| # | Structure of example ionizable cationic lipid |
|---|---|
| 13 | 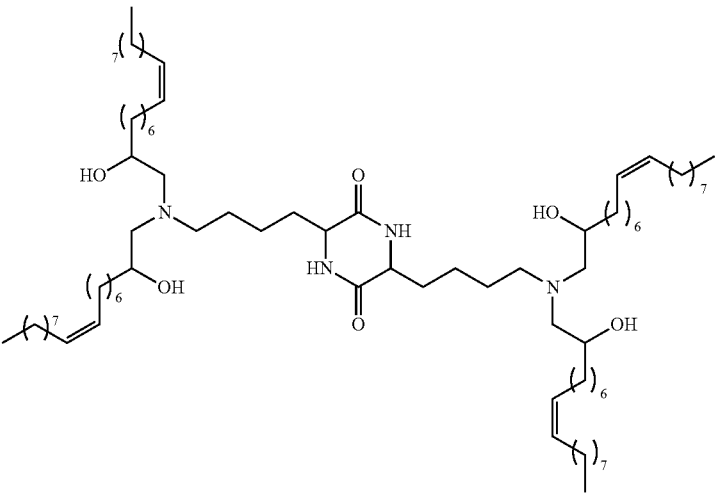 ; |
| 14 | 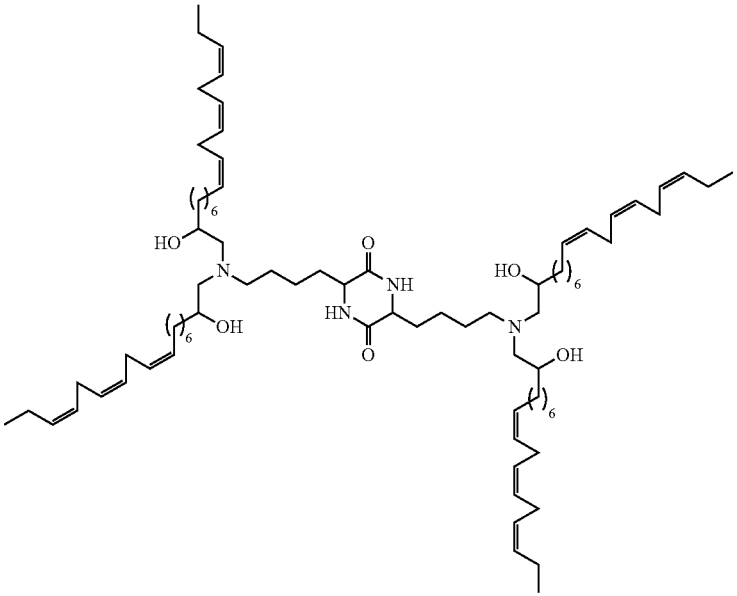 ; |
| 15 | 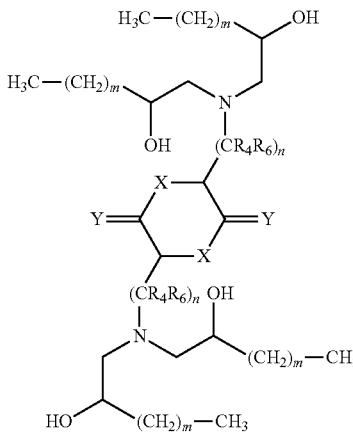 ; |

TABLE 5-continued
Example ionizable cationic lipids
| # | Structure of example ionizable cationic lipid |
|---|---|
| 16 | 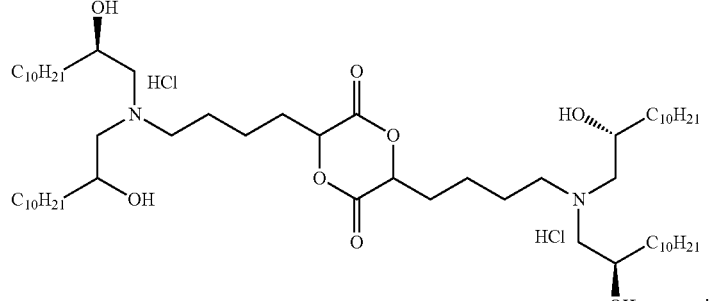 |
| 17 | 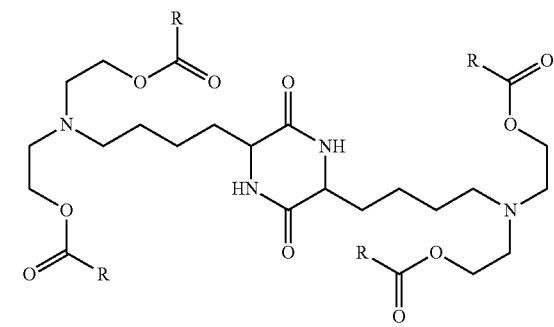 |
| 18 | 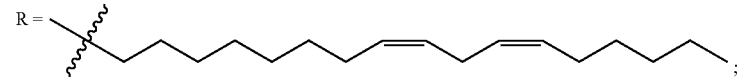 |
| 19 | 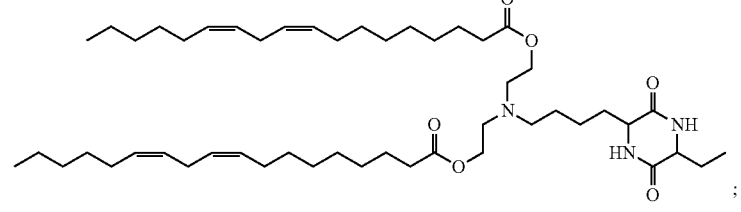 |
| 20 | 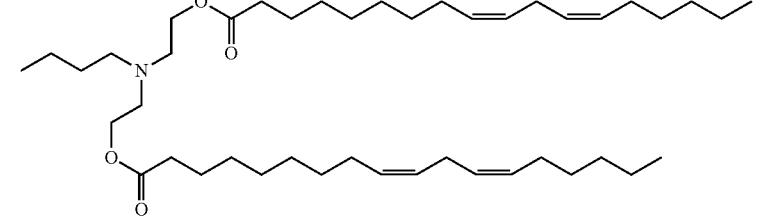 |
| 21 | 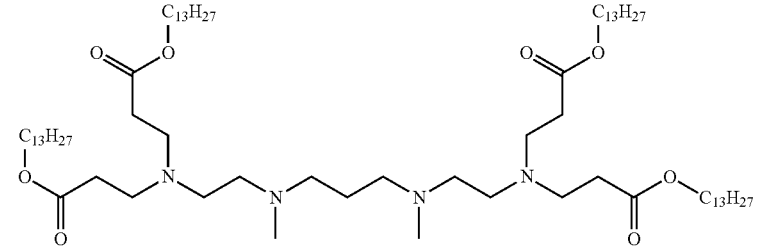 |

TABLE 5-continued
Example ionizable cationic lipids
| # | Structure of example ionizable cationic lipid |
|---|---|
| 22 | 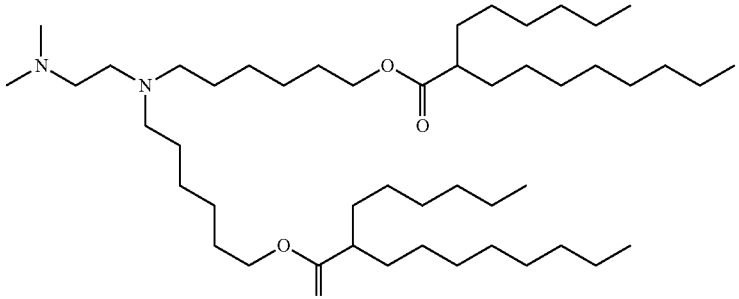 ; |
| 23 | 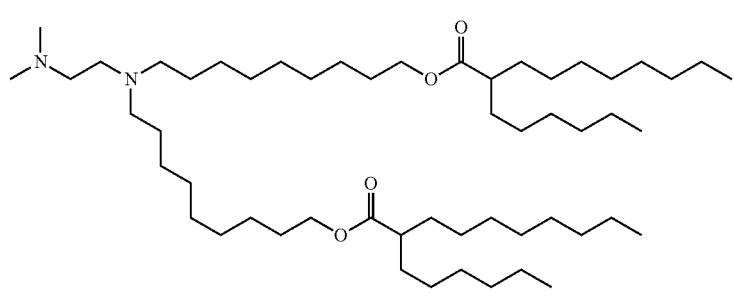 ; |
| 24 | 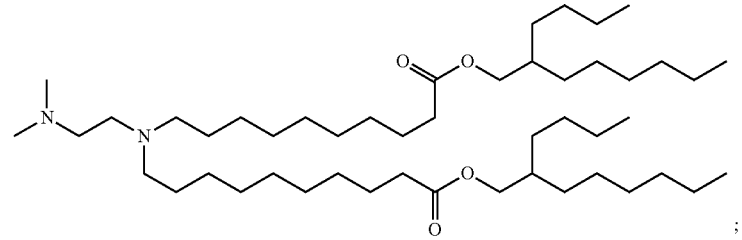 [SMILES: CCCCCCC(CCCC)COC(=O)CCCCCCCCCN(CCCCCCCCCC(=O)OCC(CCCC)CCCCCC)CCN(C)C] ; |
| 25 | 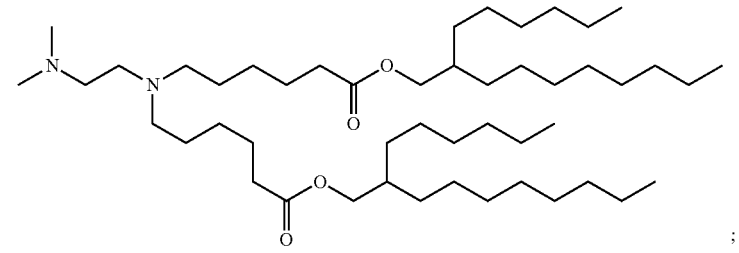 [SMILES: CCCCCCCCC(CCCCCC)COC(=O)CCCCCN(CCCCCC(=O)OCC(CCCCCC)CCCCCCCC)CCN(C)C] ; |
| 26 | 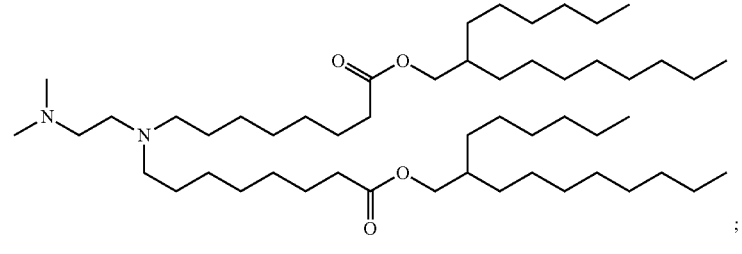 [SMILES: CCCCCCCCC(CCCCCC)COC(=O)CCCCCCCN(CCCCCCCC(=O)OCC(CCCCCC)CCCCCCCC)CCN(C)C] ; |
| 27 | 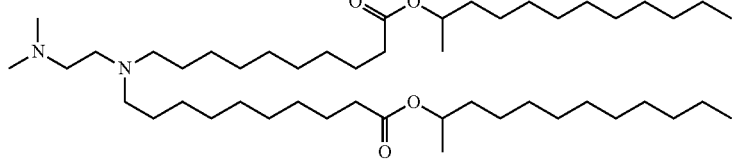 ; |

TABLE 5-continued
Example ionizable cationic lipids
| # | Structure of example ionizable cationic lipid |
|---|---|
| 28 | 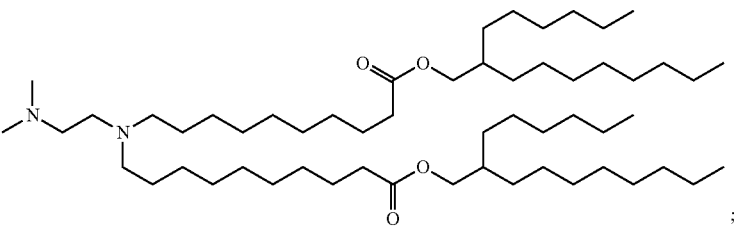 [SMILES: CCCCCCCCC(CCCCCC)COC(=O)CCCCCCCCCN(CCCCCCCCCC(=O)OCC(CCCCCC)CCCCCCCC)CCN(C)C] ; |
| 29 | 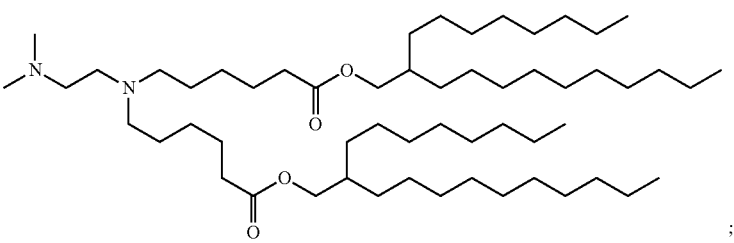 [SMILES: CCCCCCCCCCC(CCCCCCCC)COC(=O)CCCCCN(CCCCCC(=O)OCC(CCCCCCCC)CCCCCCCCCC)CCN(C)C] ; |
| 30 | 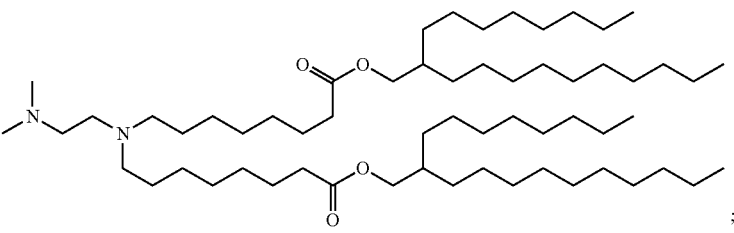 [SMILES: CCCCCCCCCCC(CCCCCCCC)COC(=O)CCCCCCCN(CCCCCCCC(=O)OCC(CCCCCCCC)CCCCCCCCCC)CCN(C)C] ; |
| 31 | 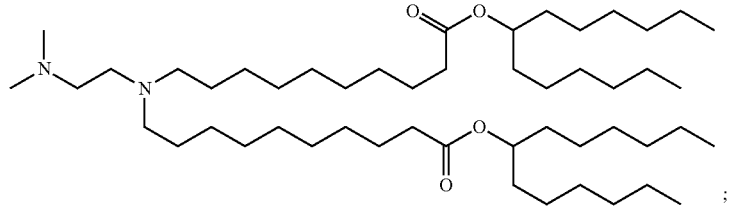 [SMILES: CCCCCCC(CCCCCC)OC(=O)CCCCCCCCCN(CCCCCCCCCC(=O)OC(CCCCCC)CCCCCC)CCN(C)C] ; |
| 32 | 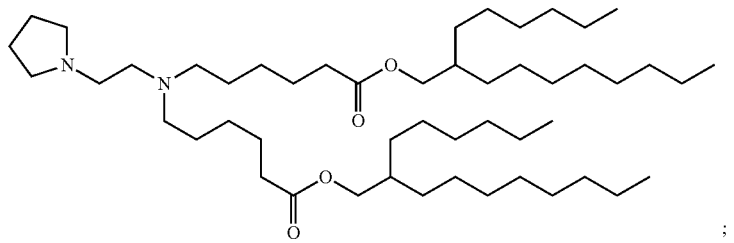 [SMILES: CCCCCCCCC(CCCCCC)COC(=O)CCCCCN(CCCCCC(=O)OCC(CCCCCC)CCCCCCCC)CCN1CCCC1] ; |
| 33 | 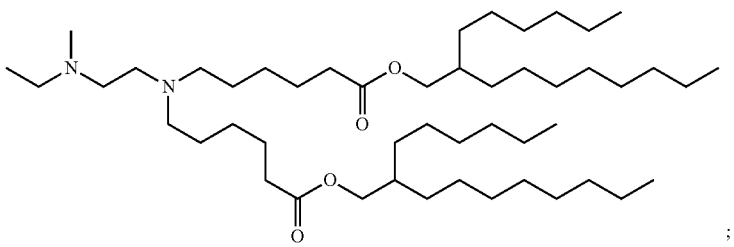 [SMILES: CCCCCCCCC(CCCCCC)COC(=O)CCCCCN(CCCCCC(=O)OCC(CCCCCC)CCCCCCCC)CCN(C)CC] ; |

TABLE 5-continued
Example ionizable cationic lipids
| # | Structure of example ionizable cationic lipid |
|---|---|
| 34 | 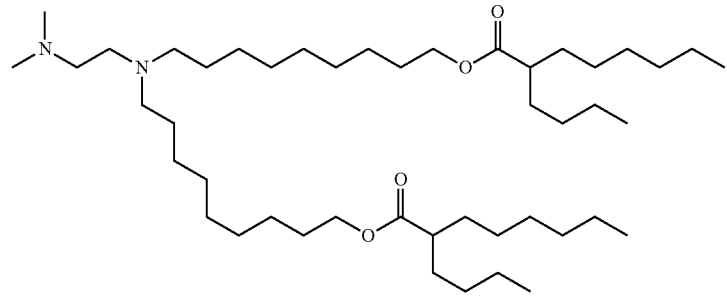 ; |
| 35 | 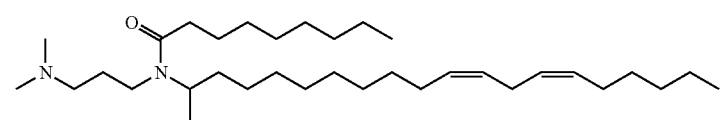 ; |
| 36 | 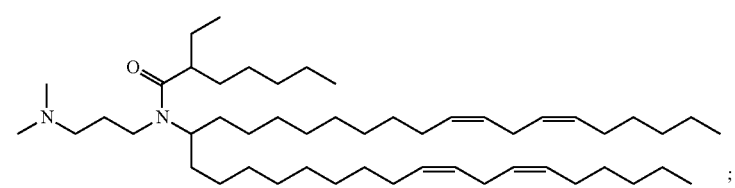 [SMILES: CCCCC/C=C\C/C=C\CCCCCCCCC(CCCCCCCC/C=C\C/C=C\CCCCC)N(CCCN(C)C)C(=O)C(CC)CCCCC] ; |
| 37 | 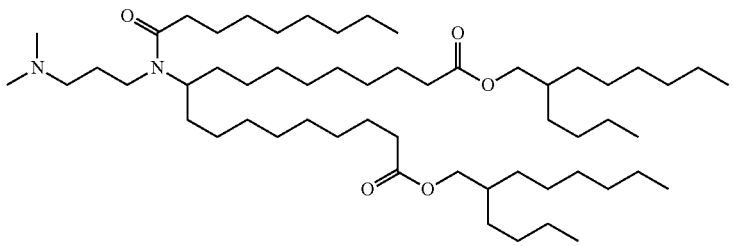 ; |
| 38 | 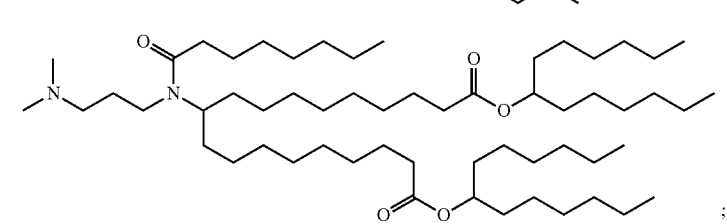 ; |
| 39 | 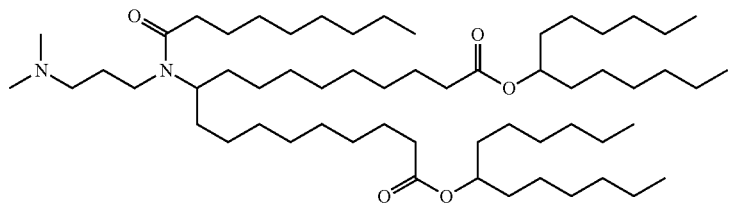 ; |
| 40 | 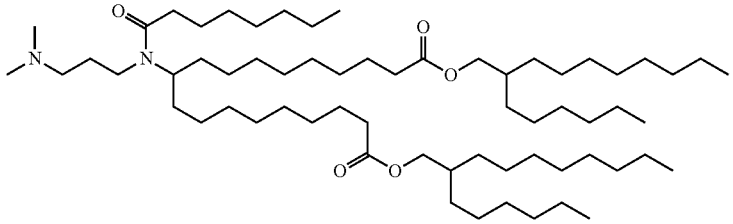 ; |

TABLE 5-continued
Example ionizable cationic lipids
| # | Structure of example ionizable cationic lipid |
|---|---|
| 41 | 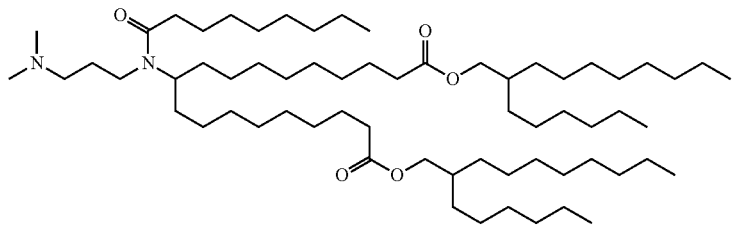 ; |
| 42 | 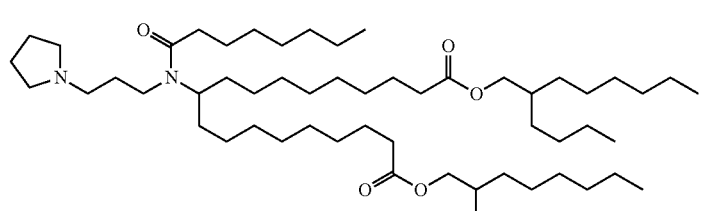 ; |
| 43 | 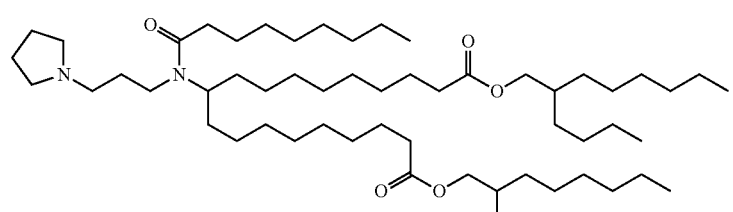 ; |
| 44 | 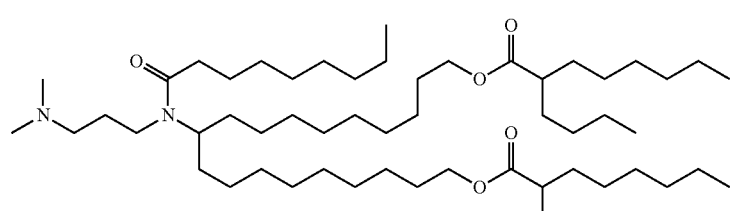 ; |
| 45 | 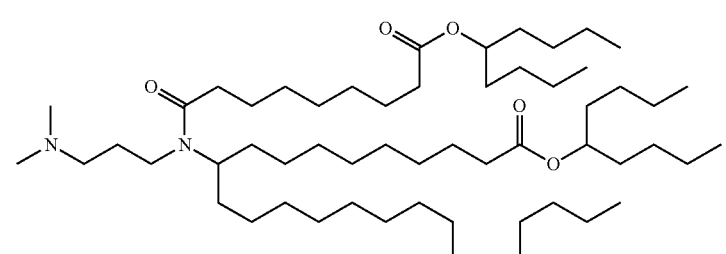 ; |
| 46 | 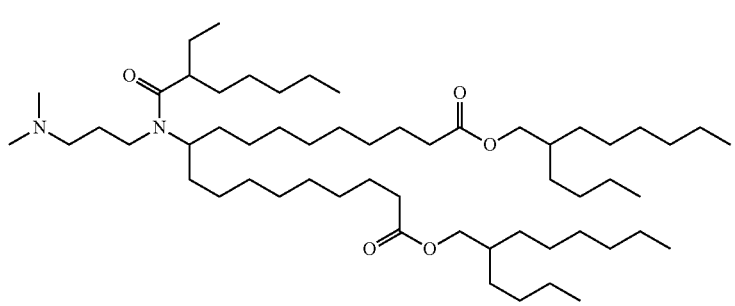 ; |

TABLE 5-continued
Example ionizable cationic lipids
| # | Structure of example ionizable cationic lipid |
|---|---|
| 47 | 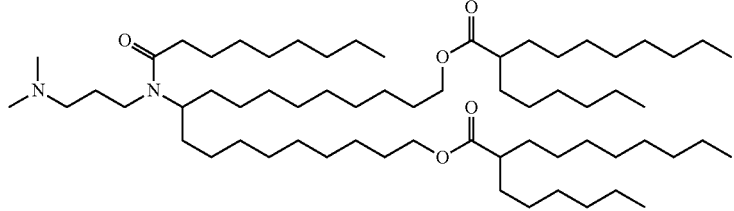 ; |
| 48 | 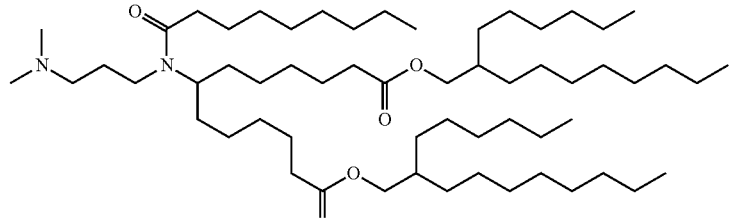 ; |
| 49 | 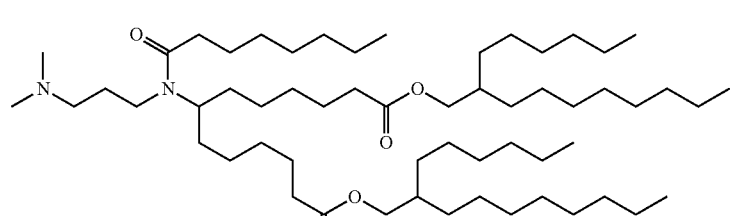 ; |
| 50 | 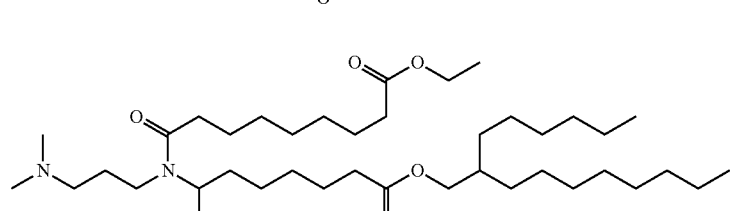 ; |
| 51 | 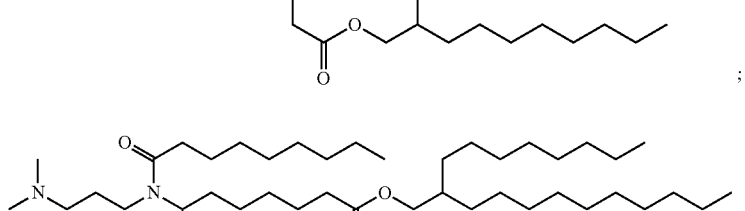 ; |
| 52 | $R^1-L^1-G^1-N(G^3-R^3)-G^2-L^2-R^2$ ; |

TABLE 5-continued
Example ionizable cationic lipids
| # | Structure of example ionizable cationic lipid |
|---|---|
| 53 | 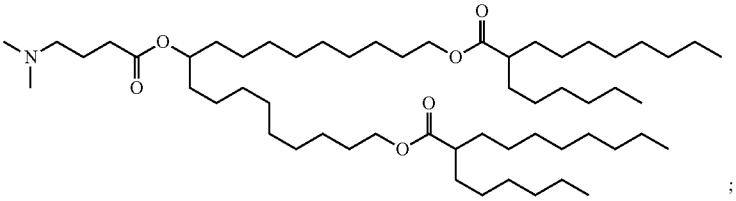 [SMILES: CCCCCCCCC(CCCCCC)C(=O)OCCCCCCCCCC(CCCCCCCCCOC(=O)C(CCCCCC)CCCCCCCC)OC(=O)CCCN(C)C] ; |
| 54 | 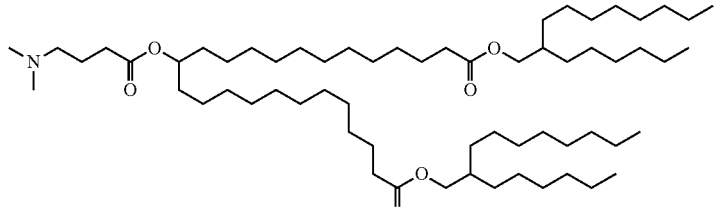 ; |
| 55 | 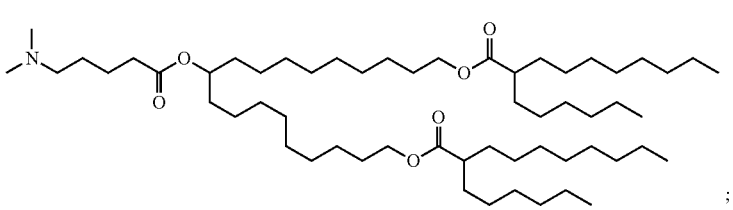 [SMILES: CCCCCCCCC(CCCCCC)C(=O)OCCCCCCCCCC(CCCCCCCCCOC(=O)C(CCCCCC)CCCCCCCC)OC(=O)CCCCN(C)C] ; |
| 56 | 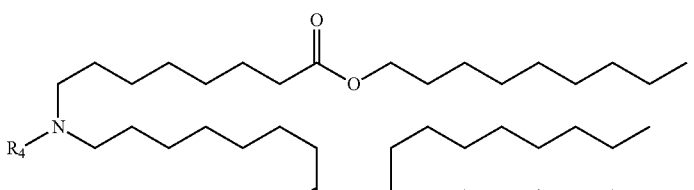 ; |
| 57 | 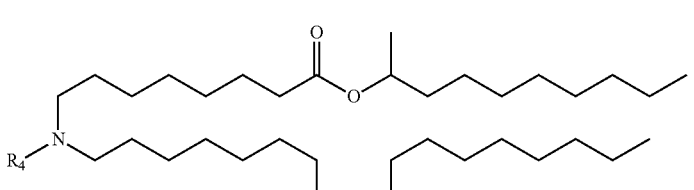 ; |
| 58 | 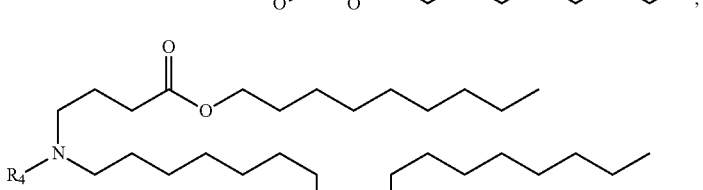 ; |
| 59 | 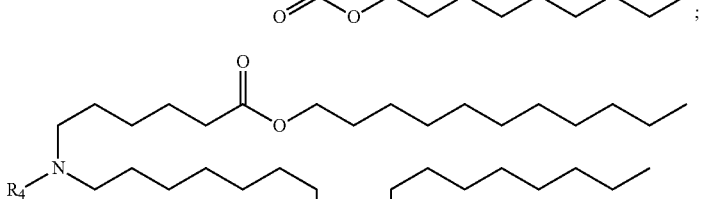 ; |

TABLE 5-continued
Example ionizable cationic lipids
| # | Structure of example ionizable cationic lipid |
|---|---|
| 60 | 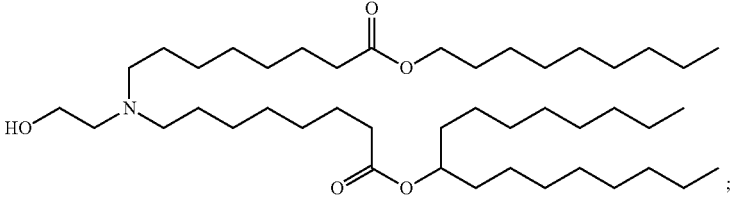 [SMILES: CCCCCCCCCOC(=O)CCCCCCCN(CCO)CCCCCCCC(=O)OC(CCCCCCCC)CCCCCCCC] |
| 61 | 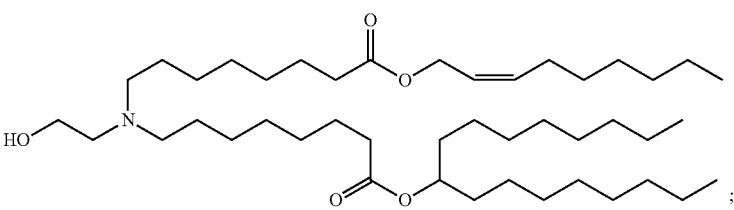 [SMILES: CCCCCC/C=C\COC(=O)CCCCCCCN(CCO)CCCCCCCC(=O)OC(CCCCCCCC)CCCCCCCC] |
| 62 | 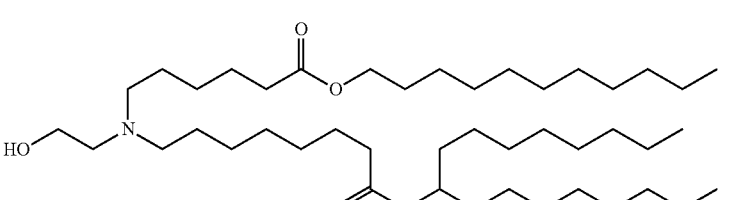 |
| 63 | 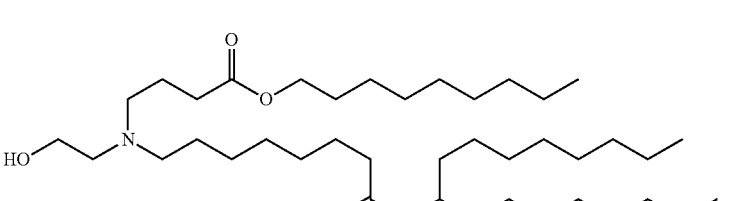 |
| 64 | 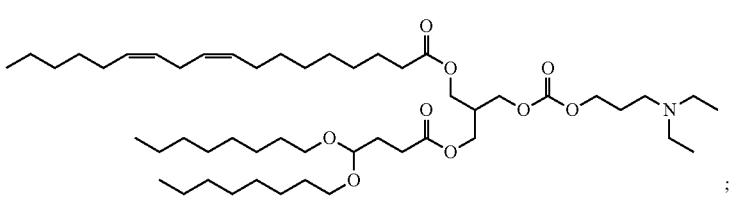 [SMILES: CCCCC/C=C\C/C=C\CCCCCCCC(=O)OCC(COC(=O)CCC(OCCCCCCCC)OCCCCCCCC)COC(=O)OCCCN(CC)CC] |
| 65 | 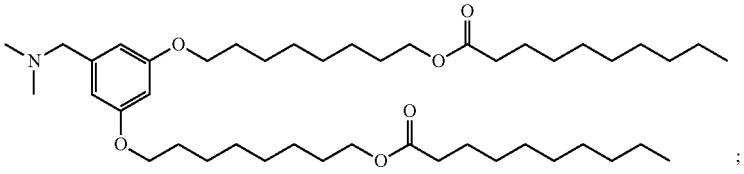 [SMILES: CCCCCCCCCC(=O)OCCCCCCCCOc1cc(CN(C)C)cc(OCCCCCCCCOC(=O)CCCCCCCCC)c1] |

TABLE 5-continued
Example ionizable cationic lipids
| # | Structure of example ionizable cationic lipid |
|---|---|
| 66 | 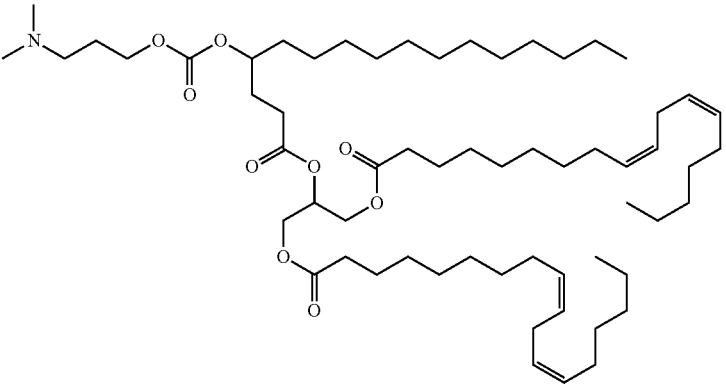 ; |
| 67 | 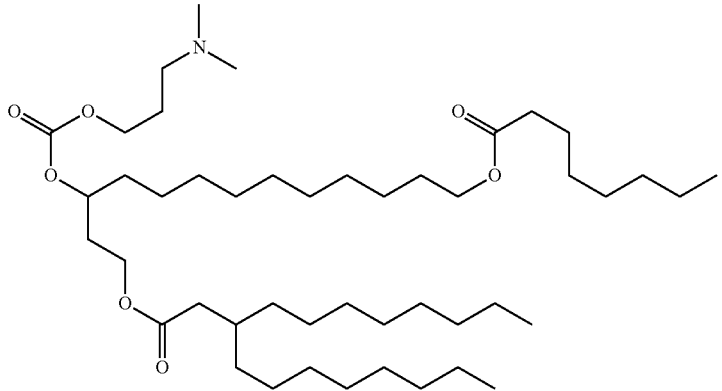 ; |
| 68 | 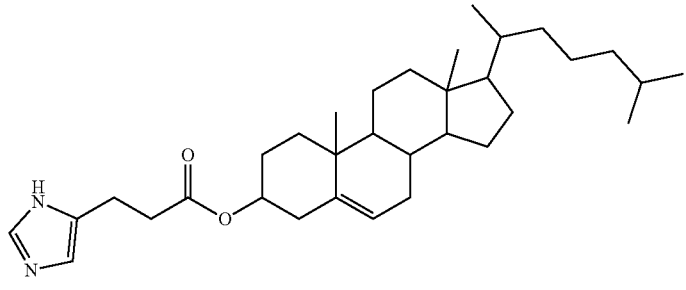 ; |
| 69 | 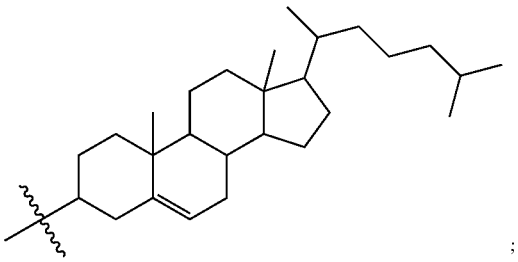 [SMILES: *C1CCC2(C)C(=CCC3C2CCC2(C)C(C(C)CCCC(C)C)CCC32)C1] ; |
| 70 | 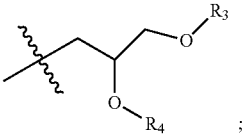 ; |
| 71 |  ; |

TABLE 5-continued

Example ionizable cationic lipids

| # | Structure of example ionizable cationic lipid |
|---|---|
| 72 | (HGT4001) ; |
| 73 | (HGT4002) ; |
| 74 | (HGT4003) ; |
| 75 | (HGT4004) ; |
| 76 | (HGT4005) |

In some embodiments of the lipid composition of the present application, the ionizable cationic lipid is present in an amount from about from about 20 to about 23. In some embodiments, the molar percentage is from about 20, 20.5, 21, 21.5, 22, 22.5, to about 23 or any range derivable therein. In other embodiments, the molar percentage is from about 7.5 to about 20. In some embodiments, the molar percentage is from about 7.5, 8, 9, 10, 11, 12, 13, 14, 15, 16, 17, 18, 19, to about 20 or any range derivable therein.

In some embodiments of the lipid composition of the present application, the lipid composition comprises the ionizable cationic lipid at a molar percentage from about 5% to about 30%. In some embodiments of the lipid composition of the present application, the lipid composition comprises the ionizable cationic lipid at a molar percentage from about 10% to about 25%. In some embodiments of the lipid composition of the present application, the lipid composition comprises the ionizable cationic lipid at a molar percentage from about 15% to about 20%. In some embodiments of the lipid composition of the present application, the lipid composition comprises the ionizable cationic lipid at a molar percentage from about 10% to about 20%. In some embodiments of the lipid composition of the present application, the lipid composition comprises the ionizable cationic lipid at a molar percentage from about 20% to about 30%. In some embodiments of the lipid composition of the present application, the lipid composition comprises the ionizable cationic lipid at a molar percentage of at least (about) 5%, at least (about) 10%, at least (about) 15%, at least (about) 20%, at least (about) 25%, or at least (about) 30%. In some embodiments of the lipid composition of the present application, the lipid composition comprises the ionizable cationic lipid at a molar percentage of at most (about) 5%, at most (about) 10%, at most (about) 15%, at most (about) 20%, at most (about) 25%, or at most (about) 30%.

Selective Organ Targeting (SORT) Lipids

In some embodiments of the lipid composition of the present application, the lipid (e.g., nanoparticle) composition is preferentially delivered to a target organ. In some embodiments, the target organ is a lung, a lung tissue or a lung cell. As used herein, the term "preferentially delivered" is used to refer to a composition, upon being delivered, which is delivered to the target organ (e.g., lung), tissue, or cell in at least 25% (e.g., at least 30%, 35%, 40%, 45%, 50%, 55%, 60%, 65%, 70%, or 75%) of the amount administered.

In some embodiments of the lipid composition, the lipid composition comprises one or more selective organ targeting (SORT) lipid which leads to the selective delivery of the composition to a particular organ. In some embodiments, the SORT lipid may have two or more alkyl or alkenyl chains of $C_6$-$C_{24}$.

In some embodiments of the lipid compositions, the SORT lipid comprises permanently positively charged moiety. The permanently positively charged moiety may be positively charged at a physiological pH such that the SORT lipid comprises a positive charge upon delivery of a polynucleotide to a cell. In some embodiments the positively charged moiety is quaternary amine or quaternary ammonium ion. In some embodiments, the SORT lipid comprises, or is otherwise complexed to or interacting with, a counterion.

In some embodiments of the lipid compositions, the SORT lipid is a permanently cationic lipid (i.e., comprising one or more hydrophobic components and a permanently cationic group). The permanently cationic lipid may contain a group which has a positive charge regardless of the pH. One permanently cationic group that may be used in the permanently cationic lipid is a quaternary ammonium group. The permanently cationic lipid may comprise a structural formula:

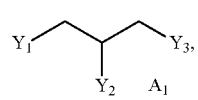

(S-I)

wherein:
$Y_1$, $Y_2$, or $Y_3$ are each independently $X_1C(O)R^1$ or $X_2N^+R_3R_4R_5$;
provided at least one of $Y_1$, $Y_2$, and $Y_3$ is $X_2N^+R_3R_4R_5$;
$R_1$ is $C_1$-$C_{24}$ alkyl, $C_1$-$C_{24}$ substituted alkyl, $C_1$-$C_{24}$ alkenyl, $C_1$-$C_{24}$ substituted alkenyl;
$X_1$ is O or $NR_a$, wherein $R_a$ is hydrogen, $C_1$-$C_4$ alkyl, or $C_1$-$C_4$ substituted alkyl;
$X_2$ is $C_1$-$C_6$ alkanediyl or $C_1$-$C_6$ substituted alkanediyl;
$R_3$, $R_4$, and $R_5$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; and
$A_1$ is an anion with a charge equal to the number of $X_2N^+R_3R_4R_5$ groups in the compound.

In some embodiments of the SORT lipids, the permanently cationic SORT lipid has a structural formula:

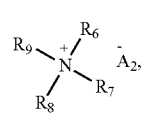

(S-II)

wherein:
$R_6$-$R_9$ are each independently $C_1$-$C_{24}$ alkyl, $C_1$-$C_{24}$ substituted alkyl, $C_1$-$C_{24}$ alkenyl, $C_1$-$C_{24}$ substituted alkenyl; provided at least one of $R_6$-$R_9$ is a group of $C_8$-$C_{24}$; and
$A_2$ is a monovalent anion.

In some embodiments of the lipid compositions, the SORT lipid is ionizable cationic lipid (i.e., comprising one or more hydrophobic components and an ionizable cationic group). The ionizable positively charged moiety may be positively charged at a physiological pH. One ionizable cationic group that may be used in the ionizable cationic lipid is a tertiary ammine group. In some embodiments of the lipid compositions, the SORT lipid has a structural formula:

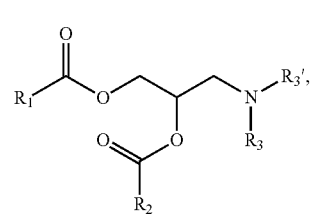

(S-I'a)

wherein:
$R_1$ and $R_2$ are each independently alkyl$_{(C8-C24)}$, alkenyl$_{(C8-C24)}$, or a substituted version of either group; and
$R_3$ and $R_3{}'$ are each independently alkyl$_{(C\leq 6)}$ or substituted alkyl$_{(C\leq 6)}$.

In some embodiments of the lipid compositions, the SORT lipid comprises a head group of a particular structure. In some embodiments, the SORT lipid comprises a headgroup having a structural formula:

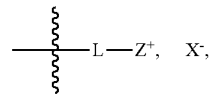

wherein L is a linker; $Z^+$ is positively charged moiety and $X^-$ is a counterion. In some embodiment, the linker is a biodegradable linker. The biodegradable linker may be degradable under physiological pH and temperature. The biodegradable linker may be degraded by proteins or enzymes from a subject. In some embodiments, the positively charged moiety is a quaternary ammonium ion or quaternary amine.

In some embodiments of the lipid compositions, the SORT lipid has a structural formula:

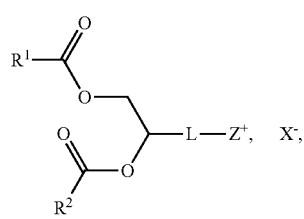

wherein $R^1$ and $R^2$ are each independently an optionally substituted $C_6$-$C_{24}$ alkyl, or an optionally substituted $C_6$-$C_{24}$ alkenyl.

In some embodiments of the lipid compositions, the SORT lipid has a structural formula:

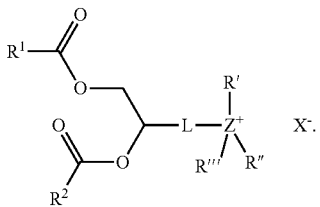

In some embodiments of the lipid compositions, the SORT lipid comprises a Linker (L). In some embodiments, L is

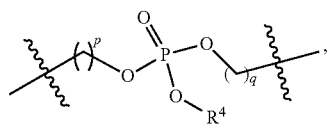

wherein:
p and q are each independently 1, 2, or 3; and
$R^4$ is an optionally substituted $C_1$-$C_6$ alkyl
In some embodiments of the lipid compositions, the SORT lipid has a structural formula:

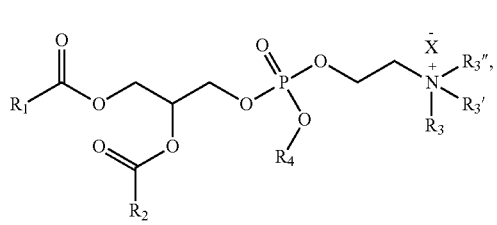
(IA)

wherein:
$R_1$ and $R_2$ are each independently alkyl$_{(C8-C24)}$, alkenyl$_{(C8-C24)}$, or a substituted version of either group;
$R_3$, $R_3'$, and $R_3''$ are each independently alkyl$_{(C\leq 6)}$ or substituted alkyl$_{(C\leq 6)}$;
$R_4$ is alkyl$_{(C\leq 6)}$ or substituted alkyl$_{(C\leq 6)}$; and
$X^-$ is a monovalent anion.
In some embodiments of the lipid compositions, the SORT lipid is a phosphatidylcholine (e.g., 14:0 EPC). In some embodiments, the phosphatidylcholine compound is further defined as:

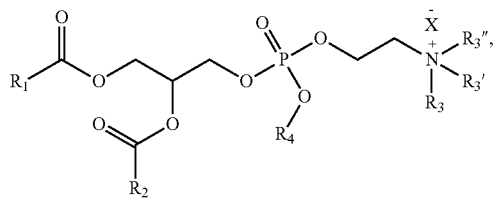
(IA)

wherein:
$R_1$ and $R_2$ are each independently alkyl$_{(C8-C24)}$, alkenyl$_{(C8-C24)}$, or a substituted version of either group;

$R_3$, $R_3'$, and $R_3''$ are each independently alkyl$_{(C\leq 6)}$ or substituted alkyl$_{(C\leq 6)}$; and $X^-$ is a monovalent anion.

In some embodiments of the lipid compositions, the SORT lipid is a phosphocholine lipid. In some embodiments, the SORT lipid is an ethylphosphocholine. The ethylphosphocholine may be, by way of example, without being limited to, 1,2-dimyristoleoyl-sn-glycero-3-ethylphosphocholine, 1,2-dioleoyl-sn-glycero-3-ethylphosphocholine, 1,2-distearoyl-sn-glycero-3-ethylphosphocholine, 1,2-dipalmitoyl-sn-glycero-3-ethylphosphocholine, 1,2-dimyristoyl-sn-glycero-3-ethylphosphocholine, 1,2-dilauroyl-sn-glycero-3-ethylphosphocholine, 1-palmitoyl-2-oleoyl-sn-glycero-3-ethylphosphocholine.

In some embodiments of the lipid compositions, the SORT lipid has a structural formula:

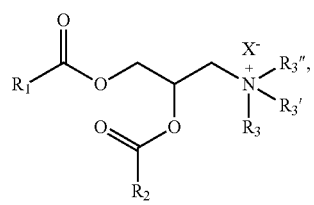
(S-I')

wherein:
$R_1$ and $R_2$ are each independently alkyl$_{(C8-C24)}$, alkenyl$_{(C8-C24)}$, or a substituted version of either group;

$R_3$, $R_3'$, and $R_3''$ are each independently alkyl$_{(C\leq 6)}$ or substituted alkyl$_{(C\leq 6)}$;

$X^-$ is a monovalent anion.

By way of example, and without being limited thereto, a SORT lipid of the structural formula of the immediately preceding paragraph is 1,2-dioleoyl-3-trimethylammonium-propane (18:1 DOTAP) (e.g., chloride salt).

In some embodiments of the lipid compositions, the SORT lipid has a structural formula:

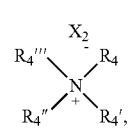
(S-II')

wherein:
$R_4$ and $R_4'$ are each independently alkyl$_{(C6-C24)}$, alkenyl$_{(C6-C24)}$, or a substituted version of either group;

$R_4''$ is alkyl$_{(C\leq 24)}$, alkenyl$_{(C\leq 24)}$, or a substituted version of either group;

$R_4'''$ is alkyl$_{(C1-C8)}$, alkenyl$_{(C2-C8)}$, or a substituted version of either group; and $X_2$ is a monovalent anion.

By way of example, and without being limited thereto, a SORT lipid of the structural formula of the immediately preceding paragraph is dimethyldioctadecylammonium (DDAB) (e.g., bromide salt).

In some embodiments of the lipid compositions, the SORT lipid has a structural formula:

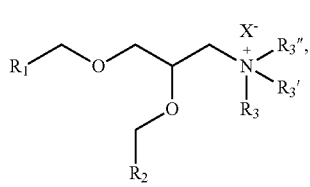
(S-III)

wherein:

R₁ and R₂ are each independently alkyl$_{(C8-C24)}$, alkenyl$_{(C8-C24)}$, or a substituted version of either group;

R₃, R₃', and R₃" are each independently alkyl$_{(C≤6)}$ or substituted alkyl$_{(C≤6)}$; and X⁻ is a monovalent anion.

By way of example, and without being limited thereto, a SORT lipid of the structural formula of the immediately preceding paragraph is N-[1-(2, 3-dioleyloxy)propyl]-N,N,N-trimethylammonium chloride (DOTMA).

In some embodiments of the lipid compositions, the SORT lipid is an anionic lipid. In some embodiments of the lipid compositions, the SORT lipid has a structural formula:

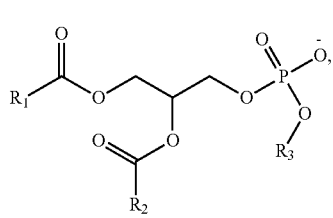
(S-IV)

wherein:

R₁ and R₂ are each independently alkyl$_{(C8-C24)}$, alkenyl$_{(C8-C24)}$, or a substituted version of either group;

R₃ is hydrogen, alkyl$_{(C≤6)}$, or substituted alkyl$_{(C≤6)}$, or —Y₁—R₄, wherein:

Y₁ is alkanediyl$_{(C≤6)}$ or substituted alkanediyl$_{(C≤6)}$; and

R₄ is acyloxy$_{(C≤8-24)}$ or substituted acyloxy$_{(C≤8-24)}$.

In some embodiments of the lipid compositions, the SORT lipid comprises one or more selected from the lipids set forth in Table 6.

TABLE 6

Example SORT lipids

| Lipid Name | Structure |
|---|---|
| 1,2-Dioleoyl-3-dimethylammonium-propane (18:1 DODAP) | 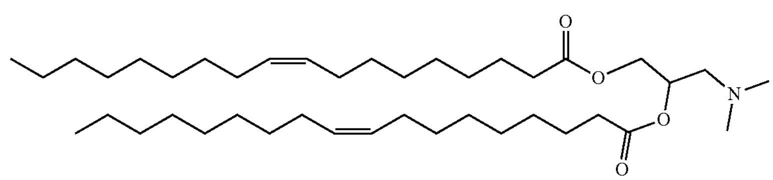 [SMILES: CCCCCCCC/C=C\CCCCCCCC(=O)OCC(CN(C)C)OC(=O)CCCCCCC/C=C\CCCCCCCC] |
| 1,2-dimyristoyl-3-trimethylammonium-propane (14:0 TAP) (e.g., chloride salt) | 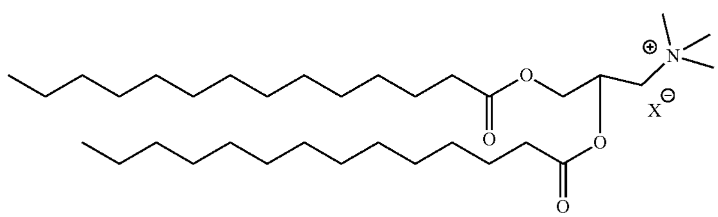 |
| 1,2-dipalmitoyl-3-trimethylammonium-propane (16:0 TAP) (e.g., chloride salt) | 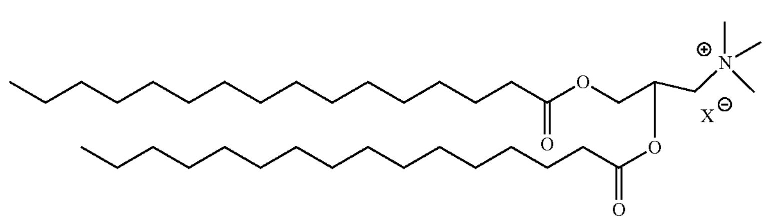 |
| 1,2-stearoyl-3-trimethylammonium-propane (18:0 TAP) (e.g., chloride salt) | 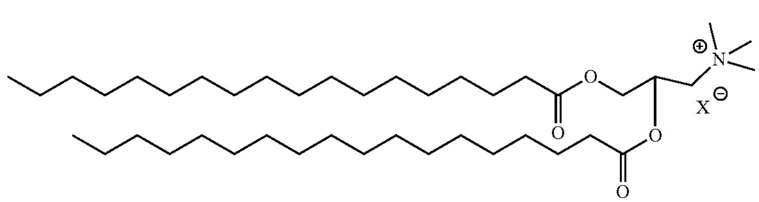 |

TABLE 6-continued

Example SORT lipids

| Lipid Name | Structure |
| --- | --- |
| 1,2-Dioleoyl-3-trimethylammonium-propane (18:1 DOTAP) (e.g., chloride salt) | |
| 1,2-Di-O-octadecenyl-3-trimethylammonium propane (DOTMA) (e.g., chloride salt) | |
| Dimethyldioctadec-ylammonium(DDAB) (e.g., bromide salt) | |
| 1,2-dilauroyl-sn-glycero-3-ethylphos-phocholine (12:0 EPC) (e.g., chloride salt) | |
| 1,2-Dioleoyl-sn-glycero-3-ethylphos-phocholine (14:0 EPC) (e.g., chloride salt) | |
| 1,2-dimyristoleoyl-sn-glycero-3-ethylphos-phocholine (14:1 EPC) (e.g., triflate salt) | |
| 1,2-dipalmitoyl-sn-glycero-3-ethylphos-phocholine (16:0 EPC) (e.g., chloride salt) | |
| 1,2-distearoyl-sn-glycero-3-ethylphos-phocholine (18:0 EPC) (e.g., chloride salt) | |
| 1,2-dioleoyl-sn-glycero-3-ethylphos-phocholine (18:1 EPC) (e.g., chloride salt) | |
| 1-palmitoyl-2-oleoyl-sn-glycero-3-ethyl-phosphocholine (16:0-18:1 EPC) (e.g., chloride salt) | |

TABLE 6-continued

Example SORT lipids

| Lipid Name | Structure |
|---|---|
| 1,2-di-O-octadecen-yl-3-trimethyl-ammonium propane (18:1 DOTMA) (e.g., chloride salt) | 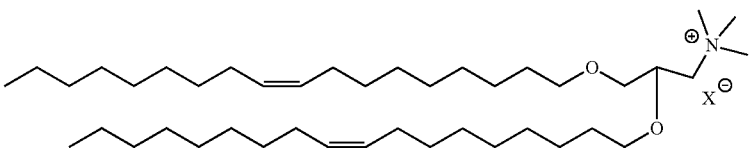 |

X⁻ is a counterion (e.g., Cl⁻, Br⁻, etc.)

In some embodiments of the lipid composition of the present application, the lipid composition comprises the SORT lipid at a molar percentage from about 20% to about 65%. In some embodiments of the lipid composition of the present application, the lipid composition comprises the SORT lipid at a molar percentage from about 25% to about 60%. In some embodiments of the lipid composition of the present application, the lipid composition comprises the SORT lipid at a molar percentage from about 30% to about 55%. In some embodiments of the lipid composition of the present application, the lipid composition comprises the SORT lipid at a molar percentage from about 20% to about 50%. In some embodiments of the lipid composition of the present application, the lipid composition comprises the SORT lipid at a molar percentage from about 30% to about 60%. In some embodiments of the lipid composition of the present application, the lipid composition comprises the SORT lipid at a molar percentage from about 25% to about 60%. In some embodiments of the lipid composition of the present application, the lipid composition comprises the SORT lipid at a molar percentage of at least (about) 25%, at least (about) 30%, at least (about) 35%, at least (about) 40%, at least (about) 45%, at least (about) 50%, at least (about) 55%, at least (about) 60%, or at least (about) 65%. In some embodiments of the lipid composition of the present application, the lipid composition comprises the SORT lipid at a molar percentage of at most (about) 25%, at most (about) 30%, at most (about) 35%, at most (about) 40%, at least (about) 45%, at most (about) 50%, at most (about) 55%, at most (about) 60%, or at most (about) 65%. In some embodiments of the lipid composition of the present application, the lipid composition comprises the SORT lipid at a molar percentage of about 20%, 25%, 30%, 35%, 40%, 45%, 50%, 55%, 60%, or 65%, or of a range between (inclusive) any two of the foregoing values.

Additional Lipids

In some embodiments of the lipid composition of the present application, the lipid composition further comprises an additional lipid including but not limited to a steroid or a steroid derivative, a PEG lipid, and a phospholipid.

Phospholipids or Other Zwitterionic Lipids

In some embodiments of the lipid composition of the present application, the lipid composition further comprises a phospholipid. In some embodiments, the phospholipid may contain one or two long chain (e.g., $C_6$-$C_{24}$) alkyl or alkenyl groups, a glycerol or a sphingosine, one or two phosphate groups, and, optionally, a small organic molecule. The small organic molecule may be an amino acid, a sugar, or an amino substituted alkoxy group, such as choline or ethanolamine. In some embodiments, the phospholipid is a phosphatidylcholine. In some embodiments, the phospholipid is distearoylphosphatidylcholine or dioleoylphosphatidylethanolamine. In some embodiments, other zwitterionic lipids are used, where zwitterionic lipid defines lipid and lipid-like molecules with both a positive charge and a negative charge.

In some embodiments of the lipid compositions, the phospholipid is not an ethylphosphocholine.

In some embodiments of the lipid composition of the present application, the compositions may further comprise a molar percentage of the phospholipid to the total lipid composition from about 20 to about 23. In some embodiments, the molar percentage is from about 20, 20.5, 21, 21.5, 22, 22.5, to about 23 or any range derivable therein. In other embodiments, the molar percentage is from about 7.5 to about 60. In some embodiments, the molar percentage is from about 7.5, 8, 9, 10, 11, 12, 13, 14, 15, 16, 17, 18, 19, to about 20 or any range derivable therein.

In some embodiments of the lipid composition of the present application, the lipid composition comprises the phospholipid at a molar percentage from about 8% to about 23%. In some embodiments of the lipid composition of the present application, the lipid composition comprises the phospholipid at a molar percentage from about 10% to about 20%. In some embodiments of the lipid composition of the present application, the lipid composition comprises the phospholipid at a molar percentage from about 15% to about 20%. In some embodiments of the lipid composition of the present application, the lipid composition comprises the phospholipid at a molar percentage from about 8% to about 15%. In some embodiments of the lipid composition of the present application, the lipid composition comprises the phospholipid at a molar percentage from about 10% to about 15%. In some embodiments of the lipid composition of the present application, the lipid composition comprises the phospholipid at a molar percentage from about 12% to about 18%. In some embodiments of the lipid composition of the present application, the lipid composition comprises the phospholipid at a molar percentage of at least (about) 8%, at least (about) 10%, at least (about) 12%, at least (about) 15%, at least (about) 18%, at least (about) 20%, or at least (about) 23%. In some embodiments of the lipid composition of the present application, the lipid composition comprises the phospholipid at a molar percentage of at most (about) 8%, at most (about) 10%, at most (about) 12%, at most (about) 15%, at most (about) 18%, at most (about) 20%, or at most (about) 23%.

Steroids or Steroid Derivatives

In some embodiments of the lipid composition of the present application, the lipid composition further comprises a steroid or steroid derivative. In some embodiments, the steroid or steroid derivative comprises any steroid or steroid derivative. As used herein, in some embodiments, the term "steroid" is a class of compounds with a four ring 17 carbon cyclic structure which can further comprises one or more substitutions including alkyl groups, alkoxy groups, hydroxy groups, oxo groups, acyl groups, or a double bond between two or more carbon atoms. In one aspect, the ring structure of a steroid comprises three fused cyclohexyl rings and a fused cyclopentyl ring as shown in the formula:

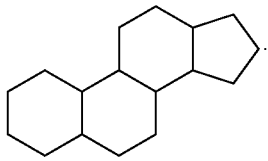 [SMILES: C1CCC2C(C1)CCC1C3CCCC3CCC21]

In some embodiments, a steroid derivative comprises the ring structure above with one or more non-alkyl substitutions. In some embodiments, the steroid or steroid derivative is a sterol wherein the formula is further defined as:

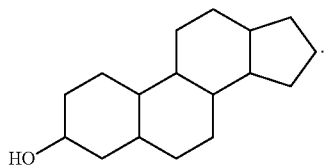

In some embodiments of the present application, the steroid or steroid derivative is a cholestane or cholestane derivative. In a cholestane, the ring structure is further defined by the formula:

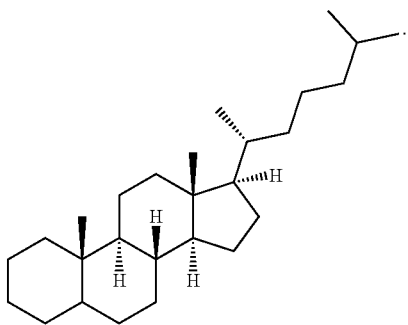

As described above, a cholestane derivative includes one or more non-alkyl substitution of the above ring system. In some embodiments, the cholestane or cholestane derivative is a cholestene or cholestene derivative or a sterol or a sterol derivative. In other embodiments, the cholestane or cholestane derivative is both a cholestere and a sterol or a derivative thereof.

In some embodiments of the lipid composition, the compositions may further comprise a molar percentage of the steroid to the total lipid composition from about 40 to about 46. In some embodiments, the molar percentage is from about 40, 41, 42, 43, 44, 45, to about 46 or any range derivable therein. In other embodiments, the molar percentage of the steroid relative to the total lipid composition is from about 15 to about 40. In some embodiments, the molar percentage is 15, 16, 18, 20, 22, 24, 26, 28, 30, 32, 34, 36, 38, or 40, or any range derivable therein.

In some embodiments of the lipid composition of the present application, the lipid composition comprises the steroid or steroid derivative at a molar percentage from about 15% to about 46%. In some embodiments of the lipid composition of the present application, the lipid composition comprises the steroid or steroid derivative at a molar percentage from about 20% to about 40%. In some embodiments of the lipid composition of the present application, the lipid composition comprises the steroid or steroid derivative at a molar percentage from about 25% to about 35%. In some embodiments of the lipid composition of the present application, the lipid composition comprises the steroid or steroid derivative at a molar percentage from about 30% to about 40%. In some embodiments of the lipid composition of the present application, the lipid composition comprises the steroid or steroid derivative at a molar percentage from about 20% to about 30%. In some embodiments of the lipid composition of the present application, the lipid composition comprises the steroid or steroid derivative at a molar percentage of at least (about) 15%, of at least (about) 20%, of at least (about) 25%, of at least (about) 30%, of at least (about) 35%, of at least (about) 40%, of at least (about) 45%, or of at least (about) 46%. In some embodiments of the lipid composition of the present application, the lipid composition comprises the steroid or steroid derivative at a molar percentage of at most (about) 15%, of at most (about) 20%, of at most (about) 25%, of at most (about) 30%, of at most (about) 35%, of at most (about) 40%, of at most (about) 45%, or of at most (about) 46%.

Polymer-Conjugated Lipids

In some embodiments of the lipid composition of the present application, the lipid composition further comprises a polymer conjugated lipid. In some embodiments, the polymer conjugated lipid is a PEG lipid. In some embodiments, the PEG lipid is a diglyceride which also comprises a PEG chain attached to the glycerol group. In other embodiments, the PEG lipid is a compound which contains one or more $C_6$-$C_{24}$ long chain alkyl or alkenyl group or a $C_6$-$C_{24}$ fatty acid group attached to a linker group with a PEG chain. Some non-limiting examples of a PEG lipid includes a PEG modified phosphatidylethanolamine and phosphatidic acid, a PEG ceramide conjugated, PEG modified dialkylamines and PEG modified 1,2-diacyloxypropan-3-amines, PEG modified diacylglycerols and dialkylglycerols. In some embodiments, PEG modified diastearoylphosphatidylethanolamine or PEG modified dimyristoyl-sn-glycerol. In some embodiments, the PEG modification is measured by the molecular weight of PEG component of the lipid. In some embodiments, the PEG modification has a molecular weight from about 100 to about 15,000. In some embodiments, the molecular weight is from about 200 to about 500, from about 400 to about 5,000, from about 500 to about 3,000, or from about 1,200 to about 3,000. The molecular weight of the PEG modification is from about 100, 200, 400, 500, 600, 800, 1,000, 1,250, 1,500, 1,750, 2,000, 2,250, 2,500, 2,750, 3,000, 3,500, 4,000, 4,500, 5,000, 6,000, 7,000, 8,000, 9,000, 10,000, 12,500, to about 15,000. Some non-limiting examples of lipids that may be used in the present application are taught by U.S. Pat. No. 5,820,873, WO 2010/141069, or U.S. Pat. No. 8,450,298, which is incorporated herein by reference.

In some embodiments of the lipid composition of the present application, the PEG lipid has a structural formula:

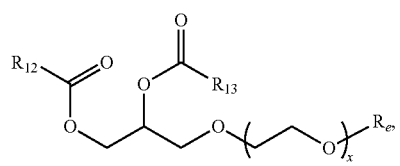

wherein: $R_{12}$ and $R_{13}$ are each independently alkyl$_{(C \leq 24)}$, alkenyl$_{(C \leq 24)}$, or a substituted version of either of these groups; $R_e$ is hydrogen, alkyl$_{(C \leq 8)}$, or substituted alkyl$_{(C \leq 8)}$; and x is 1-250. In some embodiments, $R_e$ is alkyl$_{(C \leq 8)}$ such as methyl. $R_{12}$ and $R_{13}$ are each independently alkyl$_{(C \leq 4-20)}$. In some embodiments, x is 5-250. In one embodiment, x is 5-125 or x is 100-250. In some embodiments, the PEG lipid is 1,2-dimyristoyl-sn-glycerol, methoxypolyethylene glycol.

In some embodiments of the lipid composition of the present application, the PEG lipid has a structural formula:

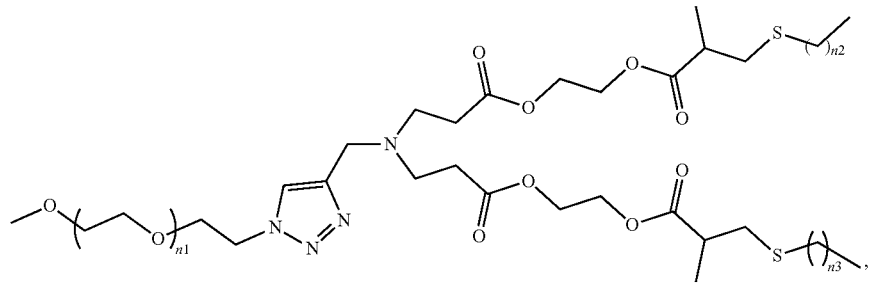

wherein: $n_1$ is an integer between 1 and 100 and $n_2$ and $n_3$ are each independently selected from an integer between 1 and 29. In some embodiments, $n_1$ is 5, 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100, or any range derivable therein. In some embodiments, $n_1$ is from about 30 to about 50. In some embodiments, $n_2$ is from 5 to 23. In some embodiments, $n_2$ is 11 to about 17. In some embodiments, $n_3$ is from 5 to 23. In some embodiments, $n_3$ is 11 to about 17.

In some embodiments of the lipid composition of the present application, the compositions may further comprise a molar percentage of the PEG lipid to the total lipid composition from about 4.0 to about 4.6. In some embodiments, the molar percentage is from about 4.0, 4.1, 4.2, 4.3, 4.4, 4.5, to about 4.6 or any range derivable therein. In other embodiments, the molar percentage is from about 1.5 to about 4.0. In some embodiments, the molar percentage is from about 1.5, 1.75, 2, 2.25, 2.5, 2.75, 3, 3.25, 3.5, 3.75, to about 4.0 or any range derivable therein.

In some embodiments of the lipid composition of the present application, the lipid composition comprises the polymer-conjugated lipid at a molar percentage from about 0.5% to about 10%. In some embodiments of the lipid composition of the present application, the lipid composition comprises the polymer-conjugated lipid at a molar percentage from about 1% to about 10%. In some embodiments of the lipid composition of the present application, the lipid composition comprises the polymer-conjugated lipid at a molar percentage from about 2% to about 10%. In some embodiments of the lipid composition of the present application, the lipid composition comprises the polymer-conjugated lipid at a molar percentage from about 1% to about 8%. In some embodiments of the lipid composition of the present application, the lipid composition comprises the polymer-conjugated lipid at a molar percentage from about 2% to about 7%. In some embodiments of the lipid composition of the present application, the lipid composition comprises the polymer-conjugated lipid at a molar percentage from about 3% to about 5%. In some embodiments of the lipid composition of the present application, the lipid composition comprises the polymer-conjugated lipid at a molar percentage from about 5% to about 10%. In some embodiments of the lipid composition of the present application, the lipid composition comprises the polymer-conjugated lipid at a molar percentage of at least (about) 0.5%, at least (about) 1%, at least (about) 1.5%, at least (about) 2%, at least (about) 2.5%, at least (about) 3%, at least (about) 3.5%, at least (about) 4%, at least (about) 4.5%, at least (about) 5%, at least (about) 5.5%, at least (about) 6%, at least (about) 6.5%, at least (about) 7%, at least (about) 7.5%, at least (about) 8%, at least (about) 8.5%, at least (about) 9%, at least (about) 9.5%, or at least (about) 10%. In some embodiments of the lipid composition of the present application, the lipid composition comprises the polymer-conjugated lipid at a molar percentage of at most (about) 0.5%, at most (about) 1%, at most (about) 1.5%, at most (about) 2%, at most (about) 2.5%, at most (about) 3%, at most (about) 3.5%, at most (about) 4%, at most (about) 4.5%, at most (about) 5%, at most (about) 5.5%, at most (about) 6%, at most (about) 6.5%, at most (about) 7%, at most (about) 7.5%, at most (about) 8%, at most (about) 8.5%, at most (about) 9%, at most (about) 9.5%, or at most (about) 10%.

Pharmaceutical Compositions

Therapeutic or Prophylactic Agents

In another aspect, provided herein is a pharmaceutical composition comprising a therapeutic agent (or prophylactic agent) assembled with a lipid composition as described herein.

In some embodiments of the pharmaceutical composition, the therapeutic agent (or prophylactic agent) comprises a compound, a polynucleotide, a polypeptide, or a combination thereof. In some embodiments, the compound, the polynucleotide, the polypeptide, or a combination thereof is exogenous or heterologous to the cell or the subject being treated by the pharmaceutical compositions described herein. In some embodiments, the therapeutic agent (or prophylactic agent) comprises a compound described herein. In some embodiments, the therapeutic agent (or prophylactic agent) comprises a polynucleotide described herein. In some embodiments, the therapeutic agent (or prophylactic agent) comprises a polypeptide described herein. In some embodiments, the therapeutic agent (or prophylactic agent) comprises a compound, a polynucleotide, a polypeptide, or a combination thereof.

In some embodiments, the pharmaceutical composition comprises a therapeutic agent (or prophylactic agent) for treating a lung disease such as asthma, COPD, or lung cancer. In some embodiments, the therapeutic agent (or prophylactic agent) comprises a steroid such as prednisone, hydrocortisone, prednisolone, methylprednisolone, or dexamethasone. In some embodiments, the therapeutic agent (or prophylactic agent) comprises Abraxane, Afatinib Dimaleate, Afinitor, Afinitor Disperz, Alecensa, Alectinib, Alimta, Alunbrig, Atezolizumab, Avastin, Bevacizumab, Brigatinib, Capmatinib Hydrochloride, Carboplatin, Ceritinib, Crizotinib, Cyramza, Dabrafenib Mesylate, Dacomitinib, Docetaxel, Doxorubicin Hydrochloride, Durvalumab, Entrectinib, Erlotinib Hydrochloride, Everolimus, Gavreto, Gefitinib, Gilotrif, Gemcitabine, Ipilimumab, Iressa, Keytruda, Lorbrena, Mekinist, Methotrexate Sodium, Necitumumab, Nivolumab, Osimertinib Mesylate, Paclitaxel, Pembrolizumab, Pemetrexed Disodium, Pralsetinib, Ramucirumab, Retevmo, Selpercatinib, Tabrecta, Tafinlar, Tagrisso, Trametinib Dimethyl Sulfoxide, Vizimpro, Vinorelbine Tartrate, Xalkori, Yervoy, Zirabev, Zykadia, Carboplatin, Gemcitabine-cisplatin, Afinitor, Atezolizumab, Durvalumab, Etopophos, Etoposide, Hycamtin, Imfinzi, Keytruda, Lurbinectedin, Methotrexate Sodium, Nivolumab, Opdivo, Pembrolizumab, Tecentriq, Topotecan Hydrochloride, Trexall, or Zepzelca. Other non-limiting examples of the therapeutic agents (or prophylactic agents) comprising compounds include small molecule selected from 7-Methoxypteridine, 7 Methylpteridine, abacavir, abafungin, abarelix, acebutolol, acenaphthene, acetaminophen, acetanilide, acetazolamide, acetohexamide, acetretin, acrivastine, adenine, adenosine, alatrofloxacin, albendazole, albuterol, alclofenac, aldesleukin, alemtuzumab, alfuzosin, alitretinoin, allobarbital, allopurinol, all-transretinoic acid (ATRA), aloxiprin, alprazolam, alprenolol, altretamine, amifostine, amiloride, aminoglutethimide, aminopyrine, amiodarone HCl, amitriptyline, amlodipine, amobarbital, amodiaquine, amoxapine, amphetamine, amphotericin, amphotericin B, ampicillin, amprenavir, amsacrine, amylnitrate, amylobarbitone, anastrozole, anrinone, anthracene, anthracyclines, aprobarbital, arsenic trioxide, asparaginase, aspirin, astemizole, atenolol, atorvastatin, atovaquone, atrazine, atropine, atropine azathioprine, auranofin, azacitidine, azapropazone, azathioprine, azintamide, azithromycin, aztreonum, baclofen, barbitone, BCG live, beclamide, beclomethasone, bendroflumethiazide, benezepril, benidipine, benorylate, benperidol, bentazepam, benzamide, benzanthracene, benzathine penicillin, benzhexol HCl, benznidazole, benzodiazepines, benzoic acid, bephenium hydroxynaphthoate, betamethasone, bevacizumab (avastin), bexarotene, bezafibrate, bicalutamide, bifonazole, biperiden, bisacodyl, bisantrene, bleomycin, bleomycin, bortezomib, brinzolamide, bromazepam, bromocriptine mesylate, bromperidol, brotizolam, budesonide, bumetanide, bupropion, busulfan, butalbital, butamben, butenafine HCl, butobarbitone, butobarbitone (butethal), butoconazole, butoconazole nitrate, butylparaben, caffeine, calcifediol, calciprotriene, calcitriol, calusterone, cambendazole, camphor, camptothecin, camptothecin analogs, candesartan, capecitabine, capsaicin, captopril, carbamazepine, carbimazole, carbofuran, carboplatin, carbromal, carimazole, carmustine, cefamandole, cefazolin, cefixime, ceftazidime, cefuroxime axetil, celecoxib, cephradine, cerivastatin, cetrizine, cetuximab, chlorambucil, chloramphenicol, chlordiazepoxide, chlormethiazole, chloroquine, chlorothiazide, chlorpheniramine, chlorproguanil HCl, chlorpromazine, chlorpropamide, chlorprothixene, chlorpyrifos, chlortetracycline, chlorthalidone, chlorzoxazone, cholecalciferol, chrysene, cilostazol, cimetidine, cinnarizine, cinoxacin, ciprofibrate, ciprofloxacin HCl, cisapride, cisplatin, citalopram, cladribine, clarithromycin, clemastine fumarate, clioquinol, clobazam, clofarabine, clofazimine, clofibrate, clomiphene citrate, clomipramine, clonazepam, clopidogrel, clotiazepam, clotrimazole, clotrimazole, cloxacillin, clozapine, cocaine, codeine, colchicine, colistin, conjugated estrogens, corticosterone, cortisone, cortisone acetate, cyclizine, cyclobarbital, cyclobenzaprine, cyclobutane-spirobarbiturate, cycloethane-spirobarbiturate, cycloheptane-spirobarbiturate, cyclohexane-spirobarbiturate, cyclopentane-spirobarbiturate, cyclophosphamide, cyclopropane-spirobarbiturate, cycloserine, cyclosporin, cyproheptadine, cytarabine, cytosine, dacarbazine, dactinomycin, danazol, danthron, dantrolene sodium, dapsone, darbepoetin alfa, darodipine, daunorubicin, decoquinate, dehydroepiandrosterone, delavirdine, demeclocycline, denileukin, deoxycorticosterone, desoxymethasone, dexamethasone, dexamphetamine, dexchlorpheniramine, dexfenfluramine, dexrazoxane, dextropropoxyphene, diamorphine, diatrizoicacid, diazepam, diazoxide, dichlorophen, dichlorprop, diclofenac, dicumarol, didanosine, diflunisal, digitoxin, digoxin, dihydrocodeine, dihydroequilin, dihydroergotamine mesylate, diiodohydroxyquinoline, diltiazem HCl, diloxamide furoate, dimenhydrinate, dimorpholamine, dinitolmide, diosgenin, diphenoxylate HCl, diphenyl, dipyridamole, dirithromycin, disopyramide, disulfiram, diuron, docetaxel, domperidone, donepezil, doxazosin, doxazosin HCl, doxorubicin, doxycycline, dromostanolone propionate, droperidol, dyphylline, echinocandins, econazole, econazole nitrate, efavirenz, ellipticine, enalapril, enlimomab, enoximone, epinephrine, epipodophyllotoxin derivatives, epirubicin, epoetinalfa, eposartan, equilenin, equilin, ergocalciferol, ergotamine tartrate, erlotinib, erythromycin, estradiol, estramustine, estriol, estrone, ethacrynic acid, ethambutol, ethinamate, ethionamide, ethopropazine HCl, ethyl-4-aminobenzoate (benzocaine), ethylparaben, ethinylestradiol, etodolac, etomidate, etoposide, etretinate, exemestane, felbamate, felodipine, fenbendazole, fenbuconazole, fenbufen, fenchlorphos, fenclofenac, fenfluramine, fenofibrate, fenoldepam, fenoprofen calcium, fenoxycarb, fenpiclonil, fentanyl, fenticonazole, fexofenadine, filgrastim, finasteride, flecamide acetate, floxuridine, fludarabine, fluconazole, fluconazole, flucytosine, fludioxonil, fludrocortisone, fludrocortisone acetate, flufenamic acid, flunanisone, flunarizine HCl, flunisolide, flunitrazepam, fluocortolone, fluometuron, fluorene, fluorouracil, fluoxetine HCl, fluoxymesterone, flupenthixol decanoate, fluphenthixol decanoate, flurazepam, flurbiprofen, fluticasone propionate, fluvastatin, folic acid, fosenopril, fosphenytoin sodium, frovatriptan, furosemide, fulvestrant, furazolidone, gabapentin, G-BHC (Lindane), gefitinib, gemcitabine, gemfibrozil, gemtuzumab, glafenine, glibenclamide, gliclazide, glimepiride, glipizide, glutethimide, glyburide, Glyceryltrinitrate (nitroglycerin), goserelin acetate, grepafloxacin, griseofulvin, guaifenesin, guanabenz acetate, guanine, halofantrine HCl, haloperidol, hydrochlorothiazide, heptabarbital, heroin, hesperetin, hexachlorobenzene, hexethal, histrelin acetate, hydrocortisone, hydroflumethiazide, hydroxyurea, hyoscyamine, hypoxanthine, ibritumomab, ibuprofen, idarubicin, idobutal, ifosfamide, ihydroequilenin, imatinib mesylate, imipenem, indapamide, indinavir, indomethacin, indoprofen, interferon alfa-2a, interferon alfa-2b, iodamide, iopanoic acid, iprodione, irbesartan, irinotecan, isavuconazole, isocarboxazid, isoconazole, isoguanine, isoniazid, isopropylbarbiturate, isoproturon, isosorbide dinitrate, isosorbide mononitrate, isradipine, itraconazole, itraconazole, itraconazole (Itra), ivermectin, ketoconazole, ketoprofen, ketorolac, khellin, labetalol, lamivudine, lamotrigine, lanatoside C, lanosprazole, L-DOPA, leflunomide, lenalidomide, letrozole, leucovorin, leuprolide acetate, levamisole, levofloxacin, lidocaine, linuron, lisinopril, lomefloxacin, lomustine, loperamide, loratadine, lorazepam, lorefloxacin, lormetazepam, losartan mesylate, lovastatin, lysuride maleate, Maprotiline HCl, mazindol, mebendazole, Meclizine HCl, meclofenamic acid, medazepam, medigoxin, medroxyprogesterone acetate, mefenamic acid, Mefloquine HCl, megestrol acetate, melphalan, mepenzolate bromide, meprobamate, meptazinol, mercaptopurine, mesalazine, mesna, mesoridazine, mestranol, methadone, methaqualone, methocarbamol, methoin, methotrexate, methoxsalen, methsuximide, methyclothiazide, methylphenidate, methylphenobarbitone, methyl-p-hydroxybenzoate, methylprednisolone, methyltestosterone, methyprylon, methysergide maleate, metoclopramide, metolazone, metoprolol, metronidazole, Mianserin HCl, miconazole, midazolam, mifepristone, miglitol, minocycline, minoxidil, mitomycin C, mitotane, mitoxantrone, mofetilmycophenolate, molindone, montelukast, morphine, Moxifloxacin HCl, nabumetone, nadolol, nalbuphine, nalidixic acid, nandrolone, naphthacene, naphthalene, naproxen, naratriptan HCl, natamycin, nelarabine, nelfinavir, nevirapine, nicardipine HCl, nicotin amide, nicotinic acid, nicoumalone, nifedipine, nilutamide, nimodipine, nimorazole, nisoldipine, nitrazepam, nitrofurantoin, nitrofurazone, nizatidine, nofetumomab, norethisterone, norfloxacin, norgestrel, nortriptyline HCl, nystatin, oestradiol, ofloxacin, olanzapine, omeprazole, omoconazole, ondansetron HCl, oprelvekin, ornidazole, oxaliplatin, oxamniquine, oxantelembonate, oxaprozin, oxatomide, oxazepam, oxcarbazepine, oxfendazole, oxiconazole, oxprenolol, oxyphenbutazone, oxyphencyclimine HCl, paclitaxel, palifermin, pamidronate, p-aminosalicylic acid, pantoprazole, paramethadione, paroxetine HCl, pegademase, pegaspargase, pegfilgrastim, pemetrexeddisodium, penicillamine, pentaerythritol tetranitrate, pentazocin, pentazocine, pentobarbital, pentobarbitone, pentostatin, pentoxifylline, perphenazine, perphenazine pimozide, perylene, phenacemide, phenacetin, phenanthrene, phenindione, phenobarbital, phenolbarbitone, phenolphthalein, phenoxybenzamine, phenoxybenzamine HCl, phenoxymethyl penicillin, phensuximide, phenylbutazone, phenytoin, pindolol, pioglitazone, pipobroman, piroxicam, pizotifen maleate, platinum compounds, plicamycin, polyenes, polymyxin B, porfimersodium, posaconazole (Posa), pramipexole, prasterone, pravastatin, praziquantel, prazosin, prazosin HCl, prednisolone, prednisone, primidone, probarbital, probenecid, probucol, procarbazine, prochlorperazine, progesterone, proguanil HCl, promethazine, propofol, propoxur, propranolol, propylparaben, propylthiouracil, prostaglandin, pseudoephedrine, pteridine-2-methyl-thiol, pteridine-2-thiol, pteridine-4-methyl-thiol, pteridine-4-thiol, pteridine-7-methyl-thiol, pteridine-7-thiol, pyrantelembonate, pyrazinamide, pyrene, pyridostigmine, pyrimethamine, quetiapine, quinacrine, quinapril, quinidine, quinidine sulfate, quinine, quininesulfate, rabeprazole sodium, ranitidine HCl, rasburicase, ravuconazole, repaglinide, reposal, reserpine, retinoids, rifabutine, rifampicin, rifapentine, rimexolone, risperidone, ritonavir, rituximab, rizatriptan benzoate, rofecoxib, ropinirole HCl, rosiglitazone, saccharin, salbutamol, salicylamide, salicylic acid, saquinavir, sargramostim, secbutabarbital, secobarbital, sertaconazole, sertindole, sertraline HCl, simvastatin, sirolimus, sorafenib, sparfloxacin, spiramycin, spironolactone, stanolone, stanozolol, stavudine, stilbestrol, streptozocin, strychnine, sulconazole, sulconazole nitrate, sulfacetamide, sulfadiazine, sulfamerazine, sulfamethazine, sulfamethoxazole, sulfanilamide, sulfathiazole, sulindac, sulphabenzamide, sulphacetamide, sulphadiazine, sulphadoxine, sulphafurazole, sulphamerazine, sulpha-methoxazole, sulphapyridine, sulphasalazine, sulphinpyrazone, sulpiride, sulthiame, sumatriptan succinate, sunitinib maleate, tacrine, tacrolimus, talbutal, tamoxifen citrate, tamulosin, targretin, taxanes, tazarotene, telmisartan, temazepam, temozolomide, teniposide, tenoxicam, terazosin, terazosin HCl, terbinafine HCl, terbutaline sulfate, terconazole, terfenadine, testolactone, testosterone, tetracycline, tetrahydrocannabinol, tetroxoprim, thalidomide, thebaine, theobromine, theophylline, thiabendazole, thiamphenicol, thioguanine, thioridazine, thiotepa, thotoin, thymine, tiagabine HCl, tibolone, ticlopidine, tinidazole, tioconazole, tirofiban, tizanidine HCl, tolazamide, tolbutamide, tolcapone, topiramate, topotecan, toremifene, tositumomab, tramadol, trastuzumab, trazodone HCl, tretinoin, triamcinolone, triamterene, triazolam, triazoles, triflupromazine, trimethoprim, trimipramine maleate, triphenylene, troglitazone, tromethamine, tropicamide, trovafloxacin, tybamate, ubidecarenone (coenzyme Q10), undecenoic acid, uracil, uracil mustard, uric acid, valproic acid, valrubicin, valsartan, vancomycin, venlafaxine HCl, vigabatrin, vinbarbital, vinblastine, vincristine, vinorelbine, voriconazole, xanthine, zafirlukast, zidovudine, zileuton, zoledronate, zoledronic acid, zolmitriptan, zolpidem, or zopiclone.

Polynucleotides

In some embodiments of the pharmaceutical compositions of the present application, the therapeutic agent (or prophylactic agent) assembled with the lipid composition comprises one or more polynucleotides. The present application is not limited in scope to any particular source, sequence, or type of polynucleotide; however, as one of ordinary skill in the art could readily identify related homologs in various other sources of the polynucleotide including nucleic acids from non-human species (e.g., mouse, rat, rabbit, dog, monkey, gibbon, chimp, ape, baboon, cow, pig, horse, sheep, cat and other species). It is contemplated that the polynucleotide used in the present application can comprises a sequence based upon a naturally-occurring sequence. Allowing for the degeneracy of the genetic code, sequences that have at least about 50%, usually at least about 60%, more usually about 70%, most usually about 80%, preferably at least about 90% and most preferably about 95% of nucleotides that are identical to the nucleotide sequence of the naturally-occurring sequence. In another embodiment, the polynucleotide comprises nucleic acid sequence that is a complementary sequence to a naturally occurring sequence, or complementary to 75%, 80%, 85%, 90%, 95% and 100%. Longer polynucleotides encoding 250, 500, 1000, 1212, 1500, 2000, 2500, 3000 or longer are contemplated herein.

In some embodiments, the polynucleotide used herein may be derived from genomic DNA, i.e., cloned directly from the genome of a particular organism. In preferred embodiments, however, the polynucleotide would comprise complementary DNA (cDNA). Also contemplated is a cDNA plus a natural intron or an intron derived from another gene; such engineered molecules are sometime referred to as "mini-genes." At a minimum, these and other nucleic acids of the present application may be used as molecular weight standards in, for example, gel electrophoresis. The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

In some embodiments, the polynucleotide comprises one or more segments comprising a small interfering ribonucleic acid (siRNA), a short hairpin RNA (shRNA), a micro-ribonucleic acid (miRNA), a primary micro-ribonucleic acid (pri-miRNA), a long non-coding RNA (lncRNA), a messenger ribonucleic acid (mRNA), a clustered regularly interspaced short palindromic repeats (CRISPR) related nucleic acid, a CRISPR-RNA (crRNA), a single guide ribonucleic acid (sgRNA), a trans-activating CRISPR ribonucleic acid (tracrRNA), a plasmid deoxyribonucleic acid (pDNA), a transfer ribonucleic acid (tRNA), an antisense oligonucleotide (ASO), an antisense ribonucleic acid (RNA), a guide ribonucleic acid, deoxyribonucleic acid (DNA), a double stranded deoxyribonucleic acid (dsDNA), a single stranded deoxyribonucleic acid (ssDNA), a single stranded ribonucleic acid (ssRNA), a or double stranded ribonucleic acid (dsRNA). In some embodiments, the polynucleotide encodes at least one of the therapeutic agent (or prophylactic agent) described herein. In some embodiments, the polynucleotide encodes at least one guide polynucleotide, such as guide RNA (gRNA) or guide DNA (gDNA), for complexing with a guide RNA guided nuclease described herein. In some embodiments, the polynucleotide encodes at least one guide polynucleotide guided heterologous nuclease. The nuclease may be an endonuclease. Non-limiting example of the guide polynucleotide guided heterologous endonuclease may be selected from CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), eukaryotic Argonaute (eAgo), and Natronobacterium gregoryi Argonaute (NgAgo)); Adenosine deaminases acting on RNA (ADAR); CIRT, PUF, homing endonuclease, or any functional fragment thereof, any derivative thereof; any variant thereof; and any fragment thereof.

In some embodiments, the therapeutic (or prophylactic) agent is a transfer ribonucleic acid (tRNA) that introduces an amino acid into a growing peptide chain of a protein of a target gene. The target gene can be one set forth in Table 7.

TABLE 7

Example target genes for transfer RNA therapy

| Target | Gene Name | Corresponding Protein | Disease |
|---|---|---|---|
| CFTR | CFTR | Cystic fibrosis transmembrane conductance regulator | Cystic fibrosis |
| DNAH5 | DNAH5 | Dynein axonemal heavy chain 5 | Primary ciliary dyskinesia |
| DNAH11 | DNAH11 | Dynein axonemal heavy chain 11 | Primary ciliary dyskinesia |
| BMPR2 | BMPR2 | Bone morphogenetic protein receptor type 2 | Pulmonary arterial hypertension |
| FAH | FAH | Fumarylacetoacetate hydrolase | Tyrosinemia |
| PAH | PAH | Phenylalanine hydroxylase | Phenylketonuria |
| IDUA | IDUA | Alpha-L-iduronidase | Mucopolysaccharidosis i |
| COLAA3 | COL4A3 | Collagen type IV alpha 3 chain | Alport syndrome |
| COL4A4 | COL4A4 | Collagen type IV alpha 4 chain | Alport syndrome |
| COL4A5 | COL4A5 | Collagen type IV alpha 5 chain | Alport syndrome |
| PKD1 | PKD | Polycystin 1 | Polycystic kidney disease |
| PKD2 | PKD2 | Polycystin 2 | Polycystic kidney disease |
| PKHD1 | PKHDI | Fibrocystin (or polyductin) | Polycystic kidney disease |
| SLC3A1 | SLC3A1 | Solute carrier family 3 member 1 | Cystinuria |
| SLC7A9 | SLC7A9 | Solute carrier family 7 member 9 | Cystinuria |
| PAX9 | PAX9 | Paired box gene 9 | Aniridia |
| MYO7A | MYO7A | Myosin VIIA | Usher syndrome |
| CDH23 | CDH23 | Cadherin related 23 | Usher syndrome |
| USH2A | USH2A | Usherin | Usher syndrome |
| CLRN1 | CLRNI | Clarin 1 | Usher syndrome |
| GJB2 | GJB2 | Gap junction beta-2 protein | Non-syndromic hearing loss |
| GJB6 | GJB6 | Gap junction beta-6 protein | Non-syndromic hearing loss |
| RHO | RHO | Rhodopsin | Retinitis pigmentosa |
| DMPK | DMPK | dystrophia myotonica protein kinase | Myotonic dystrophy type 1 |
| DMD | DMD | Dystrophin | Muscular dystrophy |
| SCN1A | SCN1A | Sodium voltage-gated channel alpha subunit 1 | Dravet syndrome |
| SCN1B | SCN1B | Sodium voltage-gated channel beta subunit 1 | Dravet syndrome |
| F8 | F8 | Coagulation factor VIII | Hemophilia a |
| F9 | F9 | Coagulation factor IX | Hemophilia b |
| NGLY1 | NGLY1 | N-glycanase 1 | N-glycanase 1 deficiency |
| p53 | p53 | Tumor protein p53 | Cancer |
| CLN1 | PPT1 | Palmitoyl-protein thioesterase 1 | Batten disease |
| CLN2 | TPP1 | Tripeptidyl peptidase 1 | Late infantile ceroid lipofuscinoses |
| HERG | hERG | Kv11.1 (alpha subunit of potassium ion channel) | Long qt syndrome |
| PPT1 | PPT1 | Palmitoyl-protein thioesterase 1 | Infantile ceroid lipofuscinoses |
| ATM | ATM | ATM serine/threonine kinase | Ataxia telangiectasia |
| FBN1 | FBN1 | Fibrillin 1 | Usher syndrome type 1 |

Some embodiments of the therapeutic agent (or prophylactic agent) provided herein comprise a heterologous polypeptide comprising an actuator moiety. The actuator moiety can be configured to complex with a target polynucleotide corresponding to a target gene. In some embodiments, administration of the therapeutic agent (or prophylactic agent) results in a modified expression or activity of the target gene. The modified expression or activity of the target gene can be detectable, for example, in at least about 5%, 10%, 15%, or 20% lung epithelial cells of said subject, in at least about 2%, 5%, or 10% lung ciliated cells of said subject, in at least about 5%, 10%, 15%, or 20% lung secretory cells of said subject, in at least about 5%, 10%, 15%, or 20% lung club cells of said subject, in at least about 5%, 10%, 15%, or 20% lung goblet cells of said subject, or in at least about 5%, 10%, 15%, or 20% lung basal cells of said subject, or a combination thereof. Biomarkers for characterizing the cell types might be known in the field, such as those described herein below in the Examples section. The therapeutic agent (or prophylactic agent) may comprise a heterologous polynucleotide encoding an actuator moiety. The actuator moiety may be configured to complex with a target polynucleotide corresponding to a target gene. The heterologous polynucleotide may encode a guide polynucleotide configured to direct the actuator moiety to the target polynucleotide. The actuator moiety may comprise a heterologous endonuclease or a fragment thereof (e.g., directed by a guide polynucleotide to specifically bind the target polynucleotide). The heterologous endonuclease may be (1) part of a ribonucleoprotein (RNP) and (2) complexed with the guide polynucleotide. The heterologous endonuclease may be part of a clustered regularly interspaced short palindromic repeats (CRISPR)/CRISPR-associated (Cas) protein complex. The heterologous endonuclease may be a clustered regularly interspaced short palindromic repeats (CRISPR)-associated (Cas) endonuclease. The heterologous endonuclease may comprise a deactivated endonuclease. The deactivated endonuclease may be fused to a regulatory moiety. The regulatory moiety may comprise a transcription activator, a transcription repressor, an epigenetic modifier, or a fragment thereof.

In some embodiments, the polynucleotide encodes at least one guide polynucleotide (such as guide RNA (gRNA) or guide DNA (gDNA)) guided heterologous endonuclease. In some embodiments, the polynucleotide encodes at least one guide polynucleotide and at least one heterologous endonuclease, where the guide polynucleotide can be complexed with and guides the at least one heterologous endonuclease to cleave a genetic locus of any one of the genes described herein. In some embodiments, the polynucleotide encodes at least one guide polynucleotide guided heterologous endonuclease such as Cas9, Cas12, Cas13, Cpf1 (or Cas12a), C2C1, C2C2 (or Cas13a), Cas13b, Cas13c, Cas13d, Cas14, C2C3, Cas1, Cas1B, Cas2, Cas3, Cas4, Cas5, Cas5e (CasD), Cas6, Cas6e, Cas6f, Cas7, Cas8a, Cas8a1, Cas8a2, Cas8b, Cas8c, Csn1, Csx12, Cas10, Cas10d, CasIO, CasIOd, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, CsxIO, Csx16, CsaX, Csx3, Csx1, Csx15, Csf1, Csf2, Csf3, Csf4, or Cul966; any derivative thereof; any variant thereof; or any fragment thereof. In some embodiments, Cas13 can include, but are not limited to, Cas13a, Cas13b, Cas13c, and Cas 13d (e.g., CasRx).

In some embodiments, the heterologous endonuclease comprises a deactivated endonuclease, optionally fused to a regulatory moiety, such as an epigenetic modifier to remodel the epigenome that mediates the expression of the selected genes of interest. In some cases, the epigenetic modifier can include methyltransferase, demethylase, dismutase, an alkylating enzyme, depurinase, oxidase, photolyase, integrase, transposase, recombinase, polymerase, ligase, helicase, glycosylase, acetyltransferase, deacetylase, kinase, phosphatase, ubiquitin-activating enzymes, ubiquitin-conjugating enzymes, ubiquitin ligase, deubiquitinating enzyme, adenylate-forming enzyme, AMPylator, de-AMPylator, SUMOylating enzyme, deSUMOylating enzyme, ribosylase, deribosylase, N-myristoyltransferase, chromotine remodeling enzyme, protease, oxidoreductase, transferase, hydrolase, lyase, isomerase, synthase, synthetase, or demyristoylation enzyme. In some instances, the epigenetic modifier can comprise one or more selected from the group consisting of p300, TET1, LSD1, HDAC1, HDAC8, HDAC4, HDAC11, HDT1, SIRT3, HST2, CobB, SIRT5, SIR2A, SIRT6, NUE, vSET, SUV39H1, DIM5, KYP, SUVR4, Set4, Set1, SETD8, and TgSET8.

In some embodiments, the polynucleotide encodes a guide polynucleotide (such as guide RNA (gRNA) or guide DNA (gDNA)) that is at least partially complementary to the genomic region of a gene, where upon binding of the guide polynucleotide to the gene the guide polynucleotide recruits the guide polynucleotide guided nuclease to cleave and genetically modified the region. Examples of the genes that may be modified by the guide polynucleotide guided nuclease include CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, or FBN1.

In some embodiments, the polynucleotide comprises or encodes at least one mRNA that, upon expression of the mRNA, restores the function of a defective gene in a subject being treated by the pharmaceutical composition described herein. For example, the polynucleotide comprises or encodes an mRNA that expresses a wild type CFTR protein, which may be used to rescue a subject who is afflicted with inborn mutation in CFTR protein. Other examples of mRNA that can be expressed from the polynucleotide includes mRNA that encodes DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, or FBN1.

In some embodiments, the polynucleotides of the present application comprise at least one chemical modifications of the one or more nucleotides. In some embodiments, the chemical modification increases specificity of the guide polynucleotide (such as guide RNA (gRNA) or guide DNA (gDNA)) binding to a complementary genomic locus (e.g., the genomic locus of any one of the genes described herein). In some embodiments, the at least one chemical modification increases resistance to nuclease digestion, when then polynucleotide is administered to a subject in need thereof. In some embodiments, the at least one chemical modification decreases immunogenicity, when then polynucleotide is administered to a subject in need thereof. In some embodiments, the at least one chemical modification stabilizes scaffold such as a tRNA scaffold. Such chemical modification may have desirable properties, such as enhanced resistance to nuclease digestion or increased binding affinity with a target genomic locus relative to a polynucleotide without the at least one chemical modification.

In some embodiments, the at least one chemical modification comprises modification to sugar moiety. In some embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In some embodiments, substituted sugars comprise more than one non-bridging sugar substituent, for example, 2'-F-5'-methyl sugar moieties.

Nucleosides comprising 2'-substituted sugar moieties are referred to as 2'-substituted nucleosides. In some embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In some embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In some embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O(CH$_2$)$_2$—O—N(CH$_3$)$_2$, —O(CH$_2$)$_2$O (CH$_2$)$_2$N(CH$_3$)$_2$, and O—CH$_2$—C(=O)—N(H)CH$_3$.

In some embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In some such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof; 4'-C(CH$_3$)(CH$_3$)—O-2' and analogs thereof; 4'-CH$_2$—N(OCH$_3$)-2' and analogs thereof; 4'-CH$_2$—O—N(CH$_3$)-2'; 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group; 4'-CH$_2$—C(H)(CH$_3$)-2'; and 4'-CH$_2$—C(=CH$_2$)-2' and analogs thereof.

In some embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Methoxy(ethyleneoxy) (4'-CH(CH$_2$OMe)-O-2') BNA (also referred to as constrained MOE or cMOE).

In some embodiments, bicyclic sugar moieties and nucleosides incorporating such bicyclic sugar moieties are further defined by isomeric configuration. For example, a nucleoside comprising a 4'-2' methylene-oxy bridge, may be in the .alpha.-L configuration or in the .beta.-D configuration. Previously, α-L-methyleneoxy (4'-CH$_2$—O-2') bicyclic nucleosides have been incorporated into antisense polynucleotides that showed antisense activity.

In some embodiments, substituted sugar moieties comprise one or more non-bridging sugar substituent and one or more bridging sugar substituent (e.g., 5'-substituted and 4'-2' bridged sugars, wherein LNA is substituted with, for example, a 5'-methyl or a 5'-vinyl group).

In some embodiments, modified sugar moieties are sugar surrogates. In some such embodiments, the oxygen atom of the naturally occurring sugar is substituted, e.g., with a sulfur, carbon or nitrogen atom. In some such embodiments, such modified sugar moiety also comprises bridging and/or non-bridging substituents as described above. For example, certain sugar surrogates comprise a 4'-sulfur atom and a substitution at the 2'-position and/or the 5' position. By way of additional example, carbocyclic bicyclic nucleosides having a 4'-2' bridge have been described.

In some embodiments, sugar surrogates comprise rings having other than 5-atoms. For example, in some embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA), and fluoro HNA (F-HNA).

In some embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In some embodiments, at least one of $q_1$, $q_2$, $q_3$, $q_4$, $q_5$, $q_6$ and $q_7$ is methyl. In some embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds.

Combinations of modifications are also provided without limitation, such as 2'-F-5'-methyl substituted nucleosides and replacement of the ribosyl ring oxygen atom with S and further substitution at the 2'-position or alternatively 5'-substitution of a bicyclic nucleic acid. In some embodiments, a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described.

In some embodiments, the present application provides polynucleotide comprising modified nucleosides. Those modified nucleotides may include modified sugars, modified nucleobases, and/or modified linkages. The specific modifications are selected such that the resulting polynucleotide possesses desirable characteristics. In some embodiments, polynucleotide comprises one or more RNA-like nucleosides. In some embodiments, polynucleotide comprises one or more DNA-like nucleotides.

In some embodiments, nucleosides of the present application comprise one or more unmodified nucleobases. In certain embodiments, nucleosides of the present application comprise one or more modified nucleobases.

In some embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and 0-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl $CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-13][1,4]benzoxazin-2 (3H)-one), carbazole cytidine ($^2$H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone.

In some embodiments, the present application provides poylnucleotide comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C (O)(NH)—S—); siloxane (—O—Si(H)$_2$—O—); and N,N'-dimethylhydrazine (—$CH_2$—N($CH_3$)—N($CH_3$)—). Modified linkages, compared to natural phosphodiester linkages, can be used to alter, typically increase, nuclease resistance of the oligonucleotide. In some embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The polynucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Additional modifications may also be made at other positions on the oligonucleotide, particularly the 3' position of the sugar on the 3' terminal nucleotide and the 5' position of 5' terminal nucleotide. For example, one additional modification of the ligand conjugated polynucleotides of the present application involves chemically linking to the oligonucleotide one or more additional non-ligand moieties or conjugates which enhance the activity, cellular distribution or cellular uptake of the oligonucleotide. Such moieties include but are not limited to lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety.

In some embodiments, the polynucleotides described herein comprise or encode at least one tRNA described herein. In some embodiments, the tRNA expressed from the polynucleotide restores the function of at least one defective tRNA in a subject who is being treated by the pharmaceutical composition described herein. In some embodiments, the at least one tRNA expressed by the polynucleotide described herein may include tRNA that encodes alanine, arginine, asparagine, aspartic acid, cysteine, glutamic acid, glutamine, glycine, histidine, hydroxyproline, isoleucine, leucin, lysine, methionine, phenylaniline, proline, pyroglutamic acid, serine, threonine, tryptophan, tyrosine, or valine. In some embodiments, the at least one tRNA expressed by the polynucleotide described herein may include tRNA that encodes arginine, tryptophan, glutamic acid, glutamine, serine, tyrosine, lysine, leucine, glycine, or cysteine. In some embodiments, the tRNA encoded by the polynucleotide described herein may restore the expression of any one of the genes described herein. In some embodiments, the tRNA encoded by the polynucleotide described herein may restore the expression of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, or FBN1.

Polypeptides

In some embodiments of the pharmaceutical compositions of the present application, the therapeutic agent (or prophylactic agent) assembled with the lipid composition comprises one or more one or more polypeptides. Some polypeptide may include enzymes such as any one of the nuclease enzymes described herein. For example, the nuclease enzyme may include from CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), eukaryotic Argonaute (eAgo), and Natronobacterium gregoryi Argonaute (NgAgo)); Adenosine deaminases acting on RNA (ADAR); CIRT, PUF, homing endonuclease, or any functional fragment thereof, any derivative thereof; any variant thereof; and any fragment thereof. In some embodiments, the nuclease enzyme may include Cas proteins such as Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. In some embodiments, the Cas protein may be complexed with a guide polynucleotide described herein to be form a CRISPR ribonucleoprotein (RNP).

The nuclease in the compositions described herein may be Cas9 (e.g., from *S. pyogenes* or *S. pneumonia*). The CRISPR enzyme can direct cleavage of one or both strands at the location of a target sequence, such as within the target sequence and/or within the complement of the target sequence of any one of the genes described herein. For example, the CRISPR enzyme may be directed and cleaved a genomic locus of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, or FBN1.

The CRISPR enzyme may be mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, the present application provides polypeptide containing one or more therapeutic proteins. The therapeutic proteins that may be included in the composition include a wide range of molecules such as cytokines, chemokines, interleukins, interferons, growth factors, coagulation factors, anti-coagulants, blood factors, bone morphogenic proteins, immunoglobulins, and enzymes. Some non-limiting examples of particular therapeutic proteins include Erythropoietin (EPO), Granulocyte colony-stimulating factor (G-CSF), Alpha-galactosidase A, Alpha-L-iduronidase, Thyrotropin α, N-acetylgalactosamine-4-sulfatase (rhASB), Dornase alfa, Tissue plasminogen activator (TPA) Activase, Glucocerebrosidase, Interferon (IF) β-1a, Interferon β-1b, Interferon γ, Interferon α, TNF-α, IL-1 through IL-36, Human growth hormone (rHGH), Human insulin (BHI), Human chorionic gonadotropin α, Darbepoetin α, Follicle-stimulating hormone (FSH), and Factor VIII.

In some embodiments, the polypeptide comprises a peptide sequence that is at least partially identical to any of the therapeutic agent (or prophylactic agent) comprising a peptide sequence. For example, the polypeptide may comprise a peptide sequence that is at least partially identical to an antibody (e.g., a monoclonal antibody) for treating a lung disease such as lung cancer.

In some embodiments, the polypeptide comprises a peptide or protein that restores the function of a defective protein in a subject being treated by the pharmaceutical composition described herein. For example, the polynucleotide comprises a peptide or protein that restores function of cystic fibrosis transmembrane conductance regulator (CFTR) protein, which may be used to rescue a subject who is afflicted with inborn error leading to the expression of the mutated CFTR protein. Other examples of the rescue may include administering to a subject in need thereof a polypeptide comprising a peptide or protein of wild type Dynein axonemal heavy chain 5, Dynein axonemal heavy chain 11, Bone morphogenic protein receptor type 2, Fumarylacetoacetate hydrolase, Phenylalanine hydroxylase, Alpha-L-iduronidase, Collagen type IV alpha 3 chain, Collagen type IV alpha 4 chain, Collagen type IV alpha 5 chain, Polycystin 1, Polycystin 2, Fibrocystin (or polyductin), Solute carrier family 3 member 1, Solute carrier family 7 member 9, Paired box gene 9, Myosin VIIA, Cadherin related 23, Usherin, Clarin 1, Gap junction beta-2 protein, Gap junction beta-6 protein, Rhodopsin, dystrophia myotonica protein kinase, Dystrophin, Sodium voltage-gated channel alpha subunit 1, Sodium voltage-gated channel beta subunit 1, Coagulation factor VIII, Coagulation factor IX, N-glycanase 1, Tumor protein p53, Palmitoyl-protein thioesterase 1, Tripeptidyl peptidase 1, Kv11.1 (alpha subunit of potassium ion channel), Palmitoyl-protein thioesterase 1, ATM serine/threonine kinase, or Fibrillin 1.

In some embodiments, the pharmaceutical composition of the present application comprises a plurality of payloads assembled with (e.g., encapsulated within) a lipid composition. The plurality of payloads assembled with the lipid composition may be configured for gene-editing or gene-expression modification. The plurality of payloads assembled with the lipid composition may comprise a polynucleotide encoding an actuator moiety (e.g., comprising a heterologous endonuclease such as Cas) or a polynucleotide encoding the actuator moiety. The plurality of payloads assembled with the lipid composition may further comprise one or more (e.g., one or two) guide polynucleotides. The plurality of payloads assembled with the lipid composition may further comprise one or more donor or template polynucleotides. The plurality of payloads assembled with the lipid composition may comprise a ribonucleoprotein (RNP).

In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is no more than (about) 20:1, no more than (about) 15:1, no more than (about) 10:1, or no more than (about) 5:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is no less than (about) 20:1, no less than (about) 15:1, no less than (about) 10:1, or no less than (about) 5:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 5:1 to about 20:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 10:1 to about 20:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 15:1 to about 20:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 5:1 to about 10:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 5:1 to about 15:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 5:1 to about 20:1. In some embodiments of the pharmaceutical composition of the present application, the therapeutic agent (or prophylactic agent) is a polynucleotide, and a molar ratio of nitrogen in the lipid composition to phosphate in the polynucleotide (N/P ratio) is from about 15:1 to about 20:1.

In some embodiments of the pharmaceutical composition of the present application, a molar ratio of the therapeutic agent to total lipids of the lipid composition is from about 1:1 to about 1:100. In some embodiments of the pharmaceutical composition of the present application, a molar ratio of the therapeutic agent to total lipids of the lipid composition is from about 1:1 to about 1:50. In some embodiments of the pharmaceutical composition of the present application, a molar ratio of the therapeutic agent to total lipids of the lipid composition is from about 50:1 to about 1:100. In some embodiments of the pharmaceutical composition of the present application, a molar ratio of the therapeutic agent to total lipids of the lipid composition is from about 1:1 to about 1:20. In some embodiments of the pharmaceutical composition of the present application, a molar ratio of the therapeutic agent to total lipids of the lipid composition is from about 20:1 to about 1:50. In some embodiments of the pharmaceutical composition of the present application, a molar ratio of the therapeutic agent to total lipids of the lipid composition is from about 50:1 to about 1:70. In some embodiments of the pharmaceutical composition of the present application, a molar ratio of the therapeutic agent to total lipids of the lipid composition is from about 70:1 to about 1:100. In some embodiments of the pharmaceutical composition of the present application, a molar ratio of the therapeutic agent to total lipids of the lipid composition is no more than (about) 1:1, no more than (about) 1:5, no more than (about) 1:10, no more than (about) 1:15, no more than (about) 1:20, no more than (about) 1:25, no more than (about) 1:30, no more than (about) 1:35, no more than (about) 1:40, no more than (about) 1:45, no more than (about) 1:50, no more than (about) 1:60, no more than (about) 1:70, no more than (about) 1:80, no more than (about) 1:90, or more than (about) 1:100. In some embodiments of the pharmaceutical composition of the present application, a molar ratio of the therapeutic agent to total lipids of the lipid composition is no less than (about) 1:1, no less than (about) 1:5, no less than (about) 1:10, no less than (about) 1:15, no less than (about) 1:20, no less than (about) 1:25, no less than (about) 1:30, no less than (about) 1:35, no less than (about) 1:40, no less than (about) 1:45, no less than (about) 1:50, no less than (about) 1:60, no less than (about) 1:70, no less than (about) 1:80, no less than (about) 1:90, or less than (about) 1:100.

In some embodiments of the pharmaceutical composition of the present application, at least (about) 85%, at least (about) 86%, at least (about) 87%, at least (about) 88%, at least (about) 89%, at least (about) 90%, at least (about) 91%, at least (about) 92%, at least (about) 93%, at least (about) 94%, at least (about) 95%, at least (about) 96%, at least (about) 97%, at least (about) 98%, at least (about) 99%, or (about) 100% of the therapeutic agent is encapsulated in particles of the lipid compositions.

In some embodiments of the pharmaceutical composition of the present application, the lipid composition comprises a plurality of particles characterized by one or more characteristics of the following: (1) a (e.g., average) size of 100 nanometers (nm) or less; (2) a polydispersity index (PDI) of no more than about 0.2; and (3) a zeta potential of −10 millivolts (mV) to 10 mV. In some embodiments of the pharmaceutical composition of the present application, the lipid composition comprises a plurality of particles with a (e.g., average) size from about 50 nanometers (nm) to about 100 nanometers (nm). In some embodiments of the pharmaceutical composition of the present application, the lipid composition comprises a plurality of particles with a (e.g., average) size from about 70 nanometers (nm) to about 100 nanometers (nm). In some embodiments of the pharmaceutical composition of the present application, the lipid composition comprises a plurality of particles with a (e.g., average) size from about 50 nanometers (nm) to about 80 nanometers (nm). In some embodiments of the pharmaceutical composition of the present application, the lipid composition comprises a plurality of particles with a (e.g., average) size from about 60 nanometers (nm) to about 80 nanometers (nm). In some embodiments of the pharmaceutical composition of the present application, the lipid composition comprises a plurality of particles with a (e.g., average) size of at most about 100 nanometers (nm), at most about 90 nanometers (nm), at most about 85 nanometers (nm), at most about 80 nanometers (nm), at most about 75 nanometers (nm), at most about 70 nanometers (nm), at most about 65 nanometers (nm), at most about 60 nanometers (nm), at most about 55 nanometers (nm), or at most about 50 nanometers (nm). In some embodiments of the pharmaceutical composition of the present application, the lipid composition comprises a plurality of particles with a (e.g., average) size of at least about 100 nanometers (nm), at least about 90 nanometers (nm), at least about 85 nanometers (nm), at least about 80 nanometers (nm), at least about 75 nanometers (nm), at least about 70 nanometers (nm), at least about 65 nanometers (nm), at least about 60 nanometers (nm), at least about 55 nanometers (nm), or at least about 50 nanometers (nm). The (e.g., average) size may be determined by size exclusion chromatography (SEC). The (e.g., average) size may be determined by spectroscopic method(s) or image-based method(s), for example, dynamic light scattering, static light scattering, multi-angle light scattering, laser light scattering, or dynamic image analysis, or a combination thereof.

In some embodiments of the pharmaceutical composition of the present application, the lipid composition comprises a plurality of particles with a polydispersity index (PDI) from about 0.05 to about 0.5. In some embodiments of the pharmaceutical composition of the present application, the lipid composition comprises a plurality of particles with a polydispersity index (PDI) from about 0.1 to about 0.5. In some embodiments of the pharmaceutical composition of the present application, the lipid composition comprises a plurality of particles with a polydispersity index (PDI) from about 0.1 to about 0.3. In some embodiments of the pharmaceutical composition of the present application, the lipid composition comprises a plurality of particles with a polydispersity index (PDI) from about 0.2 to about 0.5. In some embodiments of the pharmaceutical composition of the present application, the lipid composition comprises a plurality of particles with a polydispersity index (PDI) of no more than about 0.5, no more than about 0.4, no more than about 0.3, no more than about 0.2, no more than about 0.1, or no more than about 0.05.

In some embodiments of the pharmaceutical composition of the present application, the lipid composition comprises a plurality of particles with a negative zeta potential of −5 millivolts (mV) or less. In some embodiments of the pharmaceutical composition of the present application, the lipid composition comprises a plurality of particles with a negative zeta potential of −10 millivolts (mV) or less. In some embodiments of the pharmaceutical composition of the present application, the lipid composition comprises a plurality of particles with a negative zeta potential of −15 millivolts (mV) or less. In some embodiments of the pharmaceutical composition of the present application, the lipid composition comprises a plurality of particles with a negative zeta potential of −20 millivolts (mV) or less. In some embodiments of the pharmaceutical composition of the present application, the lipid composition comprises a plurality of particles with a negative zeta potential of −30 millivolts (mV) or less. In some embodiments, the lipid composition comprises a plurality of particles with a zeta potential of 0 millivolts (mV) or less. In some embodiments, the lipid composition comprises a plurality of particles with a zeta potential of 5 millivolts (mV) or less. In some embodiments, the lipid composition comprises a plurality of particles with a zeta potential of 10 millivolts (mV) or less. In some embodiments of the pharmaceutical composition of the present application, the lipid composition comprises a plurality of particles with a negative zeta potential of 15 millivolts (mV) or less. In some embodiments of the pharmaceutical composition of the present application, the lipid composition comprises a plurality of particles with a negative zeta potential of 20 millivolts (mV) or less.

In some embodiments of the pharmaceutical composition of the present application, the lipid composition comprises a plurality of particles with a negative zeta potential of −5 millivolts (mV) or more. In some embodiments of the pharmaceutical composition of the present application, the lipid composition comprises a plurality of particles with a negative zeta potential of −10 millivolts (mV) or more In some embodiments of the pharmaceutical composition of the present application, the lipid composition comprises a plurality of particles with a negative zeta potential of −15 millivolts (mV) or more. In some embodiments of the pharmaceutical composition of the present application, the lipid composition comprises a plurality of particles with a negative zeta potential of −20 millivolts (mV) or more. In some embodiments of the pharmaceutical composition of the present application, the lipid composition comprises a plurality of particles with a negative zeta potential of −30 millivolts (mV) or more. In some embodiments, the lipid composition comprises a plurality of particles with a zeta potential of 0 millivolts (mV) or more. In some embodiments, the lipid composition comprises a plurality of particles with a zeta potential of 5 millivolts (mV) or more. In some embodiments, the lipid composition comprises a plurality of particles with a zeta potential of 10 millivolts (mV) or more. In some embodiments of the pharmaceutical composition of the present application, the lipid composition comprises a plurality of particles with a zeta potential of 15 millivolts (mV) or more. In some embodiments of the pharmaceutical composition of the present application, the lipid composition comprises a plurality of particles with a zeta potential of 20 millivolts (mV) or more.

In some embodiments of the pharmaceutical composition of the present application, the lipid composition has an apparent ionization constant (pKa) outside a range of 6 to 7. In some embodiments of the pharmaceutical composition of the present application, the lipid composition has an apparent pKa of about 8 or higher, about 9 or higher, about 10 or higher, about 11 or higher, about 12 or higher, or about 13 or higher. In some embodiments of the pharmaceutical composition of the present application, the lipid composition has an apparent pKa of about 8 to about 13. In some embodiments of the pharmaceutical composition of the present application, the lipid composition has an apparent pKa of about 8 to about 10. In some embodiments of the pharmaceutical composition of the present application, the lipid composition has an apparent pKa of about 9 to about 11. In some embodiments of the pharmaceutical composition of the present application, the lipid composition has an apparent pKa of about 10 to about 13. In some embodiments of the pharmaceutical composition of the present application, the lipid composition has an apparent pKa of about 8 to about 12. In some embodiments of the pharmaceutical composition of the present application, the lipid composition has an apparent pKa of about 10 to about 12.

In some embodiments of the pharmaceutical composition of the present application, the SORT lipid in the pharmaceutical composition effects a delivery of the therapeutic agent characterized by one or more of the following: (a) a greater therapeutic effect in a cell of the subject compared to that achieved with a reference lipid composition; (b) a therapeutic effect in a greater plurality of cells of the subject compared to that achieved with a reference lipid composition; (c) a therapeutic effect in a first plurality of cells of a first cell type and in a greater second plurality of cells of a second cell type; and (d) a greater therapeutic effect in a first cell of a first cell type of the subject compared to that in a second cell of a second cell type of the subject. In some embodiments, the first cell type is different from the second cell type.

In some embodiments of the pharmaceutical composition of the present application, the cell is a lung cell. In some embodiments, the lung cell is a lung airway cell. Examples of lung airway cells that can be targeted by the delivery of the present application includes but is not limited to basal cell, secretory cell such as goblet cell and club cell, ciliated cell and any combination thereof. The cells may be located in the trachea, bronchi, bronchioles, or other parts of the lung or associated areas.

In some embodiments of the pharmaceutical composition of the present application, the therapeutic effect is characterized by a therapeutically effective amount of the therapeutic agent, for example, in a lung, a lung cell, a plurality of lung cells, or a lung cell type of the subject. In some embodiments, the therapeutic effect is characterized by an activity of the therapeutic agent, for example, in a lung, a lung cell, a plurality of lung cells, or a lung cell type of the subject. In some embodiments, the therapeutic effect is characterized by an effect of the therapeutic agent, for example, in a lung, a lung cell, a plurality of lung cells, or a lung cell type of the subject. In some embodiments, the greater therapeutic effect is characterized by a greater therapeutic amount of the therapeutic agent. In some embodiments, the greater therapeutic effect is characterized by a greater activity of the therapeutic agent. In some embodiments, the greater therapeutic effect is characterized by a greater effect of the therapeutic agent.

In some embodiments of the pharmaceutical composition of the present application, the SORT lipid in the pharmaceutical composition effects delivery of the therapeutic agent to the cell of the subject characterized by a greater therapeutic effect compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the pharmaceutical composition of the present application, the SORT lipid in the pharmaceutical composition achieves about 1.1-fold to about 20-fold therapeutic effect compared to that achieved with a reference lipid composition. In some embodiments, the SORT lipid achieves about 1.1-fold to about 10-fold therapeutic effect compared to that achieved with a reference lipid composition. In some embodiments, the SORT lipid achieves about 5-fold to about 10-fold therapeutic effect compared to that achieved with a reference lipid composition. In some embodiments, the SORT lipid achieves about 10-fold to about 20-fold therapeutic effect compared to that achieved with a reference lipid composition. In some embodiments, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect compared to that achieved with a reference lipid composition.

In some embodiments of the pharmaceutical composition of the present application, the SORT lipid in the pharmaceutical composition achieves about 1.1-fold to about 20-fold greater therapeutic effect compared to that achieved with a reference lipid composition in cells selected from basal cell, secretory cell such as goblet cell and club cell, ciliated cell and any combination thereof. In some embodiments, the SORT lipid achieves about 1.1-fold to about 10-fold therapeutic effect compared to that achieved with a reference lipid composition in cells selected from basal cell, secretory cell such as goblet cell and club cell, ciliated cell and any combination thereof. In some embodiments, the SORT lipid achieves about 5-fold to about 10-fold greater therapeutic effect compared to that achieved with a reference lipid composition in cells selected from basal cell, secretory cell such as goblet cell and club cell, ciliated cell and any combination thereof. In some embodiments, the SORT lipid achieves about 10-fold to about 20-fold greater therapeutic effect compared to that achieved with a reference lipid composition in cells selected from basal cell, secretory cell such as goblet cell and club cell, ciliated cell and any combination thereof. In some embodiments, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect compared to that achieved with a reference lipid composition in cells selected from basal cell, secretory cell such as goblet cell and club cell, ciliated cell and any combination thereof.

In some embodiments of the pharmaceutical composition of the present application, the SORT lipid in the pharmaceutical composition effects delivery of the therapeutic agent to cells of the subject characterized by a therapeutic effect in a greater plurality of cells compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the pharmaceutical composition of the present application, the SORT lipid in the pharmaceutical composition achieves therapeutic effect in about 1.1-fold to about 20-fold cells compared to that achieved with a reference lipid composition. In some embodiments, the SORT lipid achieves therapeutic effect in about 1.1-fold to about 10-fold cells compared to that achieved with a reference lipid composition. In some embodiments, the SORT lipid achieves therapeutic effect in about 5-fold to about 10-fold cells compared to that achieved with a reference lipid composition. In some embodiments, the SORT lipid achieves therapeutic effect in about 10-fold to about 20-fold cells compared to that achieved with a reference lipid composition. In some embodiments, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold cells compared to that achieved with a reference lipid composition.

In some embodiments of the pharmaceutical composition of the present application, the SORT lipid in the pharmaceutical composition achieves therapeutic effect in about 1.1-fold to about 20-fold cells compared to that achieved with a reference lipid composition, wherein the cells is selected from basal cell, secretory cell such as goblet cell and club cell, ciliated cell and any combination thereof. In some embodiments, the SORT lipid achieves therapeutic effect in about 1.1-fold to about 10-fold more cells compared to that achieved with a reference lipid composition, wherein the cells are selected from basal cell, secretory cell such as goblet cell and club cell, ciliated cell and any combination thereof. In some embodiments, the SORT lipid achieves therapeutic effect in about 5-fold to about 10-fold more cells compared to that achieved with a reference lipid composition, wherein the cells are selected from basal cell, secretory cell such as goblet cell and club cell, ciliated cell and any combination thereof. In some embodiments, the SORT lipid achieves therapeutic effect in about 10-fold to about 20-fold more cells compared to that achieved with a reference lipid composition, wherein the cells are selected from basal cell, secretory cell such as goblet cell and club cell, ciliated cell and any combination thereof. In some embodiments, the SORT lipid achieves therapeutic effect in about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold more cells compared to that achieved with a reference lipid composition, wherein the cells are selected from basal cell, secretory cell such as goblet cell and club cell, ciliated cell and any combination thereof.

In some embodiments of the pharmaceutical composition of the present application, the SORT lipid in the pharmaceutical composition effects delivery of the therapeutic agent to cells of the subject characterized by a therapeutic effect in a first plurality of cells of a first cell type and in a greater therapeutic effect in a second plurality of cells of a second cell type. In some embodiments, the first cell type is different from the second cell type.

In some embodiments of the pharmaceutical composition of the present application, the first cell type is a lung cell. In some embodiments, the first cell type is a lung airway cell. Examples of lung airway cell that can be targeted by the delivery of the present application includes but is not limited to basal cell, secretory cell such as goblet cell and club cell, ciliated cell and any combination thereof.

In some embodiments of the pharmaceutical composition of the present application, the second cell type is a lung cell. In some embodiments, the second cell type is a lung airway cell. Examples of lung airway cells that can be targeted by the delivery of the present application includes but is not limited to basal cell, secretory cell such as goblet cell and club cell, ciliated cell and any combination thereof. The cells may be located in the trachea, bronchi, bronchioles, or other parts of the lung or associated areas.

In some embodiments of the pharmaceutical composition of the present application, the SORT lipid in the pharmaceutical composition achieves therapeutic effect in about 1.1-fold to about 20-fold greater second plurality of cells of the second cell type compared to the first plurality of cells of the first cell type. In some embodiments, the SORT lipid achieves therapeutic effect in about 1.1-fold to about 10-fold greater second plurality of cells of the second cell type compared to the first plurality of cells of the first cell type. In some embodiments, the SORT lipid achieves therapeutic effect in about 5-fold to about 10-fold greater second plurality of cells of the second cell type compared to the first plurality of cells of the first cell type. In some embodiments, the SORT lipid achieves therapeutic effect in about 10-fold to about 20-fold greater second plurality of cells of the second cell type compared to the first plurality of cells of the first cell type. In some embodiments, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold greater second plurality of cells of the second cell type compared to the first plurality of cells of the first cell type.

In some embodiments of the pharmaceutical composition of the present application, the SORT lipid in the pharmaceutical composition effects delivery of the therapeutic agent to cells of the subject characterized by a greater therapeutic effect in a first cell of a first cell type compared to that in a second cell of a second cell type. In some embodiments, the first cell type is different from the second cell type.

In some embodiments of the pharmaceutical composition of the present application, the first cell type is a lung cell. In some embodiments, the first cell type is a lung airway cell. Examples of lung airway cells that can be targeted by the delivery of the present application includes but is not limited to basal cell, secretory cell such as goblet cell and club cell, ciliated cell and any combination thereof. The cells may be located in the trachea, bronchi, bronchioles, or other parts of the lung or associated areas.

In some embodiments of the pharmaceutical composition of the present application, the second cell type is a lung cell. In some embodiments, the second cell type is a lung airway cell. Examples of lung airway cell that can be targeted by the delivery of the present application includes but is not limited to basal cell, secretory cell such as goblet cell and club cell, ciliated cell and any combination thereof.

In some embodiments of the pharmaceutical composition of the present application, the SORT lipid in the pharmaceutical composition achieves about 1.1-fold to about 20-fold therapeutic effect in first cell of the first cell type compared to that achieved in the second cell of the second cell type. In some embodiments, the SORT lipid achieves about 1.1-fold to about 10-fold therapeutic effect in first cell of the first cell type compared to that achieved in the second cell of the second cell type. In some embodiments, the SORT lipid achieves about 5-fold to about 10-fold therapeutic effect in first cell of the first cell type compared to that achieved in the second cell of the second cell type. In some embodiments, the SORT lipid achieves about 10-fold to about 20-fold therapeutic effect in first cell of the first cell type compared to that achieved in the second cell of the second cell type. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect in first cell of the first cell type compared to that achieved in the second cell of the second cell type.

In some embodiments, the pharmaceutical composition is an aerosol composition. In some embodiments, the aerosol composition is generated by a nebulizer at a nebulization rate of no more than 70 mL/minute. In some embodiments, the aerosol composition is generated by a nebulizer at a nebulization rate of no more than 50 mL/minute. In some embodiments, the aerosol composition is generated by a nebulizer at a nebulization rate of no more than 30 mL/minute.

In some embodiments, the aerosol composition has an average droplet size from about to about 0.5 micron (μm) to about 10 μm. In some embodiments, the aerosol composition has an average droplet size from about to about 0.5 micron (μm) to about 10 μm. In some embodiments, the aerosol composition has an average droplet size from about to about 1 micron (μm) to about 10 μm. In some embodiments, the aerosol composition has an average droplet size from about to about 0.5 micron (μm) to about 5 μm. In some embodiments, the aerosol droplets are generated by a nebulizer at a nebulization rate of no more than 70 mL/minute. In some embodiments, the aerosol droplets have a mass median aerodynamic diameter (MMAD) from about 0.5 micron (μm) to about 10 μm. In some embodiments, the droplet size varies less than about 50% for a duration of about 24 hours under a storage condition. In some embodiments, droplets of said aerosol composition are characterized by a geometric standard deviation (GSD) of no more than about 3.

In some embodiments, provided herein are (e.g., pharmaceutical) compositions that comprise components that allow for an improved efficacy or outcome based on the delivery of the polynucleotide. The compositions described elsewhere herein may be more effective at delivery to a particular cell, cell type, organ, or bodily region as compared to a reference composition or compound. The compositions described elsewhere herein may be more effective at generating increase expression of a corresponding polypeptide of a delivered polynucleotide. The compositions described elsewhere herein may be more effective at generating a larger number of cells that express a corresponding polypeptide of a delivered polynucleotide. The compositions described elsewhere herein may result in an increase uptake of the polynucleotide as compared to a reference polynucleotide. The increased uptake may be result of improved stability of polynucleotide or an improved targeting of the composition to a particular cell type or organ. In some embodiments, the SORT lipid is present in an amount in the lipid composition to effect a greater expression or activity of the polynucleotide (or corresponding polypeptide of the polynucleotide) in a cell compared to that achieved with a reference lipid composition comprising 13,16,20-tris(2-hydroxydodecyl)-13,16,20,23-tetraazapentatricontane-11,25-diol ("LF92"), a phospholipid, cholesterol, and a PEG-lipid. In some embodiments, the SORT lipid is present in an amount in the lipid composition to effect at least a 1.1 fold greater expression or activity of the polynucleotide (or corresponding polypeptide of the polynucleotide) in a cell compared to that achieved with a reference lipid composition comprising LF92, a phospholipid, cholesterol, and a PEG-lipid. In some embodiments, the SORT lipid is present in an amount in the lipid composition to effect at least a 2-fold greater expression or activity of the polynucleotide (or corresponding polypeptide of the polynucleotide) in a cell compared to that achieved with a reference lipid composition comprising LF92, a phospholipid, cholesterol, and a PEG-lipid. In some embodiments, the SORT lipid is present in an amount in the lipid composition to effect at least a 5 fold greater expression or activity of the polynucleotide (or corresponding polypeptide of the polynucleotide) in a cell compared to that achieved with a reference lipid composition comprising LF92, a phospholipid, cholesterol, and a PEG-lipid. In some embodiments, the SORT lipid is present in an amount in the lipid composition to effect at least a 10-fold greater expression or activity of the polynucleotide (or corresponding polypeptide of the polynucleotide) in a cell compared to that achieved with a reference lipid composition comprising LF92, a phospholipid, cholesterol, and a PEG-lipid.

In some embodiments, the SORT lipid is present in an amount in the lipid composition to effect an expression or activity of the polynucleotide (or corresponding polypeptide of the polynucleotide) in a greater plurality of cells compared to that achieved with a reference lipid composition comprising LF92, a phospholipid, cholesterol, and a PEG-lipid. In some embodiments, the SORT lipid is present in an amount in the lipid composition to effect an expression or activity of the polynucleotide (or corresponding polypeptide of the polynucleotide) in at least a 1.1-fold greater plurality of cells compared to that achieved with a reference lipid composition comprising LF92, a phospholipid, cholesterol, and a PEG-lipid. In some embodiments, the SORT lipid is present in an amount in the lipid composition to effect an expression or activity of the polynucleotide (or corresponding polypeptide of the polynucleotide) in at least a 2-fold greater plurality of cells compared to that achieved with a reference lipid composition comprising LF92, a phospholipid, cholesterol, and a PEG-lipid. In some embodiments, the SORT lipid is present in an amount in the lipid composition to effect an expression or activity of the polynucleotide (or corresponding polypeptide of the polynucleotide) in at least a 5-fold greater plurality of cells compared to that achieved with a reference lipid composition comprising LF92, a phospholipid, cholesterol, and a PEG-lipid. In some embodiments, the SORT lipid is present in an amount in the lipid composition to effect an expression or activity of the polynucleotide (or corresponding polypeptide of the polynucleotide) in at least a 10-fold greater plurality of cells compared to that achieved with a reference lipid composition comprising LF92, a phospholipid, cholesterol, and a PEG-lipid.

In some embodiments, the SORT lipid is present in an amount in the lipid composition to effect an uptake of the polynucleotide in a greater plurality of cells compared to that achieved with a reference lipid composition comprising LF92, a phospholipid, cholesterol, and a PEG-lipid. In some embodiments, the SORT lipid is present in an amount in the lipid composition to effect an uptake of the polynucleotide in a greater amount to a cell compared to that achieved with a reference lipid composition comprising LF92, a phospholipid, cholesterol, and a PEG-lipid.

Methods

In some embodiments, provided herein in some embodiments include a method for delivery by nebulization to lung cell(s) of a subject, the method comprising: administering to said subject a (e.g., pharmaceutical) composition (such as one described herein) comprising a therapeutic agent assembled with a lipid composition, which lipid composition (such as one described herein) comprises: (i) an ionizable cationic lipid (such as one described herein); and (ii) a selective organ targeting (SORT) lipid (such as one described herein) separate from said ionizable cationic lipid, thereby delivering said therapeutic agent to said lung cell(s) of a lung of said subject. In some embodiments, the method provides a (e.g., therapeutically) effective amount or activity of said therapeutic agent in at least about 5%, 10%, 15%, or 20% lung epithelial cells of said subject. In some embodiments, the method provides a (e.g., therapeutically) effective amount or activity of said therapeutic agent in at least about 2%, 5%, or 10% lung ciliated cells of said subject. In some embodiments, the method provides a (e.g., therapeutically) effective amount or activity of said therapeutic agent in at least about 5%, 10%, 15%, or 20% lung secretory cells of said subject. In some embodiments, the method provides a (e.g., therapeutically) effective amount or activity of said therapeutic agent in at least about 5%, 10%, 15%, or 20% lung club cells of said subject. In some embodiments, the method provides a (e.g., therapeutically) effective amount or activity of said therapeutic agent in at least about 5%, 10%, 15%, or 20% lung goblet cells of said subject. In some embodiments, the method provides a (e.g., therapeutically) effective amount or activity of said therapeutic agent in at least about 5%, 10%, 15%, or 20% lung basal cells of said subject. In some embodiments, the lipid composition comprises a phospholipid. In some embodiments, the (e.g., pharmaceutical) composition comprising said therapeutic agent assembled with said lipid composition is an aerosol composition (such as one described herein).

In some embodiments, provided herein is a method for potent delivery to a cell of a subject comprising administrating to the subject the pharmaceutical composition as described in the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (iii) a selective organ targeting (SORT) lipid separate from the ionizable cationic lipid. The lipid composition may further comprise a phospholipid.

In some embodiments of the method, the cell is a lung cell. In some embodiments, the lung cell is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid effects delivery of the therapeutic agent to the cell of the subject characterized by a greater therapeutic effect compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the method, the SORT lipid achieves about 1.1-fold to about 20-fold therapeutic effect compared to that achieved with a reference lipid composition. In some embodiments of the method, the SORT lipid achieves about 1.1-fold to about 10-fold therapeutic effect compared to that achieved with a reference lipid composition. In some embodiments of the method, the SORT lipid achieves about 1.1-fold to about 5-fold therapeutic effect compared to that achieved with a reference lipid composition. In some embodiments of the method, the SORT lipid achieves about 5-fold to about 10-fold therapeutic effect compared to that achieved with a reference lipid composition. In some embodiments of the method, the SORT lipid achieves about 10-fold to about 20-fold therapeutic effect compared to that achieved with a reference lipid composition. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect compared to that achieved with a reference lipid composition.

In some embodiments of the method, the SORT lipid achieves about 1.1-fold to about 20-fold therapeutic effect compared to that achieved with a reference lipid composition in cells selected from basal cell, secretory cell such as goblet cell and club cell, ciliated cell and any combination thereof. In some embodiments of the method, the SORT lipid achieves about 1.1-fold to about 10-fold greater therapeutic effect compared to that achieved with a reference lipid composition in cells selected from basal cell, secretory cell such as goblet cell and club cell, ciliated cell and any combination thereof. In some embodiments of the method, the SORT lipid achieves about 1.1-fold to about 5-fold greater therapeutic effect compared to that achieved with a reference lipid composition in cells selected from basal cell, secretory cell such as goblet cell and club cell, ciliated cell and any combination thereof. In some embodiments of the method, the SORT lipid achieves about 10-fold to about 20-fold greater therapeutic effect compared to that achieved with a reference lipid composition in cells selected from basal cell, secretory cell such as goblet cell and club cell, ciliated cell and any combination thereof. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect compared to that achieved with a reference lipid composition in cells selected from basal cell, secretory cell such as goblet cell and club cell, ciliated cell and any combination thereof.

In some embodiments of the method, the SORT lipid effects delivery of the therapeutic agent to cells of the subject characterized by a therapeutic effect in a greater plurality of cells compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the method, the SORT lipid achieves therapeutic effect in about 1.1-fold to about 20-fold cells compared to that achieved with a reference lipid composition. In some embodiments of the method, the SORT lipid achieves therapeutic effect in about 1.1-fold to about 10-fold cells compared to that achieved with a reference lipid composition. In some embodiments of the method, the SORT lipid achieves therapeutic effect in about 1.1-fold to about 5-fold cells compared to that achieved with a reference lipid composition. In some embodiments of the method, the SORT lipid achieves therapeutic effect in about 10-fold to about 20-fold cells compared to that achieved with a reference lipid composition. In some embodiments of the method, the SORT lipid achieves therapeutic effect in at least about 1.1-fold, at least about 5-fold, at least about 10-fold, at least about 20-fold, at least about 50-fold, or at least about 100-fold cells compared to that achieved with a reference lipid composition.

In some embodiments of the method, the SORT lipid achieves therapeutic effect in about 1.1-fold to about 20-fold cells compared to that achieved with a reference lipid composition, wherein the cells are selected from basal cell, secretory cell such as goblet cell and club cell, ciliated cell and any combination thereof. In some embodiments of the method, the SORT lipid achieves therapeutic effect in about 1.1-fold to about 10-fold cells compared to that achieved with a reference lipid composition, wherein the cells are selected from basal cell, secretory cell such as goblet cell and club cell, ciliated cell and any combination thereof. In some embodiments of the method, the SORT lipid achieves therapeutic effect in about 5-fold to about 10-fold more cells compared to that achieved with a reference lipid composition, wherein the cells are selected from basal cell, secretory cell such as goblet cell and club cell, ciliated cell and any combination thereof. In some embodiments of the method, the SORT lipid achieves therapeutic effect in about 10-fold to about 20-fold more cells compared to that achieved with a reference lipid composition, wherein the cells are selected from basal cell, secretory cell such as goblet cell and club cell, ciliated cell and any combination thereof. In some embodiments of the method, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold more cells compared to that achieved with a reference lipid composition, wherein the cells is selected from basal cell, secretory cell such as goblet cell and club cell, ciliated cell and any combination thereof.

In some embodiments of the method, the pharmaceutical composition of the present application can be administrated through any suitable routes including, for example, oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

In some embodiments of the method, the pharmaceutical composition of the present application can be administered in a local rather than systemic manner, for example, via injection of the pharmaceutical composition directly into a targeted tissue, preferably in a sustained release formulation. Local delivery can be affected in various ways, depending on the tissue to be targeted.

In some embodiments of the method, aerosols containing the composition of the present application can be inhaled (for nasal, tracheal, or bronchial delivery). In some embodiments, the composition of the present application can be injected into the site of injury, disease manifestation, or pain, for example. In some embodiments, the composition of the present application can be provided in lozenges for oral, tracheal, or esophageal application. In some embodiments, the composition of the present application can be supplied in liquid, tablet or capsule form for administration to the stomach or intestines. In some embodiments, the composition of the present application can be supplied in suppository form for rectal or vaginal application. In some embodiments, the composition of the present application can even be delivered to the eye by use of creams, drops, or even injection.

In another aspect, provided herein is a method for targeted delivery to cells of a subject, comprising administrating to the subject the pharmaceutical composition as described in the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (ii) a selective organ targeting (SORT) lipid separate from the ionizable cationic lipid. The lipid composition may further comprise a phospholipid.

In some embodiments of the method, the SORT lipid effects delivery of the therapeutic agent to a greater proportion of cell types as compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11, 25-diol ("LF92"), a phospholipid, cholesterol, and a PEG-lipid.

In some embodiments of the method, the cell is a lung cell. In some embodiments, the lung cell is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid effects delivery of the therapeutic agent to cells of the subject characterized by a therapeutic effect in a first plurality of cells of a first cell type and in a greater therapeutic effect in a second plurality of cells of a second cell type. In some embodiments, the first cell type is different from the second cell type.

In some embodiments of the method, the first cell type is a lung cell. In some embodiments, the first cell type is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the second cell type is a lung cell. In some embodiments, the second cell type is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid achieves therapeutic effect in about 1.1-fold to about 20-fold greater second plurality of cells of the second cell type compared to the first plurality of cells of the first cell type. In some embodiments of the method, the SORT lipid achieves therapeutic effect in about 1.1-fold to about 10-fold greater second plurality of cells of the second cell type compared to the first plurality of cells of the first cell type. In some embodiments of the method, the SORT lipid achieves therapeutic effect in about 1.1-fold to about 5-fold greater second plurality of cells of the second cell type compared to the first plurality of cells of the first cell type. In some embodiments of the method, the SORT lipid achieves therapeutic effect in about 10-fold to about 20-fold greater second plurality of cells of the second cell type compared to the first plurality of cells of the first cell type. In some embodiments of the method, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold greater second plurality of cells of the second cell type compared to the first plurality of cells of the first cell type.

In some embodiments of the method, the SORT lipid effects delivery of the therapeutic agent to cells of the subject characterized by a greater therapeutic effect in a first cell of a first cell type compared to that in a second cell of a second cell type. In some embodiments, the first cell type is different from the second cell type.

In some embodiments of the method, the first cell type is a lung cell. In some embodiments, the first cell type is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the second cell type is a lung cell. In some embodiments, the second cell type is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid achieves about 1.1-fold to about 20-fold therapeutic effect in first cell of the first cell type compared to that achieved in the second cell of the second cell type. In some embodiments of the method, the SORT lipid achieves about 1.1-fold to about 10-fold therapeutic effect in first cell of the first cell type compared to that achieved in the second cell of the second cell type. In some embodiments of the method, the SORT lipid achieves about 5-fold to about 10-fold therapeutic effect in first cell of the first cell type compared to that achieved in the second cell of the second cell type. In some embodiments of the method, the SORT lipid achieves about 10-fold to about 20-fold therapeutic effect in first cell of the first cell type compared to that achieved in the second cell of the second cell type. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect in first cell of the first cell type compared to that achieved in the second cell of the second cell type.

In some embodiments, the delivery of the therapeutic to a cell may alter the genome, transcriptome, or expression levels. The cell may be allowed to, or able to, propagate and the alteration may be passed on to the cells generated from the cell that the therapeutic was delivered to. In this manner, the therapeutic effect may be propagated to a larger number of cells. The alteration to the genome, transcriptome or expression level may also persist in a given cell.

Basal Cells

Basal cells are derived from undifferentiated columnar epithelium in the developing airway. They are characterized by basal position in the columnar epithelium, the presence of hemidesmosomes (characterized by alpha 6 beta 4 integrins), cytokeratins 5 and 14, and the nuclear protein p63. The distribution of basal cells varies by airway level and animal species. Airways that are larger in diameter have more basal cells than airways with smaller diameters. As the airway decreases in diameter, the number of basal cells also decreases, and none are present in the terminal bronchioles.

In another aspect, provided herein is a method for delivery to basal cells of a subject, comprising administrating to the subject the pharmaceutical composition as described in the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (ii) a selective organ targeting (SORT) lipid separate from the ionizable cationic lipid. The lipid composition may further comprise a phospholipid. In some embodiments, the basal cell is a lung basal cell.

In some embodiments of the method, the method delivers the therapeutic agent to an organ or tissue of the subject to result in a therapeutic effect detectable in basal cells in the organ or tissue of the subject. In some embodiments, the method delivers the therapeutic agent to an organ or tissue of the subject to result in a therapeutic effect detectable in at least about 5%, at least about 10%, at least about 15%, at least about 20%, at least about 30%, at least about 40%, at least about 50% basal cells in the organ or tissue of the subject.

In some embodiments of the method, the organ is lung. In some embodiments, the tissue is lung tissue. In some embodiment, the tissue is lung airway tissue. In some embodiments, the method delivers the therapeutic agent to the subject's lung to result in a therapeutic effect detectable in at least about 5%, at least about 10%, at least about 15%, at least about 20%, at least about 30%, at least about 40%, at least about 50% basal cells in the subject's lung.

In some embodiments of the method, the pharmaceutical composition is administrated to the subject through any suitable delivery. In some embodiment, the pharmaceutical composition is administrated to the subject through inhalation. In some embodiments, the pharmaceutical composition is administrated to the subject through systemic administration such as intravenous administration.

Ciliated Cells

Ciliated cells are those cells with cilia structures on the cell surface. Examples of ciliated cells include but are not limited to respiratory tract ciliated cells, oviduct ciliated cell, uterine endometrial ciliated cells, rete testis ciliated cells, ductulus efferens ciliated cells, and/or ciliated ependymal cells. Human respiratory tract ciliated cells bear 200 to 300 cilia on their surface. Cilia are elongated motile cylindrical projections from the apical cell membrane, approximately 0.25 mm in diameter, that contain microtubules and cytoplasm in continuity with that of the cell. Human tracheal cilia are 5 to 8 mm long, becoming shorter in more distal airways.

The structure of a cilium is complex and consists of an axoneme, anchored by a basal body and a rootlet to the cell, and it possesses some smaller claw-like formations on its tip. The direction in which the basal body points defines the orientation of the cilium and the direction of the effective beat. The axoneme contains nine pairs of microtubules which surround a central pair of microtubules, as well as radial spokes and peripheral nexin links, which to a great extent maintain the wheel-like arrangement of the cilium. Inner and outer arms attach to the microtubules. The main structural protein of the doublets is tubulin. The arms (inner and outer) contain dynein, which is a protein classified as an ATPase. Dynein generates the force that results in a sliding movement of the microtubules, responsible for ciliary movement. It is generally accepted that the outer dynein arms are mostly responsible for beating frequency whereas the inner dynein arms together with the radial spokes and nexin links have a role in the waveform of the beating. Changes in the structural integrity of the axoneme can result in abnormal movement that ranges from stillness to aberrant patterns of hyperactivity.

In another aspect, provided herein is a method for delivery to ciliated cells of a subject, comprising administrating to the subject the pharmaceutical composition as described in the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (ii) a selective organ targeting (SORT) lipid separate from the ionizable cationic lipid. The lipid composition may further comprise a phospholipid. In some embodiments, the ciliated cell is a lung ciliated cell.

In some embodiments of the method, the method delivers the therapeutic agent to an organ or tissue of the subject to result in a therapeutic effect detectable in ciliated cells in the organ or tissue of the subject. In some embodiments, the method delivers the therapeutic agent to an organ or tissue of the subject to result in a therapeutic effect detectable in at least about 5%, at least about 10%, at least about 15%, at least about 20%, at least about 30%, at least about 40%, at least about 50% ciliated cells in the organ or tissue of the subject.

In some embodiments, the organ is lung. In some embodiments, the tissue is lung tissue. In some embodiment, the tissue is lung airway tissue. In some embodiments, the method delivers the therapeutic agent to the subject's lung to result in a therapeutic effect detectable in at least about 5%, at least about 10%, at least about 15%, at least about 20%, at least about 30%, at least about 40%, at least about 50% ciliated cells in the subject's lung.

In some embodiments of the method, the pharmaceutical composition is administrated to the subject through any suitable delivery. In some embodiment, the pharmaceutical composition is administrated to the subject through inhalation. In some embodiments, the pharmaceutical composition is administrated to the subject through systemic administration such as intravenous administration.

Secretory Cell

"Secretory cell" refers to cells specialized for secretion. These cells are usually epithelial in origin and have characteristic, well developed rough endoplasmic reticulum or, in the case of cells secreting lipids or lipid-derived products have well developed smooth endoplasmic reticulum. Examples of secretory cells include: salivary gland cells, mammary gland cells, lacrimal gland cells, creuminous gland cells, eccrine sweat gland cells, apocrine sweat gland cells, sebaceous gland cells, Bowman's gland cells, Brunner's gland cells, seminal vesicle cells, prostate gland cells, bulbourethral gland cells, Bartholin's gland cells, gland of Littre cells, endometrial cells, goblet cells of the respiratory and digestive tracts, mucous cells of the stomach, zymogenic cells of gastric glands, oxyntic cells of gastric glands, acinar cells of the pancreas, paneth cells of the small intestine, type II pneumocytes of the lung, club cells of the lung, anterior pituitary cells, cells of the intermediate pituitary, cells of the posterior pituitary, cells of the gut and respiratory tract, cells of the thyroid gland, cells of the parathyroid gland, cells of the adrenal gland, cells of the testes, cells of the ovaries, cells of the juxtaglomerular apparatus of the kidney, cells secreting extracellular matrix (e.g., epithelial cells, nonepithelial cells (such as fibroblasts, chondrocytes, osteoblasts/osteocytes, osteoprogenitor cells), and secretory cells of the immune system (e.g., Ig producing B cells, cytokine producing T cells, etc.).

In another aspect, provided herein is a method for delivery to secretory cells of a subject, comprising administrating to the subject the pharmaceutical composition as described in the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (ii) a selective organ targeting (SORT) lipid separate from the ionizable cationic lipid. The lipid composition may further comprise a phospholipid. In some embodiments, the secretory cell is a lung secretory cell.

In some embodiments of the method, the method delivers the therapeutic agent to an organ or tissue of the subject to result in a therapeutic effect detectable in secretory cells in the organ or tissue of the subject. In some embodiments, the method delivers the therapeutic agent to an organ or tissue of the subject to result in a therapeutic effect detectable in at least about 5%, at least about 10%, at least about 15%, at least about 20%, at least about 30%, at least about 40%, at least about 50% secretory cells in the organ or tissue of the subject.

In some embodiments of the method, the organ is lung. In some embodiments, the tissue is lung tissue. In some embodiment, the tissue is lung airway tissue. In some embodiments, the method delivers the therapeutic agent to the subject's lung to result in a therapeutic effect detectable in at least about 5%, at least about 10%, at least about 15%, at least about 20%, at least about 30%, at least about 40%, at least about 50% secretory cells in the subject's lung.

In some embodiments of the method, the pharmaceutical composition is administrated to the subject through any suitable delivery. In some embodiment, the pharmaceutical composition is administrated to the subject through inhalation. In some embodiments, the pharmaceutical composition is administrated to the subject through systemic administration such as intravenous administration.

Dosing Level

In another aspect, provided is high-potency dosage form of a therapeutic agent (or prophylactic agent) formulated with a selective organ targeting (SORT) lipid, the dosage form comprising a therapeutic agent (or prophylactic agent) assembled with a lipid composition as described herein. In some embodiments, the lipid composition comprises: (i) an ionizable cationic lipid; and (ii) a selective organ targeting (SORT) lipid separate from the ionizable cationic lipid. The lipid composition may further comprise a phospholipid.

In some embodiments of the high-potency dosage form of the present application, the SORT lipid is present in the dosage form in an amount sufficient to achieve a therapeutic effect at a dose of the therapeutic agent lower than that required with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the high-potency dosage form of the present application, the SORT lipid is present in the dosage form in an amount sufficient to achieve a therapeutic effect at a dose of the therapeutic agent about 1.1-fold to about 20-fold lower than that required with a reference lipid composition. In some embodiments of the high-potency dosage form of the present application, the SORT lipid is present in the dosage form in an amount sufficient to achieve a therapeutic effect at a dose of the therapeutic agent about 1.1-fold to about 10-fold lower than that required with a reference lipid composition. In some embodiments of the high-potency dosage form of the present application, the SORT lipid is present in the dosage form in an amount sufficient to achieve a therapeutic effect at a dose of the therapeutic agent about 1.1-fold to about 5-fold lower than that required with a reference lipid composition. In some embodiments of the high-potency dosage form of the present application, the SORT lipid is present in the dosage form in an amount sufficient to achieve a therapeutic effect at a dose of the therapeutic agent about 10-fold to about 20-fold lower than that required with a reference lipid composition. In some embodiments of the high-potency dosage form of the present application, the SORT lipid is present in the dosage form in an amount sufficient to achieve a therapeutic effect at a dose of the therapeutic agent at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold lower than that required with a reference lipid composition.

In some embodiments, the therapeutic agent is present in the dosage form at a dose of about 2.0, 1.5, 1.0, 0.5, 0.2, or 0.1 milligram per kilogram (mg/kg, or mpk) body weight, or of a range between (inclusive) any two of the foregoing values.

In some embodiments, the therapeutic agent is present in the dosage form at a dose of no more than about 2 milligram per kilogram (mg/kg, or mpk) body weight. In some embodiments, the therapeutic agent is present in the dosage form at a dose of no more than about 1 milligram per kilogram (mg/kg, or mpk) body weight. In some embodiments, the therapeutic agent is present in the dosage form at a dose of no more than about 0.5 milligram per kilogram (mg/kg, or mpk) body weight. In some embodiments, the therapeutic agent is present in the dosage form at a dose of no more than about 0.2 milligram per kilogram (mg/kg, or mpk) body weight. In some embodiments, the therapeutic agent is present in the dosage form at a dose of no more than about 0.1 milligram per kilogram (mg/kg, or mpk) body weight. In some embodiments, the therapeutic agent is present in the dosage form at a concentration of no more than about 5 milligram per milliliter (mg/mL).

In some embodiments, the therapeutic agent is present in the dosage form at a concentration of about 5, 4, 3, 2, 1, 0.5, 0.2, or 0.1 milligram per milliliter (mg/mL), or of a range between (inclusive) any two of the foregoing values.

In some embodiments, the therapeutic agent is present in the dosage form at a concentration of no more than about 5 milligram per milliliter (mg/mL). In some embodiments, the therapeutic agent is present in the dosage form at a concentration of no more than about 2 milligram per milliliter (mg/mL). In some embodiments, the therapeutic agent is present in the dosage form at a concentration of no more than about 1 milligram per milliliter (mg/mL). In some embodiments, the therapeutic agent is present in the dosage form at a concentration of no more than about 0.5 milligram per milliliter (mg/mL). In some embodiments, the therapeutic agent is present in the dosage form at a concentration of no more than about 0.1 milligram per milliliter (mg/mL).

Any suitable dosage form can be prepared for delivery, for example, via oral, rectal, vaginal, transmucosal, pulmonary including intratracheal or inhaled, or intestinal administration; parenteral delivery, including intramuscular, subcutaneous, intramedullary injections, as well as intrathecal, direct intraventricular, intravenous, intraperitoneal, intranasal, or intraocular injections.

In some embodiments, the dosage form can be administered in a local rather than systemic manner, for example, via injection of the pharmaceutical composition directly into a targeted tissue, preferably in a sustained release formulation. Local delivery can be affected in various ways, depending on the tissue to be targeted.

In some embodiments, the dosage form is an inhaled aerosol containing the composition of the present for nasal, tracheal, or bronchial delivery. In some embodiments, the dosage form can be provided in lozenges for oral, tracheal, or esophageal application. In some embodiments, the dosage form can be supplied in liquid, tablet or capsule form for administration to the stomach or intestines. In some embodiments, the dosage form can be supplied in suppository form for rectal or vaginal application. In some embodiments, the dosage form can be can even be delivered to the eye by use of creams, drops, or even injection.

In some embodiments, the administration of a dose of the therapeutic agent may be repeated.

Subject

Any subject in need thereof can be treated with the method of the present application. In some embodiments, the subject has been determined to likely respond to the therapeutic agent. For example, the subject may have, is suffering from, or suspected of having a disease or condition. For the example, the disease or disorder may be selected from the group consisting of genetic respiratory disease, chronic inflammatory lung disease, pulmonary fibrosis, central nervous system (CNS) disorder, immuno-deficiency, autoimmune disease, cancer, infectious disease, liver fibrosis, cirrhosis, metabolic disorder, muscular dystrophy, and viral infection. The therapeutic or prophylactic agent(s) as described elsewhere herein may be effective for providing a therapeutic effect for the subject by a variety of mechanisms, for example, via gene therapy (e.g., requiring repeated administration), altered (e.g., increased) protein production, (e.g., in vivo) chimeric antigen receptor (CAR) T-cell generation, immuno-oncology, vaccine-based approach, reactivation of tumor suppressors, or other mechanisms.

In some embodiments, the subject has been determined to have a (e.g., missense or nonsense) mutation in a target gene. In some embodiments, the mutation in the target gene is associated with a genetic disease or disorder. In some embodiments, the target gene encodes a protein selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1.

In some embodiments, the subject has been determined to exhibit an aberrant expression or activity of a protein or polynucleotide that corresponds to a target gene. In some embodiments, the aberrant expression or activity of the protein or polynucleotide is associated with a genetic disease or disorder. In some embodiments, the protein is selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1. In some embodiments, the polynucleotide encodes a protein selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1.

In some embodiments, the subject is selected from the group consisting of mouse, rat, monkey, and human. In some embodiments, the subject is a human.

In another aspect, provided herein is a method for potent delivery of a therapeutic agent (or prophylactic agent) to a cell comprising contacting the cell with the pharmaceutical composition of the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (iii) a selective organ targeting (SORT) lipid separate from the ionizable cationic lipid. The lipid composition may further comprise a phospholipid.

In some embodiments of the method, the cell is isolated from the subject. In some embodiments of the method, the cell is a cell line. In some embodiments of the method, the cell is a lung cell. In some embodiments, the lung cell is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid effects a delivery of the therapeutic agent to the cell characterized by a greater therapeutic effect compared to that achieved with a reference lipid composition. In some embodiments, the reference lipid composition does not comprise the SORT lipid. In some embodiments, the reference lipid composition does not comprise the amount of the SORT lipid. In some embodiments, the reference lipid comprises 13,16,20-tris(2-hydroxydodecyl)-13,16,20,23-tetraazapentatricontane-11,25-diol ("LF92"), a phospholipid, cholesterol, and a PEG-lipid.

In some embodiments of the method, the SORT lipid achieves about 1.1-fold to about 20-fold therapeutic effect compared to that achieved with a reference lipid composition. In some embodiments of the method, the SORT lipid achieves about 1.1-fold to about 10-fold therapeutic effect compared to that achieved with a reference lipid composition. In some embodiments of the method, the SORT lipid achieves about 1.1-fold to about 5-fold therapeutic effect compared to that achieved with a reference lipid composition. In some embodiments of the method, the SORT lipid achieves about 10-fold to about 20-fold therapeutic effect compared to that achieved with a reference lipid composition. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect compared to that achieved with a reference lipid composition.

In some embodiments of the method, the SORT lipid effects delivery of the therapeutic agent to cells of the subject characterized by a therapeutic effect in a greater plurality of cells compared to that achieved with a reference lipid composition. In some embodiments of the method, the SORT lipid achieves therapeutic effect in about 1.1-fold to about 20-fold cells compared to that achieved with a reference lipid composition. In some embodiments of the method, the SORT lipid achieves therapeutic effect in about 1.1-fold to about 10-fold cells compared to that achieved with a reference lipid composition. In some embodiments of the method, the SORT lipid achieves therapeutic effect in about 5-fold to about 10-fold cells compared to that achieved with a reference lipid composition. In some embodiments of the method, the SORT lipid achieves therapeutic effect in about 10-fold to about 20-fold cells compared to that achieved with a reference lipid composition. In some embodiments of the method, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold cells compared to that achieved with a reference lipid composition.

In another aspect, provided herein is a method for targeted delivery of a therapeutic agent (or prophylactic agent) to a cell type comprising contacting the cell with the pharmaceutical composition of the present application. In some embodiments of the method, the pharmaceutical composition comprises a therapeutic agent (or prophylactic agent) assembled with a lipid composition as described in the present application, wherein the lipid composition comprises (i) an ionizable cationic lipid; and (ii) a selective organ targeting (SORT) lipid separate from the ionizable cationic lipid. The lipid composition may further comprise a phospholipid.

In some embodiments of the method, the cell is isolated from the subject. In some embodiments of the method, the cell is a cell line. In some embodiments of the method, the cell is a lung cell. In some embodiments, the lung cell is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the SORT lipid effects delivery of the therapeutic agent to cells of the subject characterized by a therapeutic effect in a first plurality of cells of a first cell type and in a greater therapeutic effect in a second plurality of cells of a second cell type. In some embodiments, the first cell type is different from the second cell type. In some embodiments of the method, the SORT lipid achieves therapeutic effect in about 1.1-fold to about 20-fold greater second plurality of cells of the second cell type compared to the first plurality of cells of the first cell type. In some embodiments of the method, the SORT lipid achieves therapeutic effect in about 1.1-fold to about 10-fold greater second plurality of cells of the second cell type compared to the first plurality of cells of the first cell type. In some embodiments of the method, the SORT lipid achieves therapeutic effect in about 1.1-fold to about 5-fold greater second plurality of cells of the second cell type compared to the first plurality of cells of the first cell type. In some embodiments of the method, the SORT lipid achieves therapeutic effect in about 10-fold to about 20-fold greater second plurality of cells of the second cell type compared to the first plurality of cells of the first cell type. In some embodiments of the method, the SORT lipid achieves therapeutic effect in at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold greater second plurality of cells of the second cell type compared to the first plurality of cells of the first cell type.

In some embodiments of the method, the SORT lipid effects delivery of the therapeutic agent to cells of the subject characterized by a greater therapeutic effect in a first cell of a first cell type compared to that in a second cell of a second cell type. In some embodiments, the second cell type is different from the first cell type. In some embodiments of the method, the SORT lipid achieves about 1.1-fold to about 20-fold therapeutic effect in first cell of the first cell type compared to that achieved in the second cell of the second cell type. In some embodiments of the method, the SORT lipid achieves about 1.1-fold to about 10-fold therapeutic effect in first cell of the first cell type compared to that achieved in the second cell of the second cell type. In some embodiments of the method, the SORT lipid achieves about 5-fold to about 10-fold therapeutic effect in first cell of the first cell type compared to that achieved in the second cell of the second cell type. In some embodiments of the method, the SORT lipid achieves about 10-fold to about 20-fold therapeutic effect in first cell of the first cell type compared to that achieved in the second cell of the second cell type. In some embodiments of the method, the SORT lipid achieves at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 11-fold, at least about 12-fold, at least about 13-fold, at least about 14-fold, at least about 15-fold, at least about 16-fold, at least about 17-fold, at least about 18-fold, at least about 19-fold, or at least about 20-fold therapeutic effect in first cell of the first cell type compared to that achieved in the second cell of the second cell type.

In some embodiments of the method, the first cell type is a lung cell. In some embodiments, the first cell type is a lung airway cell. Examples of lung airway cells that can be targeted by the delivery of the present application includes but is not limited to basal cell, secretory cell such as goblet cell and club cell, ciliated cell and any combination thereof.

In some embodiments of the method, the second cell type is a lung cell. In some embodiments, the second cell type is a lung airway cell. Examples of lung airway cells that can be targeted by the delivery of the present application includes but is not limited to basal cell, secretory cell such as goblet cell and club cell, ciliated cell and any combination thereof.

In some embodiments, the contacting is ex vivo. In some embodiments, the contacting is in vitro. In some embodiments, the contacting is in vivo. In some embodiments, the contacting comprises administering to a subject the composition comprising the therapeutic agent assembled with the lipid composition.

The following are examples of compositions and evaluations of compositions of the disclosure. It is understood that various other embodiments may be practiced, given the general description provided above.

LIST OF EMBODIMENTS

The following list of embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A method for potent delivery to a lung cell of a subject, comprising: administering to said subject an aerosol composition comprising a therapeutic agent assembled with a lipid composition which comprises: (i) an ionizable cationic lipid; and (ii) a selective organ targeting (SORT) lipid separate from said ionizable cationic lipid, wherein (e.g., an amount of) said SORT lipid effects delivery of said therapeutic agent to said cell of said subject characterized by a (e.g., about 1.1-, 2-, 3-, 4-, 5-, 6-, 7-, 8-, 9- or 10-fold) greater therapeutic effect compared to that achieved with a reference lipid composition (e.g., without said amount of said SORT lipid); optionally, wherein said SORT lipid is selected from those set forth in Table 6, or pharmaceutically acceptable salts thereof, or a subset of the lipids and the pharmaceutically acceptable salts thereof.

Embodiment 2. A method for potent delivery to lung cells of a subject, comprising: administering to said subject an aerosol composition comprising a therapeutic agent assembled with a lipid composition which comprises: (i) an ionizable cationic lipid; and (ii) a selective organ targeting (SORT) lipid separate from said ionizable cationic lipid, wherein (e.g., an amount of) said SORT lipid effects delivery of said therapeutic agent to cells of said subject characterized by a therapeutic effect in a (e.g., about 1.1-, 2-, 3-, 4-, 5-, 6-, 7-, 8-, 9- or 10-fold) greater plurality of lung cells compared to that achieved with a reference lipid composition (e.g., without said amount of said SORT lipid); optionally, wherein said SORT lipid is selected from those set forth in Table 6, or pharmaceutically acceptable salts thereof, or a subset of the lipids and the pharmaceutically acceptable salts thereof.

Embodiment 3. A method for targeted delivery to lung cells of a subject, comprising: administering to said subject an aerosol composition comprising a therapeutic agent assembled with a lipid composition which comprises: (i) an ionizable cationic lipid; and (ii) a selective organ targeting (SORT) lipid separate from said ionizable cationic lipid, wherein (e.g., an amount of) said SORT lipid effects delivery of said therapeutic agent to a greater proportion of cell types as compared to that achieved with a reference lipid composition; optionally, wherein said SORT lipid is selected from those set forth in Table 6, or pharmaceutically acceptable salts thereof, or a subset of the lipids and the pharmaceutically acceptable salts thereof.

Embodiment 4. A method for targeted delivery to lung cells of a subject, comprising: administering to said subject an aerosol composition comprising a therapeutic agent assembled with a lipid composition which comprises: (i) an ionizable cationic lipid; and (ii) a selective organ targeting (SORT) lipid separate from said ionizable cationic lipid, wherein (e.g., an amount of) said SORT lipid effects delivery of said therapeutic agent to cells of said subject characterized by a therapeutic effect in a first plurality of lung cells of a first cell type and in a (e.g., about 1.1-, 2-, 3-, 4-, 5-, 6-, 7-, 8-, 9- or 10-fold) greater second plurality of lung cells of a second cell type; optionally, wherein said SORT lipid is selected from those set forth in Table 6, or pharmaceutically acceptable salts thereof, or a subset of the lipids and the pharmaceutically acceptable salts thereof.

Embodiment 5. A method for targeted delivery to lung cells of a subject, comprising: administering to said subject an aerosol composition comprising a therapeutic agent assembled with a lipid composition which comprises: (i) an ionizable cationic lipid; and (ii) a selective organ targeting (SORT) lipid separate from said ionizable cationic lipid, wherein (e.g., an amount of) said SORT lipid effects a delivery of said therapeutic agent to cells of said subject characterized by a (e.g., about 1.1-, 2-, 3-, 4-, 5-, 6-, 7-, 8-, 9- or 10-fold) greater therapeutic effect in a first lung cell of a first cell type of said subject compared to that in a second lung cell of a second cell type of said subject, wherein said first cell type is different from said second cell type; optionally, wherein said SORT lipid is selected from those set forth in Table 6, or pharmaceutically acceptable salts thereof, or a subset of the lipids and the pharmaceutically acceptable salts thereof.

Embodiment 6. The method of any one of Embodiments 1-5, wherein said lipid composition further comprises (iii) a phospholipid.

Embodiment 7. The method of any one of Embodiments 1-6, wherein said administration is not intravenous administration.

Embodiment 8. The method of Embodiment 7, wherein said administration comprises administering by inhalation.

Embodiment 9. The method of any one of Embodiments 1-8, wherein said lipid composition comprises said SORT lipid at a molar percentage from about 20% to about 65%.

Embodiment 10. The method of any one of Embodiments 1-9, wherein said lipid composition comprises said ionizable cationic lipid at a molar percentage from about 5% to about 30%.

Embodiment 11. The method of any one of Embodiments 1-10, wherein said lipid composition comprises said phospholipid at a molar percentage from about 8% to about 23%.

Embodiment 12. The method of any one of Embodiments 1-11, wherein said phospholipid is not an ethylphosphocholine.

Embodiment 13. The method of any one of Embodiments 1-12, wherein said lipid composition further comprises a steroid or steroid derivative.

Embodiment 14. The method of Embodiment 13, wherein said lipid composition comprises said steroid or steroid derivative at a molar percentage from about 15% to about 46%.

Embodiment 15. The method of any one of Embodiments 1-14, wherein said lipid composition further comprises a polymer-conjugated lipid (e.g., poly(ethylene glycol) (PEG)-conjugated lipid).

Embodiment 16. The method of Embodiment 15, wherein said lipid composition comprises said polymer-conjugated lipid at a molar percentage from about 0.5% to about 10%.

Embodiment 17. The method of any one of Embodiments 1-16, wherein said therapeutic agent is a polynucleotide; and wherein a molar ratio of nitrogen in said lipid composition to phosphate in said polynucleotide (N/P ratio) is no more than about 20:1.

Embodiment 18. The method of Embodiment 17, wherein said N/P ratio is from about 5:1 to about 20:1.

Embodiment 19. The method of any one of Embodiments 1-18, wherein a molar ratio of said therapeutic agent to total lipids of said lipid composition is no more than about 1:1, 1:10, 1:50, or 1:100.

Embodiment 20. The method of any one of Embodiments 1-19, wherein at least about 85% of said therapeutic agent is encapsulated in particles of said lipid compositions.

Embodiment 21. The method of any one of Embodiments 1-20, wherein said lipid composition comprises a plurality of particles characterized by one or more characteristics of the following: (1) a (e.g., average) size of 100 nanometers (nm) or less; (2) a polydispersity index (PDI) of no more than about 0.2; and (3) a zeta potential of −10 millivolts (mV) to 10 mV.

Embodiment 22. The method of any one of Embodiments 1-21, wherein said lipid composition has an apparent ionization constant (pKa) outside a range of 6 to 7.

Embodiment 23. The method of Embodiment 22, wherein said apparent pKa of said lipid composition is of about 8 or higher.

Embodiment 24. The method of Embodiment 23, wherein said apparent pKa of said lipid composition is from about 8 to about 13.

Embodiment 25. The method of any one of Embodiments 1-24, wherein said SORT lipid comprises a permanently positively charged moiety (e.g., a quaternary ammonium ion).

Embodiment 26. The method of Embodiment 25, wherein said SORT lipid comprises a counterion.

Embodiment 27. The method of any one of Embodiments 1-26, wherein said SORT lipid is a phosphocholine lipid (e.g., saturated or unsaturated).

Embodiment 28. The method of any one of Embodiments 27, wherein said SORT lipid is an ethylphosphocholine.

Embodiment 29. The method of any one of Embodiments 1-26, wherein said SORT lipid comprises a headgroup having a structural formula:

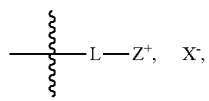

wherein L is a (e.g., biodegradable) linker; $Z^+$ is positively charged moiety (e.g., a quaternary ammonium ion); and $X^-$ is a counterion.

Embodiment 30. The method of Embodiment 29, wherein said SORT lipid has a structural formula:

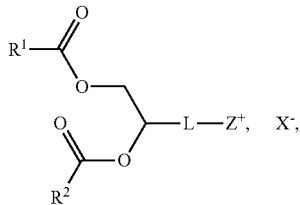

wherein $R^1$ and $R^2$ are each independently an optionally substituted $C_6$-$C_{24}$ alkyl, or an optionally substituted $C_6$-$C_{24}$ alkenyl.

Embodiment 31. The method of Embodiment 29, wherein said SORT lipid has a structural formula:

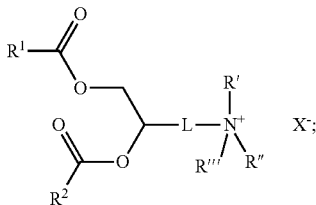

optionally, wherein L is

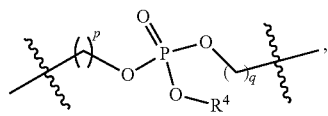

wherein: p and q are each independently 1, 2, or 3; and $R^4$ is an optionally substituted $C_1$-$C_6$ alkyl.

Embodiment 32. The method of Embodiment 29, wherein said SORT lipid has a structural formula:

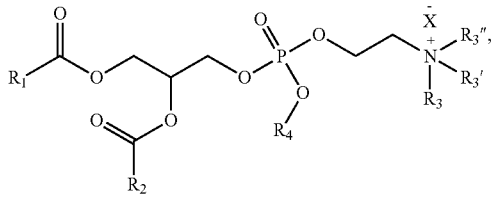

(IA)

wherein: $R_1$ and $R_2$ are each independently alkyl$_{(C8\text{-}C24)}$, alkenyl$_{(C8\text{-}C24)}$, or a substituted version of either group; $R_3$, $R_3'$, and $R_3''$ are each independently alkyl$_{(C\leq 6)}$ or substituted alkyl$_{(C\leq 6)}$; $R_4$ is alkyl$_{(C\leq 6)}$ or substituted alkyl$_{(C\leq 6)}$; and $X^-$ is a monovalent anion.

Embodiment 33. The method of any one of Embodiments 1-26, wherein said SORT lipid has a structural formula:

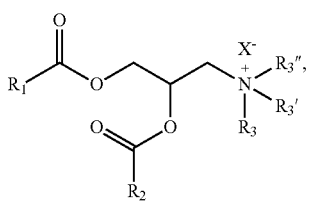

(S-I')

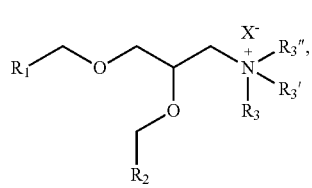

(S-III)

wherein: $R_1$ and $R_2$ are each independently alkyl$_{(C8\text{-}C24)}$, alkenyl$_{(C8\text{-}C24)}$, or a substituted version of either group; $R_3$, $R_3'$, and $R_3''$ are each independently alkyl$_{(C\leq 6)}$ or substituted alkyl$_{(C\leq 6)}$; and $X^-$ is a monovalent anion.

Embodiment 34. The method of any one of Embodiments 1-26, wherein said SORT lipid has a structural formula:

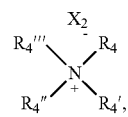

(S-II')

wherein: $R_4$ and $R_4'$ are each independently alkyl$_{(C6\text{-}C24)}$, alkenyl$_{(C6\text{-}C24)}$, or a substituted version of either group; $R_4''$ is alkyl$_{(C\leq 24)}$, alkenyl$_{(C\leq 24)}$, or a substituted version of either group; $R_4'''$ is alkyl$_{(C1\text{-}C8)}$, alkenyl$_{(C2\text{-}C8)}$, or a substituted version of either group; and $X_2$ is a monovalent anion.

Embodiment 35. The method of any one of Embodiments 1-26, wherein said SORT lipid has a structural formula:

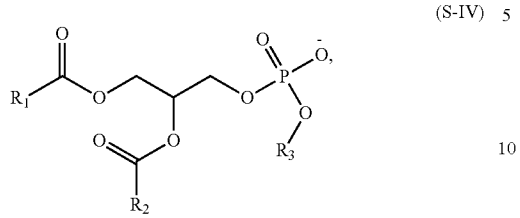

(S-IV)

wherein: $R_1$ and $R_2$ are each independently alkyl$_{(C8-C24)}$, alkenyl$_{(C8-C24)}$, or a substituted version of either group; $R_3$ is hydrogen, alkyl$_{(C\leq 6)}$, or substituted alkyl$_{(C\leq 6)}$, or —$Y_1$—$R_4$, wherein: $Y_1$ is alkanediyl$_{(C\leq 6)}$ or substituted alkanediyl$_{(C\leq 6)}$; and $R_4$ is acyloxy$_{(C\leq 8-24)}$ or substituted acyloxy$_{(C\leq 8-24)}$.

Embodiment 36. The method of any one of Embodiments 1-35, wherein the ionizable cationic lipid is a dendrimer or dendron of a generation (g) having a structural formula:

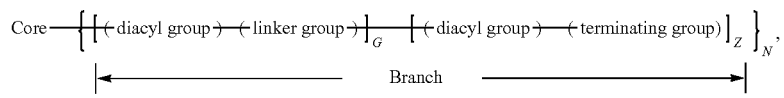

or a pharmaceutically acceptable salt thereof, wherein:
(a) the core comprises a structural formula ($X_{Core}$):

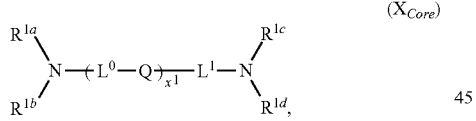

wherein:
Q is independently at each occurrence a covalent bond, —O—, —S—, —NR$^2$—, or —CR$^{3a}$R$^{3b}$—;
$R^2$ is independently at each occurrence $R^{1g}$ or -$L^2$-NR$^{1e}$R$^{1f}$;
$R^{3a}$ and $R^{3b}$ are each independently at each occurrence hydrogen or an optionally substituted (e.g., $C_1$-$C_6$, such as $C_1$-$C_3$) alkyl;
$R^{1a}$, $R^{1b}$, $R^{1c}$, $R^{1d}$, $R^{1e}$, $R^{1f}$, and $R^{1g}$ (if present) are each independently at each occurrence a point of connection to a branch, hydrogen, or an optionally substituted (e.g., $C_1$-$C_{12}$) alkyl;
$L^0$, $L^1$, and $L^2$ are each independently at each occurrence selected from a covalent bond, (e.g., $C_1$-$C_{12}$, such as $C_1$-$C_6$ or $C_1$-$C_3$) alkylene, (e.g., $C_1$-$C_{12}$, such as $C_1$-$C_8$ or $C_1$-$C_6$) heteroalkylene (e.g., $C_2$-$C_8$ alkyleneoxide, such as oligo(ethyleneoxide)), [(e.g., $C_1$-$C_6$) alkylene]-[(e.g., $C_4$-$C_6$) heterocycloalkyl]-[(e.g., $C_1$-$C_6$) alkylene], [(e.g., $C_1$-$C_6$) alkylene]-(arylene)-[(e.g., $C_1$-$C_6$) alkylene] (e.g., [(e.g., $C_1$-$C_6$) alkylene]-phenylene-[(e.g., $C_1$-$C_6$) alkylene]), (e.g., $C_4$-$C_6$) heterocycloalkyl, and arylene (e.g., phenylene); or,
alternatively, part of $L^1$ form a (e.g., $C_4$-$C_6$) heterocycloalkyl (e.g., containing one or two nitrogen atoms and, optionally, an additional heteroatom selected from oxygen and sulfur) with one of $R^{1c}$ and $R^{1d}$; and
$x^1$ is 0, 1, 2, 3, 4, 5, or 6; and
(b) each branch of the plurality (N) of branches independently comprises a structural formula ($X_{Branch}$):

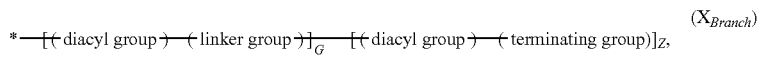

wherein:
* indicates a point of attachment of the branch to the core;
g is 1, 2, 3, or 4;
$Z = 2^{(g-1)}$;
$G = 0$, when $g = 1$; or $G = \sum_{i=0}^{i=g-2} 2^i$, when $g \neq 1$;
(c) each diacyl group independently comprises a structural formula

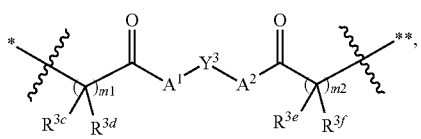

wherein:
* indicates a point of attachment of the diacyl group at the proximal end thereof;
** indicates a point of attachment of the diacyl group at the distal end thereof;
$Y^3$ is independently at each occurrence an optionally substituted (e.g., $C_1$-$C_{12}$); alkylene, an optionally substituted (e.g., $C_1$-$C_{12}$) alkenylene, or an optionally substituted (e.g., $C_1$-$C_{12}$) arenylene;
$A^1$ and $A^2$ are each independently at each occurrence —O—, —S—, or —NR$^4$—, wherein:
$R^4$ is hydrogen or optionally substituted (e.g., $C_1$-$C_6$) alkyl;
$m^1$ and $m^2$ are each independently at each occurrence 1, 2, or 3; and
$R^{3c}$, $R^{3d}$, $R^{3e}$, and $R^{3f}$ are each independently at each occurrence hydrogen or an optionally substituted (e.g., $C_1$-$C_8$) alkyl; and
(d) each linker group independently comprises a structural formula

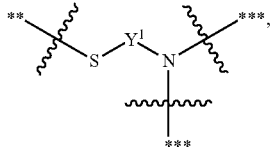

wherein:
** indicates a point of attachment of the linker to a proximal diacyl group;
*** indicates a point of attachment of the linker to a distal diacyl group;
and
$Y_1$ is independently at each occurrence an optionally substituted (e.g., $C_1$-$C_{12}$) alkylene, an optionally substituted (e.g., $C_1$-$C_{12}$) alkenylene, or an optionally substituted (e.g., $C_1$-$C_{12}$) arenylene; and
(e) each terminating group is independently selected from optionally substituted (e.g., $C_1$-$C_{18}$, such as $C_4$-$C_{18}$) alkylthiol, and optionally substituted (e.g., $C_1$-$C_{18}$, such as $C_4$-$C_{18}$) alkenylthiol.

Embodiment 37. The method of Embodiment 36, wherein $x^1$ is 0, 1, 2, or 3.

Embodiment 38. The method of Embodiment 36 or 37, wherein $R^{1a}$, $R^{1b}$, $R^{1c}$, $R^{1d}$, $R^{1e}$, $R^{1f}$, and $R^{1g}$ (if present) are each independently at each occurrence a point of connection to a branch (e.g., as indicated by *), hydrogen, or $C_1$-$C_{12}$ alkyl (e.g., $C_1$-$C_8$ alkyl, such as $C_1$-$C_6$ alkyl or $C_1$-$C_3$ alkyl), wherein the alkyl moiety is optionally substituted with one or more substituents each independently selected from —OH, $C_4$-$C_8$ (e.g., $C_4$-$C_6$) heterocycloalkyl (e.g., piperidinyl (e.g.)

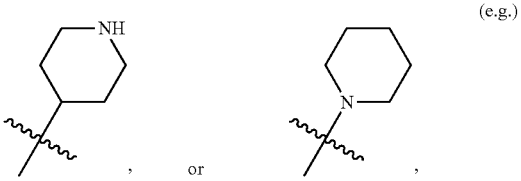 [SMILES: *C1CCNCC1 ; *N1CCCCC1]

, or ,

N—($C_1$-$C_3$ alkyl)-piperidinyl

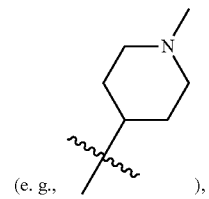

(e. g., ), piperazinyl

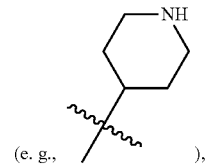

(e. g., ),

N—($C_1$-$C_3$ alkyl)-piperadizinyl

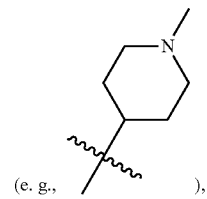

(e. g., ), morpholinyl

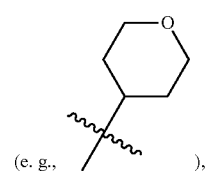

(e. g., ),

N-pyrrolidinyl

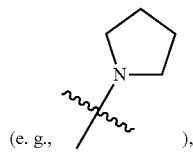

(e. g., ), pyrrolidinyl

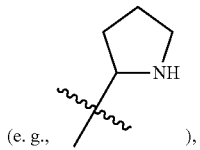

(e. g., ), or N—(C₁-C₃ alkyl)-pyrrolidinyl

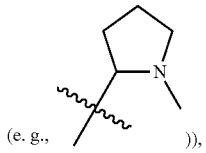 [SMILES: *C1CCCN1C]

(e. g., )), and C₃-C₅ heteroaryl (e.g., imidazolyl

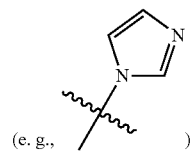 [SMILES: *n1ccnc1]

(e. g., )

or pyridinyl

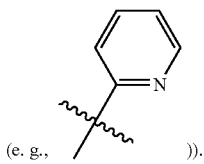

(e. g., )).

Embodiment 39. The method of Embodiment 38, wherein $R^{1a}$, $R^{1b}$, $R^{1c}$, $R^{1d}$, $R^{1e}$, $R^{1f}$, and $R^{1g}$ (if present) are each independently at each occurrence a point of connection to a branch (e.g., as indicated by *), hydrogen, or $C_1$-$C_{12}$ alkyl (e.g., $C_1$-$C_8$ alkyl, such as $C_1$-$C_6$ alkyl or $C_1$-$C_3$ alkyl), wherein the alkyl moiety is optionally substituted with one substituent —OH.

Embodiment 40. The method of any one of Embodiments 36-39, wherein $R^{3a}$ and $R^{3b}$ are each independently at each occurrence hydrogen.

Embodiment 41. The method of any one of Embodiments 36-40, wherein the plurality (N) of branches comprises at least 3 (e.g., at least 4, or at least 5) branches.

Embodiment 42. The method of any one of Embodiments 36-41, wherein g=1; G=0; and Z=1.

Embodiment 43. The method of Embodiment 42, wherein each branch of the plurality of branches comprises a structural formula *-(diacyl group)-(terminating group).

Embodiment 44. The method of any one of Embodiments 36-41, wherein g=2; G=1; and Z=2.

Embodiment 45. The method of Embodiment 44, wherein each branch of the plurality of branches comprises a structural formula

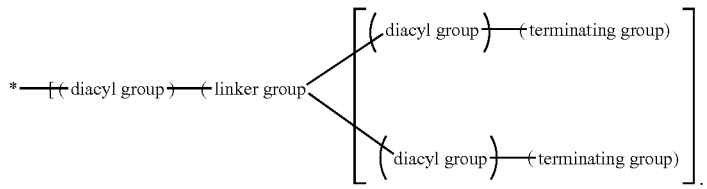

Embodiment 46. The method of any one of Embodiments 36-45, wherein the core comprises a structural formula:

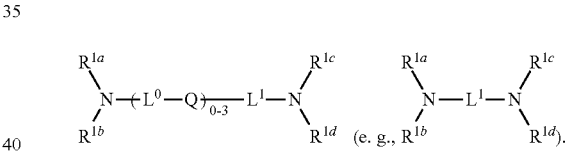

Embodiment 47. The method of any one of Embodiments 36-45, wherein the core comprises a structural formula:

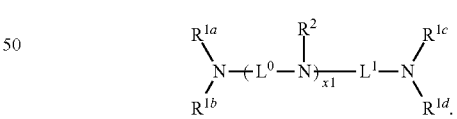

Embodiment 48. The method of Embodiment 47, wherein the core comprises a structural formula:

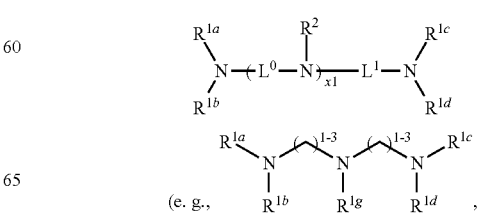

-continued

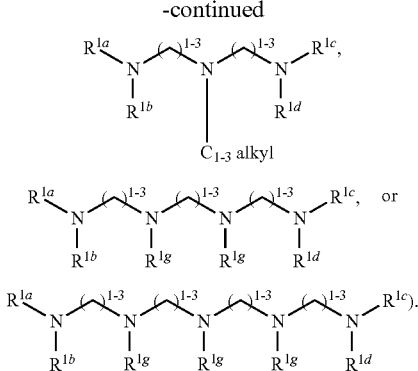

Embodiment 49. The method of Embodiment 47, wherein the core comprises a structural formula:

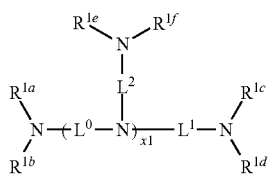

(e. g.,

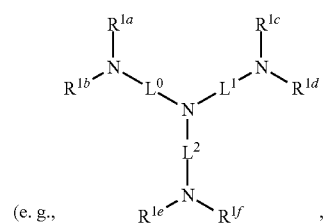

such as

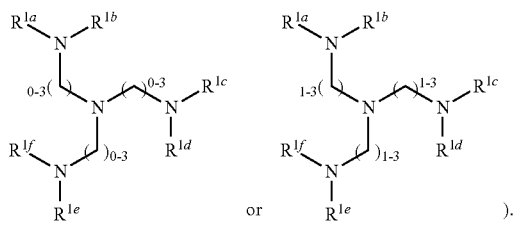

Embodiment 50. The method of any one of Embodiments 36-45, wherein the core comprises a structural formula:

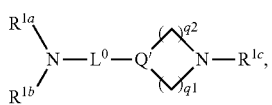

wherein Q' is $-NR^2-$ or $-CR^{3a}R^{3b}-$; $q^1$ and $q_2$ are each independently 1 or 2.

Embodiment 51. The method of Embodiment 50, wherein the core comprises a structural formula:

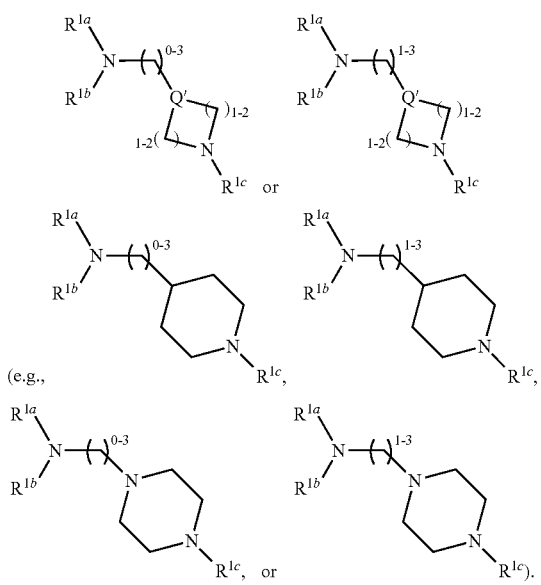

Embodiment 52. The method of any one of Embodiments 36-45, wherein the core comprises a structural formula

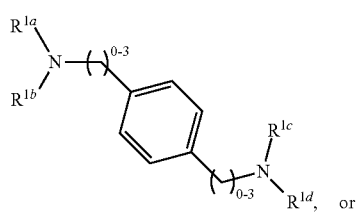

-continued

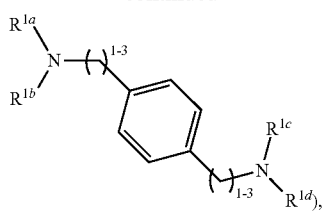

wherein ring A is an optionally substituted aryl or an optionally substituted (e.g., $C_3$-$C_{12}$, such as $C_3$-$C_5$) heteroaryl.

Embodiment 53. The method of any one of Embodiments 36-45, wherein the core comprises has a structural formula

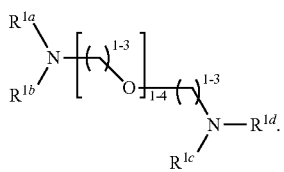

Embodiment 54. The method of any one of Embodiments 36-45, wherein the core comprises a structural formula selected from the group consisting of:

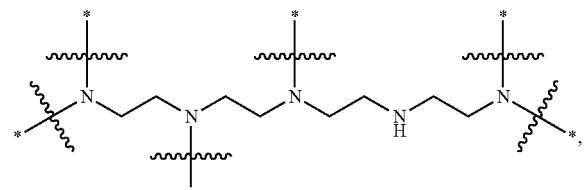

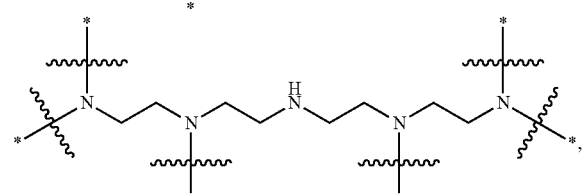

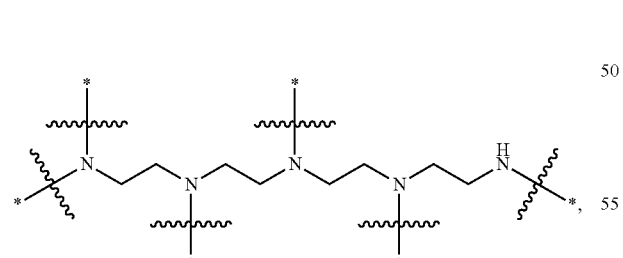

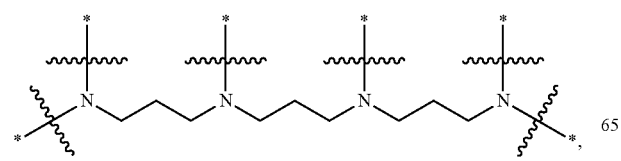

-continued

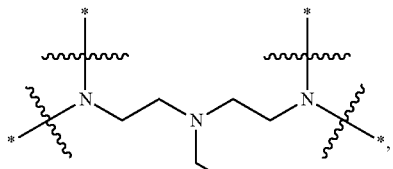

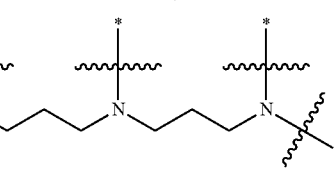

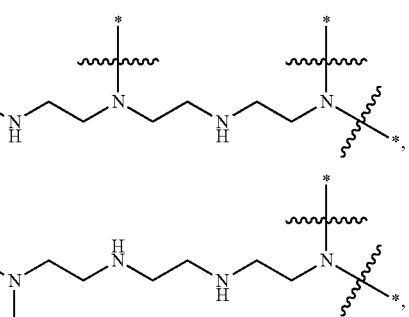

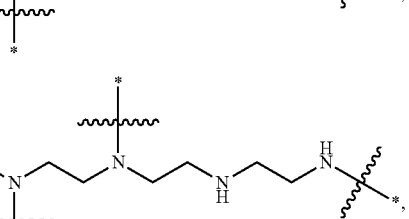

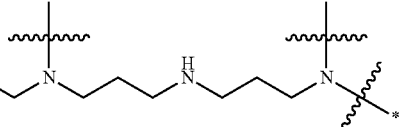

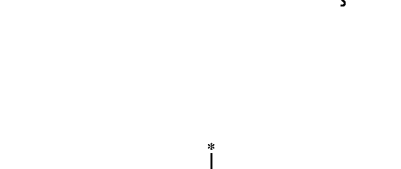

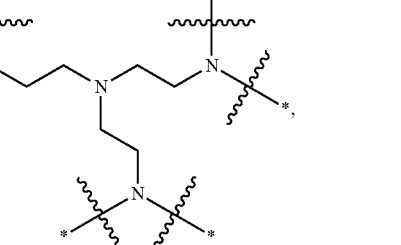

-continued
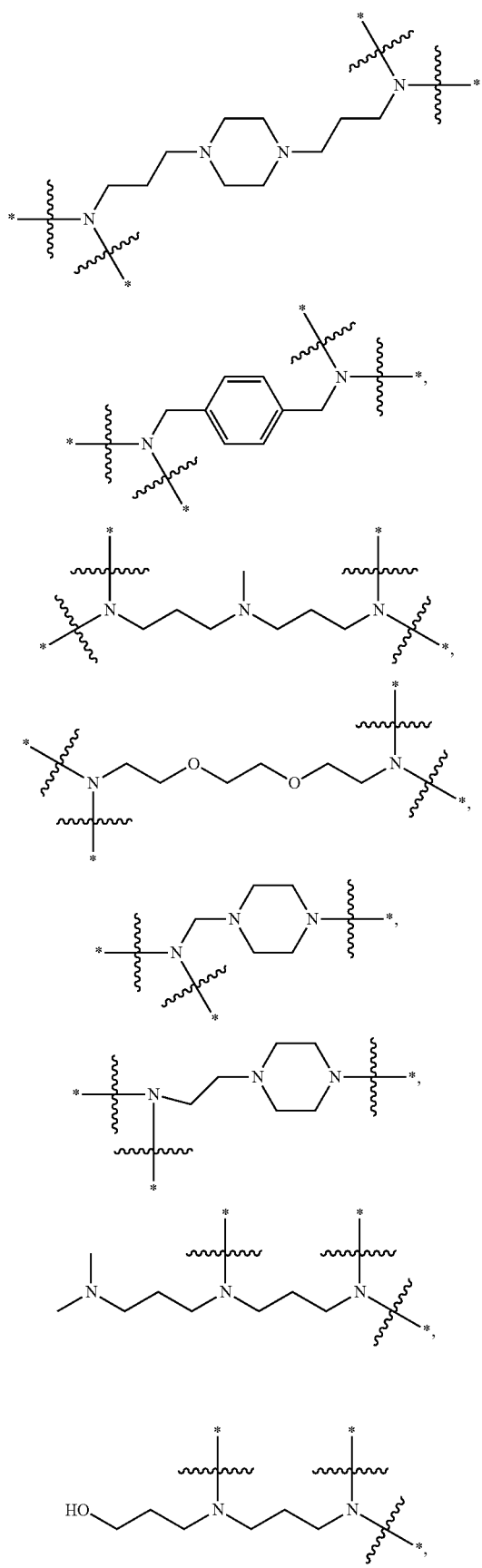
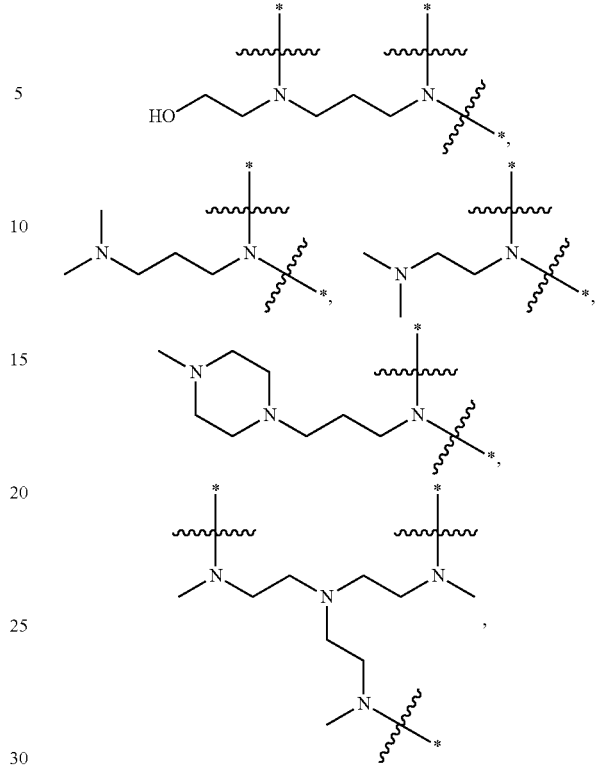
and pharmaceutically acceptable salts thereof, wherein * indicates a point of attachment of the core to a branch of the plurality of branches.
Embodiment 55. The method of any one of Embodiments 36-45, wherein the core comprises a structural formula selected from the group consisting of:
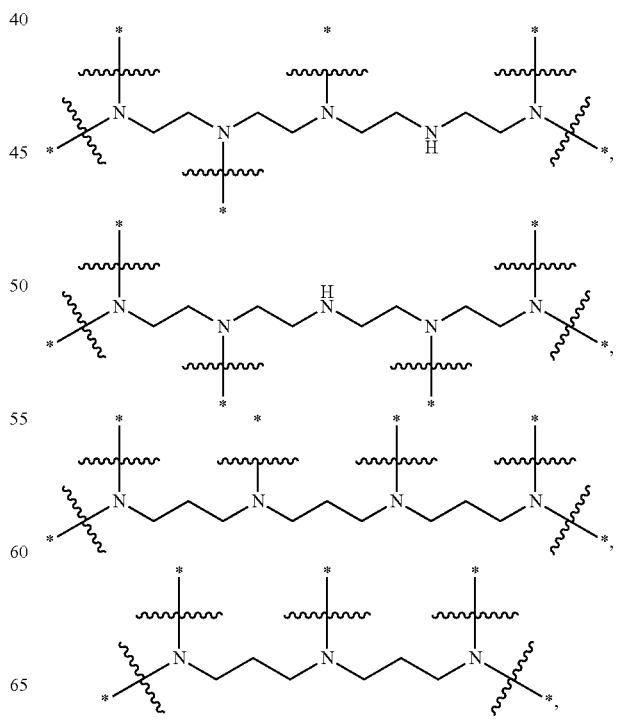

225

-continued

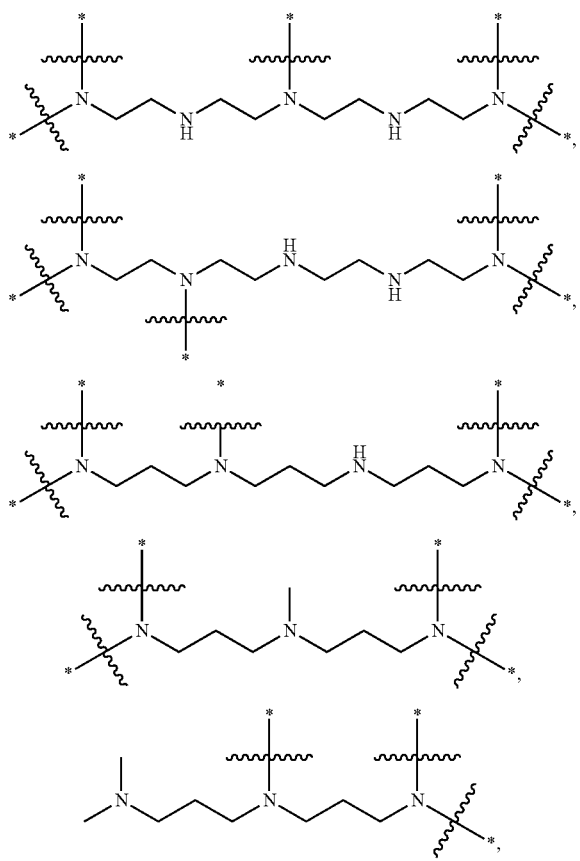

and pharmaceutically acceptable salts thereof, wherein * indicates a point of attachment of the core to a branch of the plurality of branches.

Embodiment 56. The method of any one of Embodiments 36-45, wherein the core comprises a structural formula selected from the group consisting of:

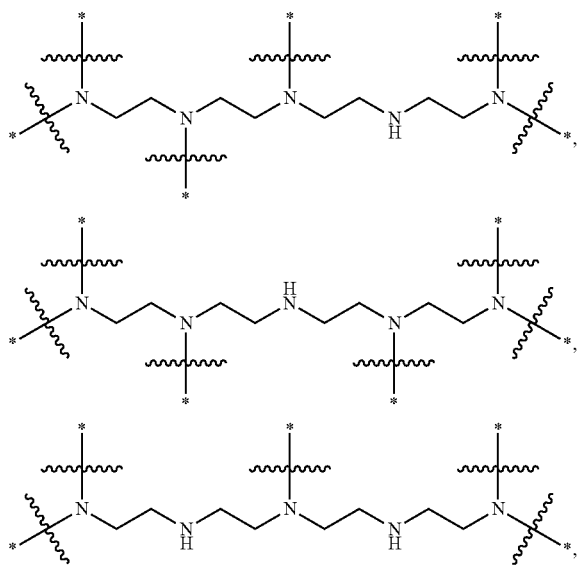

226

-continued

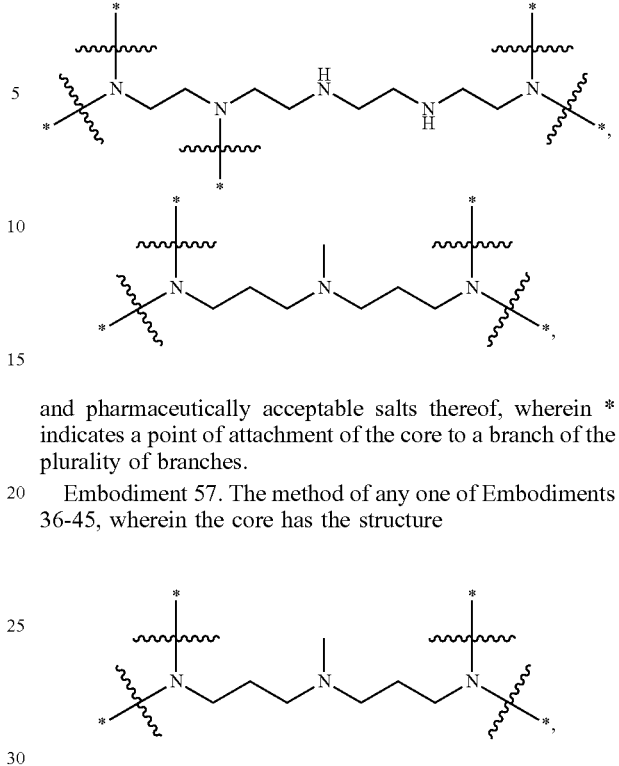

and pharmaceutically acceptable salts thereof, wherein * indicates a point of attachment of the core to a branch of the plurality of branches.

Embodiment 57. The method of any one of Embodiments 36-45, wherein the core has the structure

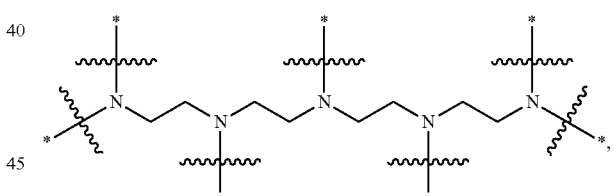

wherein * indicates a point of attachment of the core to a branch of the plurality of branches or H, wherein at least 2 (e.g., at least 3, or at least 4) branches are attached to the core.

Embodiment 58. The method of any one of Embodiments 36-45, wherein the core has the structure wherein * indicates a point of attachment of the core to a branch of the plurality of branches or H, wherein at least 4 (e.g., at least 5, or at least 6) branches are attached to the core.

Embodiment 59. The method of any one of Embodiments 36-58, wherein $A^1$ is —O— or —NH—.

Embodiment 60. The method of Embodiment 59, wherein $A^1$ is —O—.

Embodiment 61. The method of any one of Embodiments 36-60, wherein $A^2$ is —O— or —NH—.

Embodiment 62. The method of Embodiment 61, wherein $A^2$ is —O—.

Embodiment 63. The method of any one of Embodiments 36-62, wherein $Y^3$ is $C_1$-$C_{12}$ (e.g., $C_1$-$C_6$, such as $C_1$-$C_3$) alkylene.

Embodiment 64. The method of any one of Embodiments 36-63, wherein the diacyl group independently at each occurrence comprises a structural formula

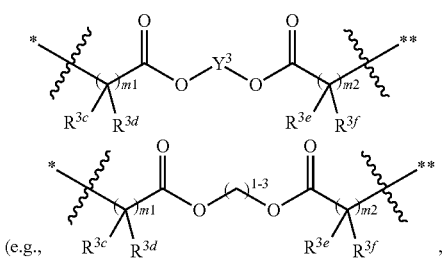

(e.g., 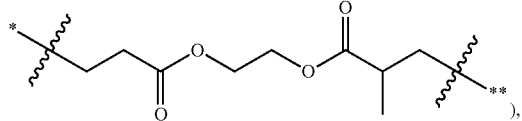), such as

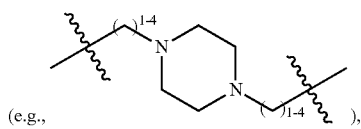

optionally wherein $R^{3c}$, $R^{3d}$, $R^{3e}$, and $R^{3f}$ are each independently at each occurrence hydrogen or $C_1$-$C_3$ alkyl.

Embodiment 65. The method of any one of Embodiments 36-64, wherein $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as —($CH_2CH_2O$)$_{1-4}$—($CH_2CH_2$)—), [($C_1$-$C_4$) alkylene]-[($C_4$-$C_6$) heterocycloalkyl]-[($C_1$-$C_4$) alkylene]

(e.g., 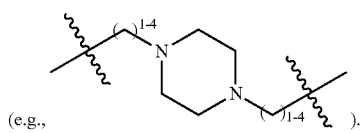), and [($C_1$-$C_4$) alkylene]-phenylene-[($C_1$-$C_4$) alkylene]

(e.g., 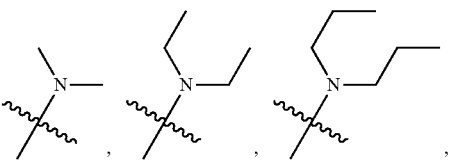).

Embodiment 66. The method of Embodiment 65, wherein $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-.

Embodiment 67. The method of Embodiment 65, wherein $L^0$, $L^1$, and $L^2$ are each independently at each occurrence $C_1$-$C_6$ alkylene (e.g., $C_1$-$C_3$ alkylene).

Embodiment 68. The method of Embodiment 65, wherein $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$—($C_1$-$C_3$ alkylene)).

Embodiment 69. The method of Embodiment 65, wherein $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene] (e.g., —($C_1$-$C_3$ alkylene)-phenylene-($C_1$-$C_3$ alkylene)-) and [($C_1$-$C_4$) alkylene]-[($C_4$-$C_6$) heterocycloalkyl]-[($C_1$-$C_4$) alkylene] (e.g., —($C_1$-$C_3$ alkylene)-piperazinyl-($C_1$-$C_3$ alkylene)-).

Embodiment 70. The method of any one of Embodiments 36-69, wherein each terminating group is independently $C_1$-$C_{18}$ (e.g., $C_4$-$C_{18}$) alkenylthiol or $C_1$-$C_{18}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —$NHCH_2CH_2CH_2CH_3$) or $C_1$-$C_8$ di-alkylamino (such as

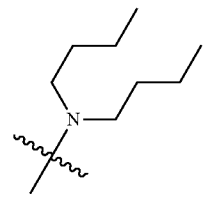

)), $C_4$-$C_6$ N-heterocycloalkyl (e.g., N-pyrrolidinyl

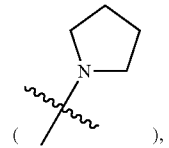

( ),

N-piperidinyl

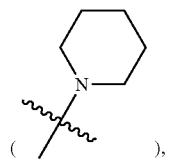

( ),

N-azepanyl

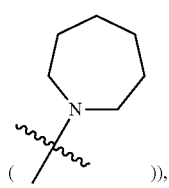

( )),

—OH, —C(O)OH, —C(O)N($C_1$-$C_3$ alkyl)-($C_1$-$C_6$ alkylene)-($C_1$-$C_{12}$ alkylamino (e.g., mono- or di-alkylamino))

(e.g., 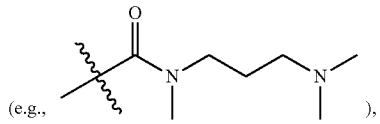 [SMILES: *C(=O)N(C)CCCN(C)C] ),

—C(O)N($C_1$-$C_3$ alkyl)-($C_1$-$C_6$ alkylene)-($C_4$-$C_6$ N-heterocycloalkyl)

(eg., 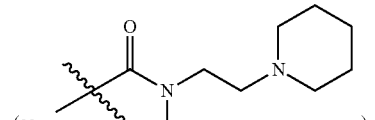 ),

—C(O)—($C_1$-$C_{12}$ alkylamino (e.g., mono- or di-alkylamino)), and (e.g., 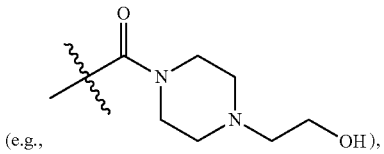 ), —C(O)—($C_4$-$C_6$ N-heterocycloalkyl) (e.g., OH), wherein the $C_4$-$C_6$ N-heterocycloalkyl moiety of any of the preceding substituents is optionally substituted with $C_1$-$C_3$ alkyl or $C_1$-$C_3$ hydroxyalkyl.

Embodiment 71. The method of Embodiment 70, wherein each terminating group is independently $C_1$-$C_{18}$ (e.g., $C_4$-$C_{18}$) alkylthiol, wherein the alkyl moiety is optionally substituted with one or more (e.g., one) substituents each independently selected from $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —NHCH$_2$CH$_2$CH$_2$CH$_3$) or $C_1$-$C_8$ di-alkylamino (such as

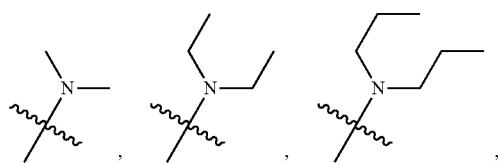,

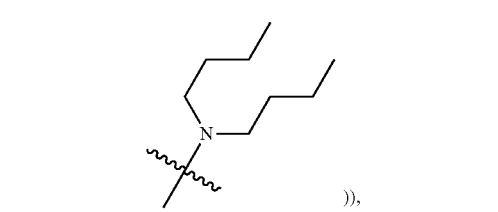 )), $C_4$-$C_6$ N-heterocycloalkyl (e.g., N-pyrrolidinyl ( 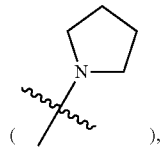 ), N-piperidinyl ( 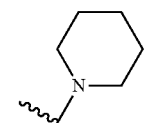 ), N-azepanyl ( 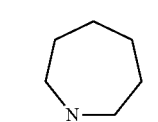 )), —OH, —C(O)OH, —C(O)N($C_1$-$C_3$ alkyl)-($C_1$-$C_6$ alkylene)-($C_1$-$C_{12}$ alkylamino (e.g., mono- or di-alkylamino))

(e.g., 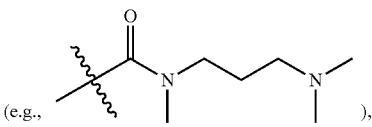 [SMILES: *C(=O)N(C)CCCN(C)C] ),

—C(O)N($C_1$-$C_3$ alkyl)-($C_1$-$C_6$ alkylene)-($C_4$-$C_6$ N-heterocycloalkyl)

(eg., 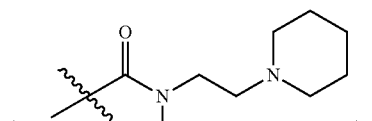 ), and —C(O)—($C_4$-$C_6$ N-heterocycloalkyl)

(e.g., 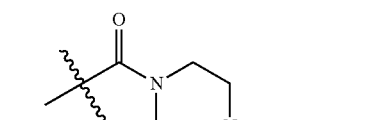 ), wherein the $C_4$-$C_6$ N-heterocycloalkyl moiety of any of the preceding substituents is optionally substituted with $C_1$-$C_3$ alkyl or $C_1$-$C_3$ hydroxyalkyl.

Embodiment 72. The method of Embodiment 71, wherein each terminating group is independently $C_1$-$C_{18}$ (e.g., $C_4$-$C_{18}$) alkylthiol, wherein the alkyl moiety is optionally substituted with one substituent —OH.

Embodiment 73. The method of Embodiment 71, wherein each terminating group is independently $C_1$-$C_{18}$ (e.g., $C_4$-$C_{18}$) alkylthiol, wherein the alkyl moiety is optionally substituted with one substituent selected from $C_1$-$C_{12}$ (e.g., $C_1$-$C_8$) alkylamino (e.g., $C_1$-$C_6$ mono-alkylamino (such as —NHCH$_2$CH$_2$CH$_2$CH$_3$) or $C_1$-$C_8$ di-alkylamino (such as

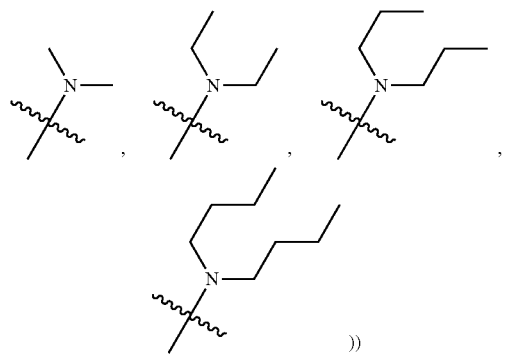

and $C_4$-$C_6$ N-heterocycloalkyl (e.g., N-pyrrolidinyl

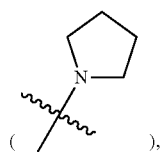

N-piperidinyl

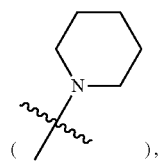

N-azepanyl

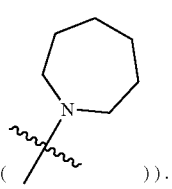

Embodiment 74. The method of Embodiment 70, wherein each terminating group is independently $C_1$-$C_{18}$ (e.g., $C_4$-$C_{18}$) alkenylthiol or $C_1$-$C_{18}$ (e.g., $C_4$-$C_{18}$) alkylthiol.

Embodiment 75. The method of Embodiment 72 or 74, wherein each terminating group is independently $C_1$-$C_{18}$ (e.g., $C_4$-$C_{18}$) alkylthiol.

Embodiment 76. The method of any one of Embodiments 36-69, wherein each terminating group is independently selected from those set forth in Table 3 or a subset thereof; or wherein each terminating group is independently selected from the group consisting of:

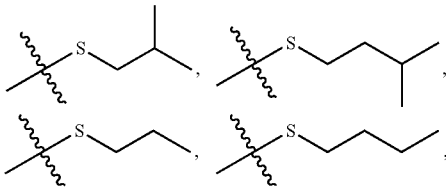

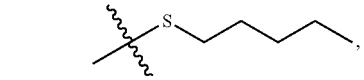

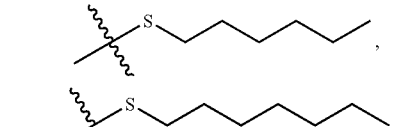

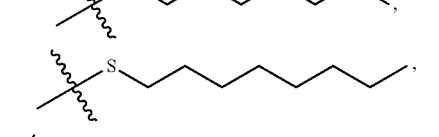

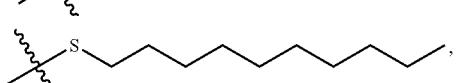

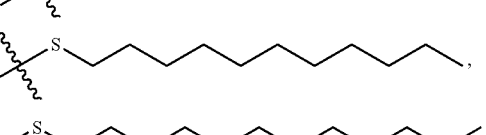

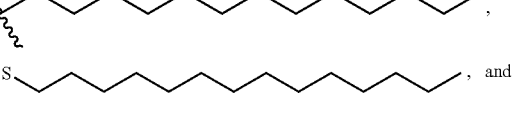

Embodiment 77. The method of any one of Embodiments 1-35, wherein the ionizable cationic lipid is selected from those set forth in Table 4 or Table 5, or pharmaceutically acceptable salts thereof, or a subset of the lipids and the pharmaceutically acceptable salts thereof.

Embodiment 78. The method of any one of Embodiments 1-77, wherein said subject has been determined to likely respond to said therapeutic agent.

Embodiment 79. The method of any one of Embodiments 1-78, wherein said subject has been determined to have a (e.g., missense or nonsense) mutation in a target gene.

Embodiment 80. The method of Embodiment 79, wherein said mutation in said target gene is associated with a genetic disease or disorder.

Embodiment 81. The method of any one of Embodiments 1-80, wherein said subject has been determined to exhibit an aberrant expression or activity of a protein or polynucleotide that corresponds to a target gene.

Embodiment 82. The method of Embodiment 81, wherein said aberrant expression or activity of said protein or polynucleotide is associated with a genetic disease or disorder.

Embodiment 83. The method of any one of Embodiments 1-82, wherein said subject is selected from the group consisting of mouse, rat, monkey, and human.

Embodiment 84. The method of Embodiment 83, wherein said subject is a human.

Embodiment 85. The method of any one of Embodiments 1-84, wherein said therapeutic agent comprises a compound, a polynucleotide, a polypeptide, or a combination thereof.

Embodiment 86. The method of Embodiment 85, wherein said therapeutic agent comprises a small interfering ribonucleic acid (siRNA), a short hairpin RNA (shRNA), a micro-ribonucleic acid (miRNA), a primary micro-ribonucleic acid (pri-miRNA), a long non-coding RNA (lncRNA), a messenger ribonucleic acid (mRNA), a clustered regularly interspaced short palindromic repeats (CRISPR) related nucleic acid, a CRISPR-RNA (crRNA), a single guide ribonucleic acid (sgRNA), a trans-activating CRISPR ribonucleic acid (tracrRNA), a plasmid deoxyribonucleic acid (pDNA), a transfer ribonucleic acid (tRNA), an antisense oligonucleotide (ASO), an antisense ribonucleic acid (RNA), a guide ribonucleic acid, deoxyribonucleic acid (DNA), a double stranded deoxyribonucleic acid (dsDNA), a single stranded deoxyribonucleic acid (ssDNA), a single stranded ribonucleic acid (ssRNA), a double stranded ribonucleic acid (dsRNA), a CRSIPR-associated (Cas) protein, or a combination thereof.

Embodiment 87. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 5%, 10%, 15%, or 20% lung epithelial cells of said subject.

Embodiment 88. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 2%, 5%, or 10% lung ciliated cells of said subject.

Embodiment 89. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 5%, 10%, 15%, or 20% lung secretory cells of said subject.

Embodiment 90. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 5%, 10%, 15%, or 20% lung club cells of said subject.

Embodiment 91. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 5%, 10%, 15%, or 20% lung goblet cells of said subject.

Embodiment 92. The method of Embodiment 86, wherein said therapeutic agent comprises a heterologous messenger ribonucleotide (mRNA); and wherein said administration results in an expression, activity, or effect of a protein encoded by said heterologous mRNA detectable in at least about 5%, 10%, 15%, or 20% lung basal cells of said subject.

Embodiment 93. The method of any one of Embodiments 87-92, wherein said protein is any one selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1.

Embodiment 94. The method of any one of Embodiments 87-92, wherein said protein corresponds to a target gene in a lung cell (e.g., a lung epithelial cell, a lung ciliated cell, a lung secretory cell, a lung club cell, a lung goblet cell, or a lung basal cell) of said subject.

Embodiment 95. The method of any one of Embodiment 87-92, wherein an expression of said heterologous mRNA produces a functional variant of said protein.

Embodiment 96. The method of any one of Embodiment 87-92, wherein an expression of said heterologous mRNA increases an amount of a functional variant of said protein as compared to an amount of said functional variant of said protein generated in absence of said administration.

Embodiment 97. The method of Embodiment 86, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 5%, 10%, 15%, or 20% lung epithelial cells of said subject.

Embodiment 98. The method of Embodiment 86 or 97, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 2%, 5%, or 10% lung ciliated cells of said subject.

Embodiment 99. The method of any one of Embodiments 86 and 97-98, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 5%, 10%, 15%, or 20% lung secretory cells of said subject.

Embodiment 100. The method of any one of Embodiments 86 and 97-99, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 5%, 10%, 15%, or 20% lung club cells of said subject.

Embodiment 101. The method of any one of Embodiments 86 and 97-100, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 5%, 10%, 15%, or 20% lung goblet cells of said subject.

Embodiment 102. The method of any one of Embodiments 86 and 97-101, wherein said therapeutic agent comprises a heterologous transfer ribonucleotide (tRNA) that introduces an amino acid into a growing peptide chain of a protein of a target gene (e.g., at a position corresponding to a mutation in said target gene encoding said protein); and wherein said administration results in an expression or activity of said protein detectable in at least about 5%, 10%, 15%, or 20% lung basal cells of said subject.

Embodiment 103. The method of any one of Embodiments 97-102, wherein said protein is any one selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1.

Embodiment 104. The method of any one of Embodiments 97-102, wherein said target gene is present in a lung cell (e.g., a lung epithelial cell, a lung ciliated cell, a lung secretory cell, a lung club cell, a lung goblet cell, or a lung basal cell) of said subject.

Embodiment 105. The method of any one of Embodiments 97-102, wherein said tRNA reduces an amount of a non-functional variant of said protein in said cell as compared to an amount of said non-functional variant of said protein generated in absence of said contacting.

Embodiment 106. The method of Embodiment 85 or 86, wherein said therapeutic agent comprises a heterologous polypeptide comprising an actuator moiety, which actuator moiety is configured to complex with a target polynucleotide corresponding to a target gene; and wherein said administration results in a modified expression or activity of said target gene detectable in at least about 5%, 10%, 15%, or 20% lung epithelial cells of said subject, in at least about 2%, 5%, or 10% lung ciliated cells of said subject, in at least about 5%, 10%, 15%, or 20% lung secretory cells of said subject, in at least about 5%, 10%, 15%, or 20% lung club cells of said subject, in at least about 5%, 10%, 15%, or 20% lung goblet cells of said subject, or in at least about 5%, 10%, 15%, or 20% lung basal cells of said subject.

Embodiment 107. The method of Embodiment 86 or 106, wherein said therapeutic agent comprises a heterologous polynucleotide encoding an actuator moiety, which actuator moiety is configured to complex with a target polynucleotide corresponding to a target gene; and wherein said administration results in a modified expression or activity of said target gene detectable in at least about 5%, 10%, 15%, or 20% lung epithelial cells of said subject, in at least about 2%, 5%, or 10% lung ciliated cells of said subject, in at least about 5%, 10%, 15%, or 20% lung secretory cells of said subject, in at least about 5%, 10%, 15%, or 20% lung club cells of said subject, in at least about 5%, 10%, 15%, or 20% lung goblet cells of said subject, or in at least about 5%, 10%, 15%, or 20% lung basal cells of said subject.

Embodiment 108. The method of Embodiment 106 or 107, wherein said heterologous polynucleotide encodes a guide polynucleotide configured to direct said actuator moiety to said target polynucleotide.

Embodiment 109. The method of Embodiment 106 or 107, wherein said actuator moiety comprises a heterologous endonuclease or a fragment thereof (e.g., directed by a guide polynucleotide to specifically bind said target polynucleotide).

Embodiment 110. The method of Embodiment 109, wherein said heterologous endonuclease is (1) part of a ribonucleoprotein (RNP) and (2) complexed with said guide polynucleotide.

Embodiment 111. The method of Embodiment 109, wherein said heterologous endonuclease is part of a clustered regularly interspaced short palindromic repeats (CRISPR)/CRISPR-associated (Cas) protein complex.

Embodiment 112. The method of Embodiment 109, wherein said heterologous endonuclease is a clustered regularly interspaced short palindromic repeats (CRISPR)-associated (Cas) endonuclease.

Embodiment 113. The method of Embodiment 109, wherein said heterologous endonuclease is selected from C2C1, C2C2, C2C3, Cas1, Cas1B, Cas2, Cas3, Cas4, Cas5, Cas5e, Cas6, Cas6e, Cas6f, Cas7, Cas8a, Cas8a1, Cas8a2, Cas8b, Cas8c, Cas9, Cas10, Cas10d, Cas10, Cas10d, Cas 11, Cas12, Cas13, Cas14, CasF, CasG, CasH, CasX, CaxY, Cpf1, Csy1, Csy2, Csy3, Cse1, Cse2, Cse3, Cse4, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, or a fragment thereof.

Embodiment 114. The method of Embodiment 109, wherein said heterologous endonuclease comprises a deactivated endonuclease, optionally fused to a regulatory moiety (e.g., comprising a transcription activator, a transcription repressor, an epigenetic modifier, or a fragment thereof).

Embodiment 115. The method of Embodiment 106 or 107, wherein said target polynucleotide corresponds to a gene encoding any protein selected from the group consisting of CFTR, DNAH5, DNAH11, BMPR2, FAH, PAH, IDUA, COL4A3, COL4A4, COL4A5, PKD1, PKD2, PKHD1, SLC3A1, SLC7A9, PAX9, MYO7A, CDH23, USH2A, CLRN1, GJB2, GJB6, RHO, DMPK, DMD, SCN1A, SCN1B, F8, F9, NGLY1, p53, PPT1, TPP1, hERG, PPT1, ATM, and FBN1.

Embodiment 116. The method of Embodiment 106 or 107, wherein said target polynucleotide corresponds to a gene in a lung cell (e.g., a lung epithelial cell, a lung ciliated cell, a lung secretory cell, a lung club cell, a lung goblet cell, or a lung basal cell) of said subject.

Embodiment 117. The method of Embodiment 106 or 107, wherein said expression or activity or said modified expression or activity is detectable at least about 4 hours after said administering.

Embodiment 118. The method of any one of Embodiments 1-117, wherein said therapeutic effect is characterized by an (e.g., therapeutically effective) amount, activity, or effect of said therapeutic agent (e.g., in a lung, a lung cell, a plurality of lung cells, or a lung cell type of said subject).

Embodiment 119. The method of any one of Embodiments 1-118, wherein said greater therapeutic effect is characterized by a greater (e.g., therapeutic) amount, activity, or effect of said therapeutic agent.

Embodiment 120. The method of any one of Embodiments 1-119, wherein said reference lipid composition does not comprise said amount of said SORT lipid.

Embodiment 121. The method of Embodiment 120, wherein said reference lipid composition does not comprise said SORT lipid.

Embodiment 122. The method of any one of Embodiments 1-121, wherein said reference lipid composition comprises 13,16,20-tris(2-hydroxydodecyl)-13,16,20,23-tetraazapentatricontane-11,25-diol ("LF92"), a phospholipid, cholesterol, and a PEG-lipid.

Embodiment 123. The method of any one of Embodiments 1-122, wherein said administering is not intravenous administration.

Embodiment 124. The method of any one of Embodiments 1-122, wherein said administering comprises systemic (e.g., intravenous) administration.

Embodiment 125. The method of any one of Embodiments 1-124, wherein said administering comprises aerosol administration (e.g., by inhalation).

Embodiment 126. The method of any one of Embodiments 1-125, wherein said cell comprises a lung airway cell (e.g., a lung ciliated cell, a lung secretory cell, a lung club cell, a lung goblet cell, a lung basal cell, or a combination thereof).

Embodiment 127. The method of any one of Embodiments 1-126, wherein said first cell type is ciliated cell, secretory cell, club cell, goblet cell, or basal cell.

Embodiment 128. The method of any one of Embodiments 1-127, wherein said first cell type is lung (e.g., airway) cell.

Embodiment 129. The method of any one of Embodiments 1-128, wherein said second cell type is ciliated cell, secretory cell, club cell, goblet cell, or basal cell.

Embodiment 130. The method of any one of Embodiments 1-129, wherein said second cell type is lung (e.g., airway) cell.

Embodiment 131. An aerosol composition comprising a therapeutic agent assembled with a lipid composition, which lipid composition comprises: (i) an ionizable cationic lipid; and (ii) a selective organ targeting (SORT) lipid separate from said ionizable cationic lipid, wherein said SORT lipid is configured to effect a delivery of said therapeutic agent characterized by one or more of the following: (a) a (e.g., 1.1- or 10-fold) greater therapeutic effect in a lung cell of said subject compared to that achieved with a reference lipid composition; (b) a therapeutic effect in a (e.g., 1.1- or 10-fold) greater plurality of lung cells (e.g., of a cell type) of said subject compared to that achieved with a reference lipid composition; (c) a therapeutic effect in a first plurality of lung cells of a first cell type and in a (e.g., 1.1- or 10-fold) greater second plurality of lung cells of a second cell type; and (d) a (e.g., 1.1- or 10-fold) greater therapeutic effect in a first lung cell of a first cell type of said subject compared to that in a second lung cell of a second cell type of said subject, wherein the aerosol composition is formulated as an aerosol; optionally, wherein said SORT lipid is selected from those set forth in Table 6, or pharmaceutically acceptable salts thereof, or a subset of the lipids and the pharmaceutically acceptable salts thereof.

Embodiment 132. The aerosol composition of Embodiment 131, wherein said lipid composition further comprises (iii) a phospholipid.

Embodiment 133. The aerosol composition of Embodiment 131 or 132, wherein said aerosol composition comprising said therapeutic agent is a pharmaceutical composition.

Embodiment 134. The aerosol composition of Embodiment 133, wherein said aerosol droplets are generated by a nebulizer at a nebulization rate of no more than 70 mL/minute.

Embodiment 135. The aerosol composition of Embodiment 133 or 134, wherein said aerosol droplets have a mass median aerodynamic diameter (MMAD) from about 0.5 micron (μm) to about 10 μm.

Embodiment 136. The aerosol composition of any one of Embodiments 133-135, wherein said droplet size varies less than about 50% for a duration of about 24 hours under a storage condition.

Embodiment 137. The aerosol composition of any one of Embodiments 133-136, wherein droplets of said aerosol composition are characterized by a geometric standard deviation (GSD) of no more than about 3.

Embodiment 138. The aerosol composition of any one of Embodiments 131-137, wherein said lipid composition comprises said SORT lipid at a molar percentage from about 20% to about 65%.

Embodiment 139. The aerosol composition of any one of Embodiments 131-138, wherein said lipid composition comprises said ionizable cationic lipid at a molar percentage from about 5% to about 30%.

Embodiment 140. The aerosol composition of any one of Embodiments 131-139, wherein said lipid composition comprises said phospholipid at a molar percentage from about 8% to about 23%.

Embodiment 141. The aerosol composition of any one of Embodiments 131-140, wherein said phospholipid is not an ethylphosphocholine.

Embodiment 142. The aerosol composition of any one of Embodiments 131-141, wherein said lipid composition further comprises a steroid or steroid derivative.

Embodiment 143. The aerosol composition of Embodiment 142, wherein said lipid composition comprises said steroid or steroid derivative at a molar percentage from about 15% to about 46%.

Embodiment 144. The aerosol composition of any one of Embodiments 131-143, wherein said lipid composition further comprises a polymer-conjugated lipid (e.g., poly(ethylene glycol) (PEG)-conjugated lipid).

Embodiment 145. The aerosol composition of Embodiment 144, wherein said lipid composition comprises said polymer-conjugated lipid at a molar percentage from about 0.5% to about 10%.

Embodiment 146. The aerosol composition of any one of Embodiments 131-145, wherein said SORT lipid comprises a permanently positively charged moiety (e.g., a quaternary ammonium ion).

Embodiment 147. The aerosol composition of any one of Embodiments 131-145, wherein said SORT lipid comprises an ionizable positively charged moiety (e.g., a tertiary amine).

Embodiment 148. The aerosol composition of Embodiment 146, wherein said SORT lipid comprises a counterion.

Embodiment 149. The aerosol composition of any one of Embodiments 131-148, wherein said SORT lipid is a phosphocholine lipid (e.g., saturated or unsaturated).

Embodiment 150. The aerosol composition of any one of Embodiments 149, wherein said SORT lipid is an ethylphosphocholine.

Embodiment 151. The aerosol composition of any one of Embodiments 131-150, wherein said SORT lipid comprises a headgroup having a structural formula:

wherein L is a (e.g., biodegradable) linker; $Z^+$ is positively charged moiety (e.g., a quaternary ammonium ion); and $X^-$ is a counterion.

Embodiment 152. The aerosol composition of Embodiment 151, wherein said SORT lipid has a structural formula:

wherein $R^1$ and $R^2$ are each independently an optionally substituted $C_6$-$C_{24}$ alkyl, or an optionally substituted $C_6$-$C_{24}$ alkenyl.

Embodiment 153. The aerosol composition of Embodiment 151, wherein said SORT lipid has a structural formula:

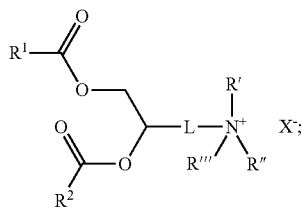

optionally, wherein L is

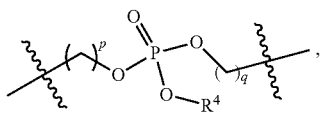

wherein: p and q are each independently 1, 2, or 3; and $R^4$ is an optionally substituted $C_1$-$C_6$ alkyl.

Embodiment 154. The aerosol composition of Embodiment 151, wherein said SORT lipid has a structural formula:

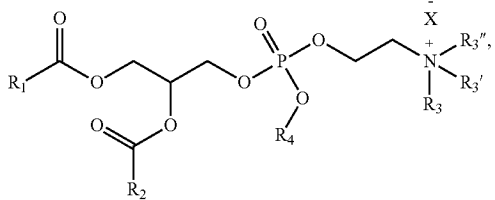

(IA)

wherein: $R_1$ and $R_2$ are each independently alkyl$_{(C8\text{-}C24)}$, alkenyl$_{(C8\text{-}C24)}$, or a substituted version of either group; $R_3$, $R_3'$, and $R_3''$ are each independently alkyl$_{(C\leq 6)}$ or substituted alkyl$_{(C\leq 6)}$; $R_4$ is alkyl$_{(C\leq 6)}$ or substituted alkyl$_{(C\leq 6)}$; and $X^-$ is a monovalent anion.

Embodiment 155. The aerosol composition of any one of Embodiments 131-148, wherein said SORT lipid has a structural formula:

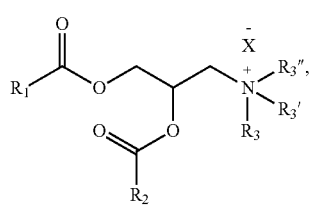

(S-I')

wherein: $R_1$ and $R_2$ are each independently alkyl$_{(C8\text{-}C24)}$, alkenyl$_{(C8\text{-}C24)}$, or a substituted version of either group; $R_3$, $R_3'$, and $R_3''$ are each independently alkyl$_{(C\leq 6)}$ or substituted alkyl$_{(C\leq 6)}$; and $X^-$ is a monovalent anion.

Embodiment 156. The aerosol composition of any one of Embodiments 131-148, wherein said SORT lipid has a structural formula:

(S-II')

wherein: $R_4$ and $R_4'$ are each independently alkyl$_{(C6\text{-}C24)}$, alkenyl$_{(C6\text{-}C24)}$, or a substituted version of either group; $R_4''$ is alkyl$_{(C\leq 24)}$, alkenyl$_{(C\leq 24)}$, or a substituted version of either group; $R_4'''$ is alkyl$_{(C1\text{-}C8)}$, alkenyl$_{(C2\text{-}C8)}$, or a substituted version of either group; and $X_2$ is a monovalent anion.

Embodiment 157. The aerosol composition of any one of Embodiments 131-148, wherein said SORT lipid has a structural formula:

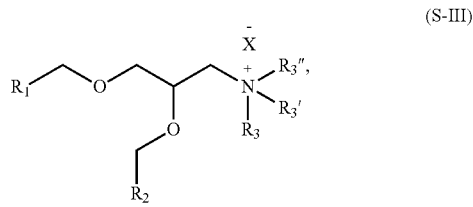

(S-III)

wherein: $R_1$ and $R_2$ are each independently alkyl$_{(C8\text{-}C24)}$, alkenyl$_{(C8\text{-}C24)}$, or a substituted version of either group; $R_3$, $R_3'$, and $R_3''$ are each independently alkyl$_{(C\leq 6)}$ or substituted alkyl$_{(C\leq 6)}$; and $X^-$ is a monovalent anion.

Embodiment 158. The pharmaceutical composition of any one of Embodiments 131-148, wherein said SORT lipid has a structural formula:

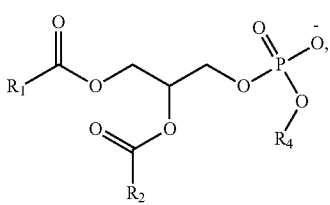

(S-IV)

wherein: $R_1$ and $R_2$ are each independently alkyl$_{(C8\text{-}C24)}$, alkenyl$_{(C8\text{-}C24)}$, or a substituted version of either group; $R_3$ is hydrogen, alkyl$_{(C\leq 6)}$, or substituted alkyl$_{(C\leq 6)}$, or —$Y_1$— $R_4$, wherein: $Y_1$ is alkanediyl$_{(C\leq 6)}$ or substituted alkanediyl$_{(C\leq 6)}$; and $R_4$ is acyloxy$_{(C\leq 8\text{-}24)}$ or substituted acyloxy$_{(C\leq 8\text{-}24)}$.

Embodiment 159. The aerosol composition of any one of Embodiments 131-158, wherein the ionizable cationic lipid is a dendrimer or dendron of a generation (g) having a structural formula:

Core—⟦⟨(diacyl group)—(linker group)⟩$_G$—⟨(diacyl group)—(terminating group)⟩$_Z$⟧$_N$,

|←——————————— Branch ———————————→| or a pharmaceutically acceptable salt thereof, wherein:

(a) the core comprises a structural formula ($X_{Core}$):

$$\begin{array}{c} R^{1a} \\ \phantom{R}\diagdown \\ N—L^0—Q—N \\ \phantom{R}\diagup \phantom{XXXXX} \diagdown \\ R^{1b} \phantom{XXXXXX} L^{1d} \end{array} \begin{array}{c} L^{1c} \\ \phantom{X} \end{array}$$ ($X_{Core}$)

wherein:

Q is independently at each occurrence a covalent bond, —O—, —S—, —NR$^2$—, or —CR$^{3a}$R$^{3b}$—;

R$^2$ is independently at each occurrence R$^{1g}$ or -L$^2$-NR$^{1e}$R$^{1f}$;

R$^{3a}$ and R$^{3b}$ are each independently at each occurrence hydrogen or an optionally substituted (e.g., C$_1$-C$_6$, such as C$_1$-C$_3$) alkyl;

R$^{1a}$, R$^{1b}$, R$^{1c}$, R$^{1d}$, R$^{1e}$, R$^{1f}$, and R$^{1g}$ (if present) are each independently at each occurrence a point of connection to a branch, hydrogen, or an optionally substituted (e.g., C$_1$-C$_{12}$) alkyl;

L$^0$, L$^1$, and L$^2$ are each independently at each occurrence selected from a covalent bond, (e.g., C$_1$-C$_{12}$, such as C$_1$-C$_6$ or C$_1$-C$_3$) alkylene, (e.g., C$_1$-C$_{12}$, such as C$_1$-C$_8$ or C$_1$-C$_6$) heteroalkylene (e.g., C$_2$-C$_8$ alkyleneoxide, such as oligo(ethyleneoxide)), [(e.g., C$_1$-C$_6$) alkylene]-[(e.g., C$_4$-C$_6$) heterocycloalkyl]-[(e.g., C$_1$-C$_6$) alkylene], [(e.g., C$_1$-C$_6$) alkylene]-(arylene)-[(e.g., C$_1$-C$_6$) alkylene] (e.g., [(e.g., C$_1$-C$_6$) alkylene]-phenylene-[(e.g., C$_1$-C$_6$) alkylene]), (e.g., C$_4$-C$_6$) heterocycloalkyl, and arylene (e.g., phenylene); or, alternatively, part of L$^1$ form a (e.g., C$_4$-C$_6$) heterocycloalkyl (e.g., containing one or two nitrogen atoms and, optionally, an additional heteroatom selected from oxygen and sulfur) with one of R$^{1c}$ and R$^{1d}$; and x$^1$ is 0, 1, 2, 3, 4, 5, or 6; and (b) each branch of the plurality (N) of branches independently comprises a structural formula ($X_{Branch}$):

*—⟦⟨(diacyl group)—(linker group)⟩$_G$—⟨(diacyl group)—(terminating) group⟩$_Z$⟧ ($X_{Branch}$), wherein:

* indicates a point of attachment of the branch to the core;

g is 1, 2, 3, or 4;

Z=2$^{(g-1)}$;

G=0, when g=1; or G=$\Sigma_{i=0}^{i=g-2}$ 2$^i$, when g≠1;

(c) each diacyl group independently comprises a structural formula

[diacyl group structure with R$^{3c}$, R$^{3d}$, A$^1$, Y$^3$, A$^2$, R$^{3e}$, R$^{3f}$, m1, m2]

wherein:

* indicates a point of attachment of the diacyl group at the proximal end thereof;

** indicates a point of attachment of the diacyl group at the distal end thereof;

Y$^3$ is independently at each occurrence an optionally substituted (e.g., C$_1$-C$_{12}$) alkylene, an optionally substituted (e.g., C$_1$-C$_{12}$) alkenylene, or an optionally substituted (e.g., C$_1$-C$_{12}$) arenylene;

A$^1$ and A$^2$ are each independently at each occurrence —O—, —S—, or —NR$^4$—, wherein:

R$^4$ is hydrogen or optionally substituted (e.g., C$_1$-C$_6$) alkyl;

m$^1$ and m$^2$ are each independently at each occurrence 1, 2, or 3; and

R$^{3c}$, R$^{3d}$, R$^{3e}$, and R$^{3f}$ are each independently at each occurrence hydrogen or an optionally substituted (e.g., C$_1$-C$_8$) alkyl; and (d) each linker group independently comprises a structural formula

[linker structure with S, Y$^1$, N and attachment points , *, ***]

wherein:

** indicates a point of attachment of the linker to a proximal diacyl group;

*** indicates a point of attachment of the linker to a distal diacyl group; and

Y$_1$ is independently at each occurrence an optionally substituted (e.g., C$_1$-C$_{12}$) alkylene, an optionally substituted (e.g., C$_1$-C$_{12}$) alkenylene, or an optionally substituted (e.g., C$_1$-C$_{12}$) arenylene; and (e) each terminating group is independently selected from optionally substituted (e.g., C$_1$-C$_{18}$, such as C$_4$-C$_{18}$) alkylthiol, and optionally substituted (e.g., C$_1$-C$_{18}$, such as C$_4$-C$_{18}$) alkenylthiol.

Embodiment 160. The aerosol composition of Embodiment 159, wherein x$^1$ is 0, 1, 2, or 3.

Embodiment 161. The aerosol composition of Embodiment 159 or 160, wherein R$^{1a}$, R$^{1b}$, R$^{1c}$, R$^{1d}$, R$^{1e}$, R$^{1f}$, and R$^{1g}$ (if present) are each independently at each occurrence a point of connection to a branch (e.g., as indicated by *), hydrogen, or C$_1$-C$_{12}$ alkyl (e.g., C$_1$-C$_8$alkyl, such as C$_1$-C$_6$ alkyl or C$_1$-C$_3$ alkyl), wherein the alkyl moiety is optionally substituted with one or more substituents each independently selected from —OH, $C_4$-$C_8$ (e.g., $C_4$-$C_6$) heterocycloalkyl (e.g., piperidinyl

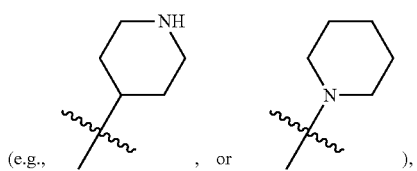 [SMILES: *C1CCNCC1 ; *N1CCCCC1]

N—($C_1$-$C_3$ alkyl)-piperidinyl

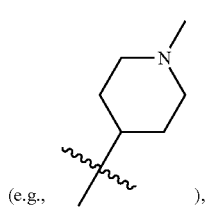

piperazinyl

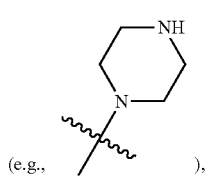

N—($C_1$-$C_3$ alkyl)-piperadizinyl

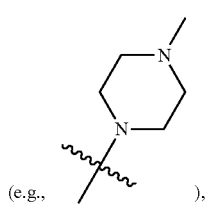

morpholinyl

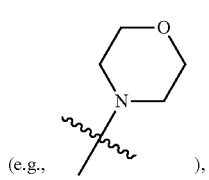

N-pyrrolidinyl

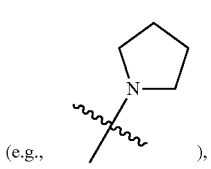 [SMILES: *N1CCCC1]

pyrrolidinyl

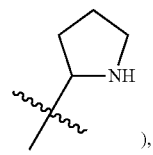

or N—($C_1$-$C_3$ alkyl)-pyrrolidinyl

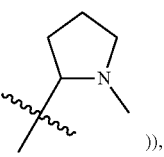

and $C_3$-$C_5$ heteroaryl (e.g., imidazolyl

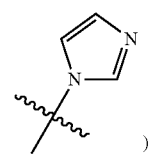

or pyridinyl

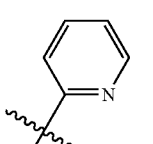

Embodiment 162. The aerosol composition of Embodiment 161, wherein $R^{1a}$, $R^{1b}$, $R^{1c}$, $R^{1d}$, $R^{1e}$, $R^{1f}$, and $R^{1g}$ (if present) are each independently at each occurrence a point of connection to a branch (e.g., as indicated by *), hydrogen, or $C_1$-$C_{12}$ alkyl (e.g., $C_1$-$C_8$alkyl, such as $C_1$-$C_6$ alkyl or $C_1$-$C_3$ alkyl), wherein the alkyl moiety is optionally substituted with one substituent —OH.

Embodiment 163. The aerosol composition of any one of Embodiments 159-162, wherein $R^{3a}$ and $R^{3b}$ are each independently at each occurrence hydrogen.

Embodiment 164. The aerosol composition of any one of Embodiments 159-163, wherein the plurality (N) of branches comprises at least 3 (e.g., at least 4, or at least 5) branches.

Embodiment 165. The aerosol composition of any one of Embodiments 159-164, wherein g=1; G=0; and Z=1.

Embodiment 166. The aerosol composition of Embodiment 165, wherein each branch of the plurality of branches comprises a structural formula *—(diacyl group)—(terminating group).

Embodiment 167. The aerosol composition of any one of Embodiments 159-164, wherein g=2; G=1; and Z=2.

Embodiment 168. The aerosol composition of Embodiment 167, wherein each branch of the plurality of branches comprises a structural formula

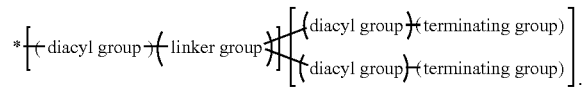

Embodiment 169. The aerosol composition of any one of Embodiments 159-168, wherein the core comprises a structural formula:

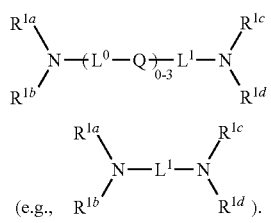

Embodiment 170. The aerosol composition of any one of Embodiments 159-168, wherein the core comprises a structural formula:

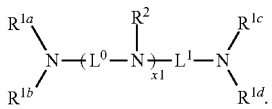

Embodiment 171. The aerosol composition of Embodiment 170, wherein the core comprises a structural formula:

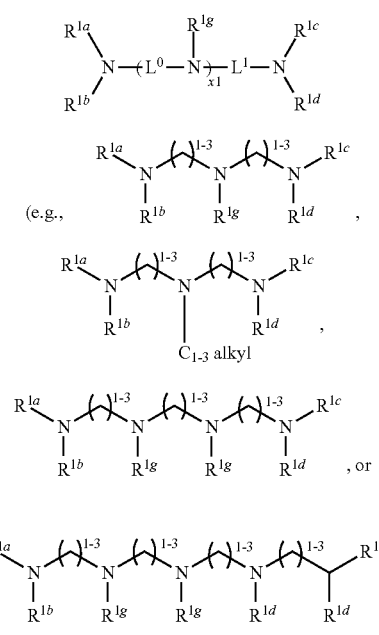

Embodiment 172. The aerosol composition of Embodiment 170, wherein the core comprises a structural formula:

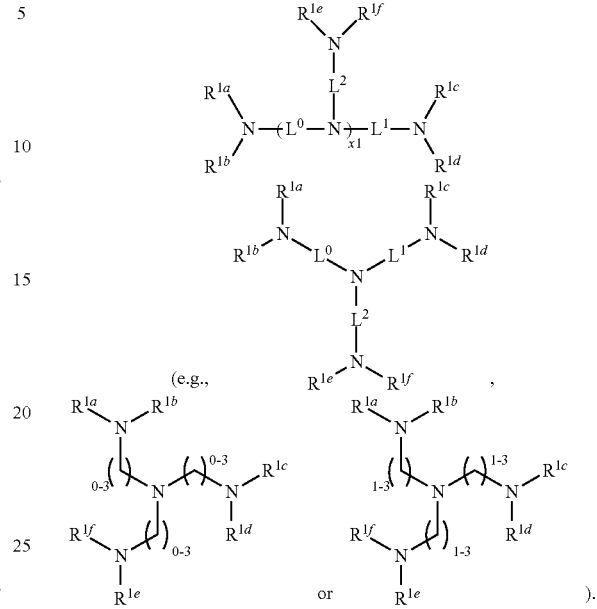

such as

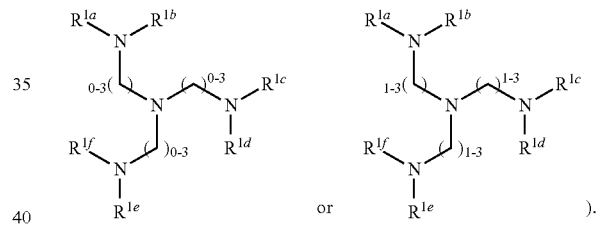

Embodiment 173. The aerosol composition of any one of Embodiments 159-168, wherein the core comprises a structural formula:

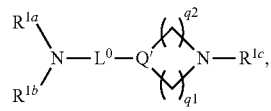

wherein Q' is $-NR^2-$ or $-CR^{3a}R^{3b}-$; $q^1$ and $q^2$ are each independently 1 or 2.

Embodiment 174. The aerosol composition of Embodiment 173, wherein the core comprises a structural formula:

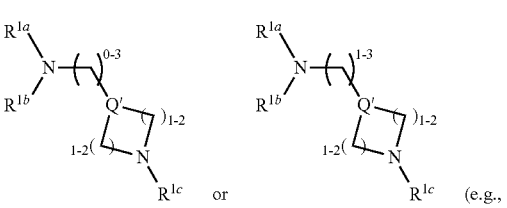

(e.g.,

247

-continued

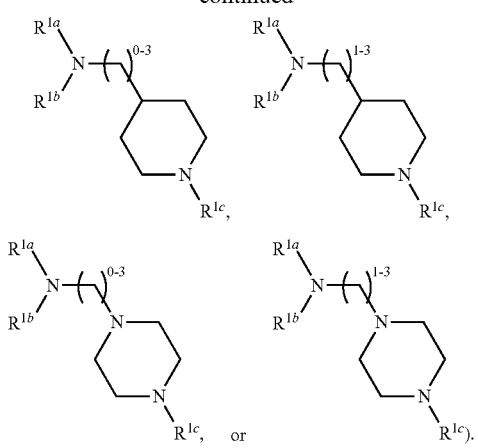

Embodiment 175. The aerosol composition of any one of Embodiments 159-168, wherein the core comprises a structural formula

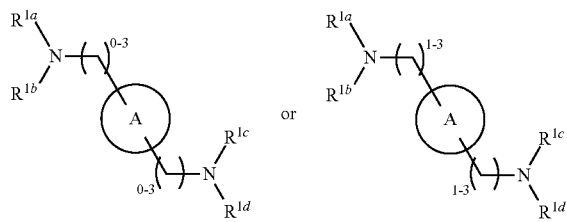

(e.g.,

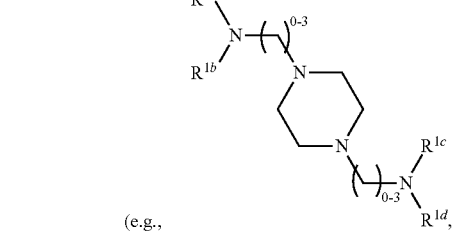

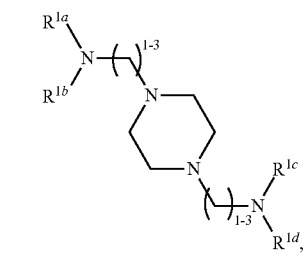

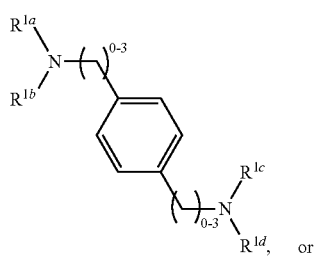

248

-continued

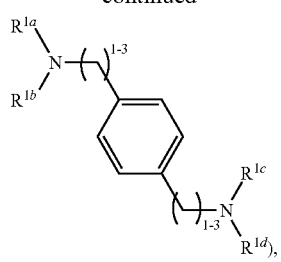

wherein ring A is an optionally substituted aryl or an optionally substituted (e.g., $C_3$-$C_{12}$, such as $C_3$-$C_5$) heteroaryl.

Embodiment 176. The aerosol composition of any one of Embodiments 159-168, wherein the core comprises has a structural formula

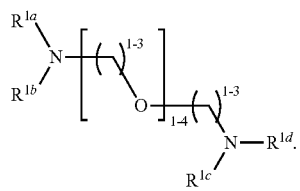

Embodiment 177. The aerosol composition of any one of Embodiments 159-168, wherein the core comprises a structural formula selected from the group consisting of:

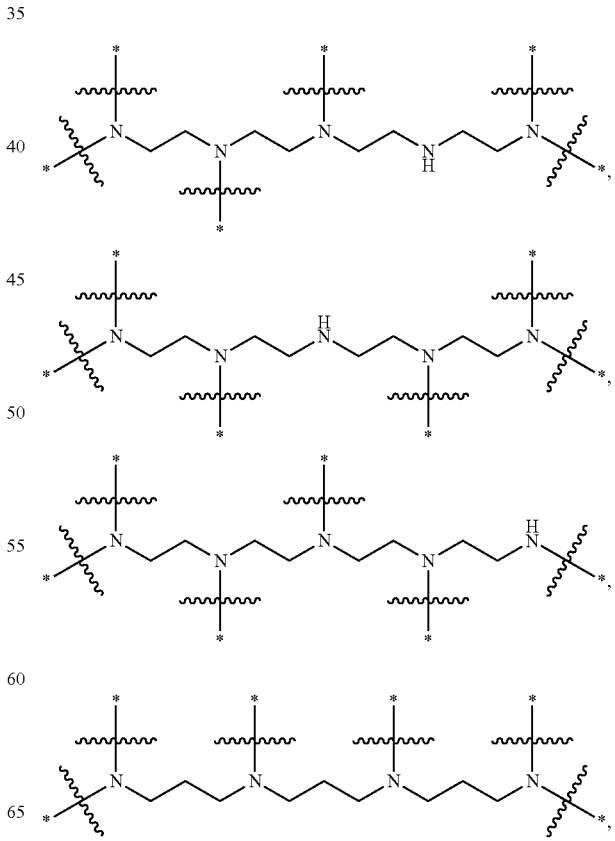

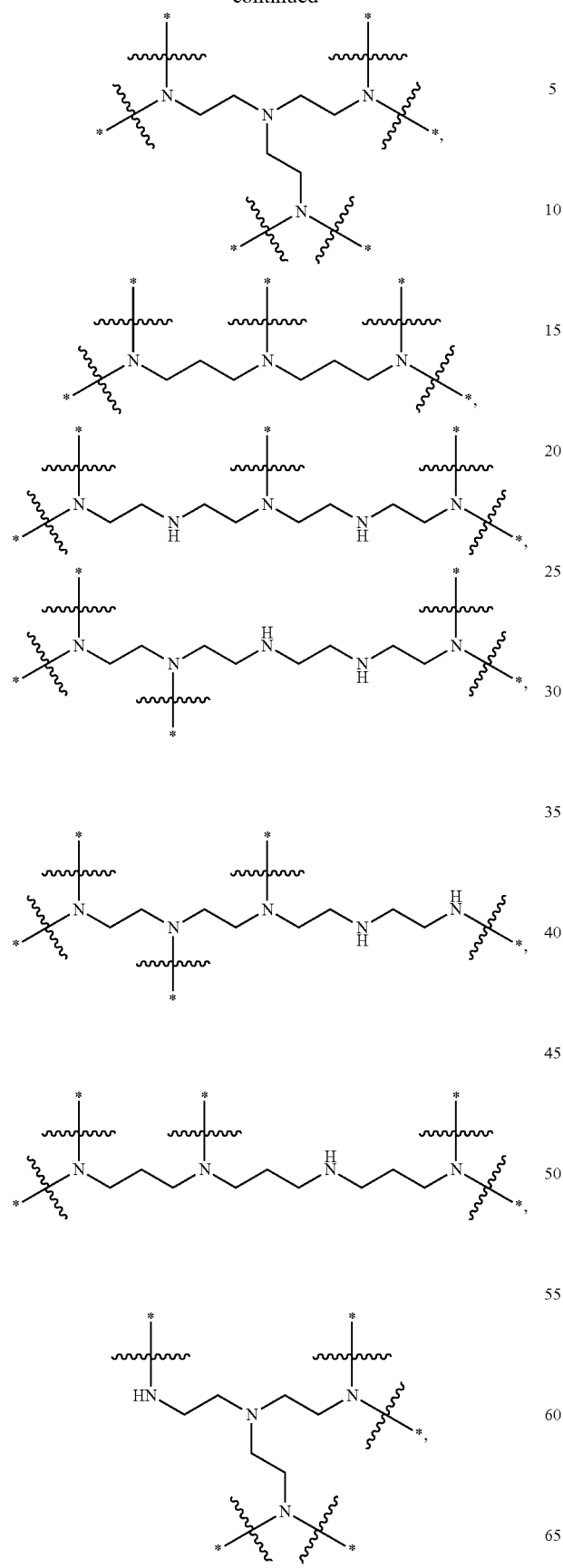
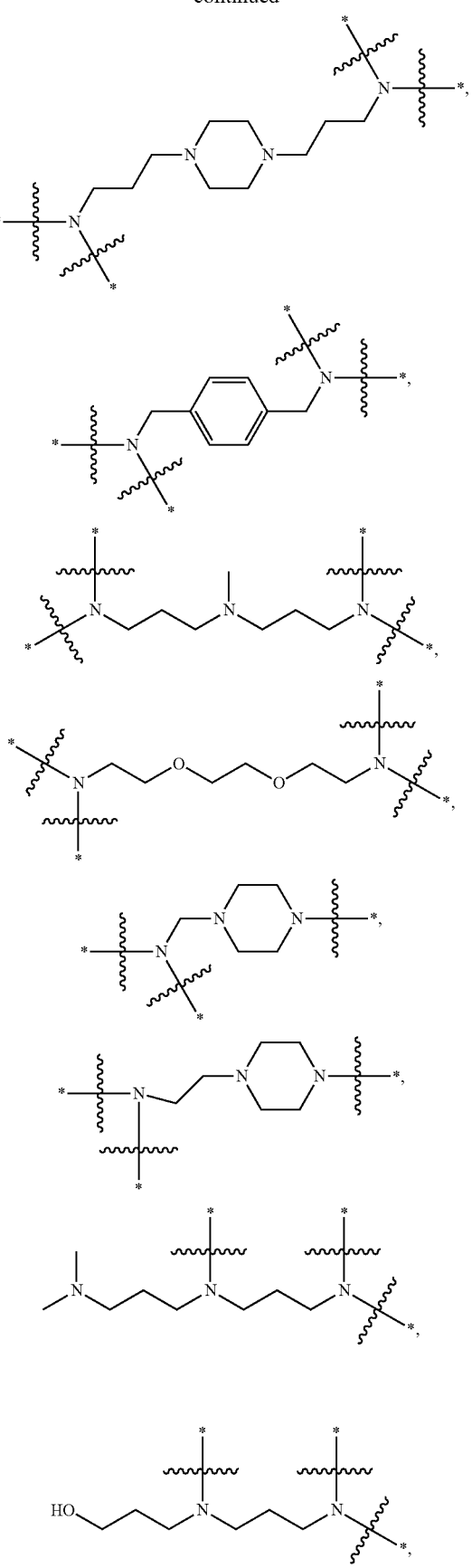

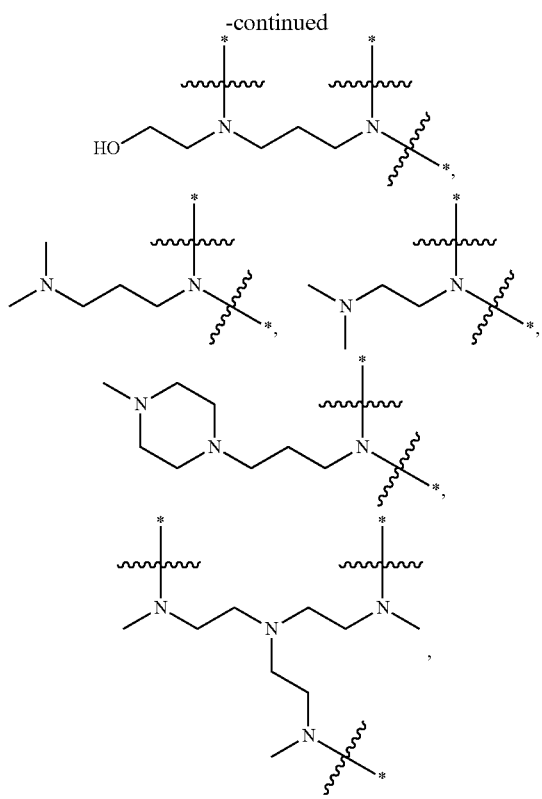

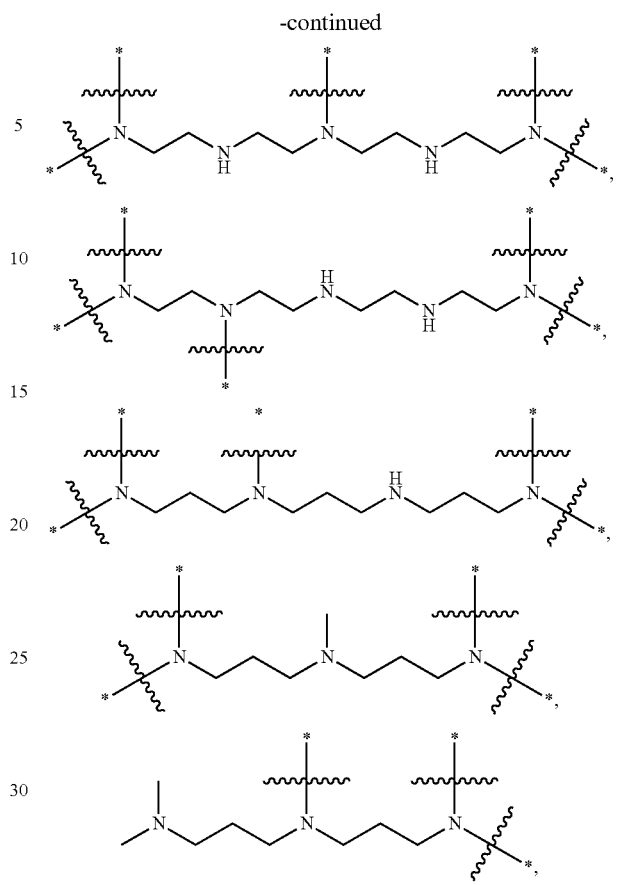

and pharmaceutically acceptable salts thereof, wherein * indicates a point of attachment of the core to a branch of the plurality of branches.

Embodiment 178. The aerosol composition of any one of Embodiments 159-168, wherein the core comprises a structural formula selected from the group consisting of:

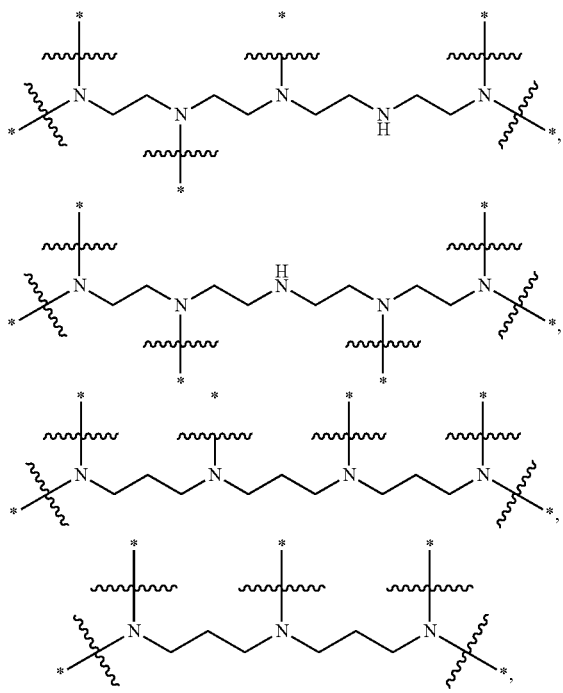

and pharmaceutically acceptable salts thereof, wherein * indicates a point of attachment of the core to a branch of the plurality of branches.

Embodiment 179. The aerosol composition of any one of Embodiments 159-168, wherein the core comprises a structural formula selected from the group consisting of:

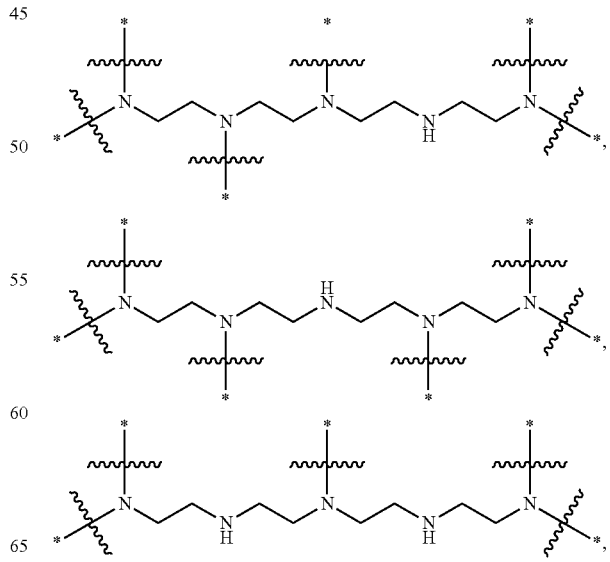

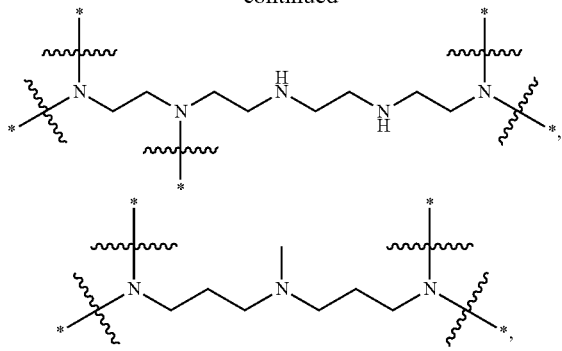

and pharmaceutically acceptable salts thereof, wherein * indicates a point of attachment of the core to a branch of the plurality of branches.

Embodiment 180. The pharmaceutical composition of any one of Embodiments 159-168, wherein the core has the structure

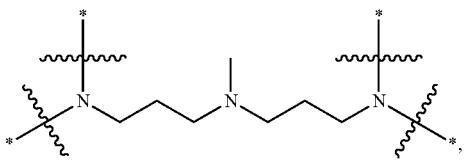

wherein * indicates a point of attachment of the core to a branch of the plurality of branches or H, wherein at least 2 (e.g., at least 3, or at least 4) branches are attached to the core.

Embodiment 181. The aerosol composition of any one of Embodiments 159-168, wherein the core has the structure

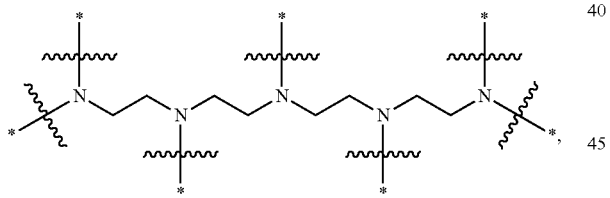

wherein * indicates a point of attachment of the core to a branch of the plurality of branches or H, wherein at least 4 (e.g., at least 5, or at least 6) branches are attached to the core.

Embodiment 182. The aerosol composition of any one of Embodiments 159-181, wherein $A^1$ is —O— or —NH—.

Embodiment 183. The aerosol composition of Embodiment 182, wherein $A^1$ is —O—.

Embodiment 184. The aerosol composition of any one of Embodiments 159-183, wherein $A^2$ is —O— or —NH—.

Embodiment 185. The aerosol composition of Embodiment 184, wherein $A^2$ is —O—.

Embodiment 186. The aerosol composition of any one of Embodiments 159-185, wherein $Y^3$ is $C_1$-$C_{12}$ (e.g., $C_1$-$C_6$, such as $C_1$-$C_3$) alkylene.

Embodiment 187. The aerosol composition of any one of Embodiments 159-186, wherein the diacyl group independently at each occurrence comprises a structural formula

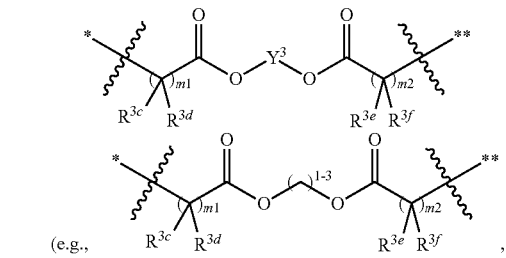

(e.g.,

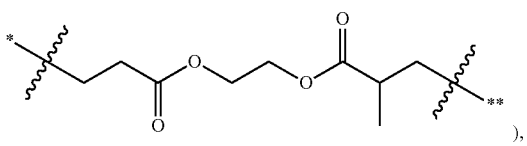

such as

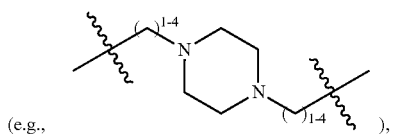

), optionally wherein $R^{3c}$, $R^{3d}$, $R^{3e}$, and $R^{3f}$ are each independently at each occurrence hydrogen or $C_1$-$C_3$ alkyl.

Embodiment 188. The aerosol composition of any one of Embodiments 159-187, wherein $L^0$, $L^1$, and $L^2$ are each independently at each occurrence selected from a covalent bond, $C_1$-$C_6$ alkylene (e.g., $C_1$-$C_3$ alkylene), $C_2$-$C_{12}$ (e.g., $C_2$-$C_8$) alkyleneoxide (e.g., oligo(ethyleneoxide), such as —$(CH_2CH_2O)_{1-4}$—$(CH_2CH_2)$—), [($C_1$-$C_4$) alkylene]-[($C_4$-$C_6$) heterocycloalkyl]-[($C_1$-$C_4$) alkylene]

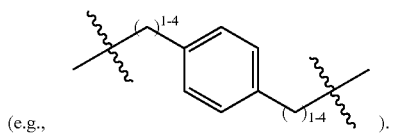

(e.g., ), and [($C_1$-$C_4$) alkylene]-phenylene-[($C_1$-$C_4$) alkylene]

(e.g., ).

Embodiment 189. The aerosol composition of Embodiment 188, wherein $L^0$, $L^1$, and $L^2$ are each independently at each occurrence selected from $C_1$-$C_6$ alkylene (e.g., $C_1$-$C_3$ alkylene), —($C_1$-$C_3$ alkylene-O)$_{1-4}$—($C_1$-$C_3$ alkylene), —($C_1$-$C_3$ alkylene)-phenylene-($C_1$-$C_3$ alkylene)-, and —($C_1$-$C_3$ alkylene)-piperazinyl-($C_1$-$C_3$ alkylene)-.

Embodiment 190. The aerosol composition of Embodiment 188, wherein $L^0$, $L^1$, and $L^2$ are each independently at each occurrence $C_1$-$C_6$ alkylene (e.g., $C_1$-$C_3$ alkylene).

Embodiment 191. The aerosol composition of Embodiment 188, wherein $L^0$, $L^1$, and $L^2$ are each independently at each occurrence $C_2$-$C_{12}$ (e.g., $C_2$-$C_8$) alkyleneoxide (e.g., —($C_1$-$C_3$ alkylene-O)$_{1-4}$—($C_1$-$C_3$ alkylene)).

Embodiment 192. The aerosol composition of Embodiment 188, wherein $L^0$, $L^1$, and $L^2$ are each independently at each occurrence selected from [($C_1$-$C_4$) alkylene]-[($C_4$-$C_6$) heterocycloalkyl]-[($C_1$-$C_4$) alkylene] (e.g., —($C_1$-$C_3$ alkylene)-phenylene-($C_1$-$C_3$ alkylene)-) and [($C_1$-$C_4$)

alkylene]-[($C_4$-$C_6$) heterocycloalkyl]-[($C_1$-$C_4$) alkylene] (e.g., —($C_1$-$C_3$ alkylene)-piperazinyl-($C_1$-$C_3$ alkylene)-).

Embodiment 193. The aerosol composition of any one of Embodiments 159-192, wherein each terminating group is independently $C_1$-$C_{18}$ (e.g., $C_4$-$C_{18}$) alkenylthiol or $C_1$-$C_{18}$ (e.g., $C_4$-$C_{18}$) alkylthiol, wherein the alkyl or alkenyl moiety is optionally substituted with one or more substituents each independently selected from halogen, $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —NHCH$_2$CH$_2$CH$_2$CH$_3$) or $C_1$-$C_8$ di-alkylamino (such as

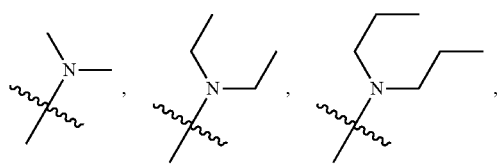

)), $C_4$-$C_6$ N-heterocycloalkyl (e.g., N-pyrrolidinyl

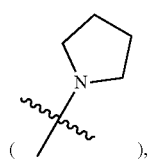

( ),

N-piperidinyl

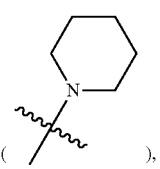 [SMILES: *N1CCCCC1]

( ),

N-azepanyl

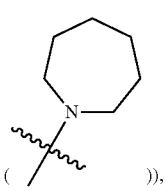

( )),

—OH, —C(O)OH, —C(O)N($C_1$-$C_3$ alkyl)-($C_1$-$C_6$ alkylene)-($C_1$-$C_{12}$ alkylamino (e.g., mono- or di-alkylamino))

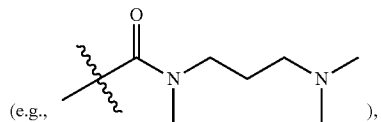 [SMILES: *C(=O)N(C)CCCN(C)C]

(e.g., ),

—C(O)N($C_1$-$C_3$ alkyl)-($C_1$-$C_6$ alkylene)-($C_4$-$C_6$ N-heterocycloalkyl)

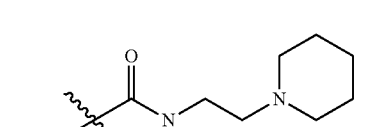

(eg., ),

—C(O)—($C_1$-$C_{12}$ alkylamino (e.g., mono- or di-alkylamino)), and —C(O)—($C_4$-$C_6$ N-heterocycloalkyl)

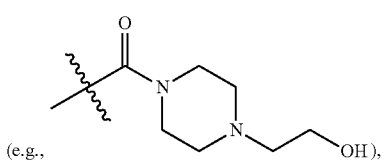 [SMILES: *C(=O)N1CCN(CCO)CC1]

(e.g., ), wherein the $C_4$-$C_6$ N-heterocycloalkyl moiety of any of the preceding substituents is optionally substituted with $C_1$-$C_3$ alkyl or $C_1$-$C_3$ hydroxyalkyl.

Embodiment 194. The aerosol composition of Embodiment 193, wherein each terminating group is independently $C_1$-$C_{18}$ (e.g., $C_4$-$C_{18}$) alkylthiol, wherein the alkyl moiety is optionally substituted with one or more (e.g., one) substituents each independently selected from $C_6$-$C_{12}$ aryl (e.g., phenyl), $C_1$-$C_{12}$ (e.g., $C_1$-$C_8$) alkylamino (e.g., $C_1$-$C_6$ mono-alkylamino (such as —NHCH$_2$CH$_2$CH$_2$CH$_3$) or $C_1$-$C_8$ di-alkylamino (such as

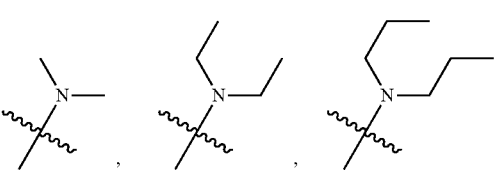

,

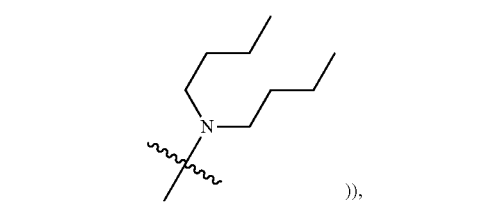

)),

C₄-C₆ N-heterocycloalkyl (e.g., N-pyrrolidinyl

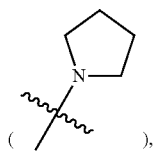

( ),

N-piperidinyl

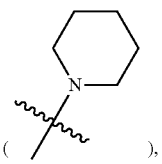 [SMILES: *N1CCCCC1]

( ),

N-azepanyl

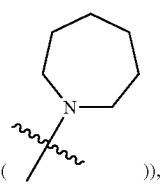

( )),

—OH, —C(O)OH, —C(O)N(C₁-C₃ alkyl)-(C₁-C₆ alkylene)-(C₁-C₁₂ alkylamino (e.g., mono- or di-alkylamino))

(e.g., 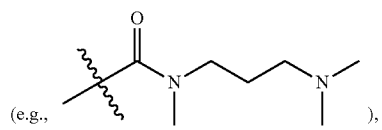 [SMILES: *C(=O)N(C)CCCN(C)C] ),

—C(O)N(C₁-C₃ alkyl)-(C₁-C₆ alkylene)-(C₄-C₆ N-heterocycloalkyl)

(eg., 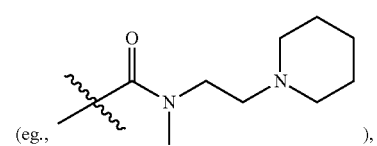 [SMILES: *C(=O)N(C)CCN1CCCCC1] ), and —C(O)—(C₄-C₆ N-heterocycloalkyl)

(e.g., 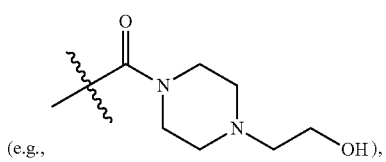 ), wherein the C₄-C₆ N-heterocycloalkyl moiety of any of the preceding substituents is optionally substituted with C₁-C₃ alkyl or C₁-C₃ hydroxyalkyl.

Embodiment 195. The aerosol composition of Embodiment 194, wherein each terminating group is independently C₁-C₁₈ (e.g., C₄-C₁₈) alkylthiol, wherein the alkyl moiety is optionally substituted with one substituent —OH.

Embodiment 196. The aerosol composition of Embodiment 194, wherein each terminating group is independently C₁-C₁₈ (e.g., C₄-C₁₈) alkylthiol, wherein the alkyl moiety is optionally substituted with one substituent selected from C₁-C₁₂ (e.g., C₁-C₈) alkylamino (e.g., C₁-C₆ mono-alkylamino (such as —NHCH₂CH₂CH₂CH₃) or C₁-C₈ di-alkylamino (such as

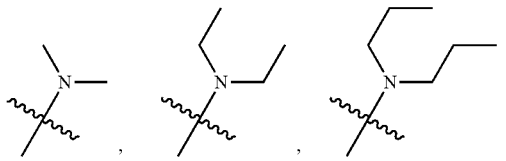

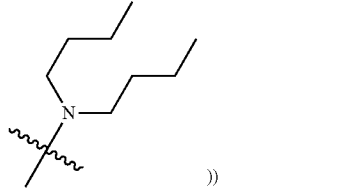 ))

and C₄-C₆ N-heterocycloalkyl (e.g., N-pyrrolidinyl

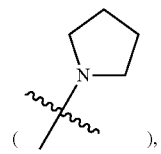

( ),

N-piperidinyl

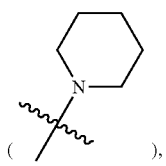

( ),

N-azepanyl

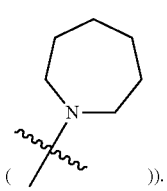

( )).

Embodiment 197. The aerosol composition of Embodiment 193, wherein each terminating group is independently C₁-C₁₈ (e.g., C₄-C₁₈) alkenylthiol or C₁-C₁₈ (e.g., C₄-C₁₈) alkylthiol.

Embodiment 198. The aerosol composition of Embodiment 195 or 197, wherein each terminating group is independently C₁-C₁₈ (e.g., C₄-C₁₈) alkylthiol.

Embodiment 199. The aerosol composition of any one of Embodiments 159-192, wherein each terminating group is independently selected from those set forth in Table 3 or a subset thereof; or wherein each terminating group is independently selected from the group consisting of:

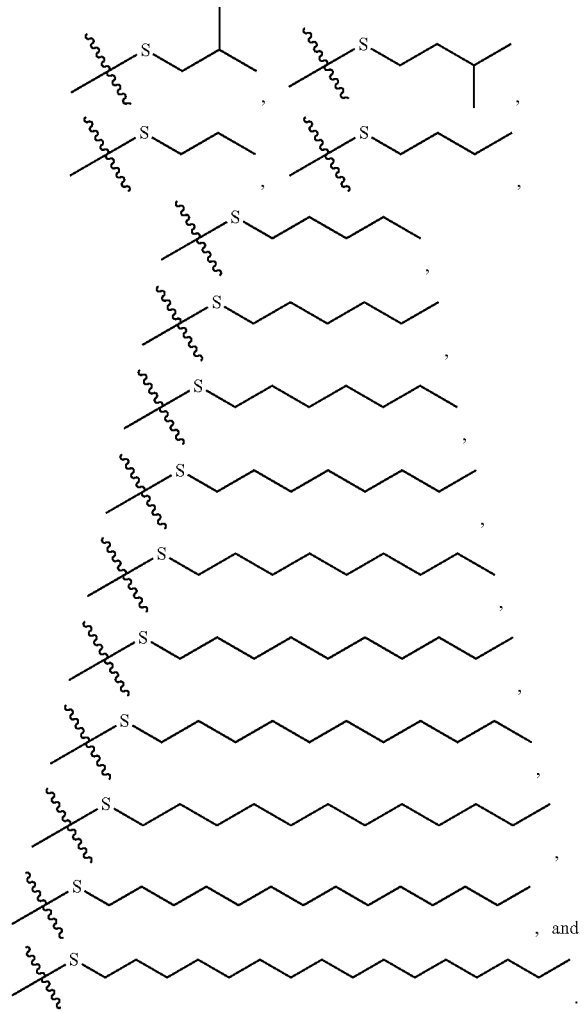

, and

.

Embodiment 200. The aerosol composition of any one of Embodiments 131-158, wherein the ionizable cationic lipid is selected from those set forth in Table 4 or Table 5, or pharmaceutically acceptable salts thereof, or a subset of the lipids and the pharmaceutically acceptable salts thereof.

Embodiment 201. A high-potency dosage form of a therapeutic agent formulated with a selective organ targeting (SORT) lipid, the dosage form comprising: said therapeutic agent assembled with a lipid composition that comprises: (i) an ionizable cationic lipid; and (ii) aid SORT lipid separate from said ionizable cationic lipid, wherein said SORT lipid is present in said dosage form in an amount sufficient to achieve a therapeutic effect at a dose of said therapeutic agent (e.g., at least about 1.1-, 2-, 3-, 4-, 5-, 6-, 7-, 8-, 9- or 10-fold) lower than that required with a reference lipid composition; optionally, wherein said SORT lipid is selected from those set forth in Table 6, or pharmaceutically acceptable salts thereof, or a subset of the lipids and the pharmaceutically acceptable salts thereof.

Embodiment 202. A high-potency dosage form of a therapeutic agent formulated with a selective organ targeting (SORT) lipid, the dosage form comprising: said therapeutic agent assembled with a lipid composition that comprises: (i) an ionizable cationic lipid; and (ii) said SORT lipid separate from said ionizable cationic lipid, wherein said therapeutic agent (e.g., heterologous polynucleotide) is present in said dosage form at a dose of no more than about 2 milligram per kilogram (mg/kg, or mpk) body weight; optionally, wherein said SORT lipid is selected from those set forth in Table 6, or pharmaceutically acceptable salts thereof, or a subset of the lipids and the pharmaceutically acceptable salts thereof.

Embodiment 203. The dosage form of Embodiment 201 or 202, wherein said lipid composition further comprises (iii) a phospholipid.

Embodiment 204. The dosage form of any one of Embodiments 201-203, wherein said dosage form is an aerosol dosage form.

Embodiment 205. The dosage form of any one of Embodiments 201-203, wherein said dosage form is an intravenous dosage form.

Embodiment 206. The dosage form of any one of Embodiments 201-205, wherein said dosage form is for lung delivery.

Embodiment 207. The dosage form of any one of Embodiments 201-206, wherein said therapeutic agent (e.g., heterologous polynucleotide) is present in said dosage form at a dose of no more than about 1.0, 0.5, 0.1, 0.05, or 0.01 mg/kg body weight.

Embodiment 208. The dosage form of any one of Embodiments 201-207, wherein said therapeutic agent (e.g., heterologous polynucleotide) is present in said dosage form at a concentration of no more than about 5 or 2 milligram per milliliter (mg/mL).

Embodiment 209. The dosage form of any one of Embodiments 201-208, wherein the dosage form is formulated as an aerosol composition according to any one of Embodiments 131-200.

Embodiment 210. A method for delivery by nebulization to lung cell(s) of a subject, the method comprising: administering to said subject an aerosol composition comprising a therapeutic agent assembled with a lipid composition, which lipid composition comprises: (i) an ionizable cationic lipid; and (ii) a selective organ targeting (SORT) lipid separate from said ionizable cationic lipid, thereby delivering said therapeutic agent to said lung cell(s) of a lung of said subject; optionally, wherein said SORT lipid is selected from those set forth in Table 6, or pharmaceutically acceptable salts thereof, or a subset of the lipids and the pharmaceutically acceptable salts thereof.

Embodiment 211. The method of Embodiment 210, wherein the method provides a (e.g., therapeutically) effective amount or activity of said therapeutic agent in at least about 5%, 10%, 15%, or 20% lung epithelial cells of said subject.

Embodiment 212. The method of Embodiment 210 or 211, wherein the method provides a (e.g., therapeutically) effective amount or activity of said therapeutic agent in at least about 2%, 5%, or 10% lung ciliated cells of said subject.

Embodiment 213. The method of any one of Embodiments 210-212, wherein the method provides a (e.g., therapeutically) effective amount or activity of said therapeutic agent in at least about 5%, 10%, 15%, or 20% lung secretory cells of said subject.

Embodiment 214. The method of any one of Embodiments 210-213, wherein the method provides a (e.g., therapeutically) effective amount or activity of said therapeutic agent in at least about 5%, 10%, 15%, or 20% lung club cells of said subject.

Embodiment 215. The method of any one of Embodiments 210-214, wherein the method provides a (e.g., therapeutically) effective amount or activity of said therapeutic agent in at least about 5%, 10%, 15%, or 20% lung goblet cells of said subject.

Embodiment 216. The method of any one of Embodiments 210-215, wherein the method provides a (e.g., therapeutically) effective amount or activity of said therapeutic agent in at least about 5%, 10%, 15%, or 20% lung basal cells of said subject.

Embodiment 217. The method of any one of Embodiments 210-216, wherein said lipid composition comprises a phospholipid.

Embodiment 218. The method of any one of Embodiments 210-217, wherein said aerosol composition comprising said therapeutic agent assembled with said lipid composition is an aerosol composition.

Embodiment 219. The method of any one of Embodiments 210-218, wherein the aerosol composition is formulated according to any one of Embodiments 131-200.

EXAMPLES

Example 1. Preparation of DOTAP or DODAP Modified Lipid Nanoparticles

Lipid nanoparticles (LNPs) are the most efficacious carrier class for in vivo nucleic acid delivery. Historically, effective LNPs are composed of 4 components: an ionizable cationic lipid, zwitterionic phospholipid, cholesterol, and lipid poly(ethylene glycol) (PEG). However, these LNPs result in only general delivery of nucleic acids, rather than organ or tissue targeted delivery. LNPs typically delivery RNAs only to the liver. Therefore, new formulations of LNPs were sought in an effort to provide targeted nucleic acid delivery.

The four canonical types of lipids were mixed in a 15:15:30:3 molar ratio, with or without the addition of a permanently cationic lipid. Briefly, LNPs were prepared by mixing a dendrimer or dendron lipid (ionizable cationic), DOPE (zwitterionic), cholesterol, DMG-PEG, and DOTAP (permanently cationic). Alternatively DOTAP can be substituted for DODAP to generate a LNP comprising DODAP. The structure of DODAP and DODAP are shown in FIG. 1. Various dendrimer or dendron lipids that may be used are shown in FIG. 2.

For preparation of the LNP formulation, a dendrimer or dendron lipid, DOPE, Cholesterol and DMG-PEG were dissolved in ethanol at desired molar ratios. The mRNA was dissolved in citrate buffer (10 mM, pH 4.0). The mRNA was then diluted into the lipids solution to achieve a weight ratio of 40:1 (total lipids:mRNA) by rapidly mixing the mRNA into the lipids solution at a volume ratio of 3:1 (mRNA: lipids, v/v). This solution was then incubated for 10 min at room temperature. For formation of DOTAP modified LNP formulations, mRNA was dissolved in 1×PBS or citrate buffer (10 mM, pH 4.0), and mixed rapidly into ethanol containing 5A2-SC8, DOPE, Cholesterol, DMG-PEG and DOTAP, fixing the weight ratio of 40:1 (total lipids:mRNA) and volume ratio of 3:1 (mRNA:lipids). Formulation are named X % DOTAP Y (or X % DODAP Y) where X represents the DOTAP (or DODAP) molar percentage in total lipids, and Y represents the type of dendrimer or dendron lipid. Alternatively, formulation may be named Y X % DOTAP or Y X % DODAP where X represents the DOTAP (or DODAP) molar percentage in total lipids, and Y represents the type of dendrimer or dendron lipid.

Example 2. SORT LNP Stability

LNPs were tested for stability. 5A2-SC8 20% DODAP ("Liver-SORT) and 5A2-SC8 50% DOTAP ("Lung-SORT") were generated using either a microfluidic mixing method or a cross/tee mixing method. The different LNP formulations were characterized by size, polydispersity index (PDI) and zeta-potential, were examined by dynamic light scattering, 3 separate times for each formulation. The characteristics of the LNPs are show in Table 8.

TABLE 8

SORT LNP characteristics

| | Size (nm) | PDI | Zeta (mV) | Encapsulation Efficiency (%) |
|---|---|---|---|---|
| Lung-SORT - microfluidic | 82.3 | 0.10 | 3.0 | 100 |
| Lung-SORT - cross/tee mixing | 78.1 | 0.09 | 2.2 | 100 |
| Liver-SORT - microfluidic | 59.1 | 0.10 | −2.3 | 97 |
| Liver-SORT - cross/tee mixing | 60.0 | 0.11 | −30 | 96 |

Figure 6:
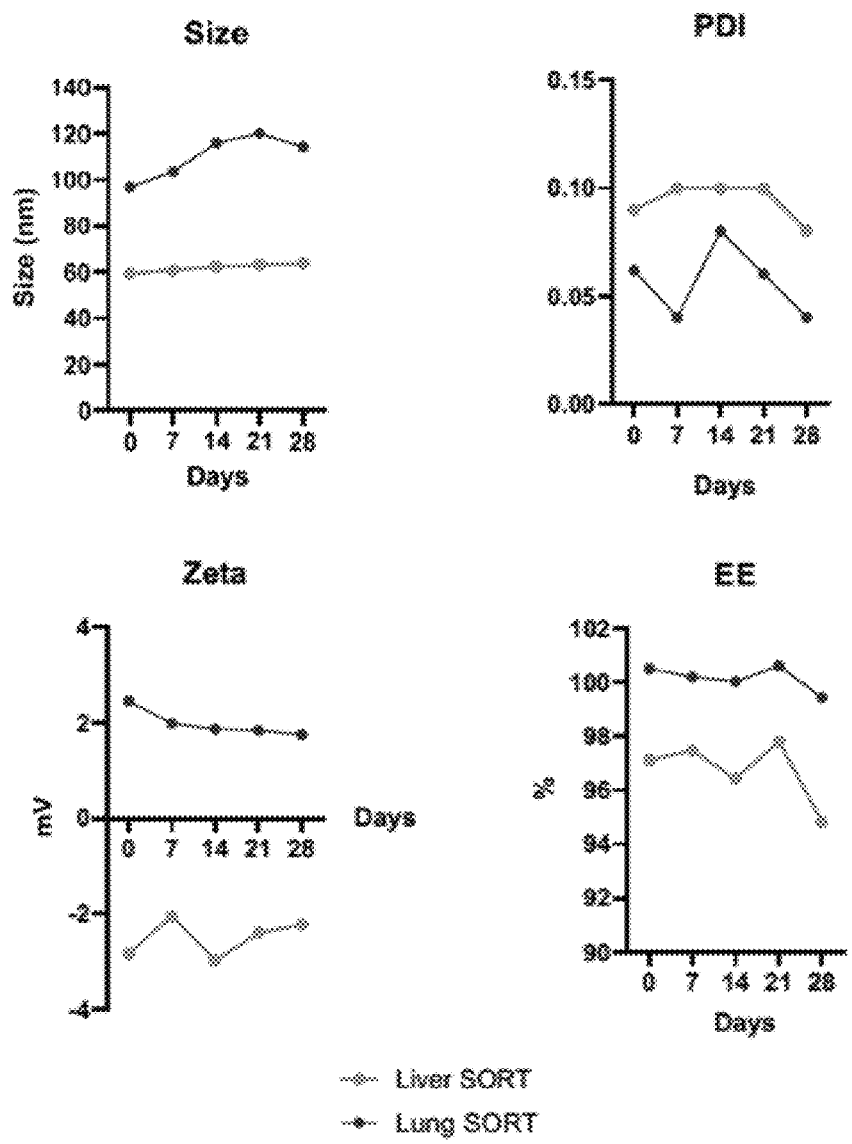
FIG. 6 shows the stability and general characteristics of various LNP compositions.

The encapsulation efficiency was tested using a Ribogreen RNA assay (Zhao et al., 2016). Briefly, mRNA was encapsulated with >95% efficiency in LNPs when the mRNA was dissolved in acidic buffer (10 mM citrate, pH 4). The characteristics were observed over 28 days for the two types of LNPs (5A2-SC8 20% DODAP ("Liver-SORT) and 5A2-SC8 50% DOTAP ("Lung-SORT")). FIG. 6 shows the changes of the characteristics of the LNP over the course of 28 days.

Figure 7:
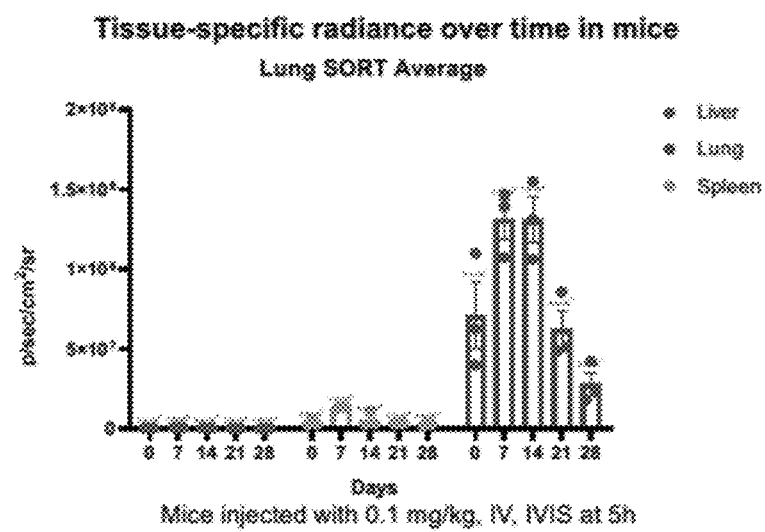
FIG. 7 shows a chart of tissue specific radiance over time in a mouse of a LNP composition ("Lung-SORT"; 5A2-SC8 DOTAP).
Figure 8:
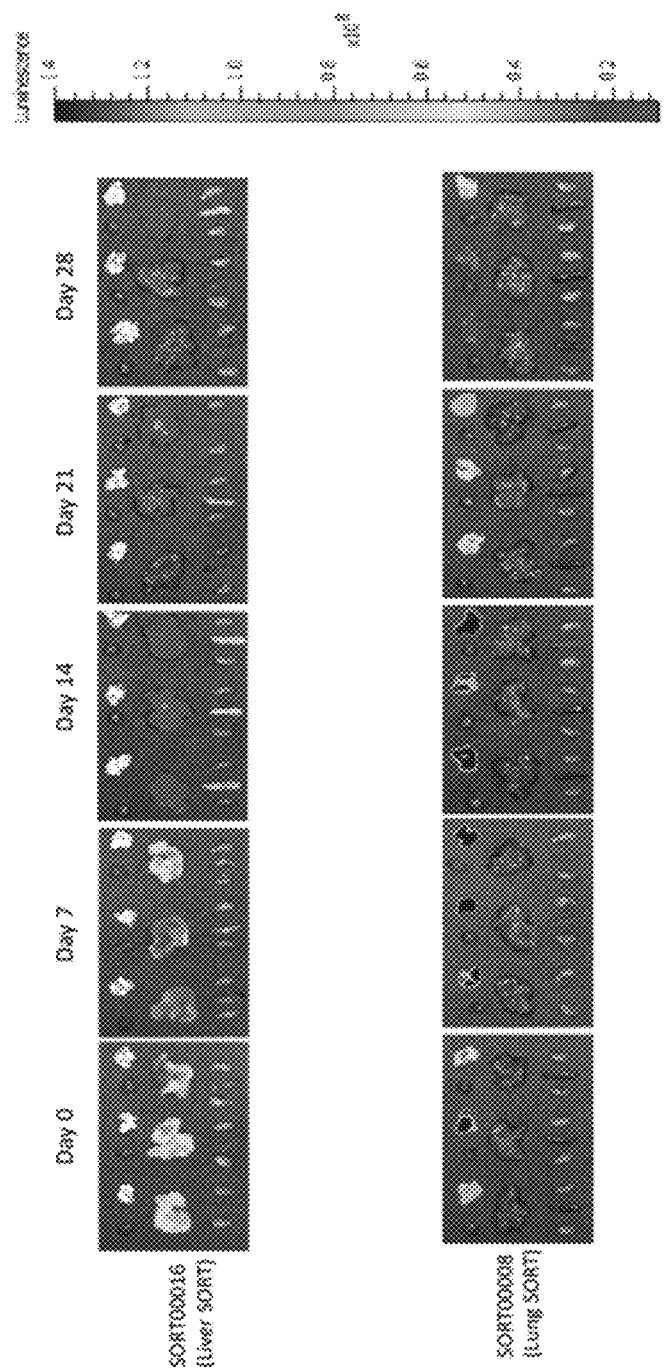
FIG. 8 shows images of tissue specific radiance over time in a mouse of a LNP composition ("Lung-SORT"; 5A2-SC8 DOTAP).

In addition, to the measure of the stability of the LNPs in solution, the stability of the LNPs and resulting mRNA expression was observed in mice. Briefly, mice were injected intravenously with 0.1 mg/kg and observed in vivo. Luciferin was added 5 hrs. after injection and visualized. As shown in FIG. 7, the Lung-SORT LNP generated tissue specific radiance in the lungs which remained high even after 14 day with a slight decay in signal by the $21^{st}$ and $28^{th}$ day. FIG. 8 shows images of the organs of the mouse at specific times periods after treated with Lung-SORT or Liver-SORT.

Example 3. Expression of TR mRNA in Different Cell Types

TR mRNA was loaded into either 20% DODAP 4A3-SC7 LNP or 10% DOTAP 5A2-SC8 LNPs and delivered into well-differentiated human bronchial epithelial cultures using apical bolus dosing. Cell expression was observed in various cell type and the percent of the cell type that expressed TR was plotted. As shown in the top panel of FIG. 3, the 20% DODAP 4A3-SC7 LNPs preferentially caused secretory cells to express TR, while 10% DOTAP 5A2-SC8 LNPs cause the ciliated cells to preferentially express TR. This preferential delivery may allow a treatment delivered to the lungs to preferentially affect a specific cell type in the lungs The TR mRNA was also loaded into LNPs without the SORT lipid (e.g. DODAP or DOTAP) to identify how the DODAP or DOTAP affected the potency. As shown in the bottom panel of FIG. 5, the LNPs comprising DOTAP or DODAP showed increase TR expression compared to their corresponding LNP without DOTAP or DODAP.

Figure 4:
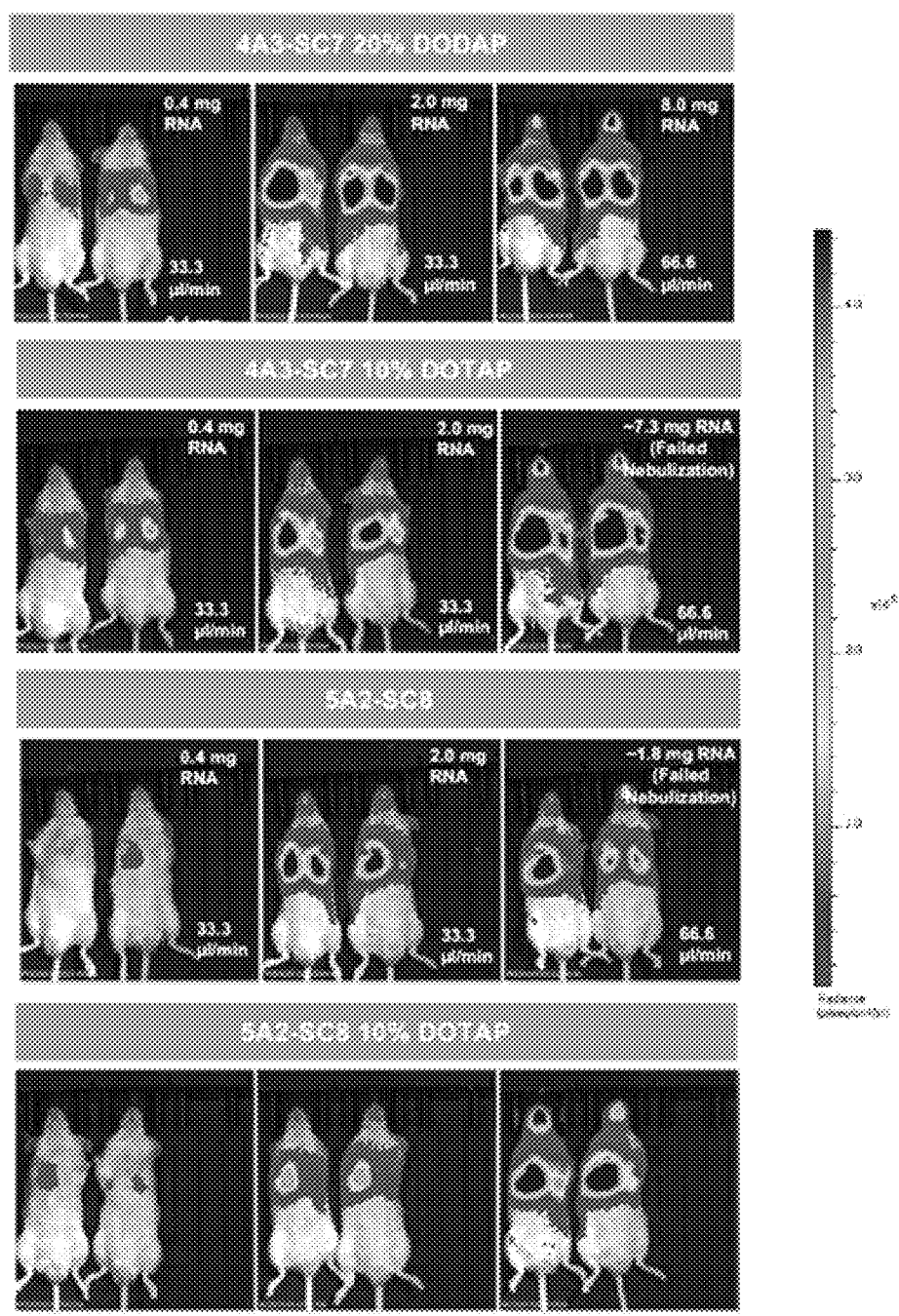
FIG. 4 shows images using in vivo imaging of bioluminescence of a mouse after inhaled aerosol delivery of a Luc mRNA/LNP using multiple compositions of LNP.

Example 4. Luciferase Activity and Histopathology from LNPs Delivered Via Inhaled Aerosol Luc mRNA was loaded into a number of LNPs including LNPs of comprising a SORT lipid and a dendrimer or dendron. LNPs of 4A3-SC7 20% DODAP, 4A3-SC7 10% DODAP, 5A2-SC8, 5A2-SC8 10% DOTAP were generated and loaded with Luc mRNA. 0.4/2/8 mg of LNP-formulatedLuc2 mRNA (1 mg/ml) was delivered into the pie chamber by nebulization (Aerogen solo), with an estimated (not measured) per mouse delivered dose of 0.01, 0.06 or 0.22 mg/kg. The mice were 7-week-old B6 male albino mice. Luciferin was administered to the mice 5 hrs. after delivery of the LNPs. The luciferase activity was detected as a measure of delivery to a target. FIG. 4 shows the distribution and expression of the luciferase in the mice demonstrating the expression was successful and delivery of the LNPs could be performed using inhaled aerosol delivery.

Example 5. Toxicity of EPC Containing LNPs

Figure 5:
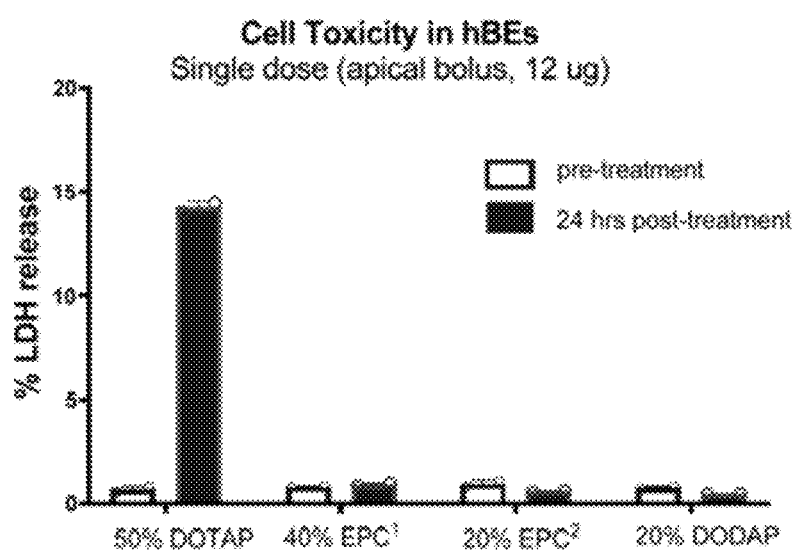
FIG. 5 shows a chart regarding cell toxicity of various LNP compositions in human bronchial epithelial (hBE) cells.

LNPs comprising ethylphosphocholine (EPC) in place of DOTAP or DODAP were tested for toxicity by using apical bolus dosing on human bronchial epithelial cells. The % of lactate dehydrogenase (LDH) that was released was used as a metric of cellular death and indicative of the toxicity of the LNP. The release of LDH was detected prior to treatment (pre-treatment) and 24 post treatment. As shown in FIG. 5, the treatment of 50% DOTAP LNP resulted in an ~15% LDH release whereas EPC didn't show a significant % LDH release. Importantly, DOTAP and EPC have a similar quaternary amine moiety, indicating that the activity for cell targeting may be similar, but that EPC is considerably less toxic.

Example 6. Production of DNAI1 mRNA

DNA corresponding to the gene of DNAI1 was synthesized at GenScript. pUC57/DNAI1 was digested with HindIII and EcoRI HF restriction enzymes. Moreover, a digested pVAX120 vector and DNAI1 cDNA were gel purified and ligated (the ORF for DNAI1 is codon optimized). Standard in vitro translation procedure was used for RNA production utilizing unmodified nucleotides. Capping reaction was carried out using Vaccinia Virus capping system and cap 2'-O-methyl transferase.

Example 7. Detection of DNAI1 mRNA Delivery to a Subject

A subject having or suspected of having primary ciliary dyskinesia (PCD) is given a treatment by administering a composition as described elsewhere herein. The subject is monitored at regular intervals for expression of DNAI1 in the lungs. A sample of lung tissue from the subject is taken comprising ciliated cells of the lung. The cells are harvested and prepared for RNA isolation. cDNA is produced from the RNA using a first strand synthesis kit and random hexamer. qPCR reactions are run using a set of forward and reverse primers and a fluorescent probe, specific to DNAI1 and a second set specific to a control or housekeeping gene for expression normalization. Expression of DNAI1 is detected using a fluorescent readout corresponding the DNAI1 probe.

Example 8. Functional Rescue in hBEs with DNAI1 mRNA

Figure 10A:
FIG. 10A shows summaries of experiments performed to measure properties of lipid compositions described herein.

Repeated doses of lipid compositions described herein were delivered to human basal epithelial cells (hBEs) deficient in DNAI1 as described in the first column of FIG. 10A. Results of the study are summarized in the left column of FIG. 10E. Cellular uptake was observed in the presence of mucus. The activity of cilia post treatment was comparable to normal controls. Normal beat frequency and synchronized wave-like motion of cilia was recovered. The first column of FIG. 10B further illustrates targeting of DNAI1-HA mRNA to ciliated cells, Immunofluorescence of DNAI1-HA and acetylated tubulin (biomarker for ciliated cells) shows the expression of DNAI1-HA in hBEs 72 h after dosing.

Example 9. Potency and Tolerability Study in Mice

Single administration and escalating doses of lipid compositions described herein comprising a luciferase mRNA payload are tested for potency and tolerability in mice. Key features of the study are summarized in the middle column of FIG. 10A. Mice are treated with a lipid composition comprising an ionizable cationic lipid (e.g., 4A3SC7, 5A2SC8) and a SORT lipid (e.g., DODAP, DOTAP) aerosolized via a nebulizer. Luciferase expression is measured to assess potency and histopathology is measured to asses tolerability. Good distribution and high levels of protein expression are observed in whole-body images of mice treated with the lipid composition, such as that depicted in the middle column of FIG. 10E. Histopathology results are comparable to control animals indicating high tolerability. The results from testing a short delivery time (e.g., 5-8 min) and low concentration used (e.g., 0.5 mg/mL) provides support for increasing the dosage.

Example 10. DNAI1 Expression in Lung Tissues of NHPs

Figure 10B:
FIG. 10B shows outcomes of experiments performed to measure properties of lipid compositions described herein.
Figure 10C:
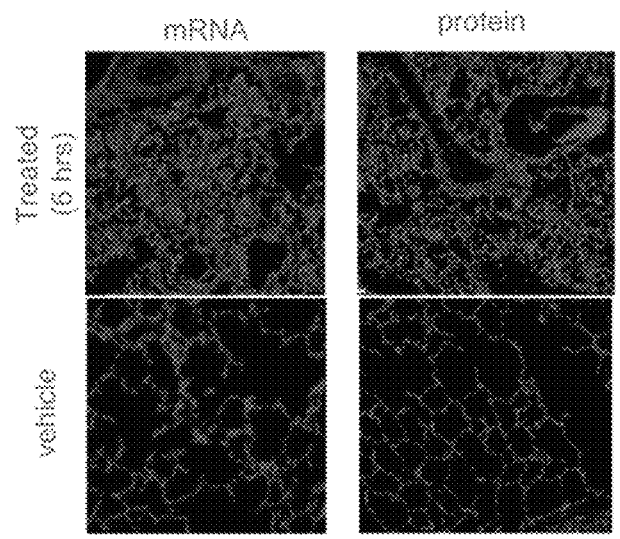
FIG. 10C illustrates positive lung labeling (red) for DNAI1 mRNA (left) and DNAI1 protein (right) in non-human primates using a lipid composition (e.g., comprising a SORT lipid) as described herein.
Figure 10D:
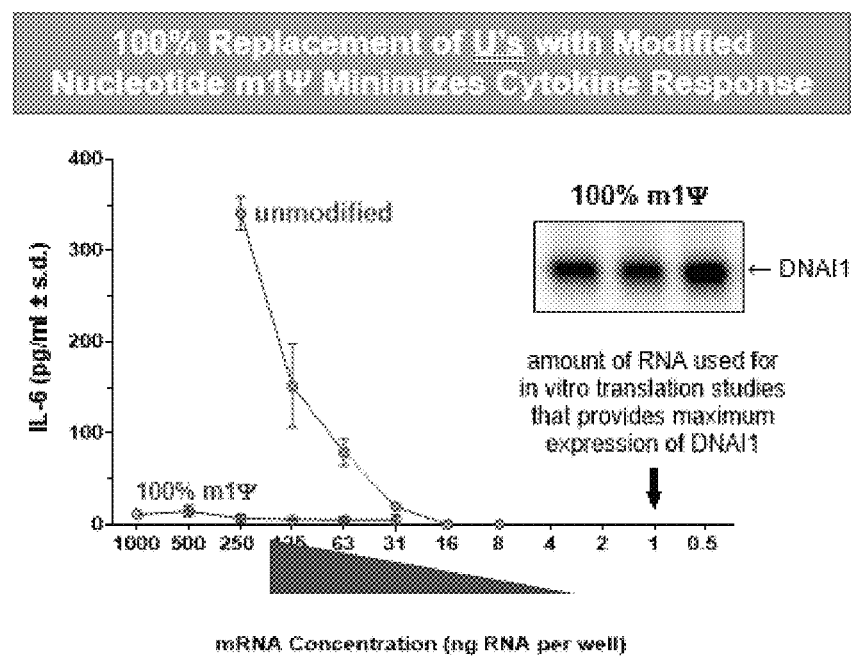
FIG. 10D illustrates that by replacing 100% of U's in the mRNA with modified nucleotide m1Ψ minimized cytokine response.
Figure 10E:
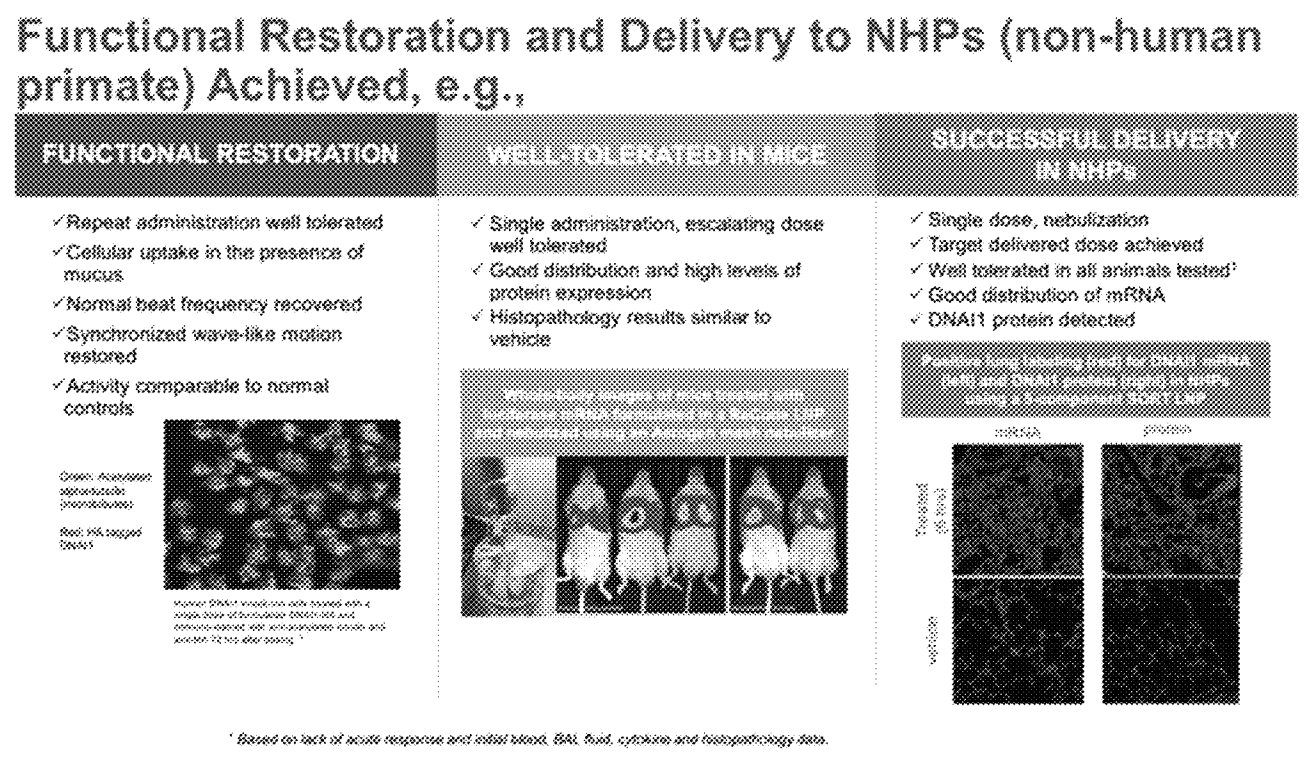

Two lipid compositions, RTX0001 (5 components) and RTX0004 (4 components), were evaluated in a non-human primate (NHP, cynomolgus macaques) study to demonstrate DNAI1 expression in lung tissues. RTX0001 comprises 4A3-SC7, DODAP, DOPE, cholesterol, and DMG-PEG at a molar ratio of 19.05:20:19.05:38.09:3.81, respectfully. RTX0004 comprises 5A2-SC8, DOPE, cholesterol, and DMG-PEG at a molar ration of 19.05:23.81:47.62:4.76, respectfully. Key features of the study are summarized in the fourth column from the left of FIG. 10A. Further experimental details are summarized in the middle column of FIG. 10B. Briefly, two formulations, one comprising a SORT LNP formulation (comprising, e.g., DODAP, DOTAP) and another comprising an LNP formulation were delivered to NHPs as a single dose via intubation. Both compositions contained DNAI1-HA mRNA. DNAI-HA mRNA and DNAI1-HA protein expression were detected in lungs of NHPs at 6 and 24 hours at doses of the aerosolized compositions of 0.1 mg/kg or less. The right column of FIG. 10C shows DNAI1-HA mRNA and corresponding protein expression observed 6 hours post treatment in the lung tissues of treated NHPs. The composition comprising a SORT molecule resulted in stronger observed expression of DNAI1-HA and DNAI1-HA mRNA in the lungs of NHPs. No adverse clinical observation or tolerability issues were detected precluding use of the formulations at higher doses or in multi-dose settings. FIG. 10D shows that that by replacing 100% of U's in the mRNA with modified nucleotide m1Ψ minimized cytokine response.

Example 11. Screening Lipid Formulations

Lipid compositions comprising an ionizable cationic lipid (e.g., 4A3SC7, 5A2SC8) with or without a SORT lipid (e.g., DODAP, DOTAP) were screened to enable longer storage and shipping, decrease required dose, shorten nebulization times (e.g., nebulization flow rate), and increase tolerability, as described in the second column from the left of FIG. 10A. Lipid compositions were screened by changing the ionizable lipid, the SORT lipid, buffer identity (e.g., PBS) and concentration, salt identity (e.g., NaCl) and concentration, cryopreservative identity (e.g., sucrose, trehalose, mannitol, xylitol, lactose) and concentration, N/P ratio, and PEG content. For screening N/P ratios: the FA, psd, % free, and yield were recorded, the potency and tolerability/toxicity (e.g., ciliary activity, LDH, cytokines) are assessed, and the nebulization time were evaluated (e.g., single dose, mice model). Various formulations were evaluated on the basis of particle size, polydispersity index (PDI), encapsulation efficiency (percent free mRNA). The lipid compositions were then screened for potency, targeting efficiency/specificity, stability, and tolerability/toxicity (e.g., ciliary activity, LDH, cytokines, blood chemistry markers) in human basal epithelial (hBE) cell cultures, mouse models, and mouse models for NHPs.

Experimental details and readouts are summarized in the second column from the left of FIG. 10A. Three different formulations with varying N/P ratios are summarized in Table 9.

Example 12. Clinical Study of mRNA Treatment for Primary Ciliary Dyskinesia

Figure 9A:
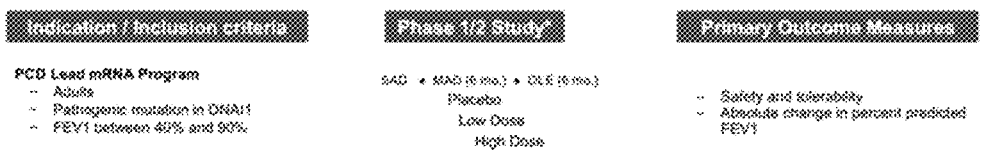
FIG. 9A shows a workflow for a safety and tolerability study in humans using a composition described herein.
Figure 9B:
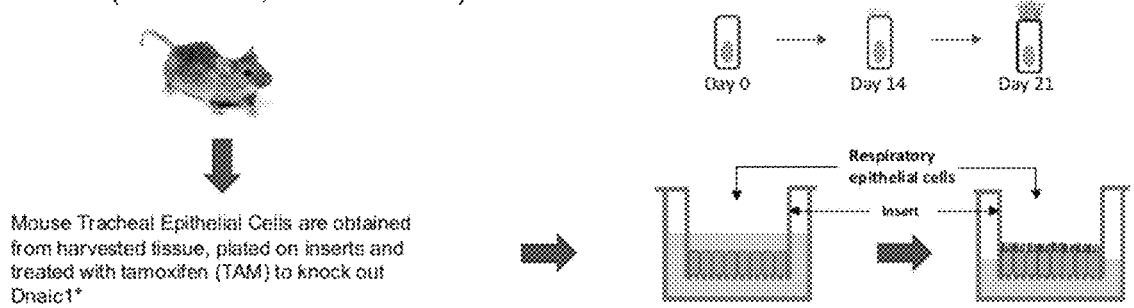
FIG. 9B illustrates an ex vivo model of ciliated epithelial cells (mouse tracheal epithelial cells or MTECs cultured at an air-liquid Interface (ALI) for testing the efficacy of rescue by the DNAI1 mRNA treatment described herein FIG. 9C illustrates that ciliary activity in KO mouse cells was rescued by the DNAI1 mRNA treatment, and the treatment effect remained stable for weeks after dosing was stopped.
Figure 9C:
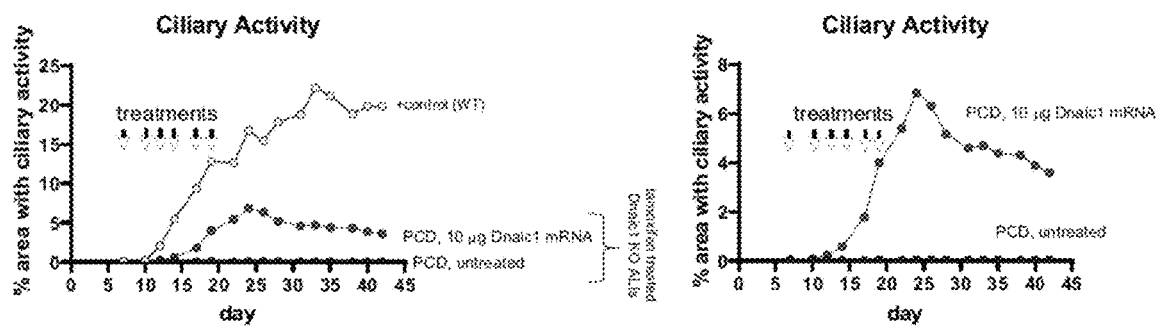

Adult subjects having or suspected of having primary ciliary dyskinesia (PCD) are given a treatment by administering a composition as described elsewhere herein. Subjects may be selected on the basis of a pathogenic mutation in DNAI1 and/or FEV1 between 40% and 90%. The study is single ascending dose (SAD), multiple ascending dose (MAD), or open-label extension (OLE) study. Subjects are sorted into placebo, low dose, and high dose treatment groups and receive a corresponding amount of formulation (or placebo). Subjects are observed for safety and tolerability and absolute change in percent predicted FEV1. Subjects treated with the formulation show signs of high tolerability and increase in percent predicted FEV1. FIG. 9A summarizes the main components of such a study. FIG. 9B illustrates an ex vivo model of ciliated epithelial cells (mouse tracheal epithelial cells or MTECs cultured at an air-liquid Interface (ALI) for testing the efficacy of rescue by the DNAI1 mRNA treatment described herein. MTECs were obtained from PCD conditional KO mouse model (Dnaic1 KO) and cultured at an air-liquid interface. The cells (ciliated, goblet, or basal) formed tight junctions and produced mucus, thus remodeling and restoring properties similar the native epithelium. FIG. 9C illustrates that ciliary activity in KO mouse cells was rescued by the DNAI1 mRNA treatment, and the treatment effect remained stable for weeks after dosing was stopped. Dnaic1 KO mouse cells were treated basally three times a week starting on day 7 during differentiation. The last dose was Armentieres on day 19.

TABLE 9

Lipid formulations tested for potency, stability, and tolerability

| | Formulation A | Formulation B | Formulation C |
|---|---|---|---|
| Concentration/potency | 0.5 mg/mL | 1 mg/mL | 1-2 mg/mL |
| Human dose | Est ≥ 0.5 mg/kg | 0.1-0.5 mg/kg | 0.1-0.3 mg/kg |
| Administration Frequency | TBD | Once or twice per week | Once or twice per two weeks |
| Tolerability | TBD | Adequate to support administration frequency | Adequate to support administration frequency |
| Sterilization | Sterile filtration | Sterile filtration | Sterile filtration |
| Stability/shelf life | 2-4 weeks at 2-8° C.; (cannot be frozen) | ≥1 year at −80 ° C.; after thaw at 5° C. ≥ 1 week | ≥2 year at −20° C.; after thaw 5° C. 1 month Alternatively, lyophilized, stored at 2-8° C. ≥ 2 years |
| Nebulization: | | | |
| Flow rate | >0.2 mL/min at 0.5 mg/mL | 0.4 mL/min at 0.5 mg/mL | >0.4 mL/min at 0.5 mg/mL |
| Device | Aerogen solo | Aerogen Solo or Pari | Breath-actuated |
| Nebulization time | TBD | 30-60 min | 30 min or less |

Moreover, aerosol compositions without the presence of lipid compositions (e.g., only salt(s), buffer(s), cryopreservative(s)) are tested to determine effect of each component and its concentration on the nebulization flow rate.

The aerosolized lipid compositions may provide synergy with the additional administration of the lipid composition through IV.

Ciliary activity in treated Dnaic1 KO culture was first detected 5 days after dosing was initiated. Activity in treated Dnaic1 KO cells reached 36% of normal (vs PCD/no TAM controls) cells by day 24. Ciliary activity in treated Dnaic1 KO cells remained above 20% of normal (more than 50% of max) cells 23 days after the last treatment (the last timepoint assessed). No ciliary activity was detected in untreated Dnaic1 KO cultures throughout the duration of the study.

Example 13. Dose Finding and Repeat Administration Studies in NHPs

Lipid compositions as described herein are used in dose finding and repeated administration studies in non-human primates (NHPs). An overview of such a study is described in the rightmost column of FIG. 10A. Lipid compositions are tested to determine clinical candidates for an investigational new drug study, determine appropriate dose and dosing frequency, determine the maximum tolerated dose, and select a nebulization device for clinical development. The three rightmost columns FIG. 10B summarize these and other goals of the study. Experimental readouts are pharmacokinetics (PK), tolerability, biodistribution, and immunological response as measured by techniques described above.

Example 14. Detection of DNAI1-HA mRNA Expression in Cells

Figure 11A:
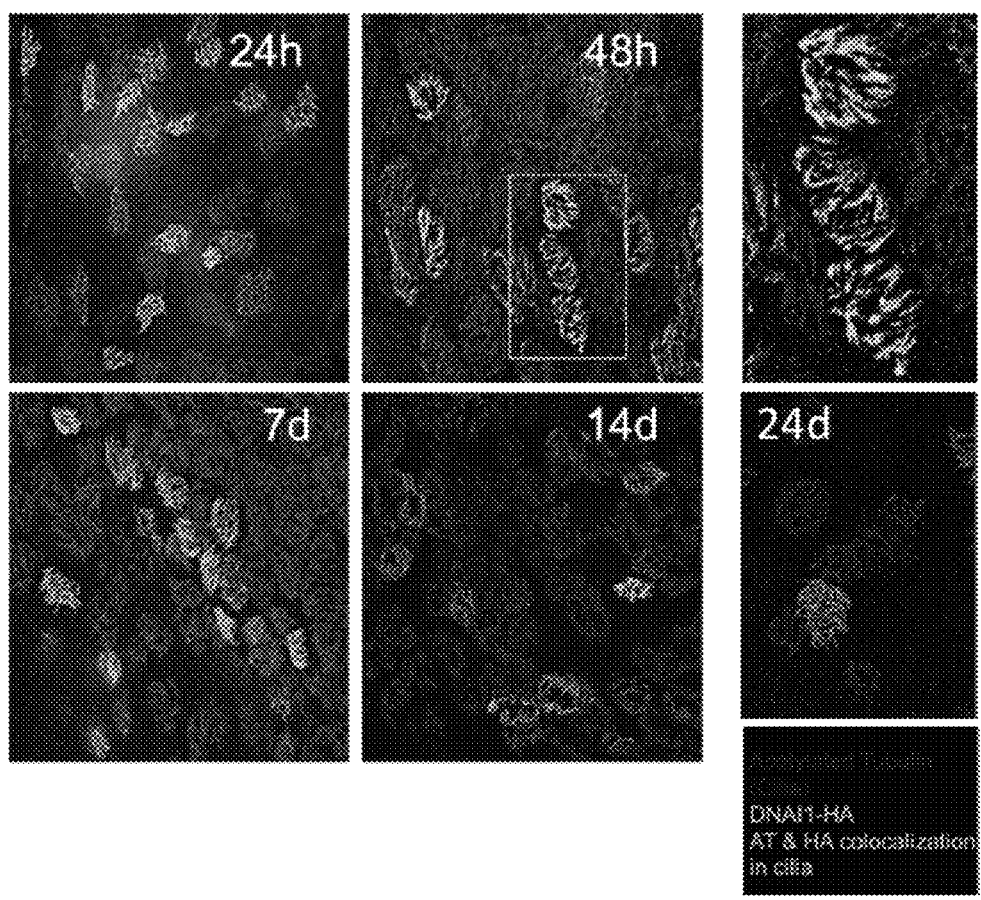
FIG. 11A shows images of immunofluorescence of human DNAI1 knock-down cells treated with LNPs containing DNAI-HA mRNA. Well-differentiated human DNAI1 knock-down cells were treated with a single dose of a formulation of DNAI1-HA mRNA described herein and immunostained with anti-acetylated tubulin and anti-HA. Integration of newly-expressed DNAI1-HA into axoneme of cilia peaked between 48 to 72 hours after treatment. DNAI1-HA was detected in ciliary axoneme for more than 24 days after single administration. Repeated administration resulted in rescue of ciliary activity that remained for weeks after the dosing was stopped.
Figure 11B:
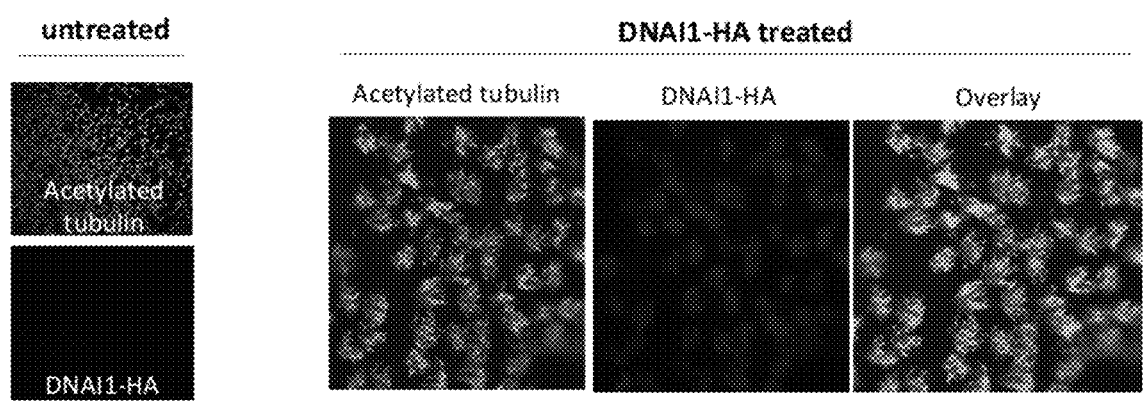
FIG. 11B illustrates that newly-made HA-tagged DNAI1 was rapidly incorporated into the cilia of human bronchial epithelial cells (hBEs). Well-differentiated human DNAI1 knock-down cells were treated (basal administration) with a single dose of LNP formulated DNAI1-HA (10 μg in 2 ml of media). Cells were immunostained with anti-acetylated tubulin and anti-HA 72 hours after dosing. More than 90% of ciliated cells was positive for DNAI1-HA.

Human DNAI1 knock-down cells were cultured at an air-liquid interface (ALI). The cultured cells were treated with a single dose of LNPs containing DNAI1-HA mRNA (10 µg/mL of media). Cells were immunostained with anti-acetylated tubulin (ciliated cell marker) and anti-HA antibodies 24 hours, 48 hours, 7 days, and 14 days after dosing. FIG. 11A shows immunofluorescence imaging of these cells at the indicated timepoints, demonstrating targeted cells successfully expressed the DNAI1-HA mRNA. Integration of DNAI1-HA into axoneme of cilia is seen to peak between 48-72 hours after treatment. Well-differentiated human DNAI1 knock-down cells were treated with a single dose of a formulation of DNAI1-HA mRNA described herein and immunostained with anti-acetylated tubulin and anti-HA. Integration of newly-expressed DNAI1-HA into axoneme of cilia peaked between 48 to 72 hours after treatment. DNAI1-HA was detected in ciliary axoneme for more than 24 days after single administration. Repeated administration resulted in rescue of ciliary activity that remained for weeks after the dosing was stopped. FIG. 11B illustrates that newly-made HA-tagged DNAI1 was rapidly incorporated into the cilia of human bronchial epithelial cells (hBEs). Well-differentiated human DNAI1 knock-down cells were treated (basal administration) with a single dose of LNP formulated DNAI1-HA (10 µg in 2 ml of media). Cells were immunostained with anti-acetylated tubulin and anti-HA 72 hours after dosing. More than 90% of ciliated cells was positive for DNAI1-HA.

Figure 12:
FIG. 12 shows a multiplexed immunofluorescence panel of the respiratory epithelium of NHPs that may be used to distinguish cell types showing newly translated DNAI1 protein.

Example 15. Biomarkers and Multiplex Immunofluorescence Panel for Epithelial Cell Types A multiplexed immunofluorescence panel was developed to distinguish certain epithelial cell types on the basis of certain biomarkers. The particular biomarkers and corresponding cell types targeted in the panel are summarized in Table 10. FIG. 12 shows the results of the panel. In each panel, the corresponding cell type is identified via immunofluorescence by the presence of a biomarker or biomarkers.

TABLE 10

Multiplex IF Panel cell types and corresponding markers

| Cell Type | Example Marker |
|---|---|
| Epithelium | EPCAM |
| Ciliated | acetylated-tubulin (AC-Tubulin) |
| Club | Secretoglobin Family 1A Member 1 (SCGB1A1) |
| Goblet | Mucin 5AC (MUC5AC) |
| Basal (stem) | Cytokeratin 5 (CK5) |

Figure 13A:
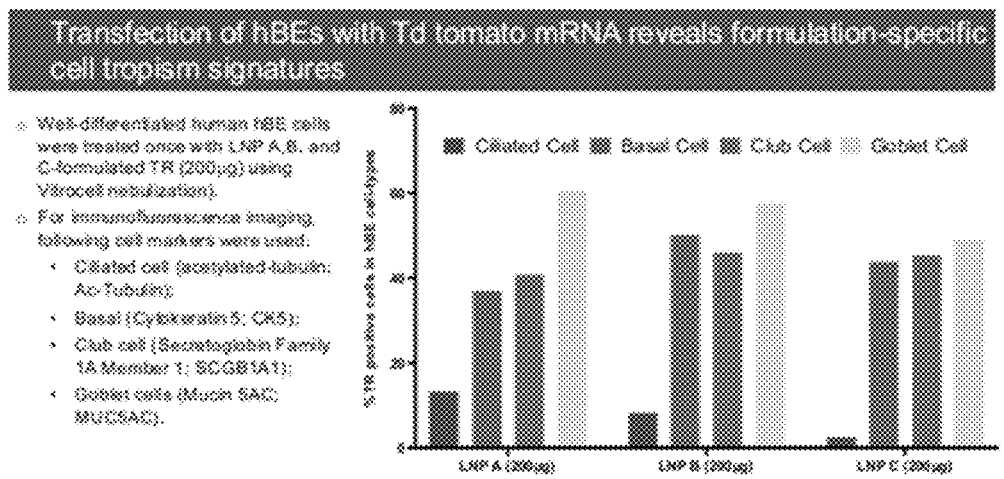
FIG. 13A shows cell tropism signatures of LNP formulations described herein.
Figure 13B:
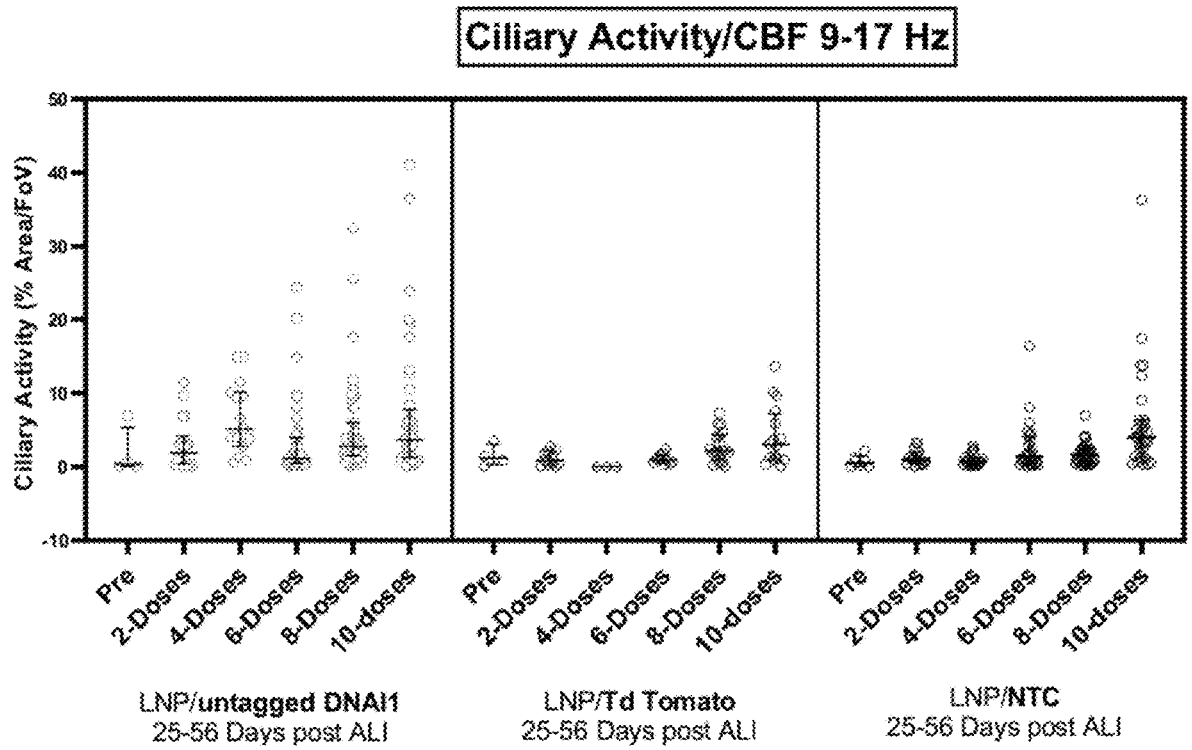
FIG. 13B illustrates aerosol administration of formulated DNAI1 mRNA rescued ciliary activity in knock-down primary hBE ALI cultures. Well-differentiated human DNAI1—knock-down cells (hBEs) were treated 2 times per week with LNP-formulated DNAi1 (300 μg per Vitrocell nebulization) starting on day 25 post ALI (culture age). Last

Example 16. Observation of Specific Cell Tropism Signatures in LNP Formulations Well-differentiated human bronchial epithelial (hBE) cells were treated once with either LNP A, B, or D (200 µg) using Vitrocell nebulization. Ciliated cells, basal cells, club cells, and goblet cells were distinguished on the basis of cell markers as detailed in Table 11. FIG. 13A shows the percentage of each cell type successfully transfected with tdTomato mRNA as measured by percentage of each cell type expressing tdTomato (% TR positive) and demonstrates specific cell tropism signatures for each LNP formulation. FIG. 13B shows illustrates aerosol administration of formulated DNAI1 mRNA rescued ciliary activity in knock-down primary hBE ALI cultures. Well-differentiated human DNAI1—knock-down cells (hBEs) were treated 2 times per week with LNP-formulated DNAi1 (300 µg per Vitrocell nebulization) starting on day 25 post ALI (culture age). Last dose was administered on day 50 post ALI. Increased ciliary activity in treated DNAI1 knock-down cultures was first detected seven days after dosing was initiated. Rescued ciliary activity had normal beat frequency (9-17 Hz) and appeared synchronized.

TABLE 11

| Cell markers for distinguishing cell types | |
|---|---|
| Ciliated cell | acylated-tubulin (Ac-Tubulin) |
| Basal cell | Cytokeratin 5 (CK5) |
| Club cell | Secretoglobin Family 1A Member 1 (SCGB1A1) |
| Goblet cell | Mucin 5AC (MUC5AC) |

Example 17. Expression of Tomato Red (TR) in Basal and Secretory Cells

Figure 14A:
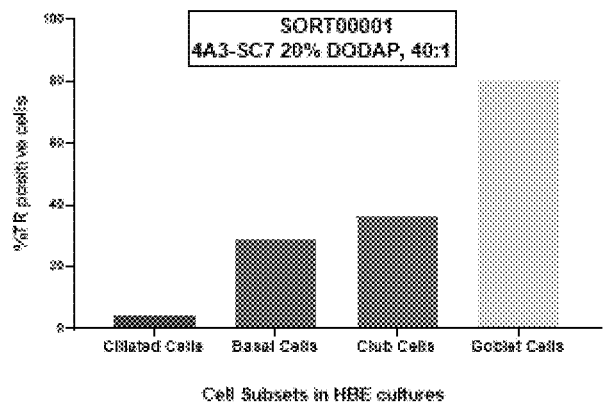
Figure 14B:
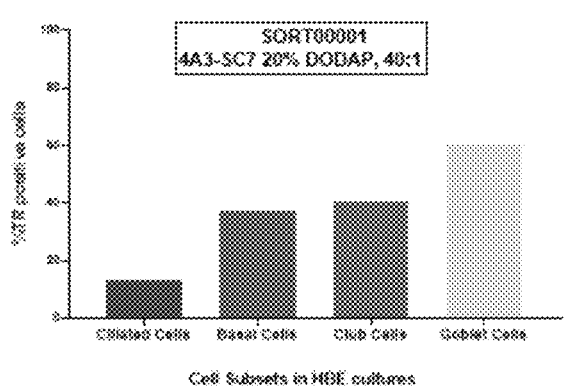
Figure 14C:
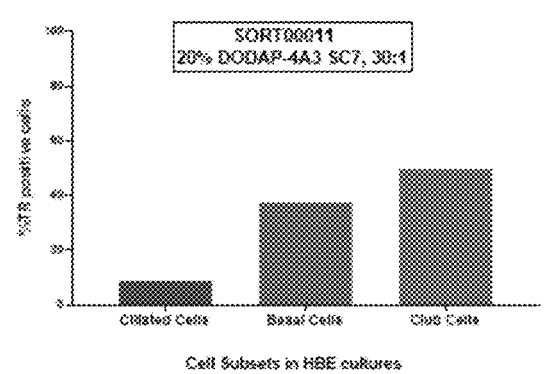
Figure 14D:
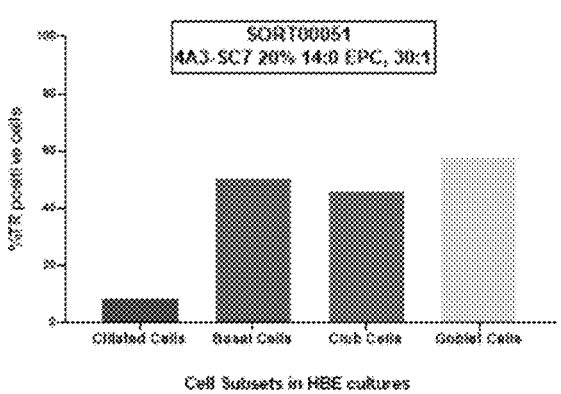
Figure 14E:
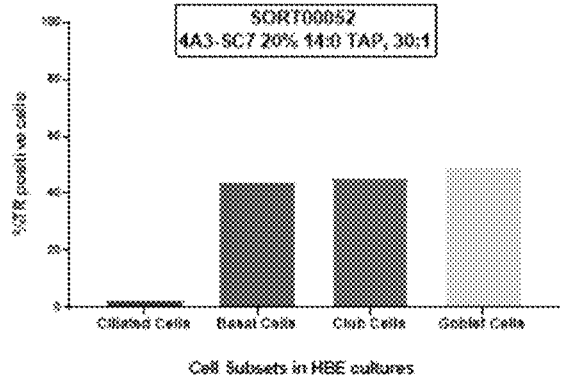

Expression of TR (Tomato Red) mRNA in different cell types in HBE cultures (human bronchial epithelial cultures) was analyzed. TR mRNA was loaded into one of 20% DODAP-4A3 SC7 40:1/PBS (FIG. 14A), 4A3-SC7-20% DODAP 40:1/Buffer 27/frozen (FIG. 14B), 4A3-SC7-20% DODAP 30:1/Buffer 27/frozen (FIG. 14C), 4A3-SC7 20% 14:0 EPC, 30:1/Buffer 27/frozen (FIG. 14D), 4A3-SC7 20% 14:0 TAP, 30:1/Buffer 27, frozen (FIG. 14E) and delivered into well-differentiated human bronchial epithelial cultures by aerosol delivery. TR protein expression in various cell-types was observed and the percent positive TR cells in different cell-types was plotted. Cell types observed and corresponding cell markers are as described in Example 16. As shown in each panel of FIG. 14, TR was seen primarily in basal and secretory cells in treated cultures. Note that HBE cultures have high numbers of goblet cells.

Figure 15:
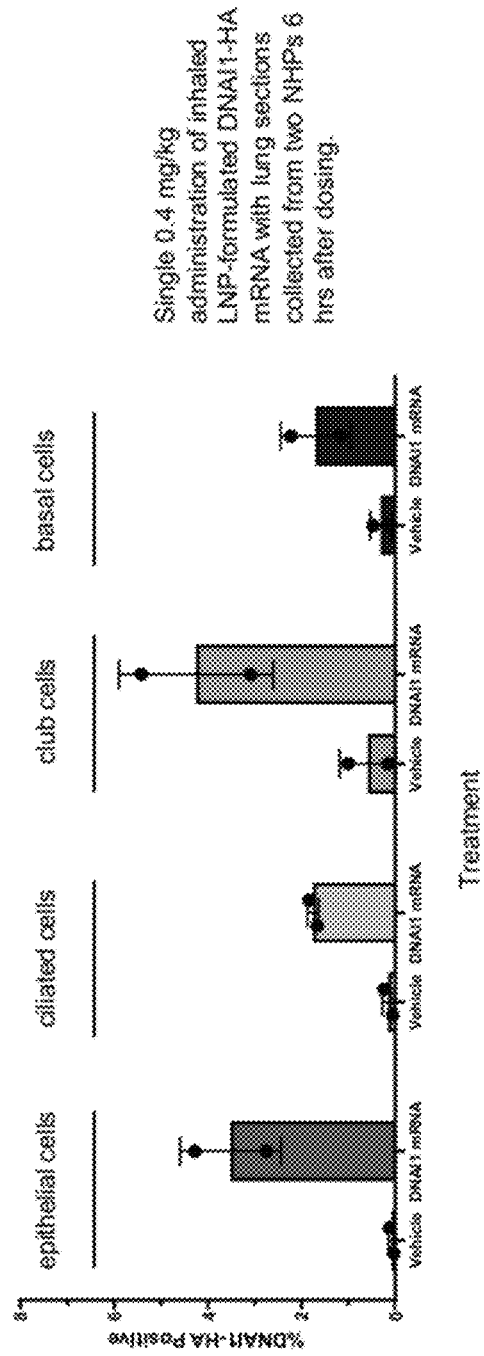
Figure 16A:
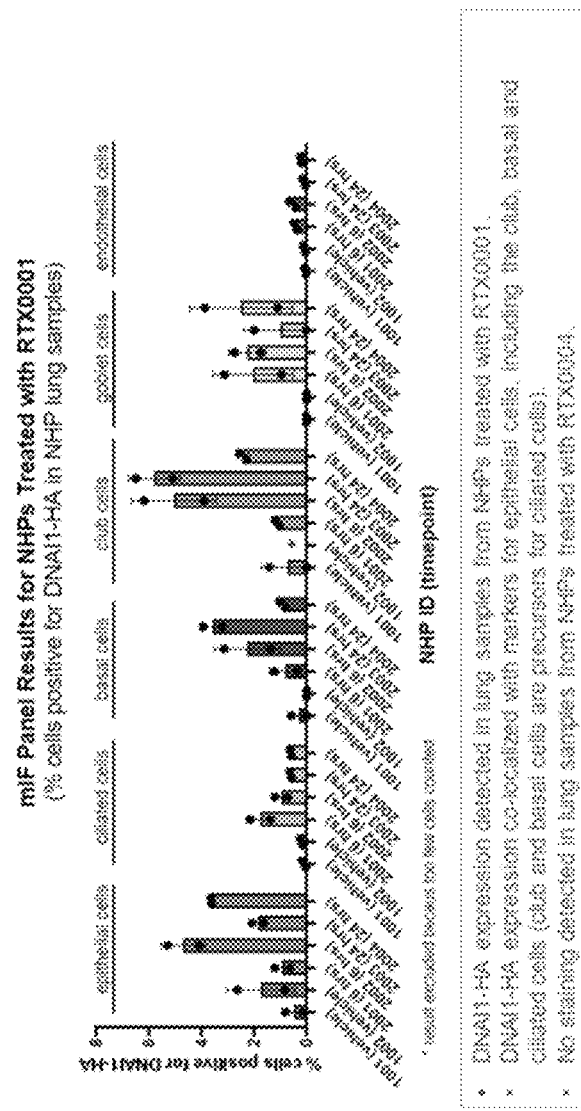
Figure 16B:
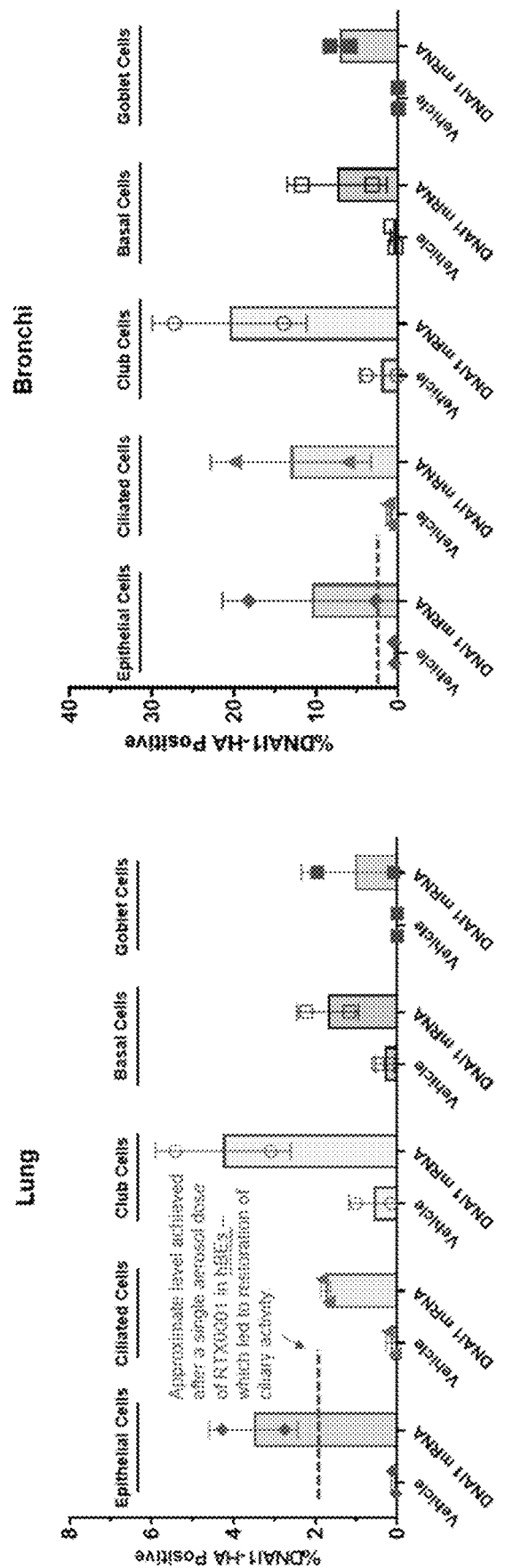

Example 18. DNAI1-HA is Expressed in Cells of the Respiratory Epithelium from NHP Lung Samples Non-human primates (NHPs) were treated by aerosol delivery with a low dose of DNAI1-HA mRNA contained in lipid compositions comprising a SORT lipid as described herein. Multiplex immunofluorescence was used to quantify DNAI1-HA expression in lung tissue blocks from treated animals. Lung tissue blocks were analyzed 6 h after treatment (6 hrs) or 24 h after treatment (24 hrs) with lipid compositions containing buffer as a control (vehicle). Cell markers for each cell type are as detailed in Example 6. As shown in FIG. 15 and FIGS. 16A-B, DNAI1-HA expression was detected in lung samples from NHPs treated with the lipid composition containing DNAI1-HA mRNA. Further, DNAI1-HA expression co-localized with markers for epithelial cells, including club, basal, and ciliated cells, indicating the lipid composition preferentially targeted the respiratory epithelium. Single 0.4 mg/kg administration of inhaled LNP-formulated DNAI1-HA mRNA was introduced to two NHPs (one male and one female). Lung and bronchial sections were collected six hours after dosing. Percentage of DNAI1-HA positive was calculated by combining cell counts from 4 lung sections (~500,000 to 1,400,0000 cells counted) and 1 bronchial section (~16,000 to 65,000 cells counted) from each animal.

Example 19. Aerosol Administration of Formulated DNAI1 mRNA Rescues Ciliary Activity in Knock-Down Primary Bronchial Human ALI Cultures Human primary bronchial epithelial DNAI1 knock-down cells were cultured at an ALI. Well-differentiated cells were treated 2×/week (T, F) with LNP C (300 µg/d using Vitrocell nebulization) starting on day 25 post ALI culture age. The last does was administered on day 50 post ALI culture. Ciliary activity was measured by cross-sectional area (CSA) and beat frequency following certain doses. FIG. 17 shows increased ciliary activity in treated DNAI1 knock-down cultures was first detected 7 days after dosing was initiated.

Example 20. Prolonged Rescue of Ciliary Activity in KO-Primary Tracheal Mouse ALI Cultures Mouse tracheal epithelial cells (MTEC) are harvested from Dnaic1 mice. The cells are cultured as described in Example 8 and grown until differentiating. The differentiating Dnaic1 knock-out (KO) mouse cells are treated with a low dose of a lipid composition comprising a SORT compound disclosed herein and carrying a DNAI1 mRNA. Ciliary activity as measured by ciliary cross-sectional area (CSA) and ciliary beat frequency (CSF) is determined at certain timepoints. Wild type (WT) and PCD/no TAM cells are used as positive controls and untreated Dnaic1 KO cells as negative controls. Ciliary activity in treated Dnaic1 KO cells may be higher than untreated Dnaic1 KO cells.

Example 21. Additional SORT Molecules

SORT lipids were screened for strong lung or spleen specificity and tolerability in mouse IV studies. The second from the left column of FIG. 10B discusses the cell tropism achieved through the SORT lipids screened. Five SORT molecules were evaluated and resulted in 2-7 times higher potency in hBEs cell cultures compared to RTX0001.

Example 22. Stability and Efficacy Study

Buffers and cryopreservatives for freezing, concentrations, osmolality and ionic strength were screened. Certain buffers provided stability across different SORT lipids and lipid compositions. The screened buffers resulted in some formulations to increase in particle size after a freeze/thaw cycle. The final particle size after a freeze/thaw cycle for all formulation resulted in acceptable ranges for particle size (<130 nm).

Potency and tolerability of formulations were tested after being stored in frozen conditions (freeze/thaw) in in vitro and in vivo nebulization experiments. Lipid compositions with SORT lipids in the screened buffer under a freeze/thaw cycle and without freeze/thaw was nebulized in hBEs. Some formulations had small change in potency (either increase or decrease), but all formulations maintained higher potency than RTX0001. The study showed that high potency was remained in the screened buffer for lipid compositions.

Example 23. Additional Screening Studies

Lipid compositions comprising SORT lipids were evaluated with a reduced 25% and 50% total lipid/mRNA ratio (N/P ratio). The 50% mRNA reduction resulted in small decrease in potency in both hBE and mouse nebulization for some lipid compositions, while other tested lipid compositions retained their potency. Two lipid compositions comprising SORT lipids were observed to have a small increase in particle size when tested with a 50% reduction in total lipid compared to RTX0001.

The lipid compositions were screened with changes in PEG lipid content and different N/P ratios. A small increase in particle size was observed with decrease in PEG lipid amount. A screened range of PEG concentration provided 120 nm particle size.

The results provide support that a change (e.g., increase) in % PEG lipid in the lipid composition may result in a change in potency (e.g., increase). In a hBE nebulization study, a decrease in PEG lipid amount resulted in an increased potency and an increase in PEG lipid amount resulted in a decrease in potency.

Example 24. SORT NHP Study

NHPs (Cynomolgus monkey, *Macaca fascicularis*, Mauritius origin, 2.5 to 3 years old, male: 2.7-3.3 kg/female: 2.5-3.0 kg; N=18 total, N=8 per dose group (4 male/4 female), N=2 vehicle control (1 male/1 female) were examined for the efficacy of aerosol delivery by inhalation using oronasal face mask. The delivery doses was 0.12 mg/kg or 0.24 mg/kg. Expression of DNAI1 was examined at six hours, 24 hours, 72 hours, or seven days after administration of RTX0052 (a lipid composition described herein. Readout for determining the efficacy of the was determined in NHPs administered with vehicle (Group 1); low dose (Group 2 with a target dose of 0.08 mg/kg; target aerosol concentration Ec of 0.0052 mg/L for 30 minutes); and high dose (Group 3 with a target dose of 0.24 mg/kg; target aerosol concentration Ec of 0.0052 mg/L for 90 minutes). FIG. 18A illustrates the aerosol concentration administered to the NHPs, and FIG. 18B illustrates exemplary measurements of the doses delivered to the NHPs. FIG. 18C illustrates characterization of the aerosol composition droplet (MMAD: mass median aerodynamic diameter; GSDL: geometric standard deviation). The droplet characterization results were within recommended range of the Organization for Economic Co-operation and Development (OECD) guidance 433 for inhalation toxicity studies with an MMAD≤4 μm and a GSD between 1.0 and 3.0.

Figure 19A:
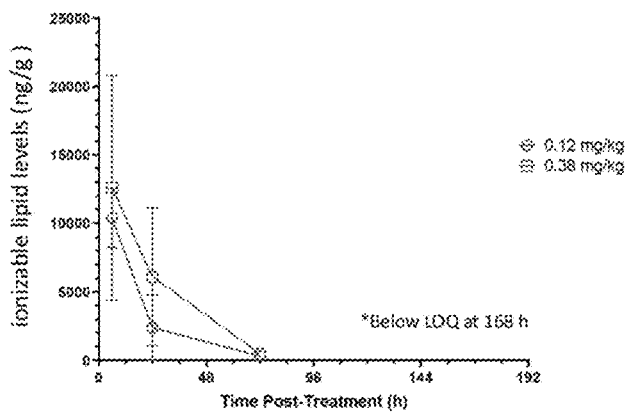
Figure 19B:
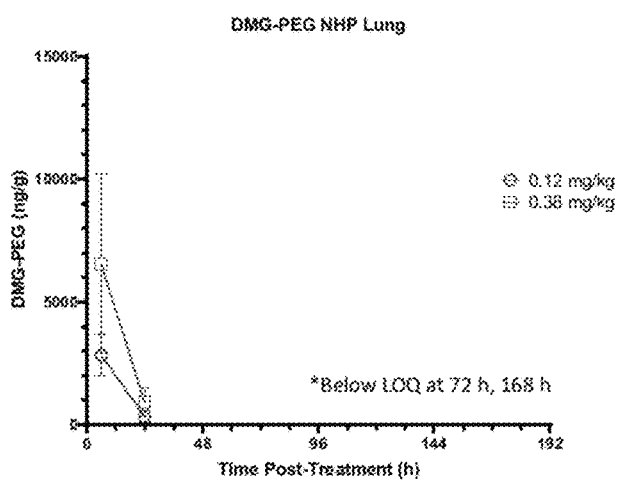
Figure 19C:
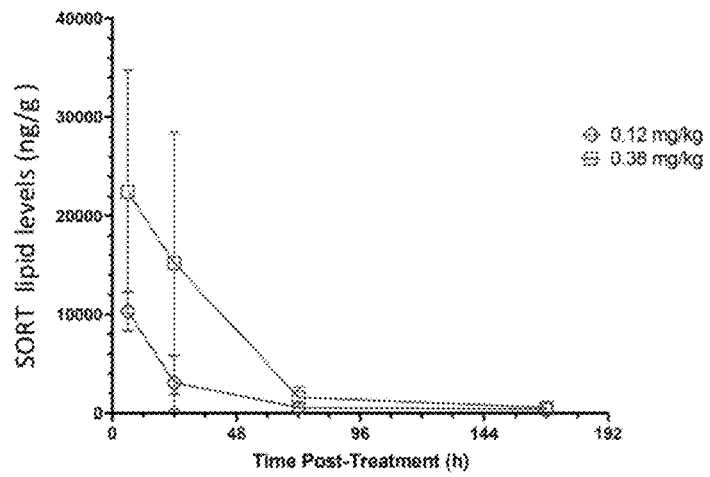
Figure 20A:
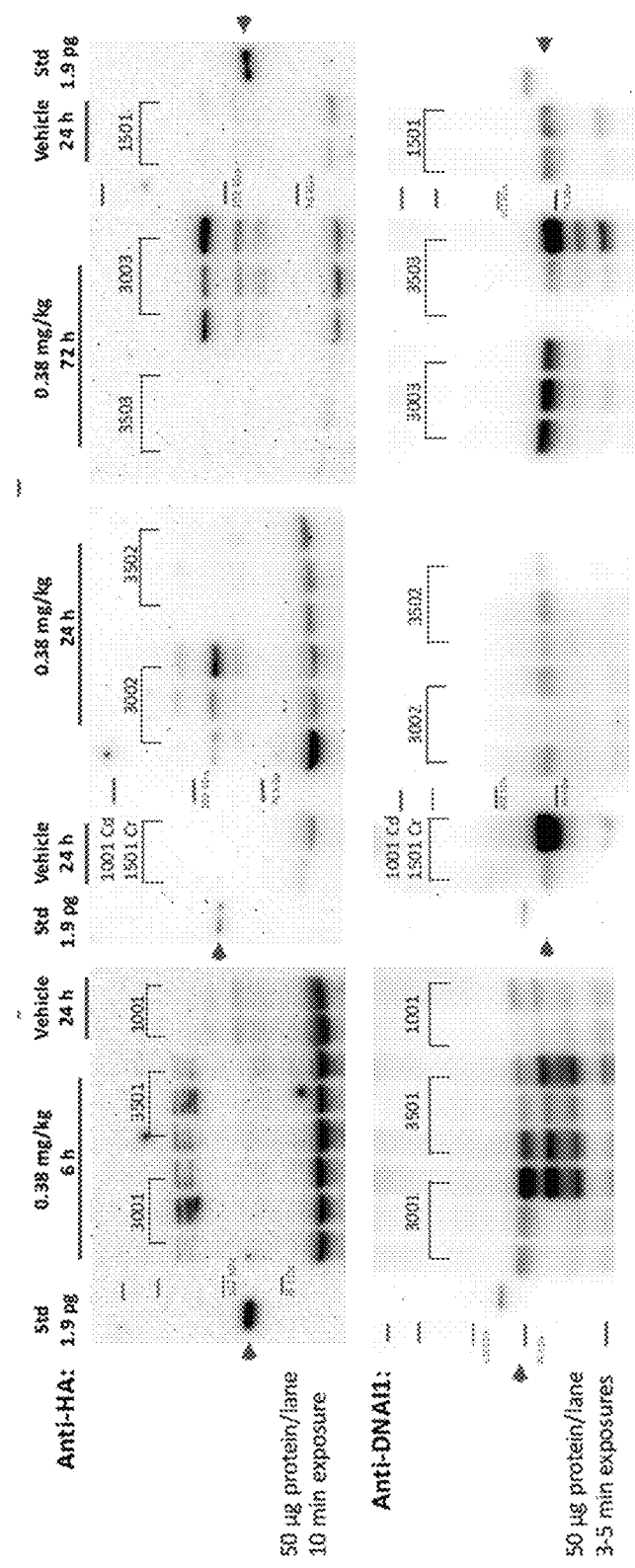
Figure 20B:
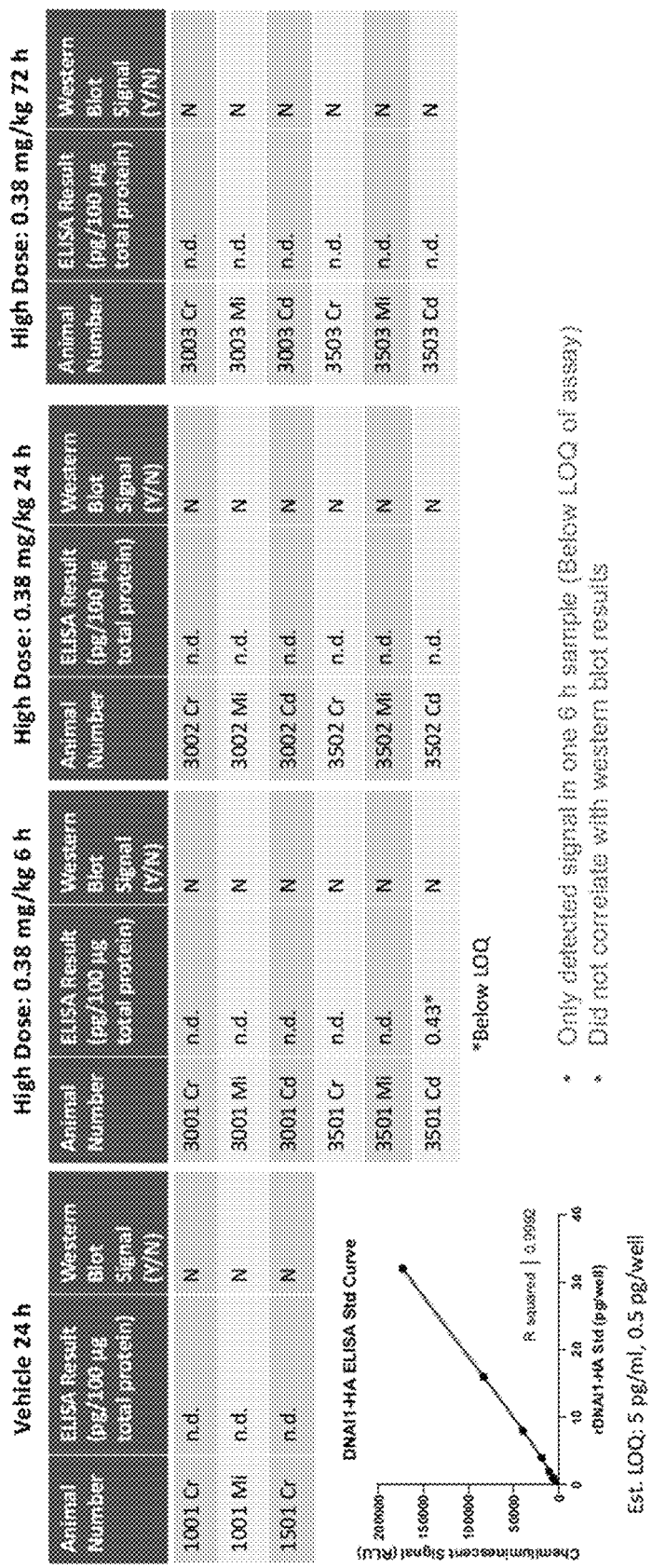

Measurement of the droplet (lipid) in NHP blood, lung, liver, and spleen tissue was determined by liquid chromatography and mass spectrometry (LC/MS-MS). Sample Matrices: Blood (plasma and blood cell fractions), Lung, Liver, Spleen. Limit of quantification (LOQ) of ionizable lipids in plasma was 4 ng/ml. LOQ of ionizable lipid in blood cell fraction was 4 ng/ml. LOQ of ionizable lipid in lung tissue cell fraction was 10 ng/ml. LOQ of PEGylation of myristoyl diglyceride (DMG-PEG) in plasma was 20 ng/ml. LOQ of DMG-PEG in blood cell fraction was 40 ng/ml. LOQ of DMG-PEG in lung tissue was 20 ng/ml. LOQ SORT lipid in lung tissue cell fraction was 10 ng/ml. LOQ of SORT lipid in plasma was 1 ng/ml. LOQ of PEGylation of SORT lipid in blood cell fraction was 1 ng/ml. LOQ of SORT lipid in lung tissue was 2 ng/ml. FIGS. 19A-C illustrate measurement of LNP lipid (stemmed from aerosol droplet) in lung in both low dose and high dose NHP group (FIG. 19A: ionizable lipid in lung; FIG. 19B: DMG-PEG in lung; and FIG. 19C: SORT lipid). Table 12 illustrates detection of DNAI1-HA in the processed sample of the NHP. For Table 12, 2 sets of lung samples per animal (6 total) processed and assayed for: Western blot: anti-HA and anti-DNAI1; and ELISA: DNAI1-HA (Capture Ab: Anti-HA, Detection Ab: anti-DNAI1). FIG. 20A illustrates DNAI1-HA protein expression in the NHP lung by Western blotting. FIG. 20B illustrates DNAI1-HA protein expression in the NHP lung by ELISA.

TABLE 12

DNAI1-HA detection in NHP sample

| Animal | Group | Necropsy | Lung Samples |
|---|---|---|---|
| 3001 | High Dose 0.38 mg/kg | 6 h | N = 3 (1 ea. Caudal, Cranial, Middle Lobe) |
| 3501 | High Dose 0.38 mg/kg | 6 h | N = 3 (1 ea. Caudal, Cranial, Middle Lobe) |
| 3002 | High Dose 0.38 mg/kg | 24 h | N = 3 (1 ea. Caudal, Cranial, Middle Lobe) |
| 3502 | High Dose 0.38 mg/kg | 24 h | N = 3 (1 ea. Caudal, Cranial, Middle Lobe) |
| 3003 | High Dose 0.38 mg/kg | 72 h | N = 3 (1 ea. Caudal, Cranial, Middle Lobe) |
| 3503 | High Dose 0.38 mg/kg | 72 h | N = 3 (1 ea. Caudal, Cranial, Middle Lobe) |
| 1001 | Vehicle | 24 h | N = 3 (1 ea. Caudal, Cranial, Middle Lobe) |
| 1501 | Vehicle | 24 h | N = 3 (1 ea. Caudal, Cranial, Middle Lobe) |

Figure 21A:
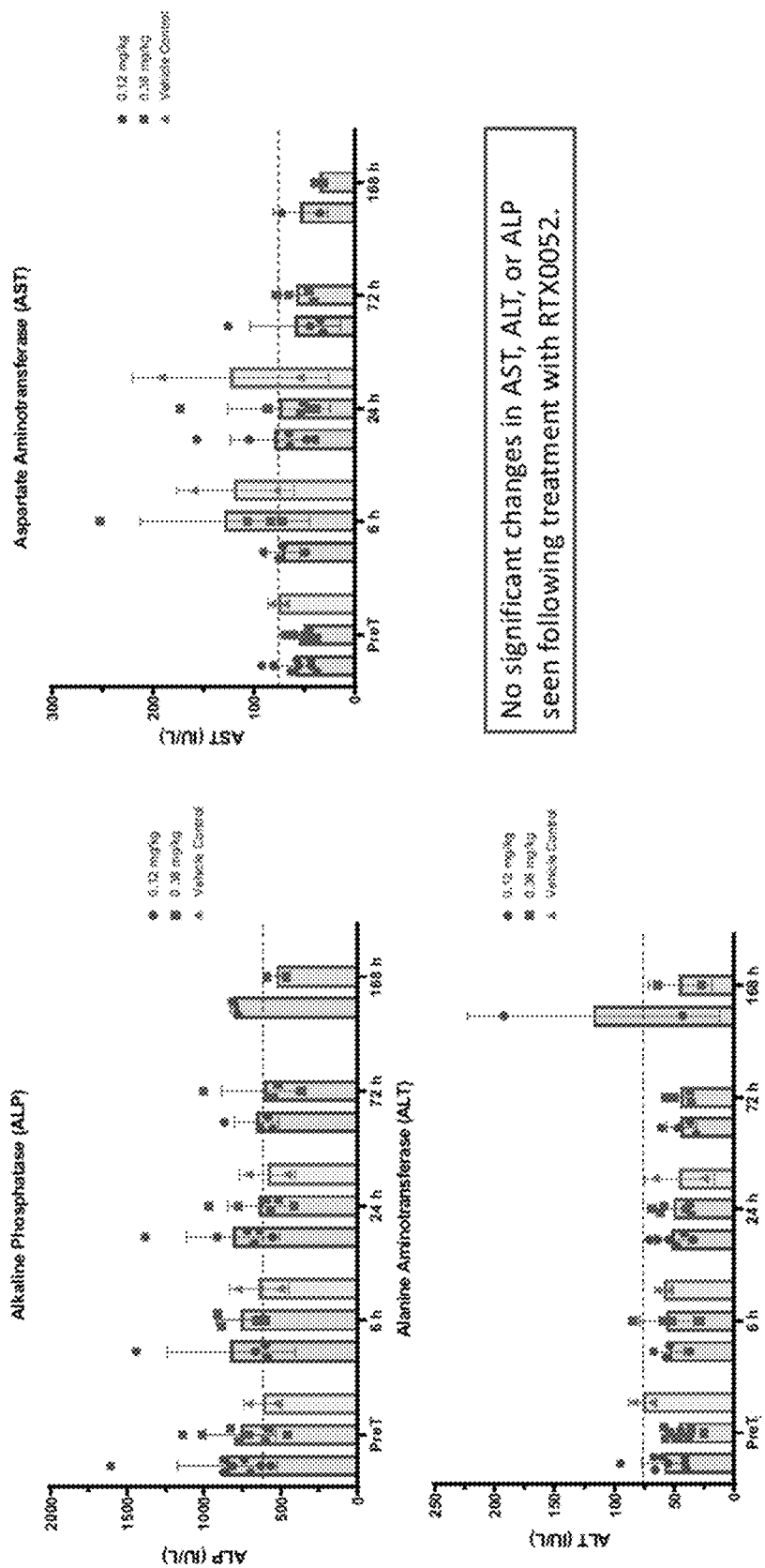
Figure 21B:
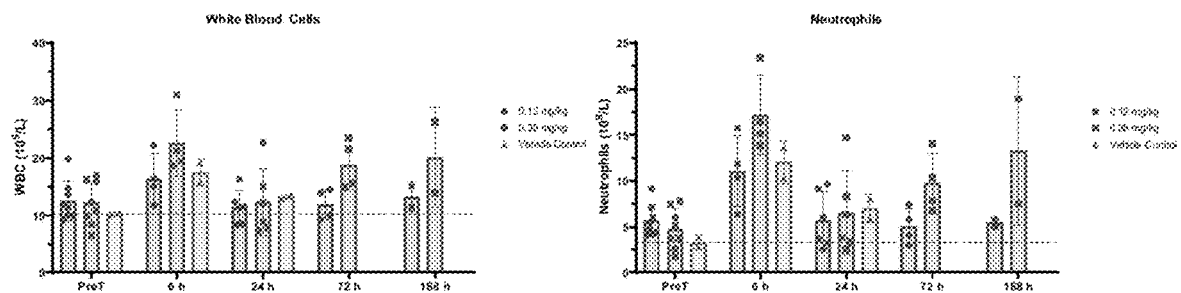
Figure 21C:
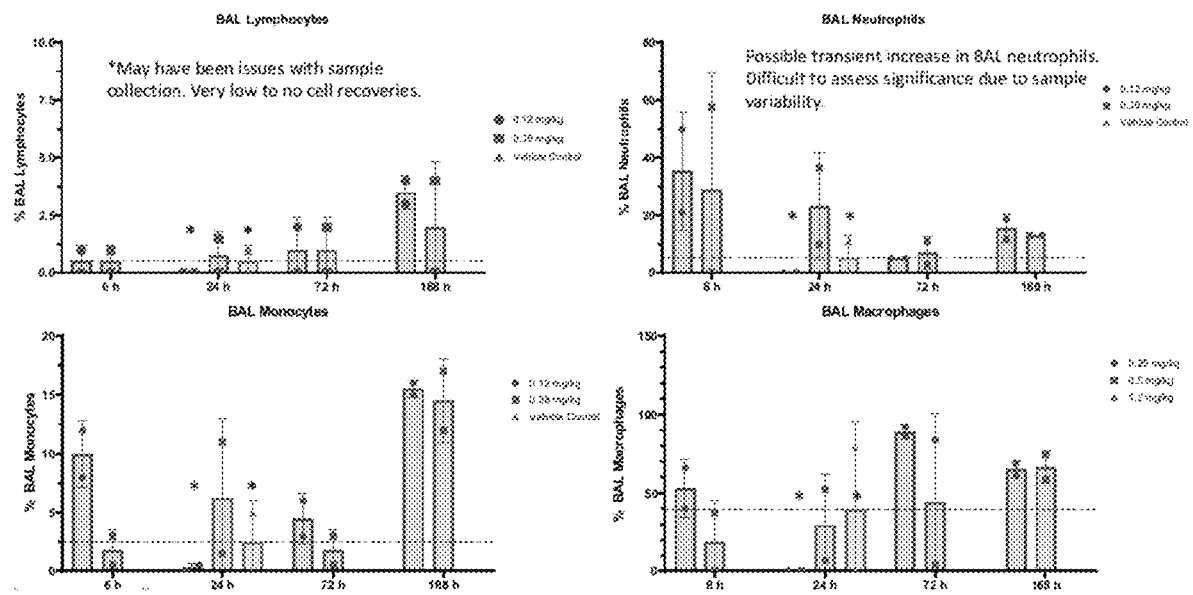
Figure 21D:
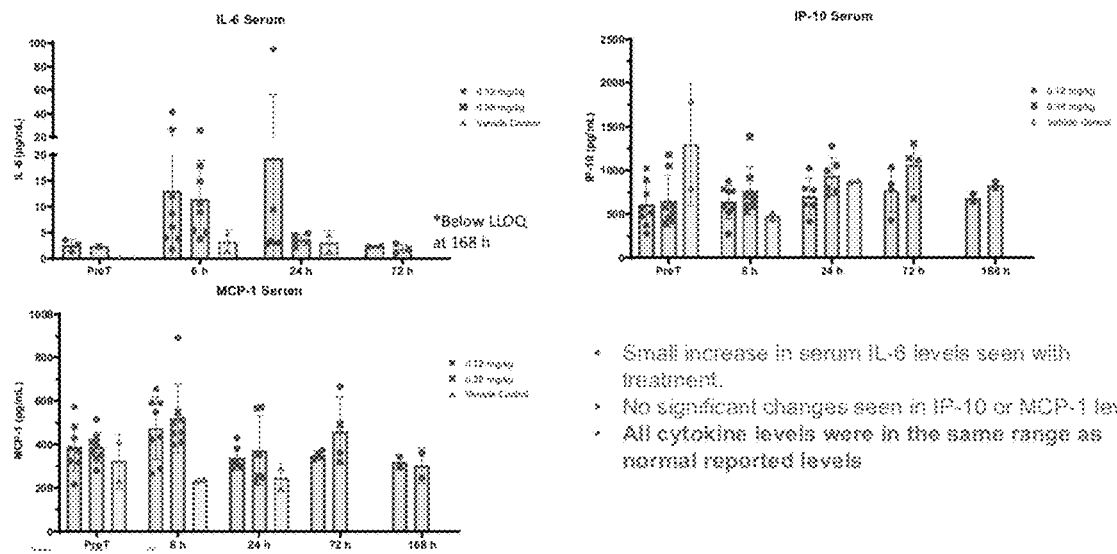
Figure 21E:
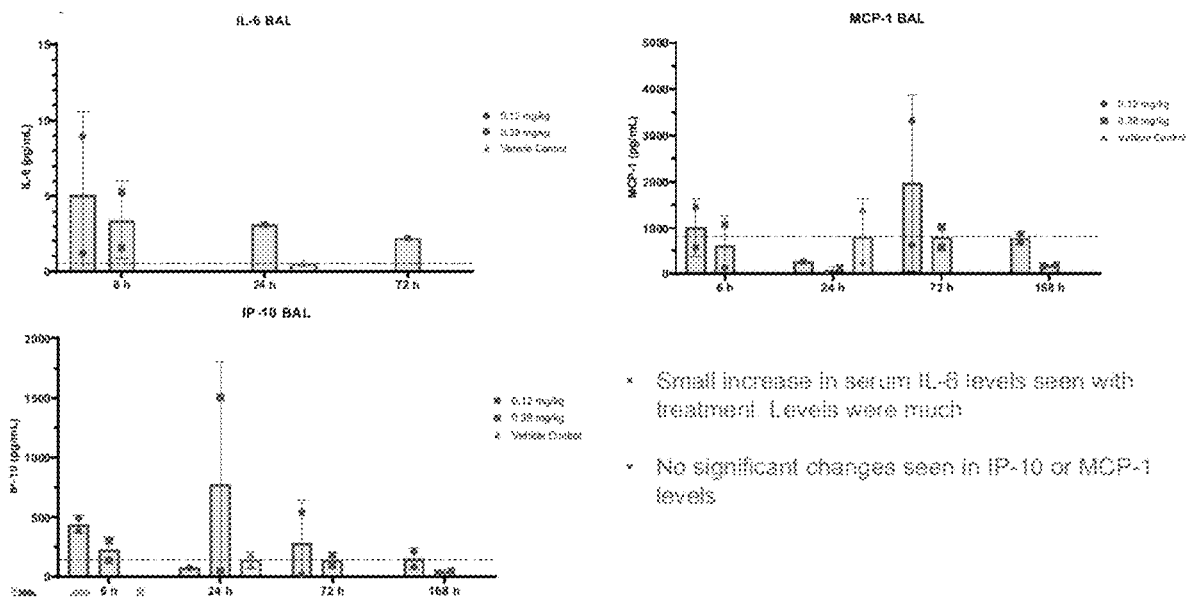
Figure 21F:
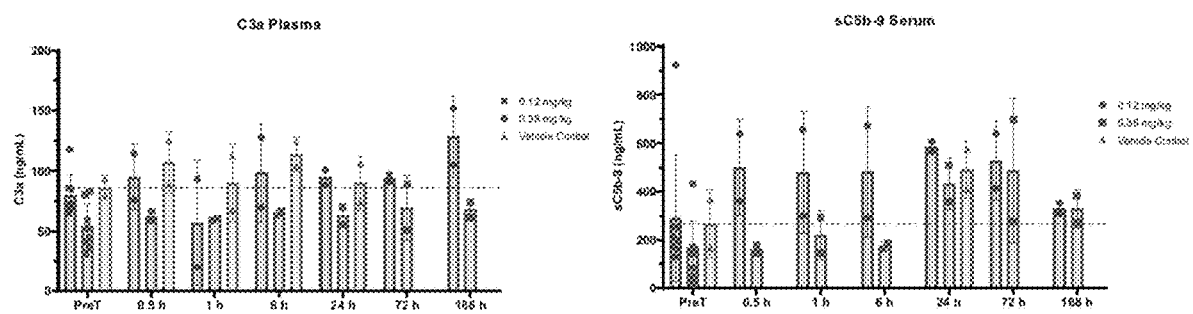
Figure 21G:
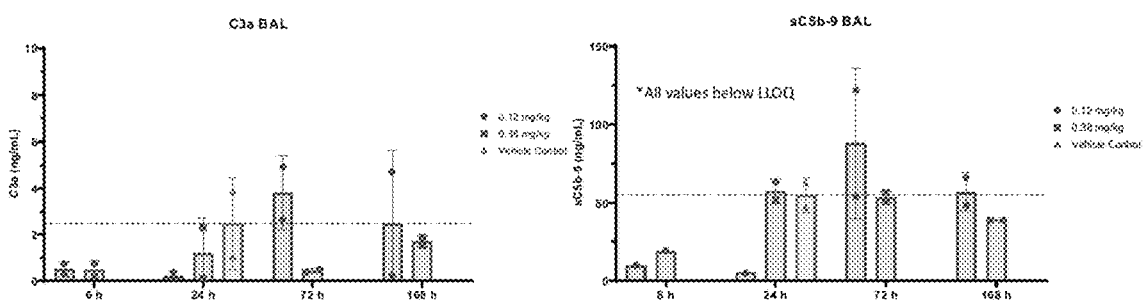

Tolerability of the RTX0052 was determined based on clinical observations; body and organ weights; clinical chemistry and hematology; bronchoalveolar lavage (BAL) cell differentials; cytokine and complement levels in serum and BAL; and histopathology. There were no adverse clinical signs observed that were considered related to treatment with RTX0052. No significant changes in body weight was observed between the treatment groups. There were also no organ weight changes (absolute and relative to body weight) that were clearly related to RTX0052. All changes observed in other tissues/organs, with/without statistical significance, in males and females at all dose levels were independent of dose and/or sex or were minor in magnitude or within ITR background ranges, thus, considered to be incidental or procedure/stress-related. FIG. 21A illustrates clinical chemistry measurements for AST, ALT, and ALP. No significant changes of AST, ALT, or ALP were observed following treatment with RTX0052. For hematology and coagulation, there were no RTX0052-DNAI1-related changes in hematology parameters measured in monkeys at 6-hour, 24-hour and 72-hour post end of exposure, and 7 days of observation after inhalation exposure. Some female monkeys had relatively higher white blood cells and neutrophils counts in blood at 6 hours, 72 hours and 7 days post end of exposure but were not considered adverse. There were no RTX0052-DNAI1-related changes in coagulation parameters measured in monkeys at 6-hour, 24-hour and 72-hour post end of exposure, and 7 days of observation after inhalation exposure. FIG. 21B illustrates the hematology counts of white blood cells and neutrophils. Some increase in neutrophils was observed in the post-treatment measurements of both vehicle and RTX0052 groups. FIG. 21C illustrates BAL cell differentials. For cytokine and complement analysis, cytokines levels were measured in NHP serum and BAL. Analytes measured included IFN-α2a, IFN-γ, IL-1β, IL-4, IL-6, IL-10, IL-17A, IP-10, MCP-1, and TNFα. All cytokine levels were in the same range as normal reported elves. BAL results were similarly normal as all cytokines were at or below serum lower limit of quantification (LLOQ) (except for IL-6, IL-10, and MCP-1). Table 13 illustrates the serum and BAL LLOQ measurements of analytes. FIG. 21D illustrates exemplary measurements of cytokine in serum. FIG. 21E illustrates exemplary measurements of cytokine in BAL. FIG. 21F illustrates exemplary complement measures of C3a and sC5b-9 measurements in plasma and serum respectively. FIG. 21G illustrates exemplary complement measures of C3a and sC5b-9 measurements in BAL.

TABLE 13

LLOQ Analyte measurement in serum and BAL

| Analyte | Serum LLOQ (pg/mL) | BAL LLOQ (pg/mL) |
|---|---|---|
| IFN-α2a | 18.36 | 9.18 |
| IFN-γ | 13.38 | 6.69 |
| IL-1β | 2.2 | 1.1 |
| IL-4 | 0.98 | 0.49 |
| IL-6 | 1 | 0.5 |
| IL-10 | 2.08 | 1.04 |
| IL-17A | 13.52 | 6.76 |
| IP-10 | 4.6 | 2.3 |
| MCP-1 | 2.66 | 1.29 |
| TNFα | 1.8 | 0.9 |

Based on the histopathology analysis performed herein, there was no evidence of test item-related macroscopic findings. All gross observations were considered to be incidental, as they were sporadic and not dose related, of low incidence, or occurred in control and treated animals or lacked the relevant histopathology correlates. Minimal to mild increase in the alveolar mixed cell infiltrates were observed in the lungs of 3/8 animals treated at target total inhaled dose level of 0.24 mg/kg. Due to low incidence and severity, this change was considered to be potentially test item-related, but non-adverse. All other microscopic observations were considered to be incidental, background or agonal changes, as they were of low incidence or severity, or occurred in control and test item-treated animals. Overall treatment was well-tolerated: No changes seen in clinical observations, clinical chemistry, or complement measurements. Slight and transient increased in blood and BAL neutrophils was observed. All cytokine levels were within the normal reported range. Small transient increase in IL-6 levels was observed in both serum and BAL. Histopathology indicated minimal to mild increase in the alveolar mixed cell infiltrates in 3/8 animals.

Example 25. SORT Rat Study

Figure 22A:
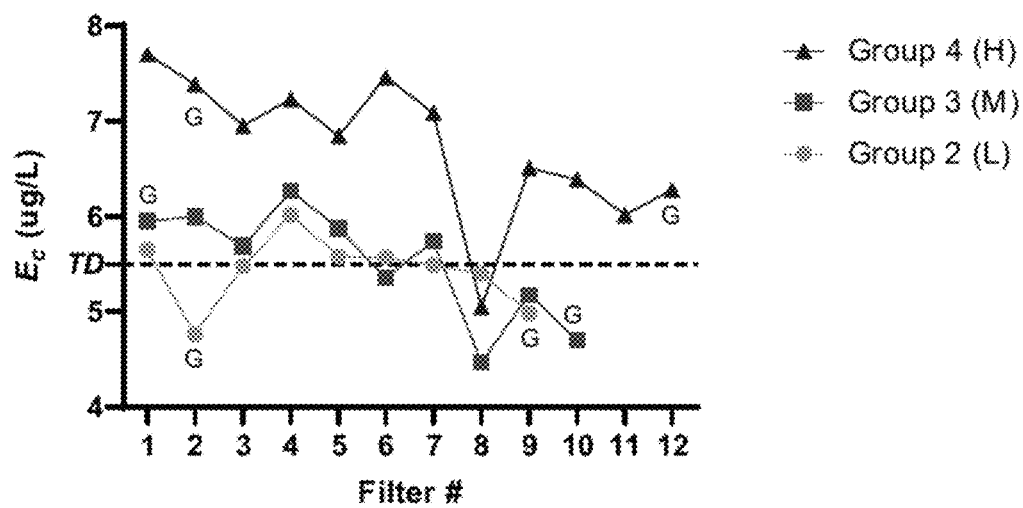
Figure 22B:
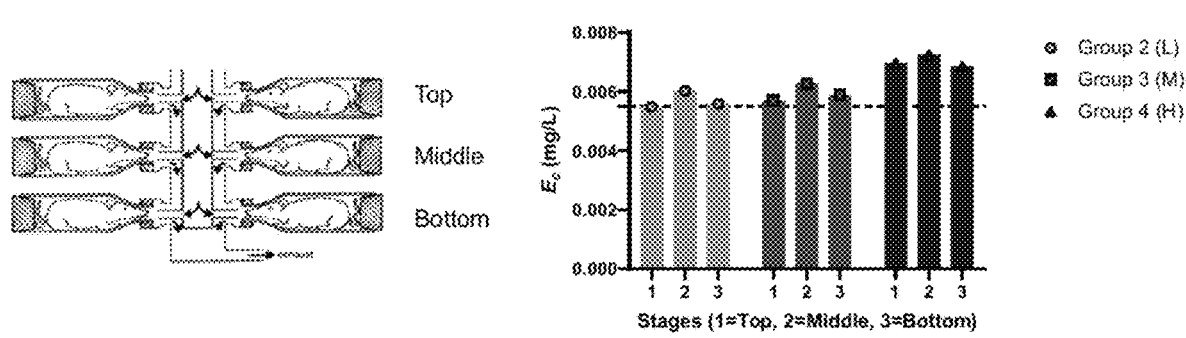

Rats (Sprague-Dawley (SD), 8 to 11 weeks old, male: 300-350 g/female: 175-250 g; N=130 total, N=40 per dose group (20 male/20 female), N=10 vehicle control (5 male/5 female)) were examined for the efficacy of aerosol delivery by inhalation using flow-past exposure system. The delivery dose was low (0.25 mg/kg target dose), mid (0.49 mg/kg target dose), or high (0.99 mg/kg target dose). Expression of DNAI1 was examined at six hours, 24 hours, 72 hours, or seven days after administration of RTX0052. Readout for determining the efficacy of the RTX0052 was determined in rats administered with vehicle (Group 1); low dose (Group 2 with a target dose of 0.25 mg/kg; target aerosol concentration Ec of 0.0055 mg/L for 60 minutes); mid dose (Group 3 with a target dose of 0.49 mg/kg; target aerosol concentration Ec of 0.0055 mg/L for 120 minutes); and high dose (Group 4 with a target dose of 0.99 mg/kg; target aerosol concentration Ec of 0.0055 mg/L for 240 minutes). FIG. 22A illustrates the aerosol concentration administered to the rats. FIG. 22B illustrates exemplary measurements aerosol homogeneity across three stages. FIG. 22C illustrates the amount of doses delivered to the rats. FIG. 22D illustrates characterization of the aerosol composition droplet (MMAD: mass median aerodynamic diameter; GSDL: geometric standard deviation). The droplet characterization results were within recommended range of the Organization for Economic Co-operation and Development (OECD) guidance 433 for inhalation toxicity studies with an MMAD≤4 μm and a GSD between 1.0 and 3.0.

Figure 23A:
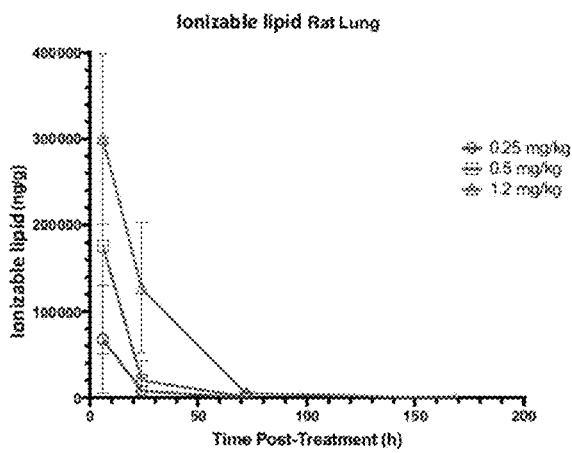
Figure 23B:
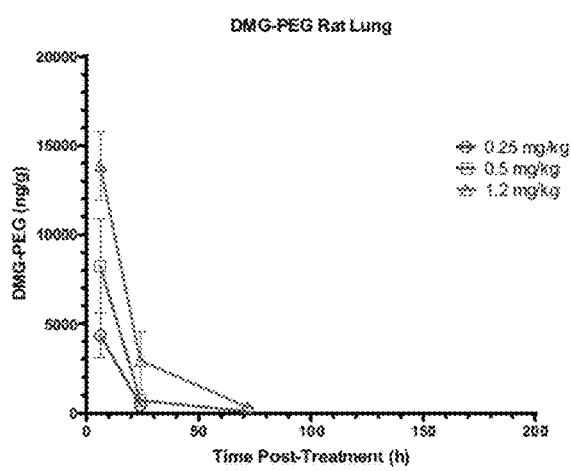
Figure 23C:
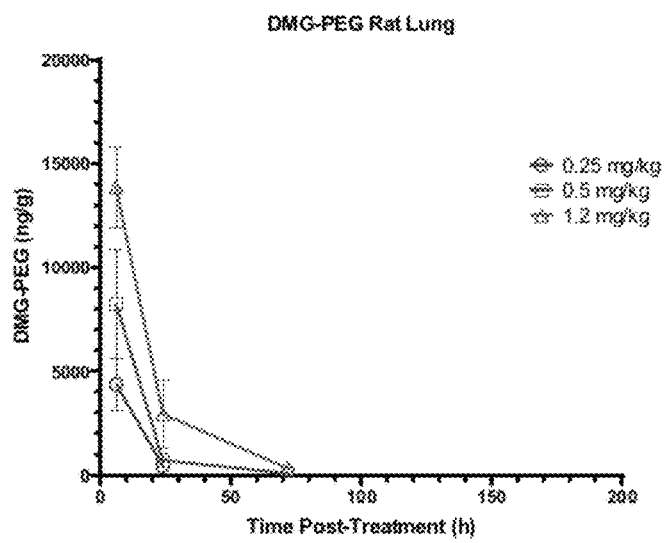
Figure 24A:
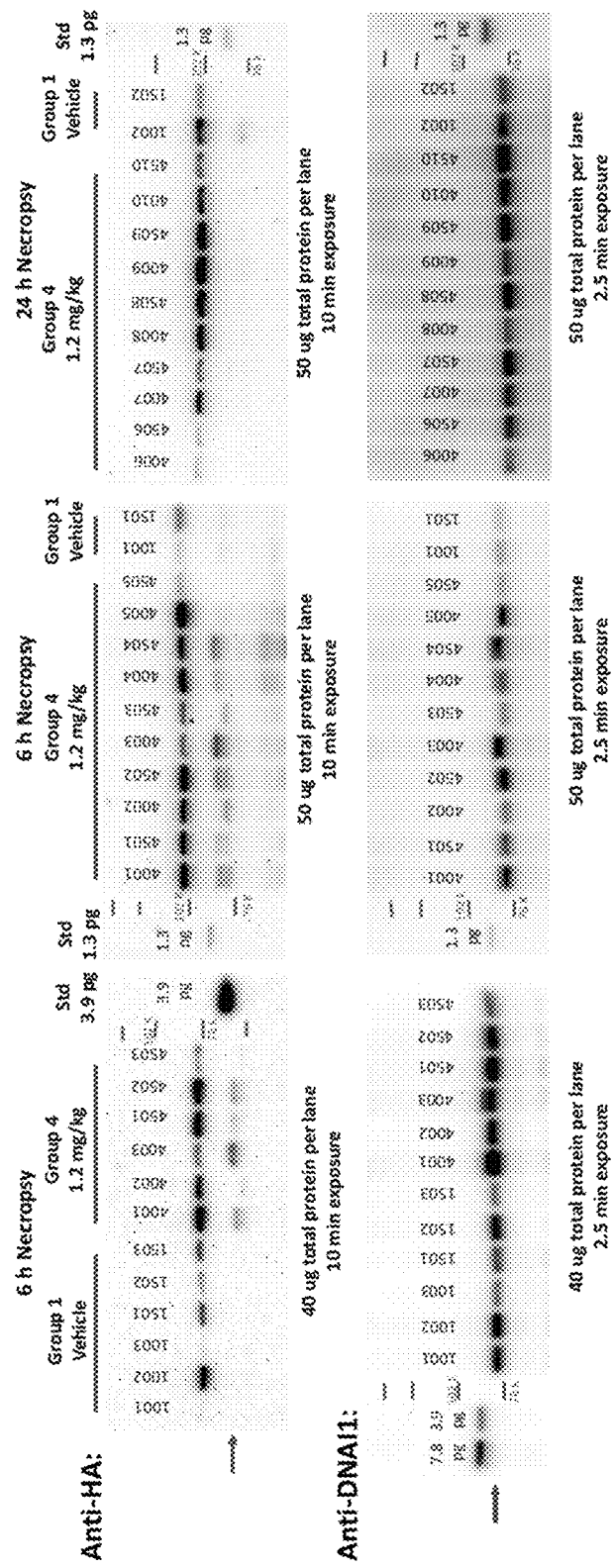
Figure 24B:
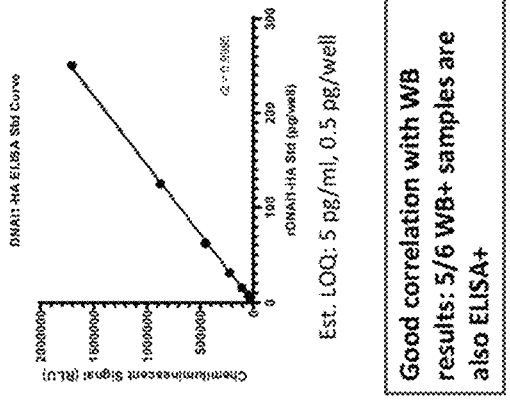

Measurement of the droplet (lipid) in rate blood, lung, liver, and spleen tissue was determined by liquid chromatography and mass spectrometry (LC/MS-MS). Sample Matrices: Blood (plasma and blood cell fractions), Lung, Liver, Spleen. Limit of quantification (LOQ) of ionizable lipids in plasma was 4 ng/ml. LOQ of ionizable lipid in blood cell fraction was 4 ng/ml. LOQ of ionizable lipid in lung tissue cell fraction was 10 ng/ml. LOQ of PEGylation of myristoyl diglyceride (DMG-PEG) in plasma was 20 ng/ml. LOQ of DMG-PEG in blood cell fraction was 40 ng/ml. LOQ of DMG-PEG in lung tissue was 20 ng/ml. LOQ SORT lipid in lung tissue cell fraction was 10 ng/ml. LOQ of SORT lipid in plasma was 1 ng/ml. LOQ of PEGylation of SORT lipid in blood cell fraction was 1 ng/ml. LOQ of SORT lipid in lung tissue was 2 ng/ml. FIGS. 23A-C illustrate measurement of LNP lipid (stemmed from aerosol droplet) in lung in low dose, mid dose, and high dose rat group (FIG. 23A: ionizable lipid in lung; FIG. 23B: DMG-PEG in lung; and FIG. 23C: SORT lipid). FIG. 24A illustrates DNAI1-HA protein expression in the rat lung by Western blotting. Six out of ten lung samples I the 1.2 mg/kg, 6 hour group were positive for DNAI1-HA. FIG. 24B illustrates DNAI1-HA protein expression in the rat lung by ELISA.

Tolerability of the RTX0052 was determined based on clinical observations. There were no clinical signs related to treatment with RTX0052-DNAI1. No significant changes in body weight between the treatment groups was observed. Food consumption was unaffected by treatment with RTX0052-DNAI1. There were no organ weight changes (absolute and relative to body weight) that were clearly related to RTX0052-DNAI1. All changes observed in other tissues/organs, with/without statistical significance, in males and females at all dose levels were independent of dose and/or sex or were minor in magnitude or within ITR background ranges, thus, considered to be incidental or procedure/stress-related.

Figure 25A:
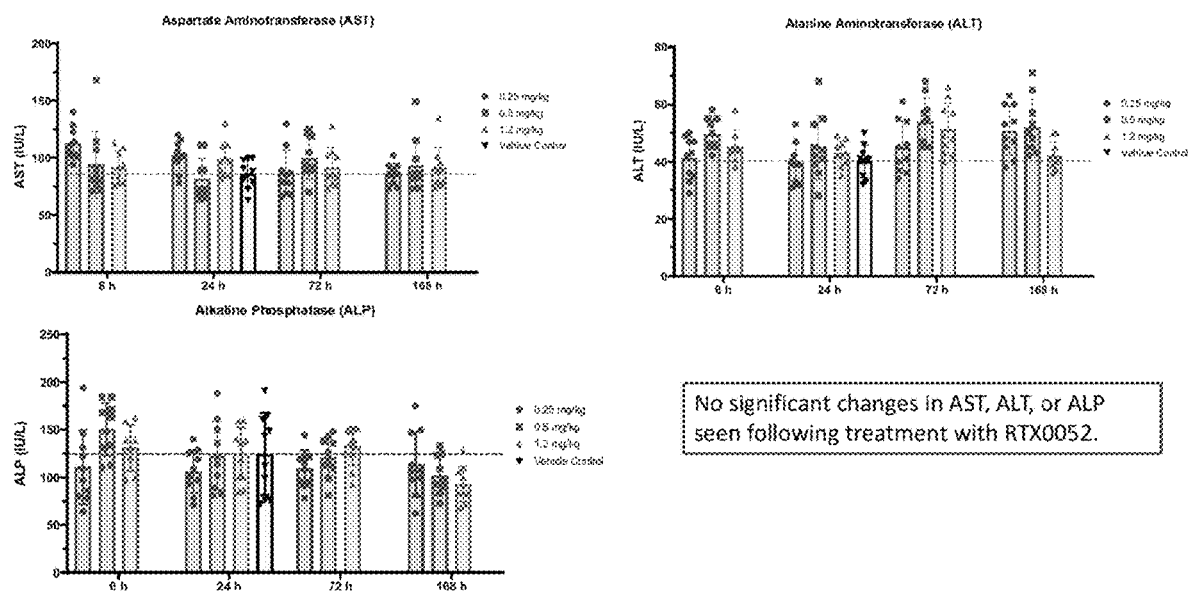
Figure 25B:
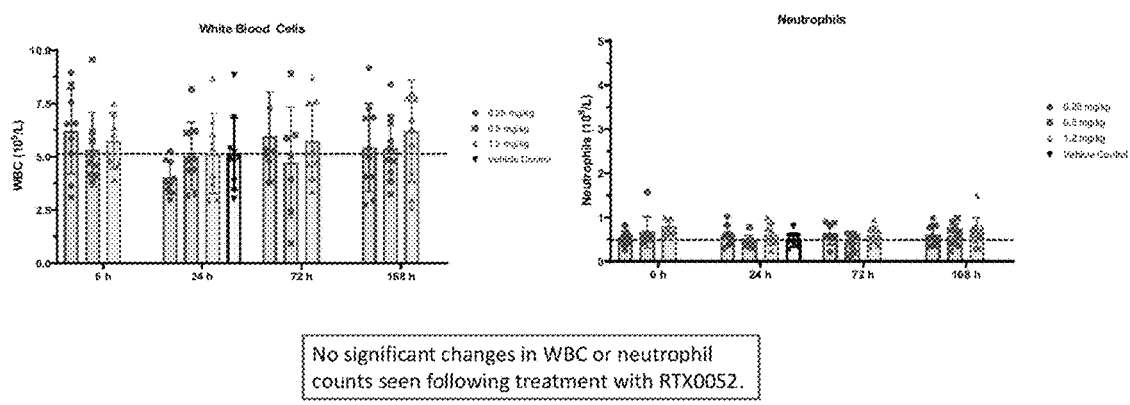
Figure 25C:
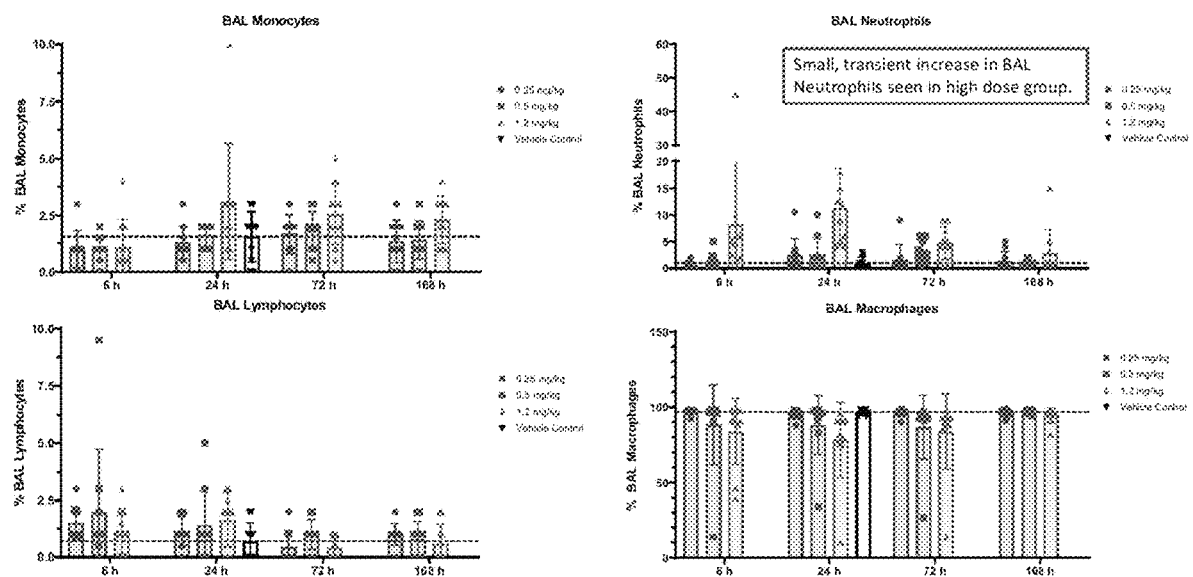
Figure 25D:
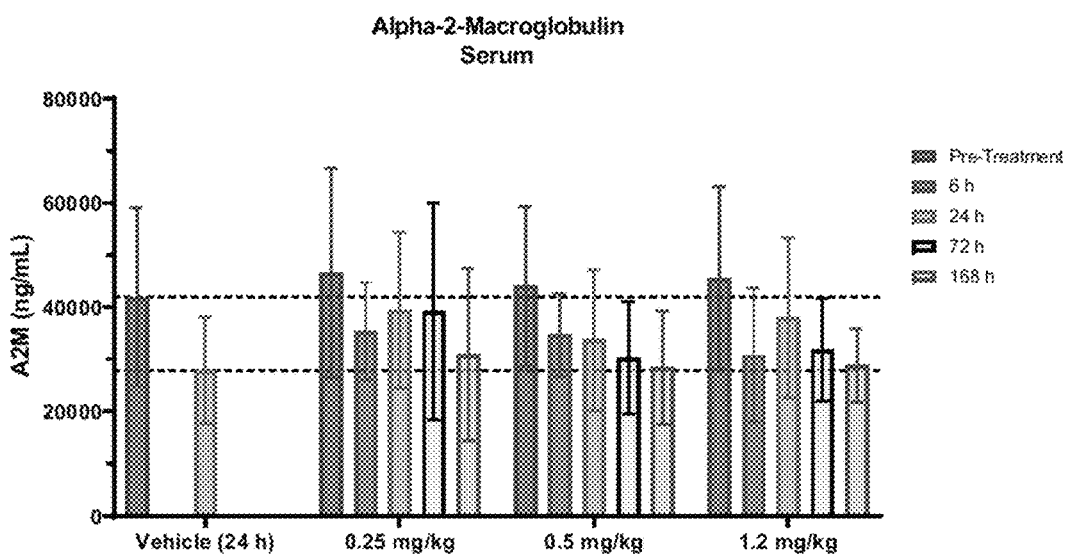

FIG. 25A illustrates clinical chemistry measurements for AST, ALT, and ALP in the treated rats. There were no RTX0052-DNAI1-related changes in clinical parameters measured in rats at 6-hour, 24-hour and 72-hour post end of exposure, and 7 days of observation after inhalation exposure. Some mean values differed from the control values, with and without statistical significance, but the differences were independent of dose and/or sex or were minor in magnitude. Thus, they were considered to have no biological significance. FIG. 25B illustrates the hematology counts of white blood cells and neutrophils in the treated rats. For hematology and coagulation, there were no RTX0052-DNAI1-related changes in hematology parameters measured in rats at 6-hour, 24-hour and 72-hour post end of exposure, and 7 days of observation after inhalation exposure. There were no RTX0052-DNAI1-related changes in coagulation parameters measured in rats at 6-hour, 24-hour and 72-hour post end of exposure, and 7 days of observation after inhalation exposure. Some mean values differed from the control values, with and without statistical significance, but the differences were independent of dose and/or sex or were minor in magnitude. Thus, they were considered to have no biological significance. Some increase in neutrophils was observed in the post-treatment measurements of both vehicle and RTX0052 groups. FIG. 25C illustrates BAL cell differentials in the treated rats. FIG. 25D illustrates exemplary measurements of alpha-2-macroglobulin in the treated rats. A2M is a documented inflammation marker in the rat. Serum levels increased 12 to 48 hours after repeated acute inflammatory stimulations. For safety evaluations, A2M was the preferred marker for the acute phase response in rats. No significant changes in A2M serum levels were observed following treatment with RTX0052.

Macroscopic finding was that regardless of the time point of termination (at 6-hour, 24-hour and 72-hour post end of exposure, and 7 days post exposure) of the treated rats, all macroscopic finding in the rats was considered incidental or spontaneous and not RTX0052-DNAI1-related. Microscopic finding was that regardless of the time point of termination (at 6-hour, 24-hour and 72-hour post end of exposure, and 7 days post exposure) of the treated rats, there were no microscopic pathology findings in the rats of this study that suggested systemic toxicity or local toxicity (oropharynx, nasopharynx, trachea, larynx, lungs) due to RTX0052-DNAI1. In one terminal Group 2 male rat (2016G), euthanized at 7 days post end of exposure, there was multifocal panlobular hepatic hemorrhagic coagulative necrosis and perilesional acute neutrophilic inflammation of the hepatic caudate lobe that correlated with its macroscopic finding. This microscopic finding was considered a spontaneous change that was not RTX0052-DNAI1-related, but rather associated with spontaneous torsion of the hepatic caudate lobe in rats (1). In another terminal Group 2 female rat (2512E), euthanized at 72-hour post end of exposure, a benign subcutaneous duct cell adenoma was noted in the inguinal skin/subcutis region. This finding was considered a spontaneous change that was not RTX0052-DNAI1-related, since it was not present in any of the Group 3 and Group 4 rats. All other microscopic findings, in the treated rats of this study were considered incidental or spontaneous, and not RTX0052-DNAI1-related. All other microscopic findings in the Control rats were considered incidental and spontaneous. LNP lipid components (ionizable lipid, DMG-PEG, and SORT lipid) were rapidly cleared from lung tissue following treatment. Measured levels for each in blood (plasma and cell fraction) were not detected or below the assay LOQs at each timepoint. Five out of ten lung samples in 1.2 mg/kg, at 6 hour post exposure were positive for DNAI1-HA protein expression by WB (FIG. 24A) and ELISA (FIG. 24B). No significant changes were seen in tolerability endpoints; clinical chemistry, hematology, BAL cell differentials, or A2M. No significant histopathology findings that indicated local or systemic toxicity were observed.

Figure 26B:
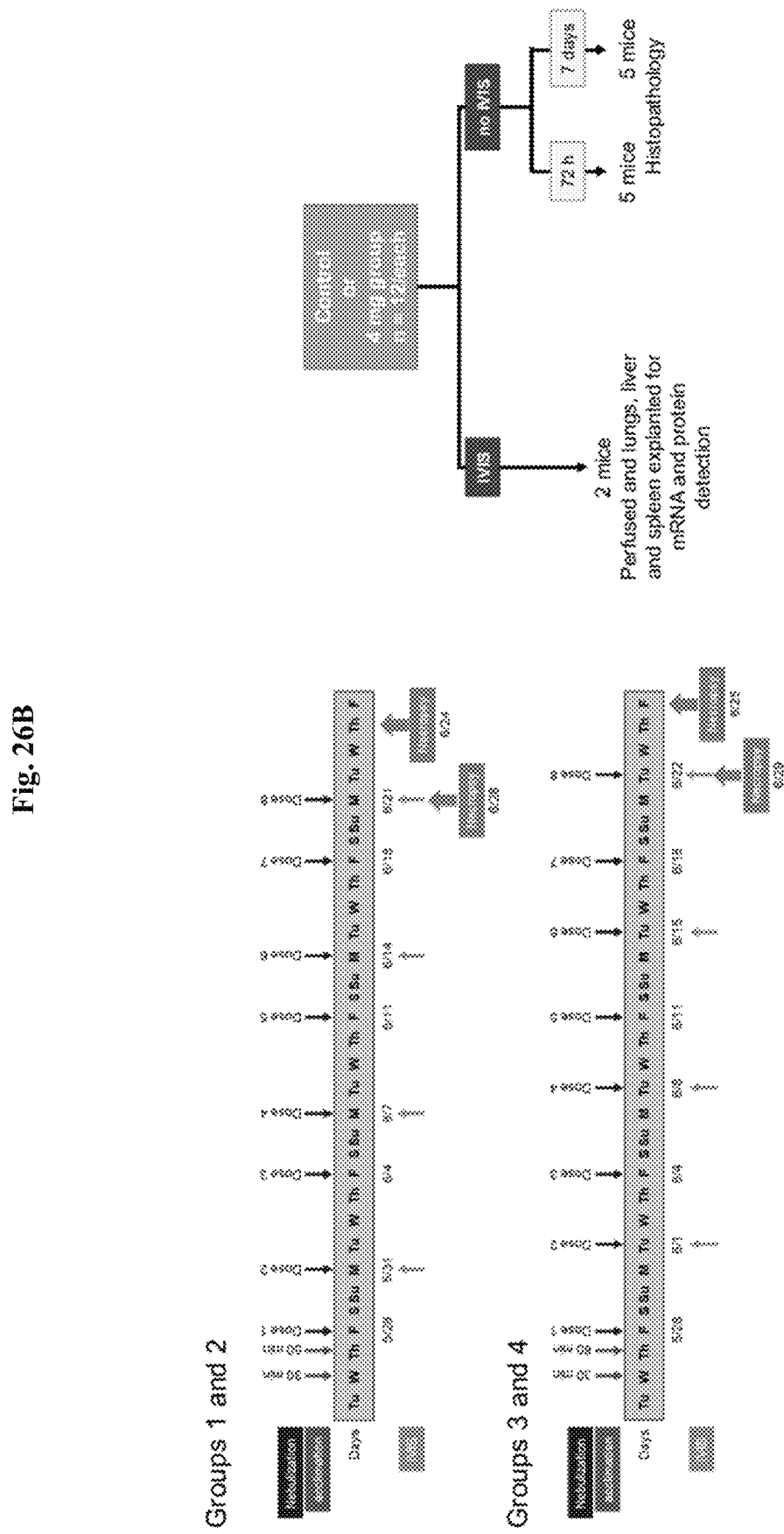

Example 26. Multi-Dose Histopathology Analysis after Aerosol Delivery of 3 Different LNP Multidose administration of 4 mg of 95% DNAI1+5% Luciferase mRNAs in buffer #27 by nebulization. Three candidate formulations (RTX0001, RTX00051, and RTX0052) were compared. Readout assays included protein detection by ELISA, mRNA levels by qPCR/dPCR at 4our h post-last dose and post-IVIS; and lung histopathology at 72 hour and 7 days post-last dosing. Multi-dose study evaluated toxicity of lead LNP candidates when administered by nebulization to mice. To deliver the LNP formulation, cages were setup for mice to acclimate for 8 days. Four groups of mice were acclimated for this study. FIG. 26A illustrates the information relating to the four groups of mice to be repeatedly treated with nebulization of LNP/DNAI1-HA mRNA. FIG. 26B illustrates the protocol for the dosing, imaging, and necropsy of the repeatedly dosed mice. In vivo imaging was conducted on the treated mice. 2 mL luciferin at 30 mg/mL in PBS were nebulized with constant flow over a period of ca.4 min; 4 h post-dosing. Animals were anesthetized with isoflurane (3% for induction, 2% for maintenance, 1 L/min oxygen flow). Ventral images were captured for 1 min (binning set to 8, f stop at 1). Calibrated units were shown as Average Radiance (photons/s/cm2/sr) representing the flux radiating omni-directionally from a user defined region. Total Flux=the radiance (photons/sec) in each pixel summed or integrated over the ROI area (cm2)×4π. Average Radiance=the sum of the radiance from each pixel inside the ROI/number of pixels or super pixels (photons/sec/cm2/sr).

Figure 27A:
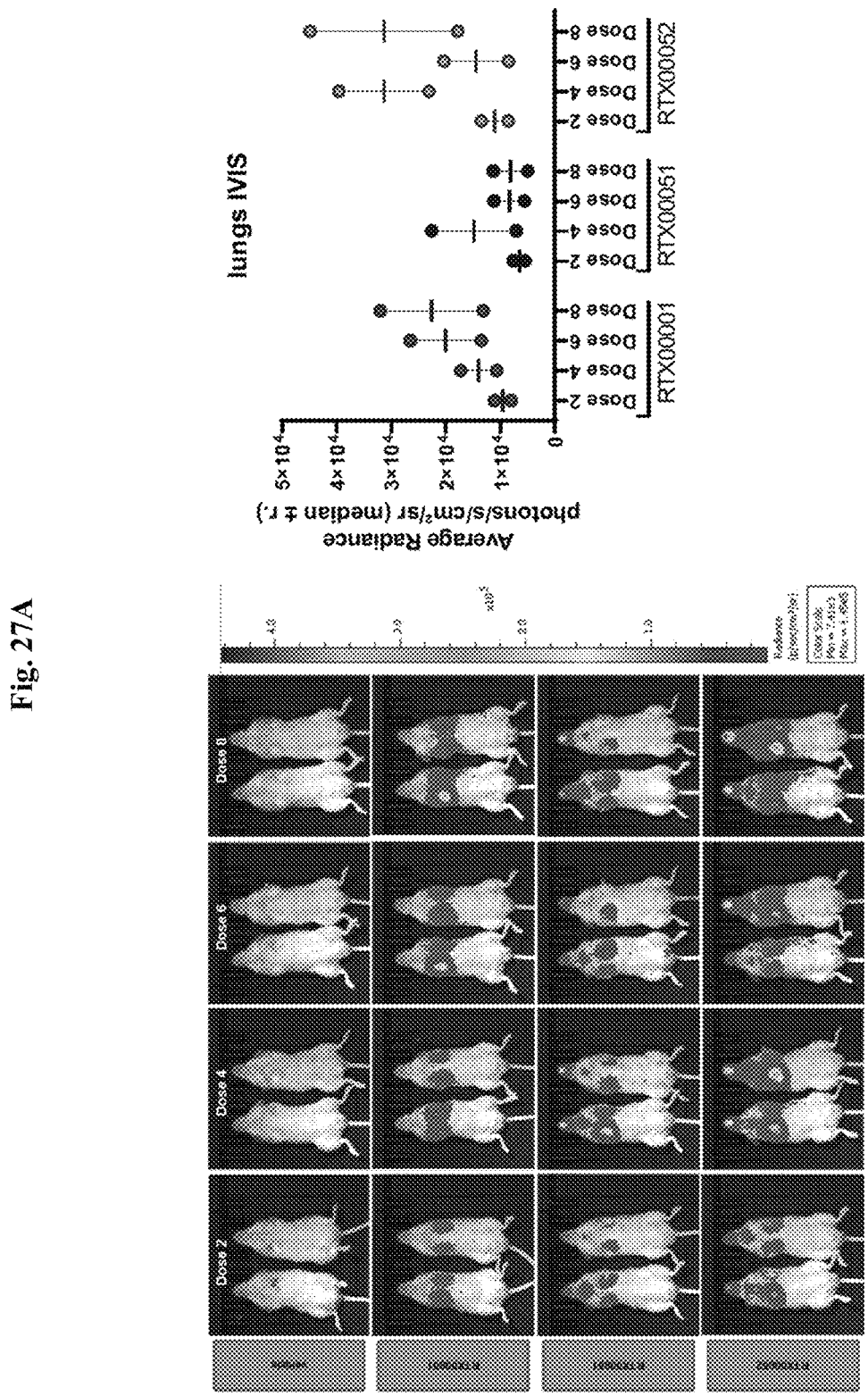
FIG. 27A-B illustrate whole body in vivo imaging (IVIS) of the repeatedly dosed mice. Animals, B6 Albino, male, about 7 weeks of age, naïve, were administered 4.0 mg of LNP-formulated DNAI1-HA/Luciferase by nebulization in 2 hours at 66.6 µL/min with Zero grade dry air flow at 2 L/min. 4 hour post-dosing, two mice were administered 2 mL of luciferin (30 mg/mL) by nebulization and imaged on IVIS within 1-15 min post-luciferin administration. Pseudo coloring was applied on the same scale for all images. Lung signal was plotted in graph of FIG. 27A. Whole body signal is plotted in the graph of FIG. 27B.
Figure 27B:
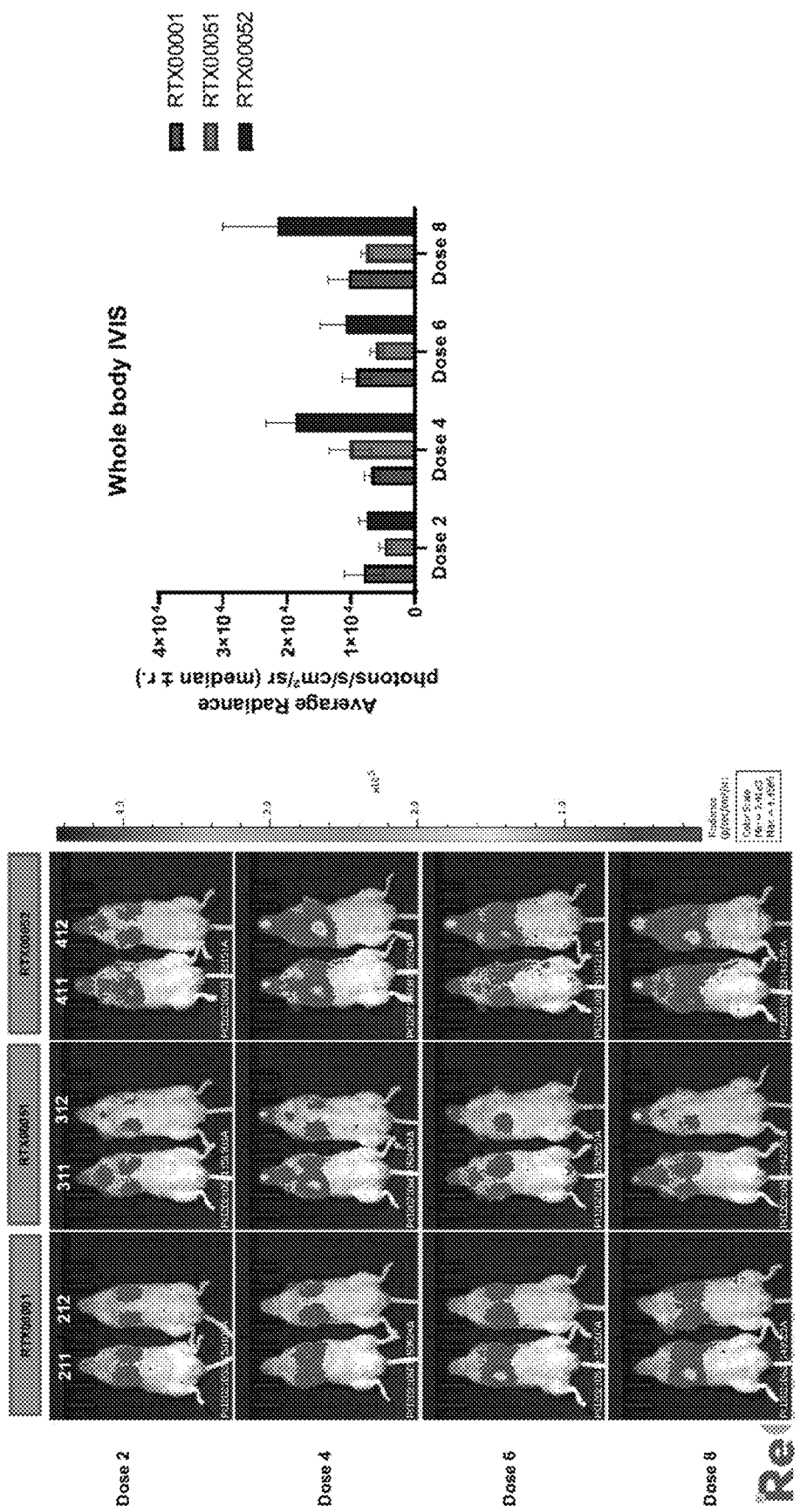
Figure 27C:
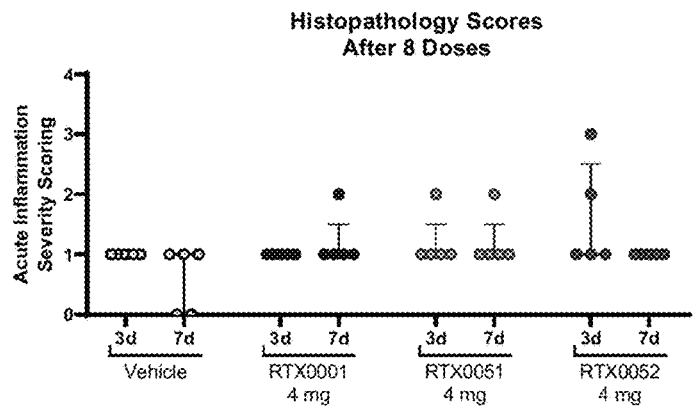
FIG. 27C illustrates histopathology results of the repeatedly dosed mice.
Figure 27D:
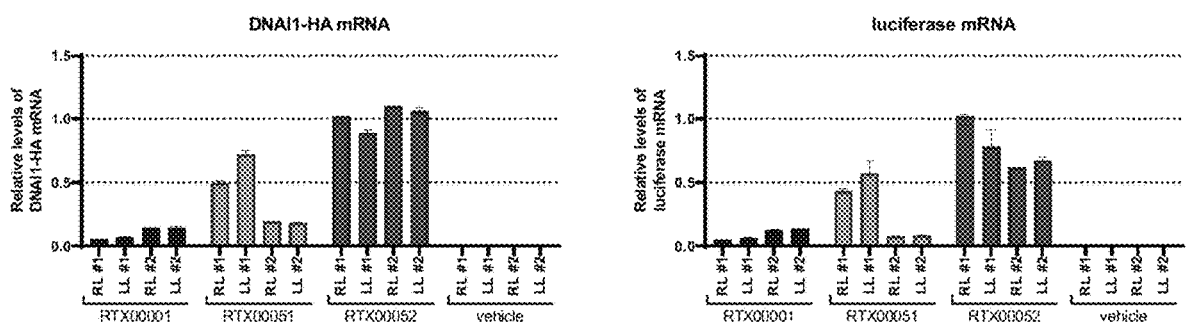
FIG. 27D illustrates qPCR results showing the relative abundance of DNAI1-HA mRNA. After the last imaging of the last dose (dose 8), 2 mice per group were perfused.
Figure 27E:
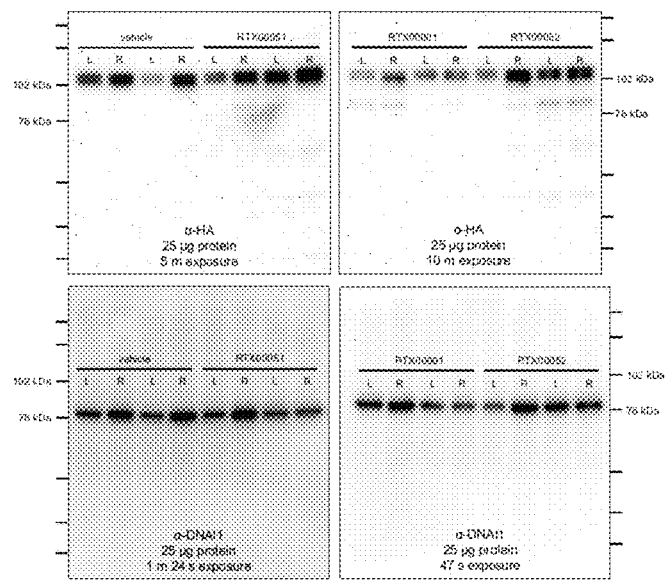
FIG. 27E illustrates Western blotting showing the protein expression of DNAI1-HA.

FIG. 27A-B illustrate whole body in vivo imaging (IVIS) of the repeatedly dosed mice. Animals, B6 Albino, male, about 7 weeks of age, naïve, were administered 4.0 mg of LNP-formulated DNAI1-HA/Luciferase by nebulization in 2 hours at 66.6 μL/min with Zero grade dry air flow at 2 L/min. 4 hour post-dosing, two mice were administered 2 mL of luciferin (30 mg/mL) by nebulization and imaged on IVIS within 1-15 min post-luciferin administration. Pseudo coloring was applied on the same scale for all images. Lung signal was plotted in graph of FIG. 27A. Whole body signal is plotted in the graph of FIG. 27B. FIG. 27C illustrates histopathology results of the repeatedly dosed mice. All formulations were well tolerated with most animals displaying minimal to mild inflammation scores. A single RTX0052-treated animal had moderate inflammation at 3 days post-exposure; however, this was resolved by 7 days with all animals showing only minimal inflammation. Tolerability data supports further studies in rats or NHPs. Histopathologic scoring system were as followed: 0 or normal: tissued considered to be normal under the conditions of the study and considering the age, sex, and strain of the animal concerned. Alterations may be present which, under other circumstances, would be considered deviation from normal; 1 or minimal: the amount of change barely exceeded that which was considered to be within normal limits; 3 or moderate: the lesion was prominent but there was significant potential for increased severity; limited tissue or organ dysfunction was possible; and 4 or severe: the degree was either as complete as considered possible or great enough in intensity or extent to expect significant tissue or organ dysfunction. FIG. 27D illustrates qPCR results showing the relative abundance of DNAI1-HA mRNA. After the last imaging of the last dose (dose 8), 2 mice per group were perfused. Spleen, liver and lungs were explanted. Half of each organ was preserved in RNAlater. Tissues were homogenized and total RNA purified with RNeasy Plus Universal Mini kit (Qiagen). Reverser transcription was performed with ProtoScript II First strand cDNA synthesis kit (NEB). Quantitative PCR was performed and analyzed. FIG. 27E illustrates Western blotting showing the protein expression of DNAI1-HA. 25 μg protein were loaded on 4-12% Bis-Tris gel. Transferred to 0.45 μm Nitrocellulose and probed with monoclonal rat anti-HA. The blot was stripped and reprobed with rabbit anti-DNAI1.

Example 27. Single Dose Inhalation Study

Figures 28A, 28B:
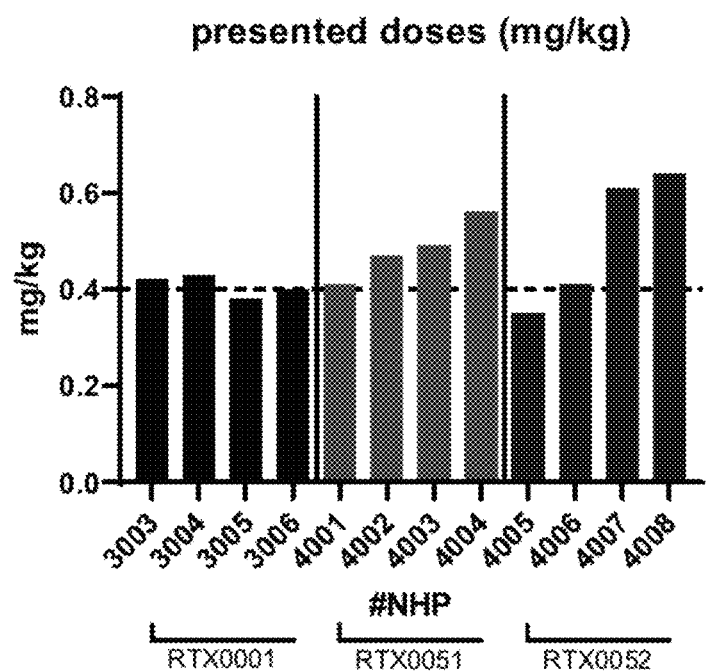
FIG. 28A illustrates delivery of 0.4 mg/kg of LNP-formulated DNAI1 mRNA by inhalation. NHPs were intubated, ventilated, and dosed for fewer than 30 minutes.
FIG. 28B illustrates LNP formulation aerosol characteristics. Aerosol particle size ranges for all three formulations were appropriate for deposition in the conducting airways.
Figure 28C:
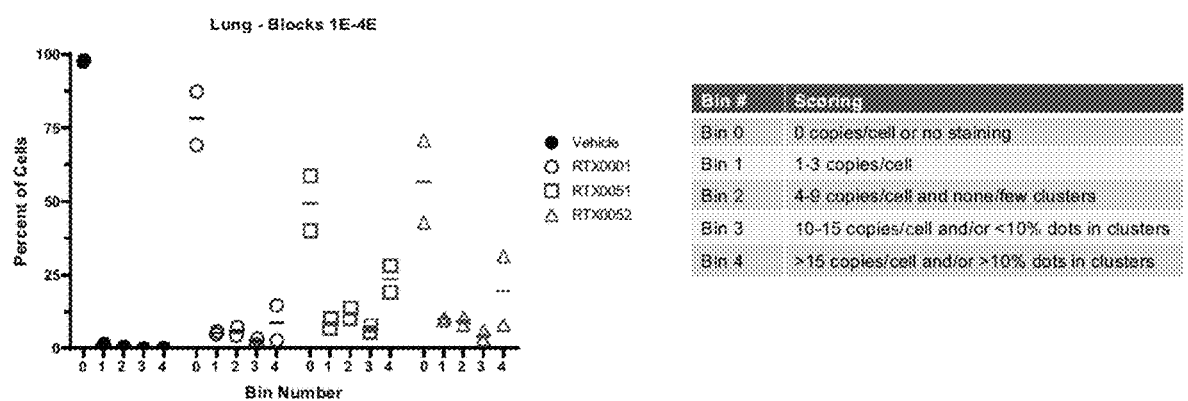
FIG. 28C illustrates biodistribution of DNAI1-HA mRNA in the targeted cells.
Figure 28D:
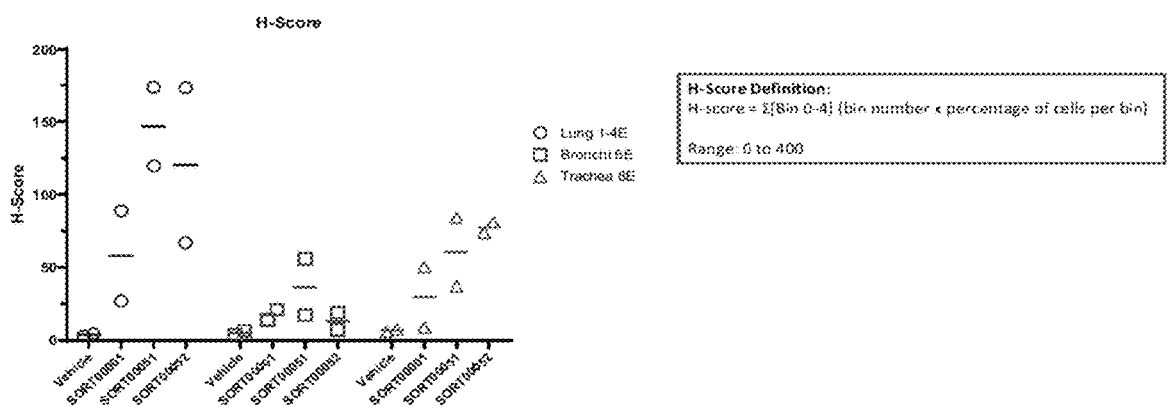
FIG. 28D illustrates DNAI1-HA mRNA ISH results by H-Score. ISH results demonstrated high levels of DNAI1-HA mRNA were delivered to lung cells with lower levels in the bronchi and trachea.
Figure 29A:
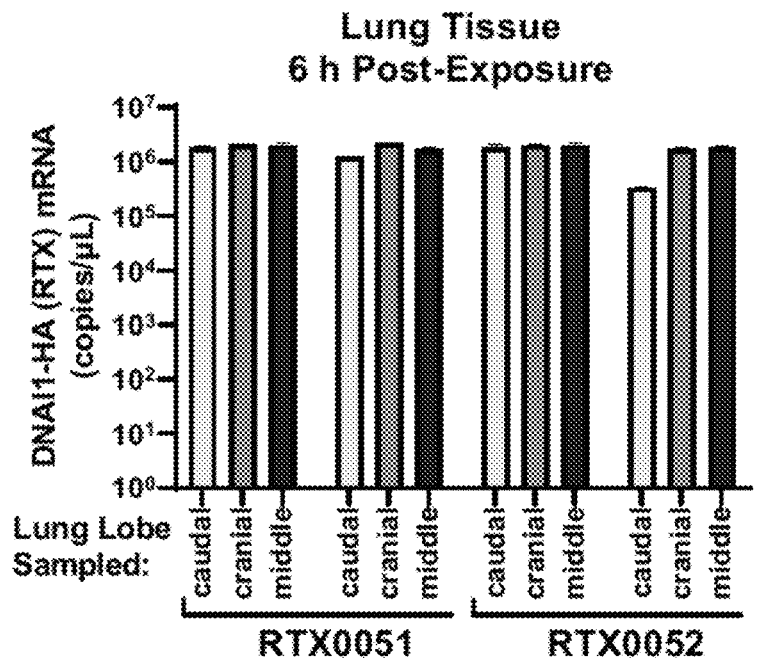
FIGS. 29A-D illustrate delivery of high levels of DNAI1-HA mRNA to the lung without exposure to liver, spleen, or blood. Digital PCR was used to measure DNAI1-HA mRNA levels in whole blood, lung, liver, and spleen tissue following a single 0.4 mg/kg administration. High levels of DNAI1-HA mRNA were detected in all three lung regions sampled at 6 hours post-exposure with RTX0051 and RTX0052. No DNAI1-HA mRNA was detected above background in spleen (6 hours, FIG. 29B), liver (6 hours, FIG. 29C), or whole blood (30 minutes or 60 minutes, FIG. 29D).
Figure 29B:
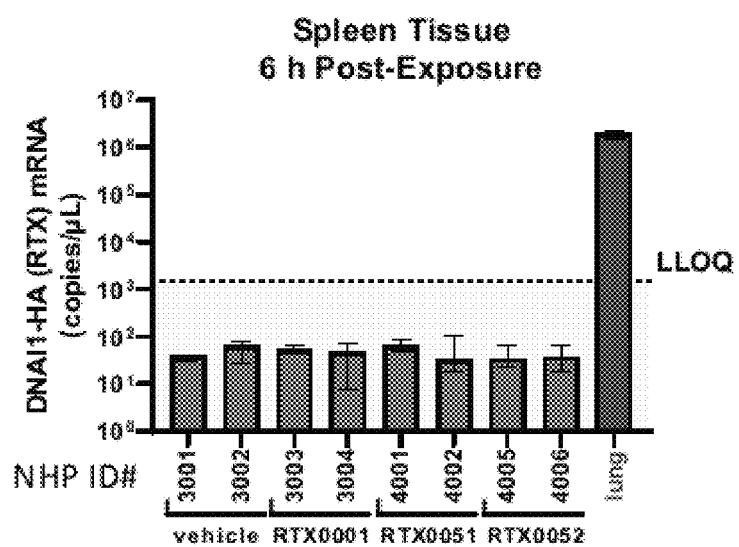
Figure 29C:
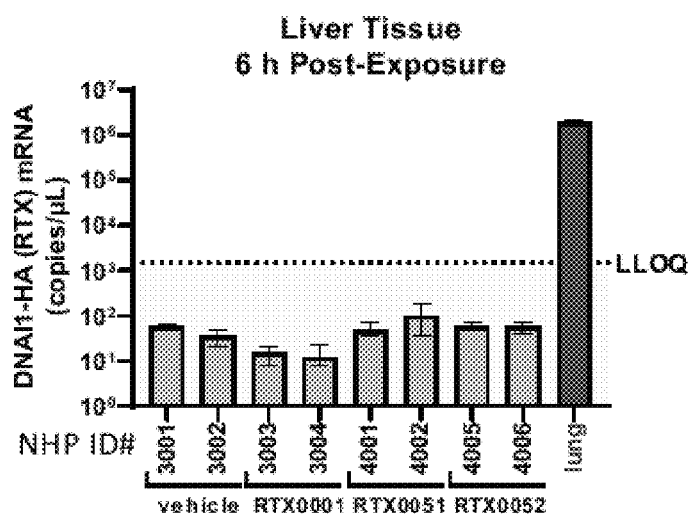
Figure 29D:
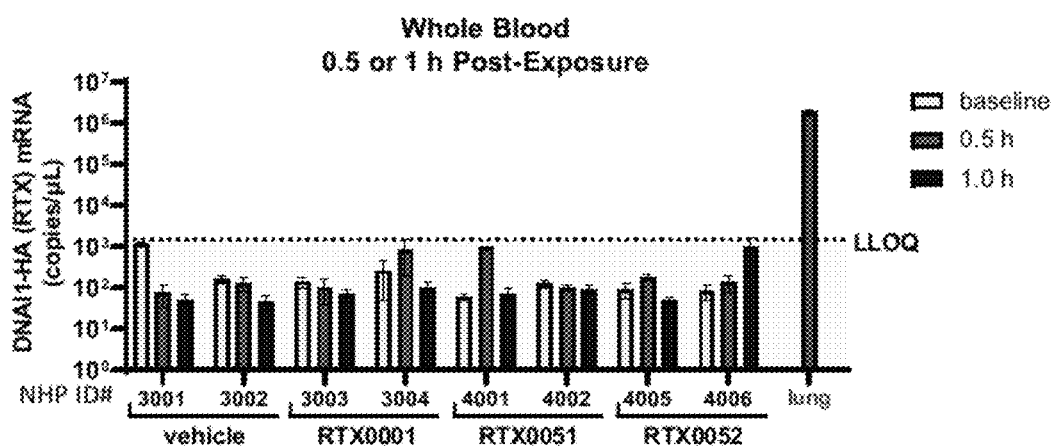

This example illustrates an exemplary experimental approaches for selecting a lipid formulation based on tolerability, biodistribution and protein expression profiles in target cells (e.g., ciliated, club, or basal cells) of the lungs. DNAI1 mRNA was selected with three optimized 5-component formulations selected for comparison in NHPs based on studies in Examples 24-26. A dose between 0.4 to 0.6 mg/kg was delivered to achieve deposition in the TB region of 1-2 μg/cm$^2$ of DNAI1 mRNA for 5 to 10-fold higher than estimated dose required for efficacy. Necropsy timepoints for clinical assessment were at six hours and at 72 hours. FIG. 28A illustrates delivery of 0.4 mg/kg of LNP-formulated DNAI1 mRNA by inhalation. NHPs were intubated, ventilated, and dosed for fewer than 30 minutes. Targeted doses of 0/4 mg/kg were reached or exceeded for all tested LNP formulation. Presented doses of LNP-formulated DNAI1 were estimated based on gravimetric analysis of glass fiber filters and confirmed by filter elution and direct RNA cargo quantification using Ribogreen fluorescence assay. FIG. 28B illustrates LNP formulation aerosol characteristics. Aerosol particle size ranges for all three formulations were appropriate for deposition in the conducting airways. FIG. 28C illustrates biodistribution of DNAI1-HA mRNA in the targeted cells. High levels of DNAI1-HA mRNA were confirmed by in situ hybridization (ISH) in the lung by qPCR six hours post exposure, while no DNAI1-HA mRNA was detected above background in spleen (at six hours), liver (at six hours), or whole blood (at 30 minutes or at 60 minutes). ISH results demonstrated that up to 30% of lung cells contained more than 15 copies of the DNAI1-HA mRNA per cell after treatment with RTX0051 or RTX0052. FIG. 28D illustrates DNAI1-HA mRNA ISH results by H-Score. ISH results demonstrated high levels of DNAI1-HA mRNA were delivered to lung cells with lower levels in the bronchi and trachea. FIGS. 29A-D illustrate delivery of high levels of DNAI1-HA mRNA to the lung without exposure to liver, spleen, or blood. Digital PCR was used to measure DNAI1-HA mRNA levels in whole blood, lung, liver, and spleen tissue following a single 0.4 mg/kg administration. High levels of DNAI1-HA mRNA were detected in all three lung regions sampled at 6 hours post-exposure with RTX0051 and RTX0052. No DNAI1-HA mRNA was detected above background in spleen (6 hours, FIG. 29B), liver (6 hours, FIG. 29C), or whole blood (30 minutes or 60 minutes, FIG. 29D).

Figure 30A:
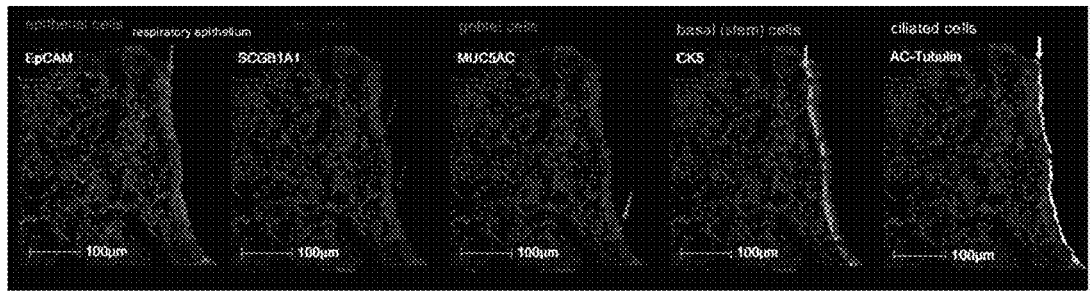
FIG. 30A illustrates multiplex immunofluorescent (IF) images for epithelial cell types.
Figure 30B:
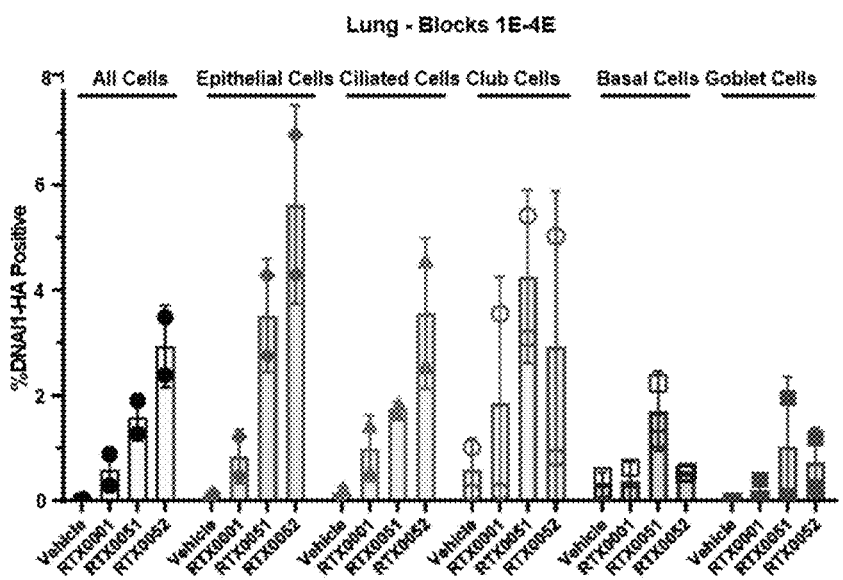
FIG. 30B illustrates multiplex IF analysis demonstrating expression of DNAI1-HA protein in target cells in lung.
Figure 30C:
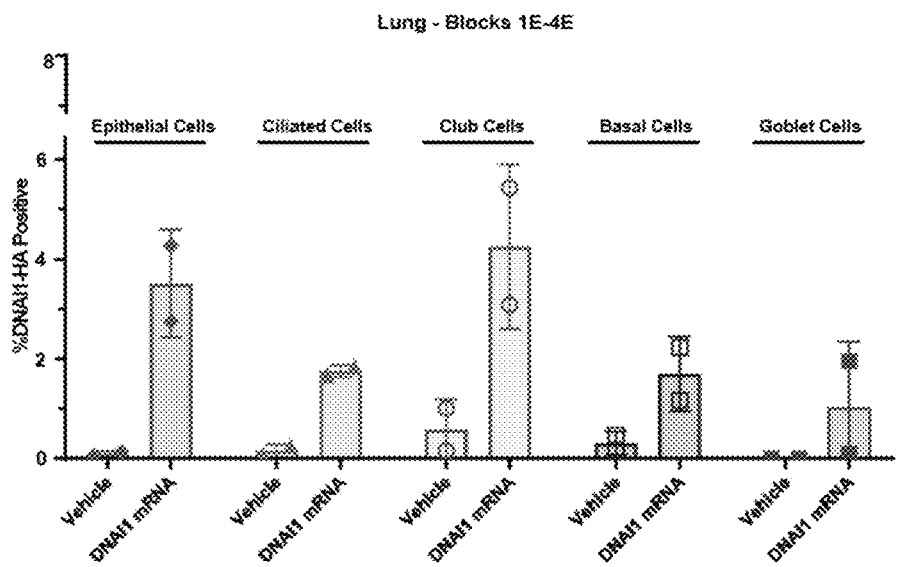
FIG. 30C illustrates multiplex IF analysis demonstrating expression of DNAI1-HA protein in target cells in lung with RTX0051.

FIG. 30A illustrates multiplex immunofluorescent (IF) images for epithelial cell types. Epithelium cell was marked with EPCAM. Ciliated cell was marked with acetylated-tubulin (AC-tubulin). Club cell was marked with secretoglobin family 1A member 1 (SCGB1A1). Goblet cell was marked with mucin 5AC (MUC5AC). Basal cell (stem cell) was marked with cytokeratin 5 (CK5). FIG. 30B illustrates multiplex IF analysis demonstrating expression of DNAI1-HA protein in target cells in lung. FIG. 30C illustrates multiplex IF analysis demonstrating expression of DNAI1-HA protein in target cells in lung with RTX0051. High sensitivity of mIF enabled detection of protein expression in tissue and cells not detectable by other protein measurement methods. Single dose of 0.4 mg/kg was administered via inhalation of LNP-formulated DNAI1-HA mRNA. Lung sections were collected from two NHPs six hours after dosing. Percentage of DNAI1-HA positive cell was calculated by combining cell counts from all 4 examined lung sections for an individual animal. Total number of cells counted per animal was about 500,000 to 1,400,000 cells. Shown are the individual data points for each treated animal and the mean±std. dev. for each group (N=2).

Figure 30D:
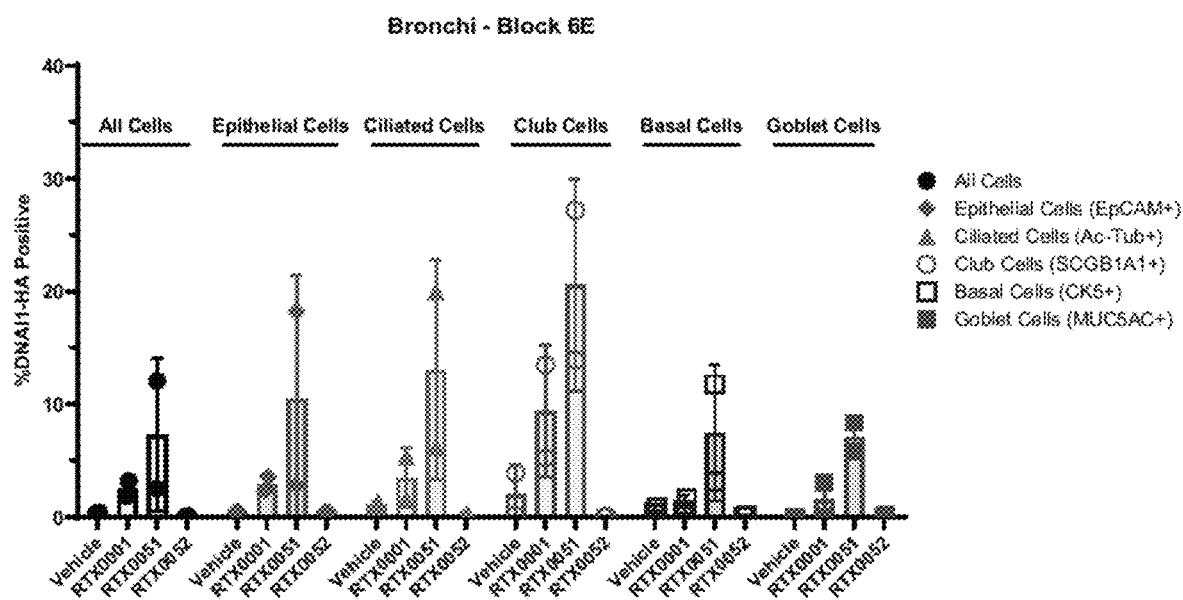
FIG. 30D illustrates multiplex IF analysis demonstrating expression of DNAI1-HA protein in target cells in bronchi.
Figure 30E:
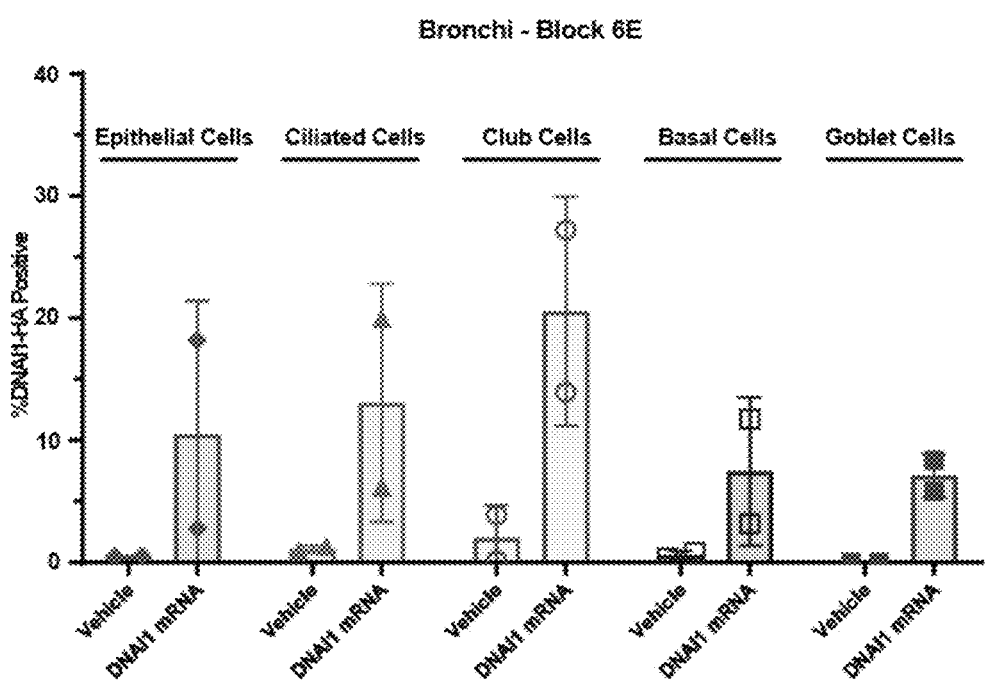
FIG. 30E illustrates multiplex IF analysis demonstrating expression of DNAI1-HA protein in target cells in bronchi with RTX0051.
Figure 30F:
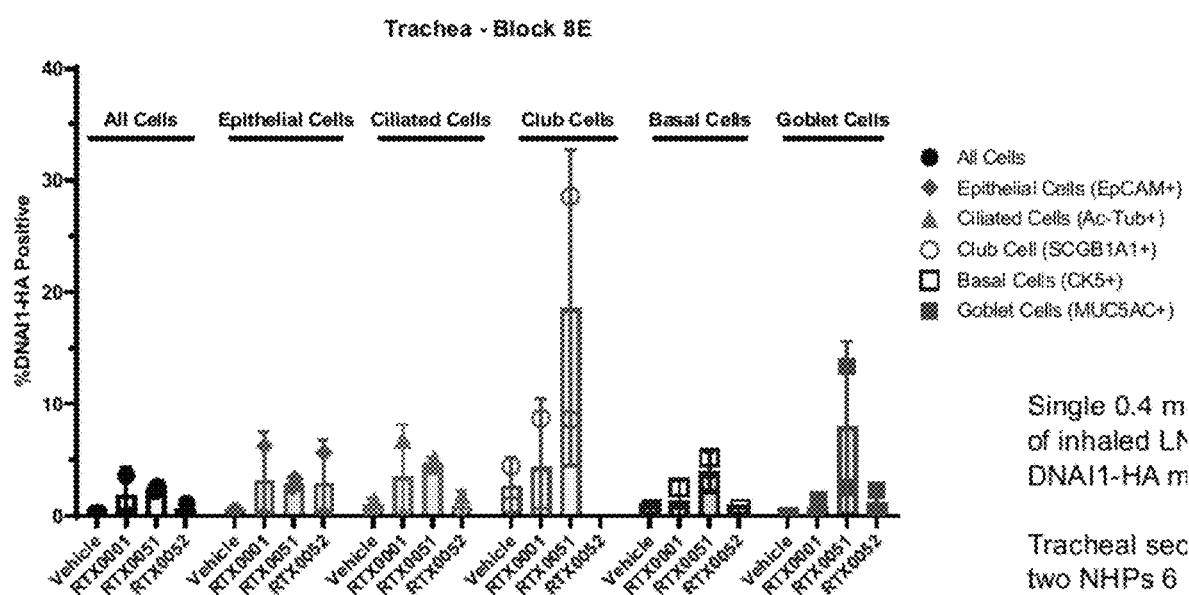
FIG. 30F illustrates multiplex IF analysis demonstrating expression of DNAI1-HA protein in target cells in trachea.
Figure 31A:
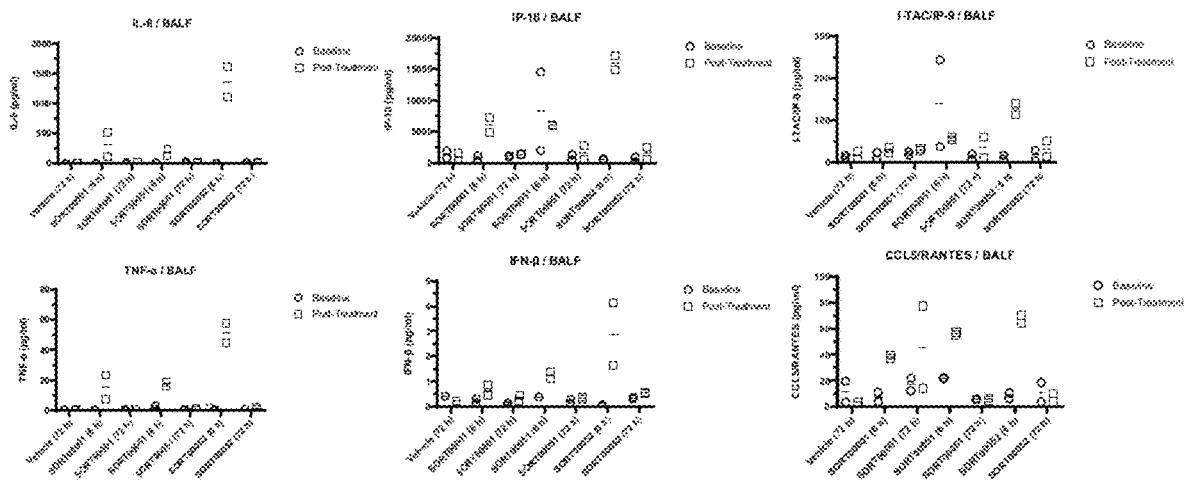
FIGS. 31A-E illustrate BAL cytokine and complement results.
Figure 31B:
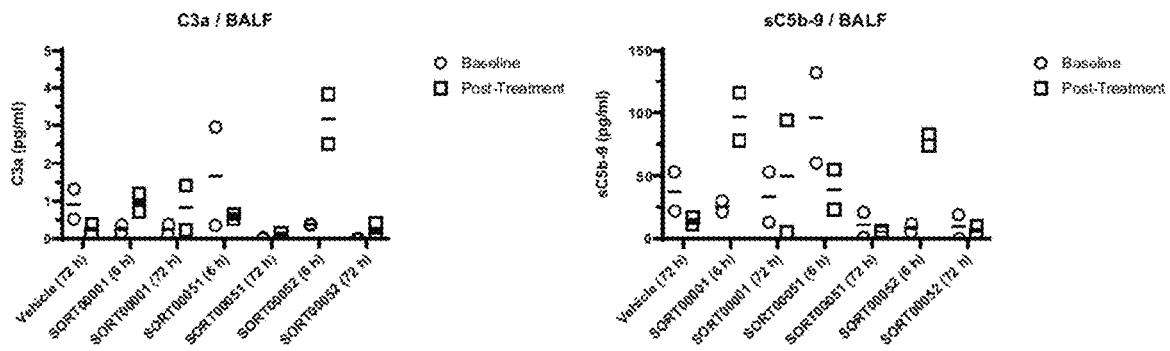
Figure 31C:
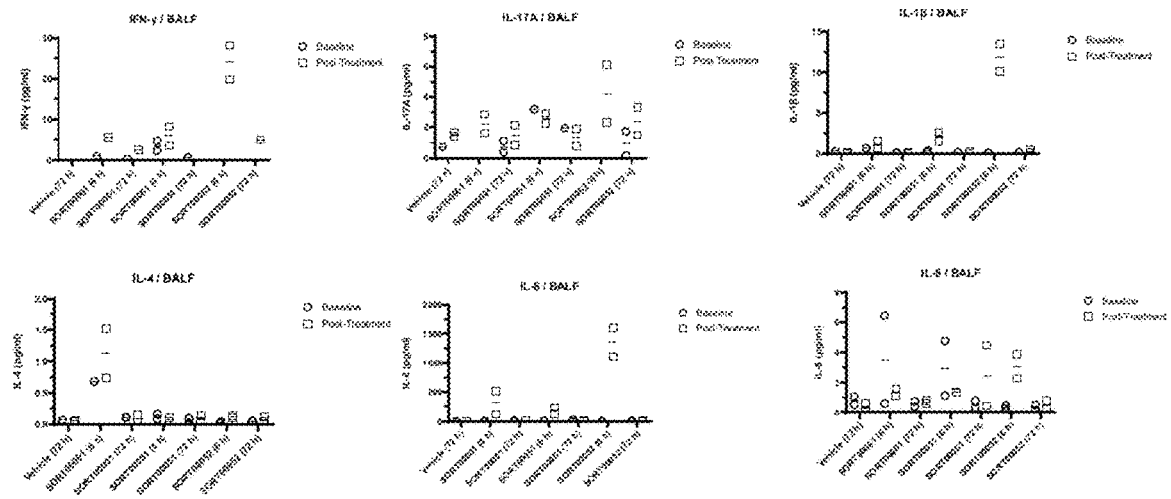
Figure 31D:
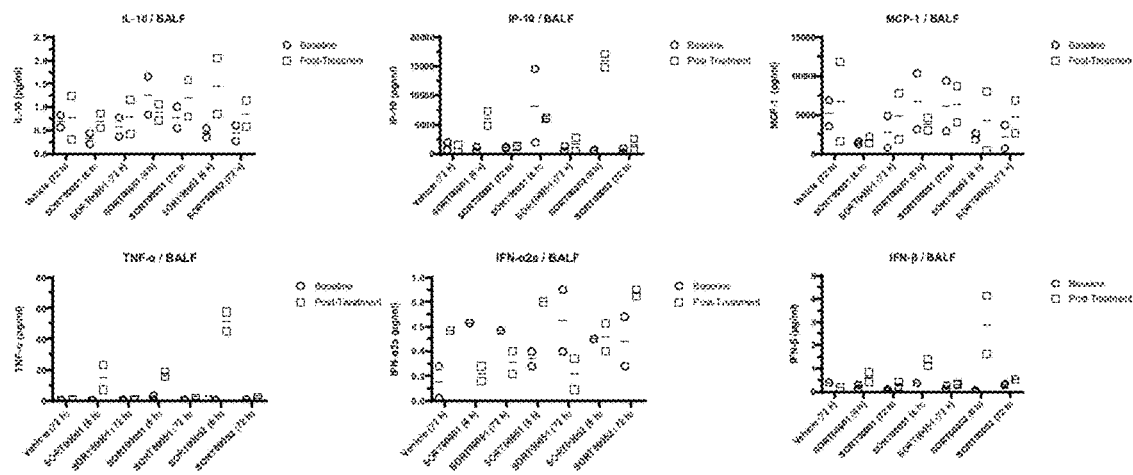
Figure 31E:
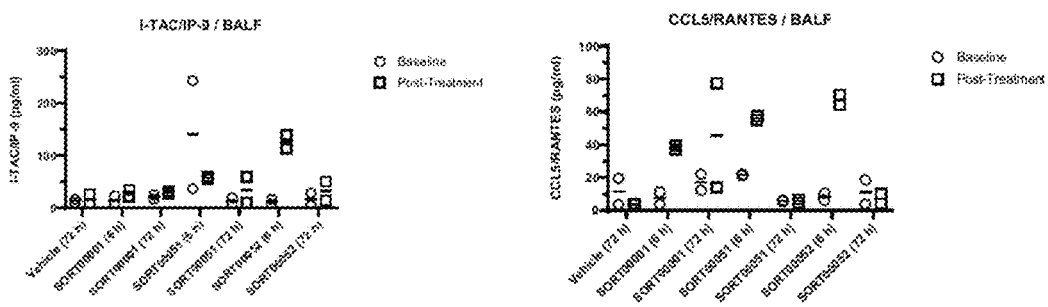
Figure 32A:
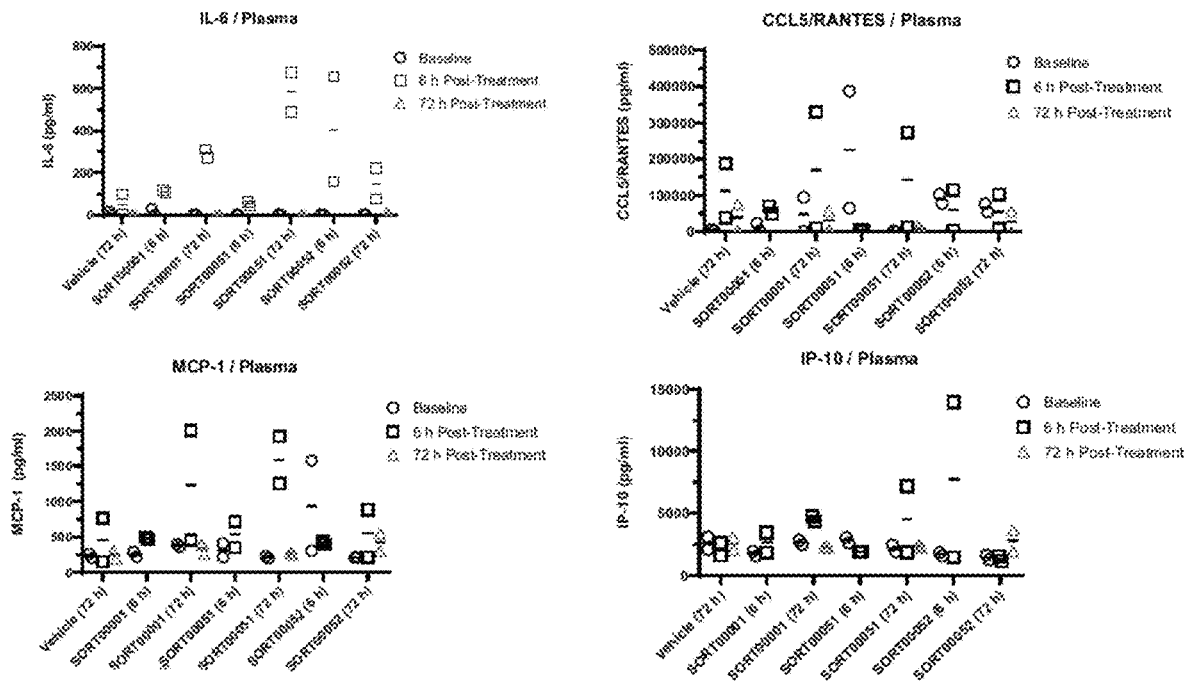
FIGS. 32A-E illustrate plasma cytokine results.
Figure 32B:
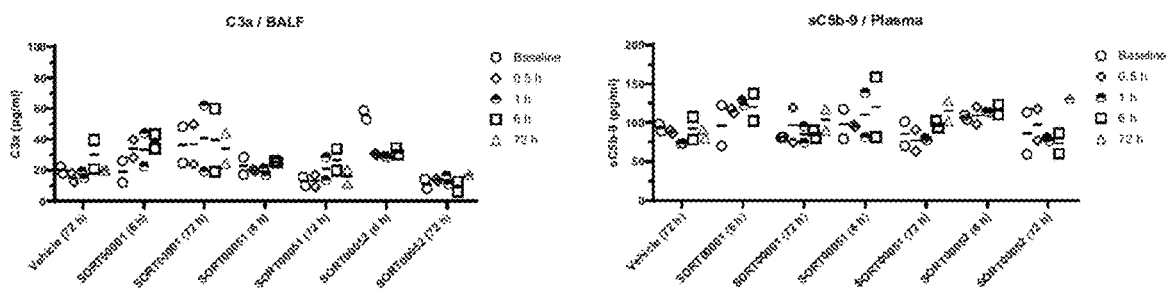
Figure 32C:
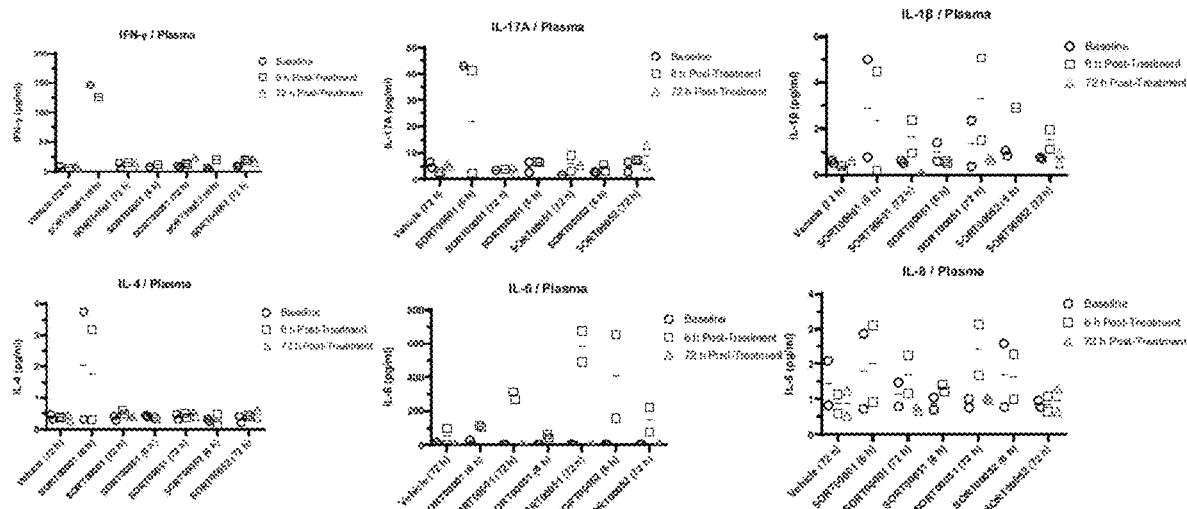
Figure 32D:
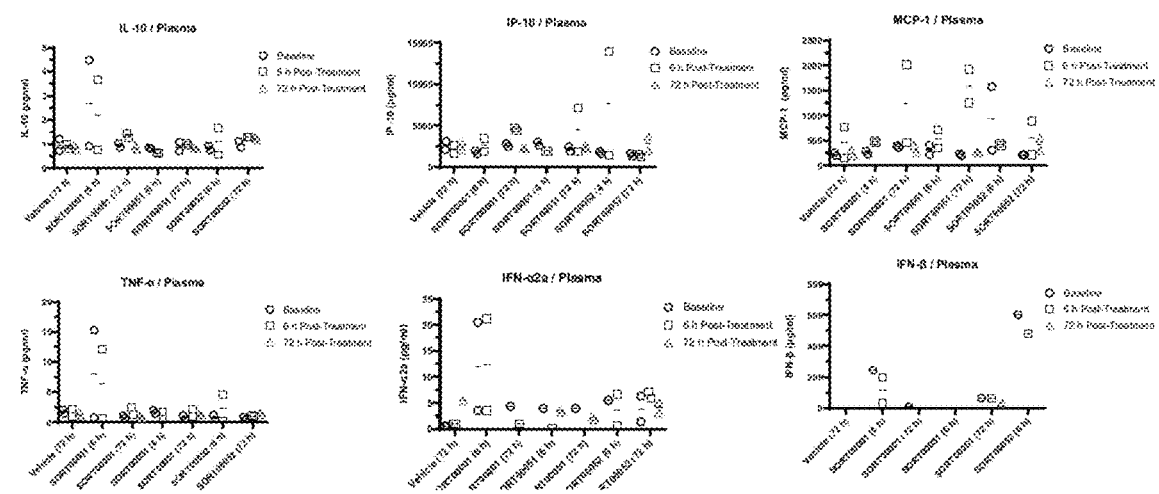
Figure 32E:
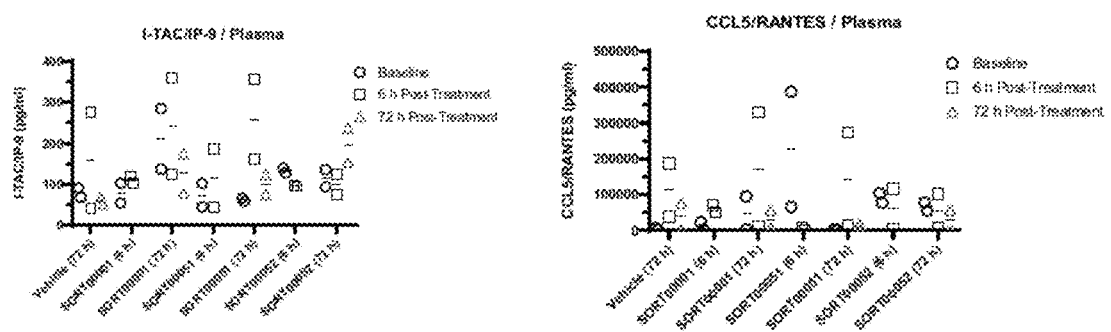

FIG. 30D illustrates multiplex IF analysis demonstrating expression of DNAI1-HA protein in target cells in bronchi. FIG. 30E illustrates multiplex IF analysis demonstrating expression of DNAI1-HA protein in target cells in bronchi with RTX0051. Single dose of 0.4 mg/kg was administered via inhalation of LNP-formulated DNAI1-HA mRNA. Bronchial sections were collected from two NHPs six hours after dosing. Percentage of DNAI1-HA positive cell was calculated from a single stained section per animal. Total number of cells counted was about 16,000 to 65,000 cells. Shown are the individual data points for each treated animal and the mean±std. dev. for each group (N=2). FIG. 30F illustrates multiplex IF analysis demonstrating expression of DNAI1-HA protein in target cells in trachea. Single dose of 0.4 mg/kg was administered via inhalation of LNP-formulated DNAI1-HA mRNA. Tracheal sections were collected from two NHPs six hours after dosing. Percentage of DNAI1-HA positive cell was calculated from a single stained section per animal. Total number of cells counted was about 16,000 to 28,000 cells. Shown are the individual data points for each treated animal and the mean±std. dev. for each group (N=2). FIG. 31A-E illustrate BAL cytokine and complement results. FIGS. 32A-E illustrate plasma cytokine results.

Figure 33:
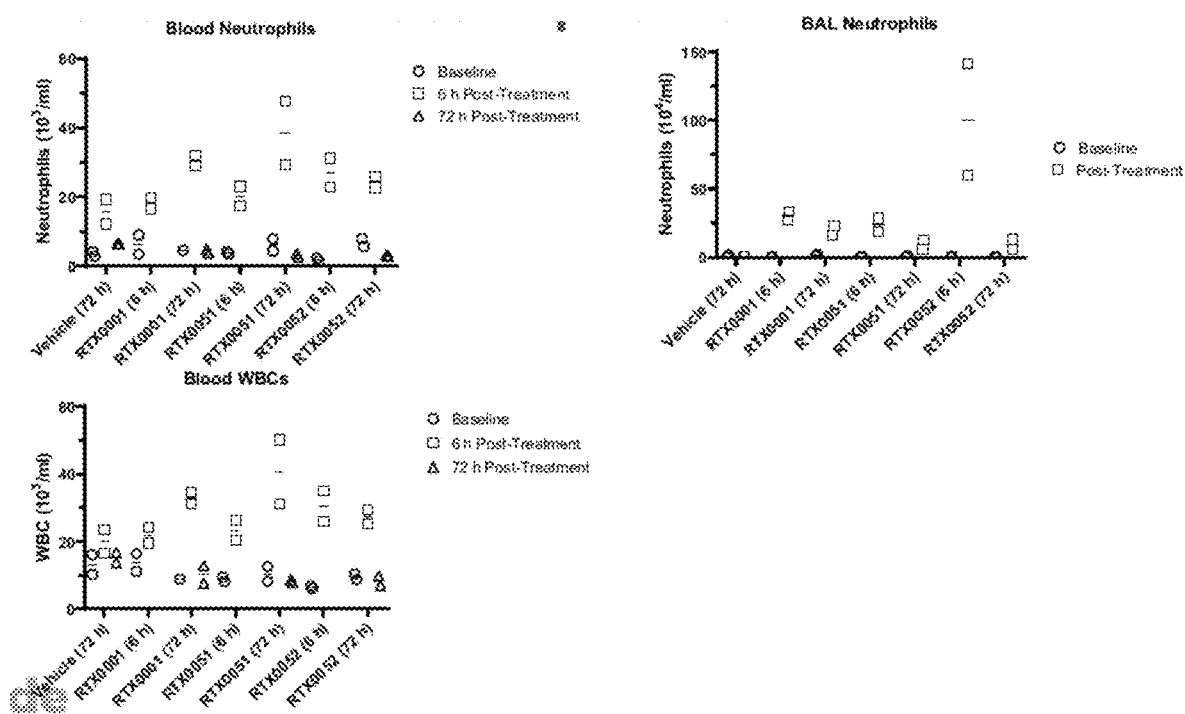
FIG. 33 illustrates transient increase in neutrophils observed in BAL and blood at six hours post-exposure.
Figure 34:
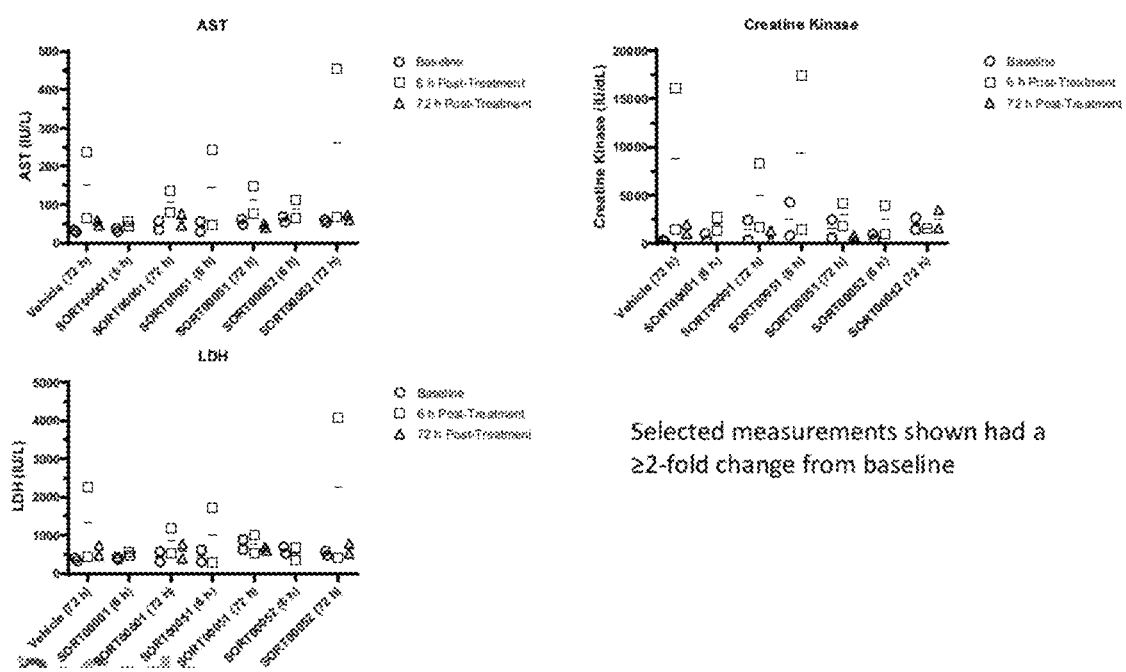
FIG. 34 illustrates selected clinical chemistry results. Small increases were observed for AST, LDH, and creatine kinase in individual animals after treatment.

FIG. 33 illustrates transient increase in neutrophils observed in BAL and blood at six hours post-exposure. Transient increases in BAL neutrophils and blood WBCs and neutrophils seen at six hours post-exposure. Levels of neutrophils and WBCs had returned to baseline at 72 hours. No other significant changes in blood or BAL cell populations was observed. FIG. 34 illustrates selected clinical chemistry results. Small increases were observed for AST, LDH, and creatine kinase in individual animals after treatment. These increases were seen in both vehicle and TA treated animals but transient and values returned to baseline by 72 hours. No significant increases were observed for rest of the blood chemistry panel. Coagulation assays showed similar results for vehicle and TA treated animals. FIG. 35 illustrates summary of tolerability as determined by clinical observations and organ weights. Animals were observed during exposure, for up to three hours post exposure and 6 hours thereafter. Cage side clinical observation (e.g. clinical signs, etc.) was performed in the AM and PM on exposure day until euthanasia. Special attention was paid to clinical signs including but not limited to apnea, dyspnea (labored breathing), malaise, marked nasal discharge, lethargy, abnormal heartbeat, cyanosis, discoloration of mucous membrane, bloody stool/urine, excessive body weight loss (>20% from baseline bodyweight). No adverse reactions were reported in any of the animals during and after exposure. No change in body weight was observed during duration of the study. Organ Weights and weights normalized to body weights were not statistically different between treatment groups. Normalized lung weights appeared to be slightly higher in the animals treated with RTX0001 and RTX0052 but no statistical significance due to small sample size. Following a single high dose administration of RTX0001, RTX0051, and RTX0052, inflammation of the lung was observed with all three formulations. The observed severity of Grade 3 (moderate) inflammation is a concern and could impact lung function at these high concentrations. While this degree of inflammation was seen with all formulations, the presentation was different. With RTX0001 and RTX0052, the early observation at 6 hours included Grade 3 multifocal neutrophilic alveolar inflammation, which by 72 hours had progressed to mixed cell inflammation (also Grade 3). At 72 hours, RTX0051 was observed with Grade 3 multifocal neutrophilic alveolar inflammation, similar to that observed at 6 hours for RTX0001 and RTX0052; it is unknown if this would have progressed to mixed cell inflammation similar to RTX0001 and RTX0052 given a later sampling.

Example 28. Single Dose Inhalation Study

Figure 36A:
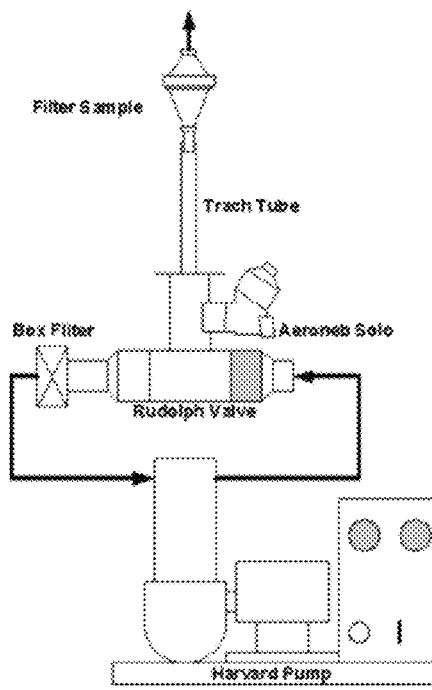
FIG. 36A illustrates a diagram of the aerosol delivery system. The amount of aerosolized drug delivered past the endotracheal tube was estimated using the test setup shown on the left. Pre-weighed glass fiber and MCE filters were attached directly at the exit of the endotracheal tube. Multiple collections were performed before, during and after treatment of the animals. The glass filters were dried and quantified using both gravimetric analysis. The MCE filters were analyzed for amount of mRNA using a RiboGreen assay.
Figure 36B:
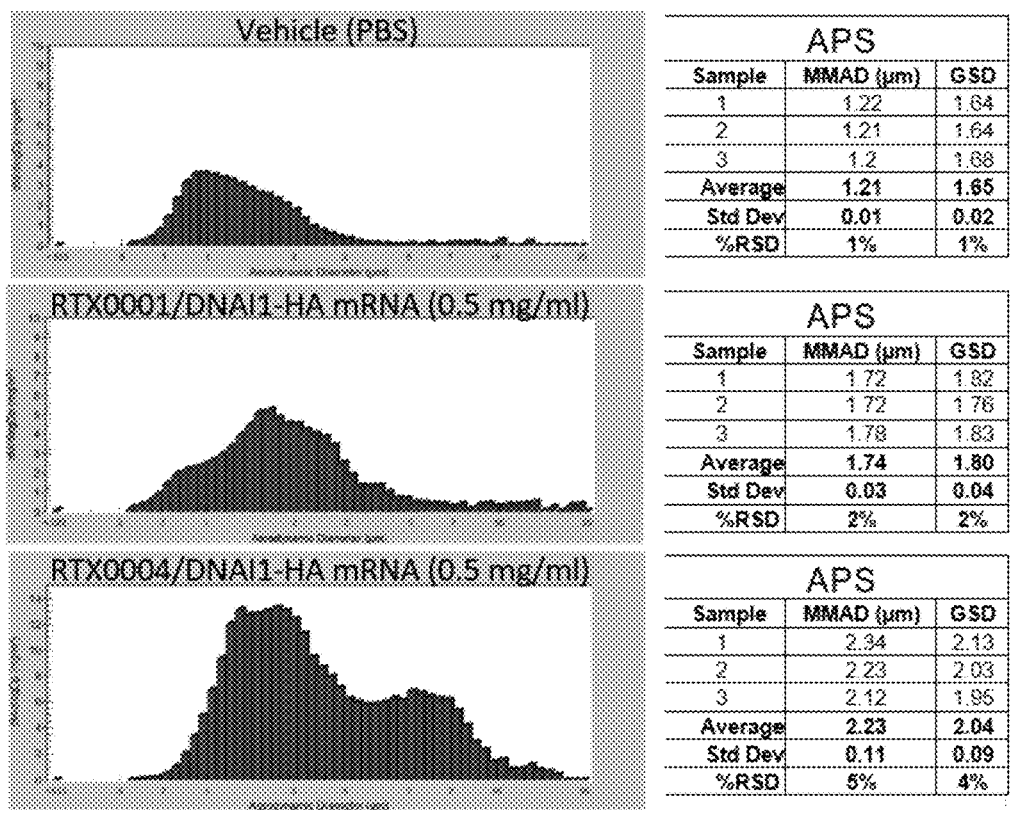
FIG. 36B illustrates the results of aerosol particle size measurements. Particle sizes for test article exposure were measured for deposition in the conducting airways (branching generations 0-15 in humans).

This example compared 4-component (RTX0004) and 5-component (SORT, RTX0001) LNPs for lung distribution of the mRNA and protein expression in target cells. The comparison included LNP formulation assessment; LNP formulation with mRNA as cargo (e.g., mRNA encoding DNAI1-GA), LNP formulation with modified nucleotide as cargo (e.g., mRNA comprising modified nucleotides); and LNP formulation with sequence optimized mRNA for stability and translation efficiency. NHPs (Mauritius cynomolgus macaques, 1-3 yrs. old, female, about 3 kg, N=4 per formulation, 2 per necropsy timepoints) were intubated and ventilated and treated with the LNPs by aerosol delivery. The target delivered dose was 0.1 mg/kg. Necropsy timepoints for assessment were at six hours and at 24 hours. FIG. 36A illustrates a diagram of the aerosol delivery system. The amount of aerosolized drug delivered past the endotracheal tube was estimated using the test setup shown on the left. Pre-weighed glass fiber and MCE filters were attached directly at the exit of the endotracheal tube. Multiple collections were performed before, during and after treatment of the animals. The glass filters were dried and quantified using both gravimetric analysis. The MCE filters were analyzed for amount of mRNA using a RiboGreen assay. FIG. 36B illustrates the results of aerosol particle size measurements. Particle sizes for test article exposure were measured for deposition in the conducting airways (branching generations 0-15 in humans).

Figure 37:
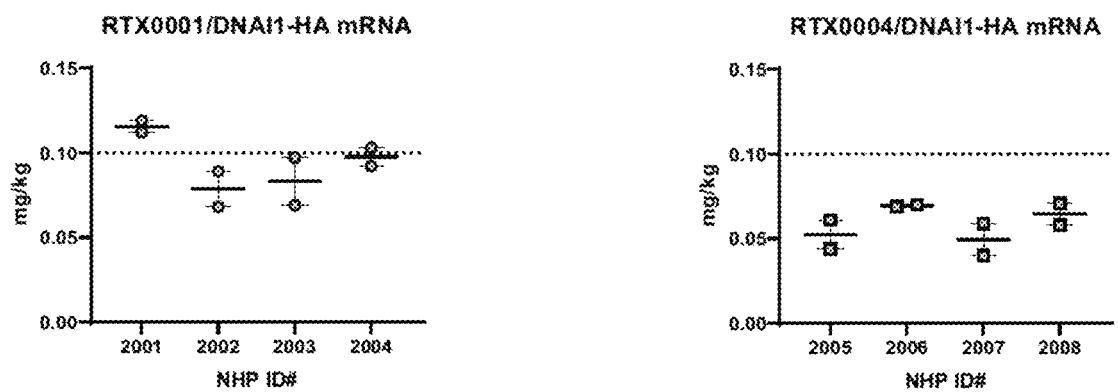
FIG. 37 illustrates DBAI1-HA mRNA dose present in the NHP. A dashed black horizontal line represents the targeted presented dose of 0.1 mg/kg. Open yellow circles show filter collections before and after dosing (GF, n=2) using RTX0001/DNAI1-HA mRNA. Open yellow squares show filter collections before and after dosing (GF, n=2) using RTX0004/DNAI1-HA mRNA. Similar results obtained for mRNA using MCE filters and a RiboGreen assay.

FIG. 37 illustrates DBAI1-HA mRNA dose present in the NHP. A dashed black horizontal line represents the targeted presented dose of 0.1 mg/kg. Open yellow circles show filter collections before and after dosing (GF, n=2) using RTX0001/DNAI1-HA mRNA. Open yellow squares show filter collections before and after dosing (GF, n=2) using RTX0004/DNAI1-HA mRNA. Similar results obtained for mRNA using MCE filters and a RiboGreen assay. FIGS. 36 and 37 collectively show that aerosol particle size ranges appropriate for deposition in the conducting airways (branching generations 0-15 in humans). Target delivered dose of 0.1 mg/kg was achieved for RTX0001/DNAI1-HA mRNA and between 25-50% lower than targeted dose for RTX0004/DNAI1-HA mRNA. Problems with clogging or changes in device performance/flow rates were not observed. Both test articles nebulized well with minimal differences in flow rates. RTX0004/DNAI1-HA mRNA had a slightly higher flow rate compared RTX0001/DNAI1-HA mRNA. The faster flow rates and lower exposures for RTX0004/DNAI1-HA mRNA could be due to the larger aerosol droplet sizes observer by APS measurements.

Figure 38A:
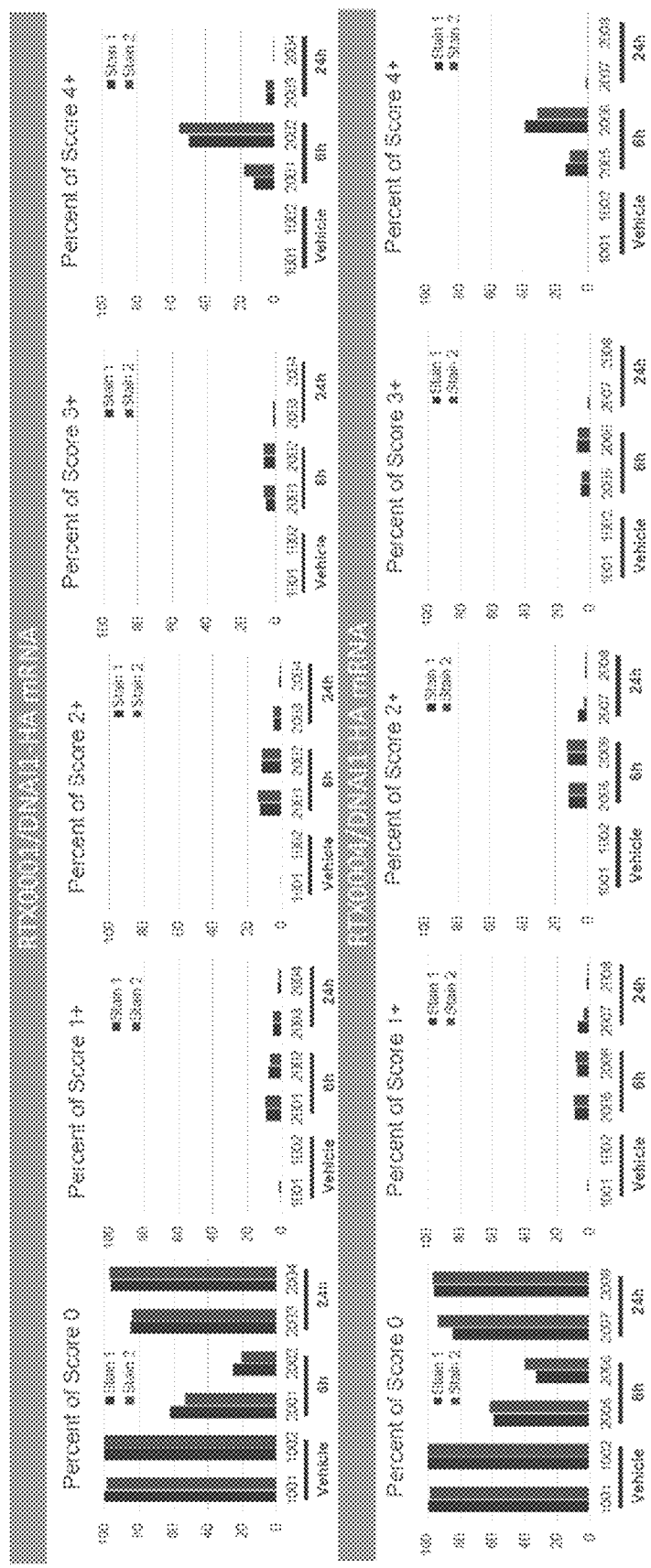
FIG. 38A illustrates DNAI1-HA mRNA ISH results for lung tissue. Data from assay qualification: 1 of 4 samples per animal analyzed. DNAI1-HA mRNA detected in all animals.
Figure 38B:
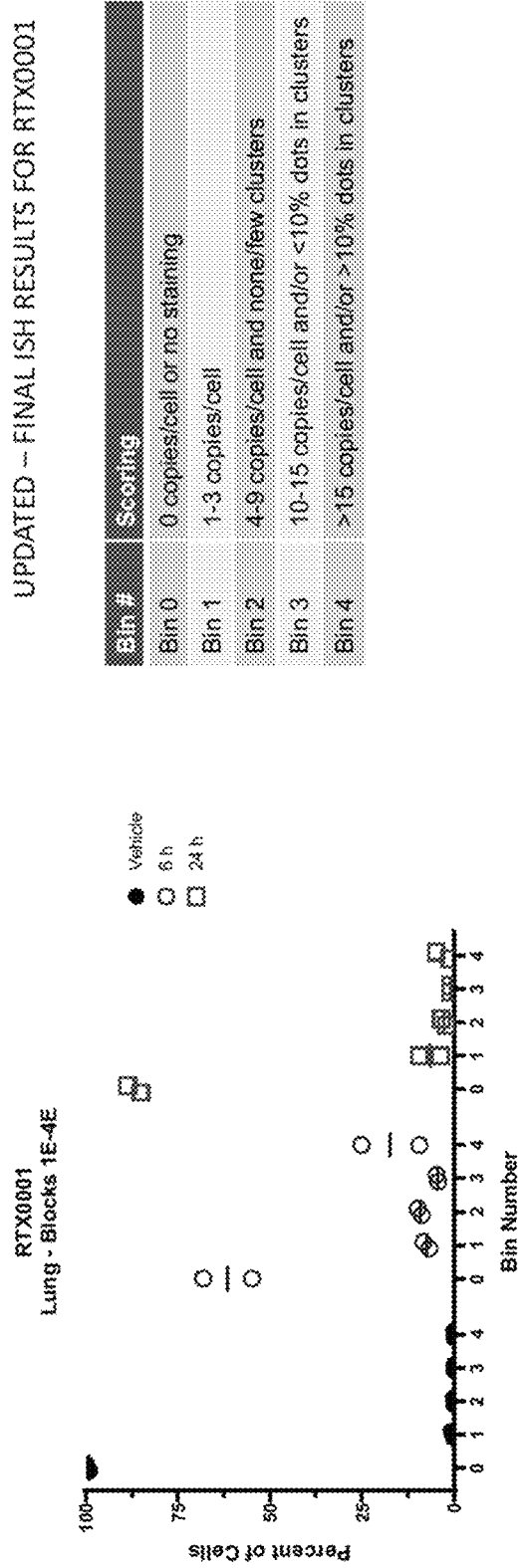
FIG. 38B illustrates that a significant fraction of lung cells contained DNAI1-HA mRNA after treatment with RTX0001 as measured by ISH and the bin scoring.
Figure 38C:
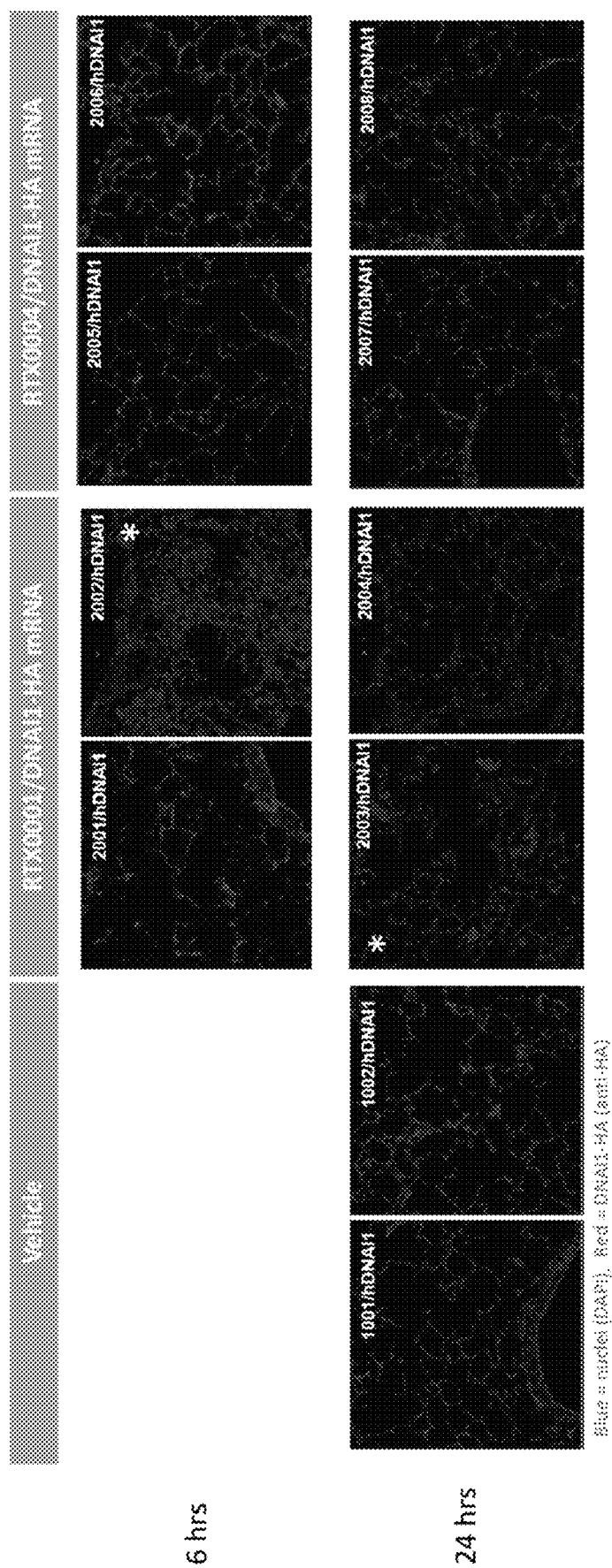
FIG. 38C illustrates the imaging of the lung tissue used for the ISH analysis.

In situ hybridization (ISH) assay was used to detect DNAI1-HA mRNA delivered to the lungs of NHPs using custom designed ISH probe. ISH results were analyzed into bins: 0+: zero minimum copies/cell; 1+: one minimum copy/cell; 2+: 4 minimum copies/cell; 3+: 10 minimum copies/cell; and 4+: 16 minimum copies/cell. FIG. 38A illustrates DNAI1-HA mRNA ISH results for lung tissue. Data from assay qualification: 1 of 4 samples per animal analyzed. DNAI1-HA mRNA detected in all animals. FIG. 38B illustrates that a significant fraction of lung cells contained DNAI1-HA mRNA after treatment with RTX0001 as measured by ISH and the bin scoring. FIG. 38B demonstrates that up to 25% of lung cells contained more than 15 copies of the DNAI1-HA mRNA per cell after treatment with RTX0001. FIG. 38C illustrates the imaging of the lung tissue used for the ISH analysis.

Figure 39A:
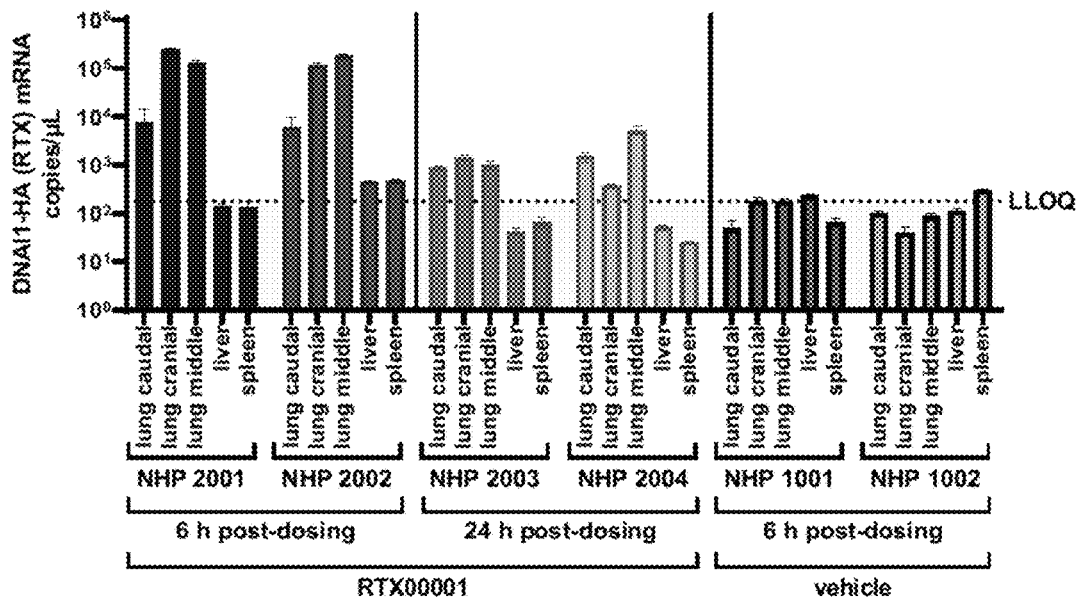
FIG. 39A illustrates that the delivery of high levels of DNAI1-HA to the lung did not lead to similar deliver to liver or spleen. Digital PCR was used to measure DNAI1-HA mRNA levels in whole blood, lung, liver, and spleen tissue following a single 0.1 mg/kg administration. High levels of DNAI1-HA mRNA were detected in all three lung regions sampled at 6 hour post-exposure with RTX0001. In spleen and liver, DNAI1-HA mRNA was only measured at or below the LLOQ of the assay.
Figure 39B:
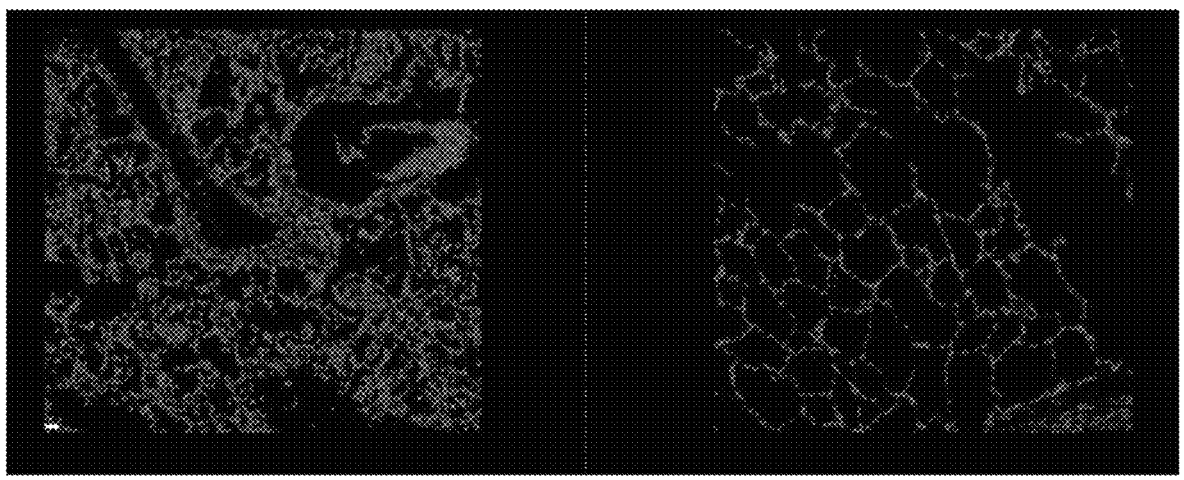
FIG. 39B illustrates the positive staining of DNAI1-HA tagged protein in NHPs. For RTX0001, DNAI1-HA was detected six hours or 24 hours after administration. Regions with higher mRNA levels correlated with regions showing highest levels of DNAI1-HA protein. DNAI1-HA mRNA was present in all eight treated animals. No signal detected in vehicle treated animals. mRNA levels were highest at six hours and lower at 24 hours.
Figure 39C:
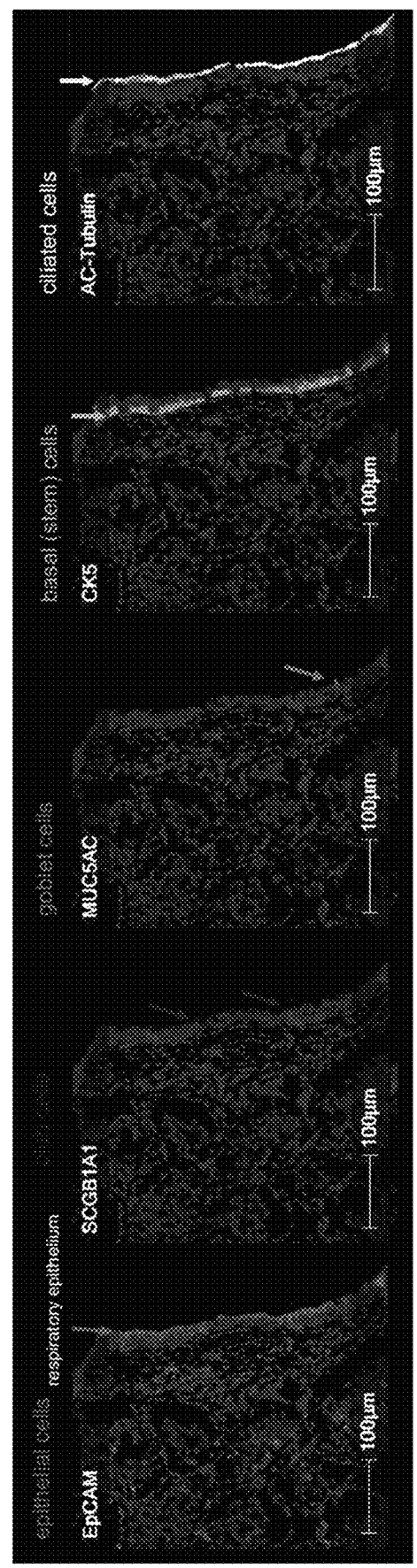
FIG. 39C illustrates multiplex IF panel for key epithelial cell types. 10 NHP FFPE lung tissue blocks (1 from each animal) were used for mIF assay qualification. Two slides from each block were stained in duplicates. The cell counts of single marker positive cells, double positive cells with DNAI1 expression, and DNAI1 MFI in double positive cells were reported.

FIG. 39A illustrates that the delivery of high levels of DNAI1-HA to the lung did not lead to similar deliver to liver or spleen. Digital PCR was used to measure DNAI1-HA mRNA levels in whole blood, lung, liver, and spleen tissue following a single 0.1 mg/kg administration. Primers used were specific for the RTX sequence optimized DNAI1-HA sequence. High levels of DNAI1-HA mRNA were detected in all three lung regions sampled at 6 hour post-exposure with RTX0001. In spleen and liver, DNAI1-HA mRNA was only measured at or below the LLOQ of the assay. FIG. 39B illustrates the positive staining of DNAI1-HA tagged protein in NHPs. For RTX0001, DNAI1-HA was detected six hours or 24 hours after administration. Regions with higher mRNA levels correlated with regions showing highest levels of DNAI1-HA protein. DNAI1-HA mRNA was present in all eight treated animals. No signal detected in vehicle treated animals. mRNA levels were highest at six hours and lower at 24 hours. mRNA levels were highest for RTX0001 treated animals compared to RTX0004 (consistent with emitted dose measurements). Using serial sections, regions with higher mRNA levels were correlated with regions showing highest levels of DNAI1-HA protein. DNAI1-HA was detected at six hours and 24 hours in NHPs treated with RTX0001. FIG. 39C illustrates multiplex IF panel for key epithelial cell types. 10 NHP FFPE lung tissue blocks (1 from each animal) were used for mIF assay qualification. Two slides from each block were stained in duplicates. The cell counts of single marker positive cells, double positive cells with DNAI1 expression, and DNAI1 MFI in double positive cells were reported. Epithelium cell was marked with EPCAM. Ciliated cell was marked with acetylated-tubulin (AC-tubulin). Club cell was marked with secreto-globin family 1A member 1 (SCGB1A1). Goblet cell was marked with mucin 5AC (MUC5AC). Basal cell (stem cell) was marked with cytokeratin 5 (CK5).

Figure 40A:
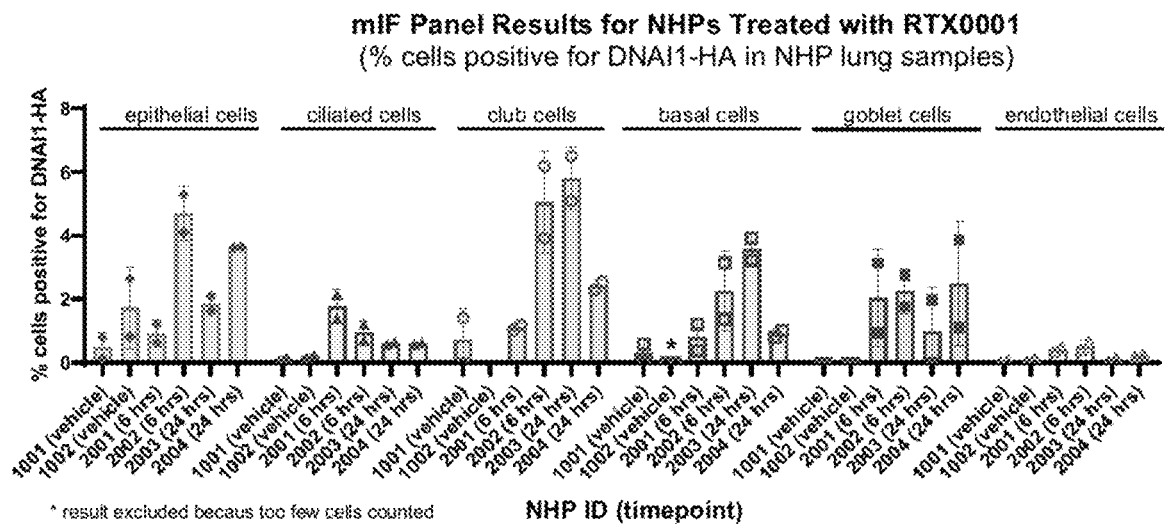
FIG. 40A illustrates multiplex IF panel results for NHP lung samples. DNAI1-HA was expressed in cells of the respiratory epithelium. Percentage of DNAI1-HA positive cell was calculated by combining cell counts from 1 examined lung section per animal. DNAI1-HA expression was detected in lung samples from NHPs treated with RTX0001. DNAI1-HA expression was co-localized with markers for epithelial cells, including the club, basal and ciliated cells (club and basal cells are precursors for ciliated cells). No staining detected was in lung samples from NHPs treated with RTX0004.
Figure 40B:
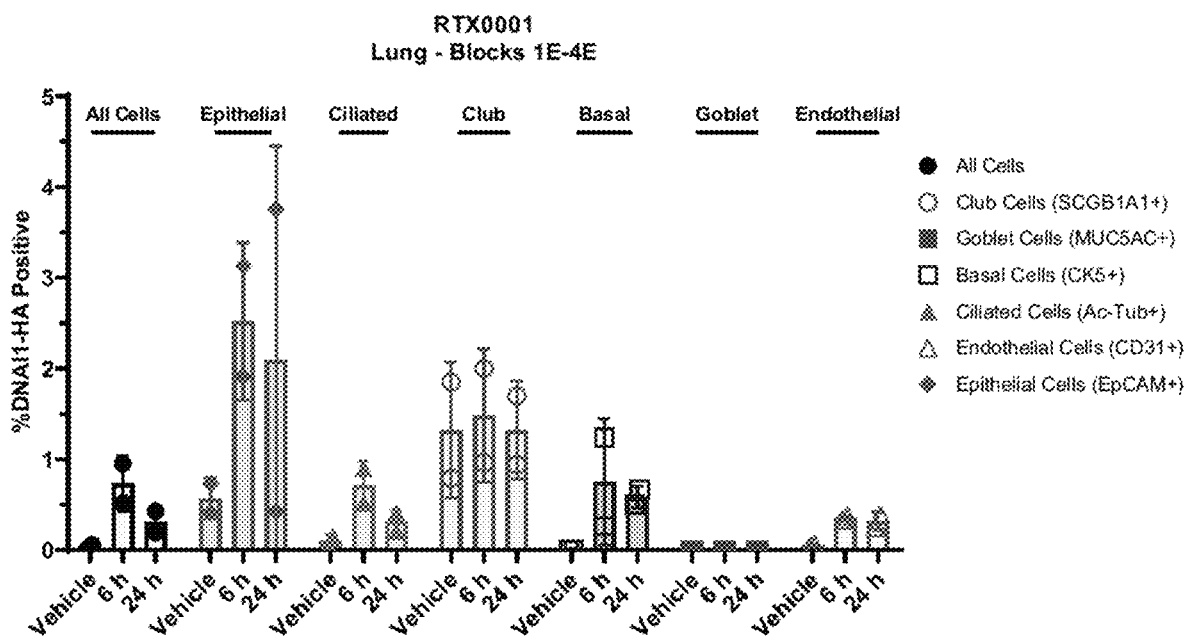
FIG. 40B illustrates multiplex IF analysis of expression of DNAI1-HA protein in target cell in the lung. Single dose of 0.1 mg/kg of RTX0001/DNAI1-HA mRNA was administered via inhalation. Lung sections were collected from two NHPs at six hours and 24 hours after dosing. Percentage of DNAI1-HA positive cell was calculated by combining cell counts from all 4 examined lung sections for an individual animal. Total number of cells counted per animal was about 690,000 to 1,100,000. Shown are the individual data points for each treated animal and the mean±std. dev. for each group (N=2).

FIG. 40A illustrates multiplex IF panel results for NHP lung samples. DNAI1-HA was expressed in cells of the respiratory epithelium. Percentage of DNAI1-HA positive cell was calculated by combining cell counts from 1 examined lung section per animal. DNAI1-HA expression was detected in lung samples from NHPs treated with RTX0001. DNAI1-HA expression was co-localized with markers for epithelial cells, including the club, basal and ciliated cells (club and basal cells are precursors for ciliated cells). No staining detected was in lung samples from NHPs treated with RTX0004. FIG. 40B illustrates multiplex IF analysis of expression of DNAI1-HA protein in target cell in the lung. Single dose of 0.1 mg/kg of RTX0001/DNAI1-HA mRNA was administered via inhalation. Lung sections were collected from two NHPs at six hours and 24 hours after dosing. Percentage of DNAI1-HA positive cell was calculated by combining cell counts from all 4 examined lung sections for an individual animal. Total number of cells counted per animal was about 690,000 to 1,100,000. Shown are the individual data points for each treated animal and the mean±std. dev. for each group (N=2).

The present study showed that the aerosol particle size was consistent with deposition in the conducting airways for both formulations, and the flow rates were consistent throughout exposures (more than >0.20 mL/min for both formulations). The exposure time for both formulations were short (between four to nine minutes). The biodistribution results indicated good distribution of mRNA, with higher levels for NHPs treated with formulation RTX0001. DNAI1 protein was detected in ciliated, club, and basal cells of animals treated with formulation RTX0001. Little or no DNAI1-HA expression was detected with RTX0004 (note: delivered dose was 25-50% lower compared to RTX0001)

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A lipid nanoparticle composition for delivering a polynucleotide to the lung cells in a subject wherein the lipid nanoparticle comprises:
   (i) a polynucleotide;
   (ii) a dendrimer ionizable cationic lipid;
   (iii) an ethylphosphocholine at a molar percentage from about 20% to about 65%;
   (iv) a phospholipid;
   (v) a cholesterol; and
   (vi) a polyethylene glycol-conjugated lipid,
   wherein the dendrimer ionizable cationic lipid is

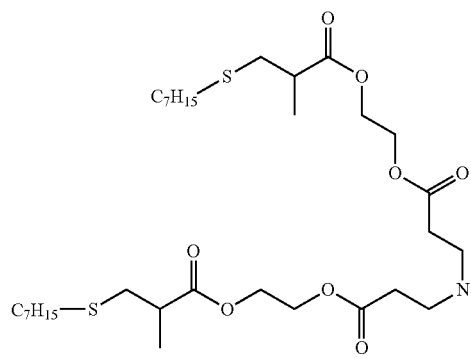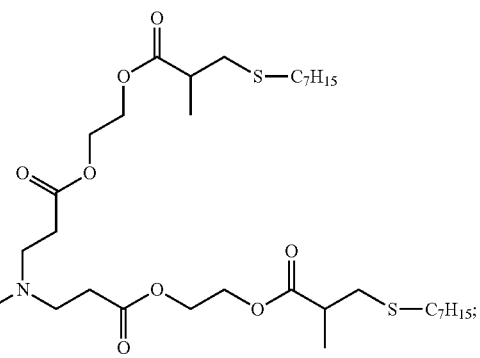

and
   wherein the lipid nanoparticle composition is an aerosol composition.

2. The composition of claim 1, wherein the composition preferentially delivers the polynucleotide to the lung cells in the subject.

3. The composition of claim 1, wherein the dendrimer ionizable cationic lipid is present in the composition at a molar percentage from about 5% to about 30%.

4. The composition of claim 1, wherein the ethylphosphocholine is present in the composition at a molar percentage from about 20% to about 40%.

5. The composition of claim 1, wherein the phospholipid is present in the composition at a molar percentage from about 7.5% to about 60%.

6. The composition of claim 1, wherein the cholesterol is present in the composition at a molar percentage from about 15% to about 46%.

7. The composition of claim 1, wherein the polyethylene glycol-conjugated lipid is present in the composition wherein the cholesterol is present in the composition at a molar percentage from about 15% to about 46%;
wherein the polyethylene glycol-conjugated lipid is present in the composition at a molar percentage from about 0.5% to about 10%; and
wherein the dendrimer ionizable cationic lipid is present in the composition at a molar percentage from about 5% to about 30%.

21. The composition of claim 1, wherein the ethylphosphocholine is 1,2-dimyristoyl-sn-glycero-3-ethylphosphocholine.

22. The composition of claim 21, wherein the 1,2-dimyristoyl-sn-glycero-3-ethylphosphocholine is present in the composition at a molar percentage from about 20% to about 40%.

23. The composition of claim 21,
wherein the 1,2-dimyristoyl-sn-glycero-3-ethylphosphocholine is present in the composition at a molar percentage from about 20% to about 40%;
wherein the phospholipid is present in the composition at a molar percentage from about 7.5% to about 60%;
wherein the cholesterol is present in the composition at a molar percentage from about 15% to about 46%;
wherein the polyethylene glycol-conjugated lipid is present in the composition at a molar percentage from about 0.5% to about 10%; and
wherein the dendrimer ionizable cationic lipid is present in the composition at a molar percentage from about 5% to about 30%.

24. The composition of claim 1, wherein the ethylphosphocholine is 1,2-dimyristoleoyl-sn-glycero-3-ethylphosphocholine.

25. The composition of claim 24, wherein the 1,2-dimyristoleoyl-sn-glycero-3-ethylphosphocholine is present in the composition at a molar percentage from about 20% to about 40%.

26. The composition of claim 24,
wherein the 1,2-dimyristoleoyl-sn-glycero-3-ethylphosphocholine is present in the composition at a molar percentage from about 20% to about 40%;
wherein the phospholipid is present in the composition at a molar percentage from about 7.5% to about 60%;
wherein the cholesterol is present in the composition at a molar percentage from about 15% to about 46%;
wherein the polyethylene glycol-conjugated lipid is present in the composition at a molar percentage from about 0.5% to about 10%; and
wherein the dendrimer ionizable cationic lipid is present in the composition at a molar percentage from about 5% to about 30%.

27. The composition of claim 1, wherein the ethylphosphocholine is 1,2-distearoyl-sn-glycero-3-ethylphosphocholine.

28. The composition of claim 27, wherein the 1,2-distearoyl-sn-glycero-3-ethylphosphocholine is present in the composition at a molar percentage from about 20% to about 40%.

29. The composition of claim 27,
wherein the 1,2-distearoyl-sn-glycero-3-ethylphosphocholine is present in the composition at a molar percentage from about 20% to about 40%;
wherein the phospholipid is present in the composition at a molar percentage from about 7.5% to about 60%;
wherein the cholesterol is present in the composition at a molar percentage from about 15% to about 46%;
wherein the polyethylene glycol-conjugated lipid is present in the composition at a molar percentage from about 0.5% to about 10%; and
wherein the dendrimer ionizable cationic lipid is present in the composition at a molar percentage from about 5% to about 30%.

30. The composition of claim 1, wherein the ethylphosphocholine is 1-palmitoyl-2-oleoyl-sn-glycero-3-ethylphosphocholine.

31. The composition of claim 30, wherein the 1-palmitoyl-2-oleoyl-sn-glycero-3-ethylphosphocholine is present in the composition at a molar percentage from about 20% to about 40%.

32. The composition of claim 30,
wherein the 1-palmitoyl-2-oleoyl-sn-glycero-3-ethylphosphocholine is present in the composition at a molar percentage from about 20% to about 40%;
wherein the phospholipid is present in the composition at a molar percentage from about 7.5% to about 60%;
wherein the cholesterol is present in the composition at a molar percentage from about 15% to about 46%;
wherein the polyethylene glycol-conjugated lipid is present in the composition at a molar percentage from about 0.5% to about 10%; and
wherein the dendrimer ionizable cationic lipid is present in the composition at a molar percentage from about 5% to about 30%.

* * * * *

UNITED STATES PATENT AND TRADEMARK OFFICE
CERTIFICATE OF CORRECTION

PATENT NO. : 12,121,610 B2
APPLICATION NO. : 18/311616
DATED : October 22, 2024
INVENTOR(S) : Mirko Hennig et al.

It is certified that error appears in the above-identified patent and that said Letters Patent is hereby corrected as shown below:

In the Claims

At Column 281, Claim number 1, Line number 3, delete "nucleotide to the lung cells in a subject wherein the lipid" and insert --nucleotide to lung cells in a subject wherein the lipid--.

Signed and Sealed this
Eleventh Day of February, 2025

Coke Morgan Stewart
*Acting Director of the United States Patent and Trademark Office*